(12) United States Patent
Kokubo et al.

(10) Patent No.: US 8,168,783 B2
(45) Date of Patent: May 1, 2012

(54) CHEMOKINE RECEPTOR ANTAGONISTS AND USE THEREOF

(75) Inventors: Masaya Kokubo, Mishima-gun (JP); Hiroshi Ochiai, Mishima-gun (JP); Yoshikazu Takaoka, Mishima-gun (JP); Shiro Shibayama, Tsukuba (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 991 days.

(21) Appl. No.: 12/094,100

(22) PCT Filed: Nov. 17, 2006

(86) PCT No.: PCT/JP2006/323015
§ 371 (c)(1),
(2), (4) Date: May 16, 2008

(87) PCT Pub. No.: WO2007/058322
PCT Pub. Date: May 24, 2007

(65) Prior Publication Data
US 2009/0169567 A1    Jul. 2, 2009

(30) Foreign Application Priority Data

Nov. 18, 2005  (JP) ................ 2005-334937
Feb. 24, 2006  (JP) ................ 2006-049378

(51) Int. Cl.
*C07D 471/10*  (2006.01)
(52) U.S. Cl. .......................................... 544/71
(58) Field of Classification Search .............. None
See application file for complete search history.

(56) References Cited

U.S. PATENT DOCUMENTS

| | | | |
|---|---|---|---|
| 3,301,857 A | 1/1967 | Berger et al. |
| 5,962,462 A | 10/1999 | Mills et al. |
| 6,291,469 B1 | 9/2001 | Fisher et al. |
| 7,176,227 B2 | 2/2007 | Yamazaki et al. |
| 2002/0018124 A1 | 2/2002 | Mottur et al. |
| 2003/0018046 A1 | 1/2003 | Bridger et al. |
| 2003/0187023 A1 | 10/2003 | Kubo et al. |
| 2003/0220341 A1 | 11/2003 | Bridger et al. |
| 2004/0019058 A1 | 1/2004 | Bridger et al. |
| 2004/0254221 A1 | 12/2004 | Yamazaki et al. |
| 2005/0165063 A1 | 7/2005 | Yamazaki et al. |
| 2007/0208007 A1 | 9/2007 | Saitou et al. |
| 2007/0208033 A1 | 9/2007 | Yamazaki et al. |
| 2008/0009495 A1 | 1/2008 | Kokubo et al. |
| 2009/0169567 A1 | 7/2009 | Kokubo et al. |
| 2009/0192182 A1 | 7/2009 | Kusumi et al. |
| 2010/0026164 A1 | 2/2010 | Honda et al. |

FOREIGN PATENT DOCUMENTS

| | | |
|---|---|---|
| EP | 0 070 171 B1 | 10/1986 |
| EP | 1 308 439 A1 | 5/2003 |
| EP | 1 378 510 A1 | 1/2004 |
| EP | 1724263 A1 | 11/2006 |
| EP | 1961744 A1 | 8/2008 |
| JP | 49-13184 | 2/1974 |
| JP | 49-72332 | 7/1974 |
| JP | 4-18092 A | 1/1992 |
| JP | 11321508 A | 11/1999 |
| JP | 2002-348288 A | 12/2002 |
| JP | 2003-104884 A | 4/2003 |
| JP | 2004-508421 A | 3/2004 |
| JP | 2004-508422 A | 3/2004 |
| JP | 2005-518397 A | 6/2005 |
| WO | 95/01358 A1 | 1/1995 |
| WO | 97/11940 A1 | 4/1997 |
| WO | 98/25605 A1 | 6/1998 |
| WO | 01/13917 A1 | 3/2001 |
| WO | WO 01/14376 A1 | 3/2001 |
| WO | 02/22599 A2 | 3/2002 |
| WO | 02/22600 A2 | 3/2002 |
| WO | 02/074770 A1 | 9/2002 |
| WO | 03/020721 A1 | 3/2003 |
| WO | 03/024941 A1 | 3/2003 |
| WO | 03/029218 A1 | 4/2003 |
| WO | 03/055876 A1 | 7/2003 |

(Continued)

OTHER PUBLICATIONS

Rautio et al., Prodrugs: Design and Clinical Applications, 7 Nat. Rev. Drug Dis., 255-70 (2008).*
Vippagunta et al., Crystalline solids, 48 Adv. Drug Delivery Rev. 3-26 (2001).*
Skerlj et al., Synthesis and SAR of Novel CXCR4 Antagonists that are Potent Inhibitors of T Tropic (XR) HIV-1 Replication, 21 Bioorg. & Med. Chem. Letts. 262-266 (2011).*

(Continued)

*Primary Examiner* — Janet Andres
*Assistant Examiner* — Timothy R Rozof
(74) *Attorney, Agent, or Firm* — Sughrue Mion, PLLC

(57) ABSTRACT

A compound represented by general formula (I):

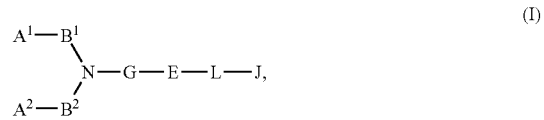

a salt thereof, a solvate thereof, or a prodrug thereof wherein all symbols are as defined in the specification has an antagonistic activity against CXCR4 and is therefore useful as a preventive and/or therapeutic agent for CXCR4-mediated diseases, for example, inflammatory and immune diseases (for example, rheumatoid arthritis, arthritis, systemic erythematosus, retinopathy, macular degeneration, pulmonary fibrosis, transplanted organ rejection, etc.), allergic diseases, infections (for example, human immunodeficiency virus infection, acquired immunodeficiency syndrome, etc.), psychoneurotic diseases, cerebral diseases, cardiac/vascular disease (for example, arteriosclerosis, myocardial infarction, stenocardia, cerebral infarction, chronic arterial occlusive disease, etc.), metabolic diseases, and cancerous diseases (for example, cancer, cancer metastasis, etc.), a preventive and/or therapeutic agent for cancerous diseases or infections, or an agent for regeneration therapy.

3 Claims, No Drawings

FOREIGN PATENT DOCUMENTS

| WO | 03/057698 A2 | 7/2003 |
|---|---|---|
| WO | WO 03/076443 A1 | 9/2003 |
| WO | 2004/024697 A1 | 3/2004 |
| WO | 2005/085209 A1 | 9/2005 |
| WO | 2006/022454 A1 | 3/2006 |

OTHER PUBLICATIONS

United States Office Action, dated Dec. 22, 2010, issued in related U.S. Appl. No. 12/301,194 to Kusumi et al.
H. Van De Waterbeemd, "Property-Based Design: Optimization of Drug Absorption and Pharmacokinetics", Journal of Medicinal Chemistry, vol. 44, No. 9, Apr. 26, 2001, pp. 1313-1333.
Extended European Search Report dated May 29, 2009.
Sudha R. Vippagunta, et al., "Crystalline solids", Advanced Drug Delivery Reviews, 2001, pp. 3-26, vol. 48.
Jantzen et al., "Modern Pharmaceutics", 1996, p. 596.
H. Soto, et al., "Gene Array Analysis Comparison between Rat Collagen-induced Arthritis and Human Rheumatoid Arthritis", Scandinavian Journal of Immunology, 2008, pp. 43-57, vol. 68.
Rheumatoid Arthritis—Prevention, http://www.webmed.com/rheumatoid-arthritis/tc/rheumatoid-arthritis-prevention, retrieved Aug. 28, 2009, pp. 1-3.
Cara A. Mosley, et al., "Recent patents regarding the discovery of small molecule CXCR4 antagonists" Expert Opin. Ther. Patents, 2009, pp. 23-38, vol. 19, No. 1.
Jan A. Burger, et al., "CXCR4 chemokine receptor antagonists: perspectives in SCLC", Expert Opin. Investig. Drugs, 2009, 481-490, vol. 18, No. 4.
Definition of Cancer; Medicine Net.com; http://www.medterms.com/script/main/art.asp?articlekey=(1 of 3), retrieved Nov. 27, 2007, pp. 1-3.
Renu Agarwal, et al., "Therapeutic potential of Curcuma longa, the golden spice of India, in drug discovery for ophthalmic diseases", Expert Opin. Drug Discov., 2009, pp. 147-158, vol. 4, No. 2.
James E. Pease, et al., "Chemokine receptor antagonists: part 2", Expert Opin Ther. Patents, 2009, pp. 199-221, vol. 19, No. 2.
Borna Mehrad, et al., "Fibrocyte CXCR4 regulation as a therapeutic target in pulmonary fibrosis", The International Journal of Biochemistry & Cell Biology, 2009, pp. 1708-1718, vol. 41.
Hirokazu Tamamura et al., "A future perspective on the development of chemokine receptor CXCR4 antagonists", Expert Opin. Drug Discov., 2008, pp. 1155-1166, vol. 3, No. 10.
Arthritis Basics; http://www.webmed.com/osteoarthritis/guide/arthritis-basic, retrieved Apr. 26, 2010, pp. 1-4.
Jason M. Link, et al., "Clues to the etiology of autoimmune diseases through analysis of immunoglobulin genes", Arthritis Research, 2002, pp. 80-83, vol. 40, No. 2.
International Search Report [PCT/ISA/210] issued Aug. 3, 2004, for PCT/JP2004/005493 counterpart of U.S. Appl. No. 12/332,716.
Christopher A. Lipinski, "Section VI—Topics in Chemistry and Drug Design", Annual Reports in Medicinal Chemistry, 1986, pp. 283-291, vol. 21.
Tara Mirzadegan, et al., "Identification of the Binding Site for a Novel Class of CCR2b Chemokine Receptor Antagonists", The Journal of Biological Chemistry, 2000, pp. 25562-25571, vol. 275, No. 33.
CA registry #85732-34-9 and CA registry #85732-35-0.
CA registry #85732-42-9.
CA registry #85732-35-0 and CA registry #121061-07-2.
CA registry #508240-62-8 and CA registry #508240-61-7.
CA registry #635713-68-7 and CA registry #635713-67-6.
Paul W. Smith, et al., "New Spiropiperidines as Potent and Selective Non-Peptide Tachykinin NK2 Receptor Antagonists", J. Med. Chem., 1995, pp. 3772-3779, vol. 38, XP009135475.
Supplementary European Search Report issued Jul. 9, 2010 in European Application No. 047279985.6 counterpart of U.S. Appl. No. 12/332,716.
American Cancer Society, "Can Cancer Be Prevented?", http://www.cancer.org/docroot/CRI/content/CRI_2_4_2x_Can_cancer_be_prevented.asp, retrieved May 27, 2010, pp. 1.
TeensHealth, "HIV and AIDS," http://kidshealth.org/teen/infections/stds/std_hiv.html, retrieved May 27, 2010, pp. 1-3.
Extended European search report dated Aug. 10, 2010, issued by the European Patent Office in counterpart European Application No. 05776646.1.
Office Action issued on Oct. 20, 2010 in counterpart European Application No. 06832893.9.
Mailey, Everett A. et al., "Synthesis of Derivatives of Alkylated and Arylated Piperidones and Piperidinols", Journal of Organic Chemistry, 1957, vol. 22, p. 1061-1065.
Winters, G. et al. "Sintesi Di Spiroidantoine Da Chetoni Eterociclici Basici", Farmaco, Edizione Scientifica, 1970, vol. 25, No. 9, p. 681-693.
US Office Action issued in related U.S. Appl. No. 12/332,716 on Mar. 29, 2011.
Extended European Search Report, dated Jul. 12, 2011 issued in corresponding European Application No. 07743395.1.
European Patent Office, Office Action dated Aug. 4, 2011, issued in European Application No. 05776646.1 in the name of Ono Pharmaceutical Co., Ltd.

* cited by examiner

CHEMOKINE RECEPTOR ANTAGONISTS AND USE THEREOF

TECHNICAL FIELD

The present invention relates to compounds having a basic group which is useful as medicaments, and use thereof.

More specifically, the present invention relates to (1) compounds represented by formula (I):

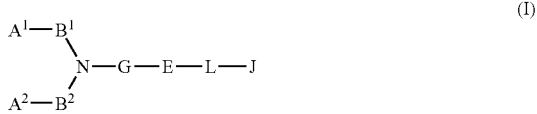

(wherein all symbols are as defined hereinafter), and salts thereof, N-oxides thereof or solvates thereof or prodrugs thereof, (2) use thereof, and (3) a method for producing the same.

Chemokine is known as a basic protein which has chemotaxis and an activating effect on endogenous leucocytes and also has strong heparin-binding abilities. It is now considered that chemokine is associated with not only control of infiltration of specific leucocytes upon inflammatory and immune responses, but also development, homing of lymphocytes under physiological conditions and migration of hemocyte precursor cells and somatic cells.

Differentiation, proliferation and cell death of blood cells are controlled by various cytokines. Inflammation occurs at a local region in a living body. Differentiation and maturation of lymphocytes, and the like are carried out at a specific site. More particularly, required various cells migrate and accumulate in the specific site and a sequence of inflammatory and immune responses arise. Thus, as well as differentiation, proliferation and death of cells, cell migration is also an essential phenomenon to an immune system.

In the living body, migration of blood cells start with shifting hemopoiesis that started at AGM (Aorta Gonad Mesonephros) region via fetal liver to permanent hematopoiesis at bone marrow in a development course. Moreover, precursors of T cells and thymus dendritic cells migrate from fetal liver into bone marrow and then into the thymus gland. They differentiate under thymus environment. The T cells are subjected to clonal selection migrates into secondary lymphoid tissues, where they contribute to immune responses in periphery. Skin Langerhans cells that caught antigen, thereby undergone activation and differentiation, migrate to T cell region in a topical lymph node, where they activate naive T cells therein as dendritic cells. The memory T cells again perform its homing into the lymph node via lymphatic and blood vessels. In addition, B cells, T cells in intestinal epithelia, γδT cells, NKT cells, and dendritic cells migrate from bone marrow not via thymus, differentiate and contribute to immune responses.

Chemokine is very involved in these various cell migrations. For example, SDF-1 (Stromal cell derived factor-1) and its receptor, CXCR4 also act on various immune and inflammatory reactions. For example, they have been reported to be associated with accumulation and activation of CD4+ T cells in a synovial membrane from a human patient suffering from rheumatoid arthritis (J. Immunol., 165, 6590-6598 (2000)). In addition, in a CIA model mouse, CXCR4 inhibitor inhibited accumulation of leucocytes in a joint and dramatically reduced arthritis score (J. Immunol., 167, 4648-4692 (2001)). In a mouse OVA-induced airway hypersensitive model, an anti-CXCR4 antibody reduced the number of eosinophiles accumulating in pulmonary interstitial tissues and prevented airway hypersensitivity (J. Immunol., 165, 499-508 (2000)). In mouse retinopathy model, an anti-SDF-1 antibody inhibits the invasion of vascular endothelial precursor cell to retina and retinal neoangiogenesis (J. Cli. I, 115, 86-93 (2005)).

There has been reported that SDF-1 and its receptor, CXCR4 play an important role in maintaining hemopoietic stem cells in bone marrow J. Exp. Med., 185, 111-120 (1997), Blood, 97, 3354-3360 (2001)). Accordingly, control of SDF-1 and CXCR4 is expected to modulate recruitment of hemopoietic stem cells to peripheral blood and is useful for peripheral blood stem cell transplantation and reproduction transplantation treatment.

SDF-1 and CXCR4 are associated with infiltration of various cancer cells such as breast cancer, prostate cancer, and ovarian cancer (Nature, 410, 50-56 (2001), Cancer Res., 62, 1832-1837 (2002), Cancer Res., 62, 5930-5938 (2002)). In a model of a SCID mouse which is transferred a human breast cancer cell strain into, an anti-CXCR4 antibody prevented metastasis of breast cancer cells to lung (Nature, 410, 50-56 (2001)). Furthermore, an anti-SDF-1 antibody inhibited neoangiogenesis around cancer and thereby inhibited cancer cell proliferation (Cell, 121, 335-348 (2005)). In human ovarian epithelial tumor, highly expression of SDF-1 promotes accumulation of plasmacytoid dendritic cells and inhibits the act of bone marrow dendritic cells associated with tumor immune and suppresses tumor immune (Nat. Med., 12, 1339 (2001)). Moreover, SDF-1 is associated with proliferation and migration of non-Hodgkin's lymphoma cells, and in a model of a NOD/SCID mouse which is transferred a human non-Hodgkin's lymphoma cells into, an anti-CXCR4 antibody inhibited proliferation of the tumor cells and improved mouse mortality (Cancer Res., 62, 3106-3112 (2002)). Furthermore, a low molecular CXCR4 antagonist increases apoptosis of intracranially transplanted amedulloblastoma in mice and decrease tumor growth (Proc. Nat. Acad. Sci. USA, 100, 13513-13518 (2003)). And it enhances the effect of an immunostimulant and an anticancer in the model of pulmonary metastasis model with malignant melanoma (Mol Cancer Ther., 5, 2592-9 (2006)).

SDF-1 and CXCR4 play an important role for formation of hippocampus dentate gyrus granulocyte, that is essential for memory and learning and are associated with development of a disease associated with adult plasticity and pathology of hippocampus, for example Alzheimer's disease, stroke and epilepsy (Development, 129, 4249-4260 (2002), Trends in Neuroscience, 25, 548-549 (2002)).

SDF-1 and CXCR4 are essential for a function of self-reactive B cells associated with development of diabetes. In NOD mouse, an anti-SDF-1 antibody reduced blood glucose level and the number of mature IgM+B cells in a periphery tissue (Immunology, 107, 222-232 (2002)). In a human arteriosclerotic plaque, SDF-1 was highly expressed and activated blood platelets (Circ. Res., 86, 131-138 (2000)).

SDF-1 and CXCR4 are involved in residence of hemopoietic stem cells and hemopoietic precursor cells in bone marrow. CXCR4 antagonist, AMD 3100 in combination with G-CSF increased the numbers of hemopoietic stem cells and hemopoietic precursor cells in periphery blood (Journal Experimental Medicine, 2001, 1307-1318 (2005)). In addition, it is known that administrating a low molecular CXCR4 antagonist to human increases neutrophilic leukocytes, lymphocytes, monocytes and the like increase in peripheral blood (Blood, 102, 2728-2730 (2003)). Therefore, a low molecular CXCR4 antagonist is expected to have an immunoenhancing effect.

In addition, the results of SDF-1/CXCR4 knock-out mice showed that SDF-1 is essential for functions of central nervous system, heart and vessels of gastrointestinal tract in addition to lymphocytes (Nature, 382, 635-639 (1996), Nature, 393, 591-594 (1998), Nature, 393, 595-599 (1998)). Accordingly, it may be associated with a disease of these tissues.

Thus, chemokine receptors are expressed at various specific cells and at a specific time. They are largely associated with the control of inflammatory- and immune responses through a mechanism by which their effector cells accumulate in a site where chemokine is produced.

Acquired immunodeficiency syndrome (also called AIDS) that caused by infection of human immunodeficiency virus (hereinafter abbreviated to HIV) is one of diseases for which therapies are the most eagerly desired lately. Once HIV infection has been established in a main target cell, CD4+ cell, HIV repetitively proliferates in a patient's body and after a while severely destroys T cells responsible for immunological functions by necrosis. In this process, immunological functions are gradually deteriorated, various immunocompromised states become to develop such as fever, diarrhea and swelling of a lymph node, and various opportunistic infections such as carinii pneumonia are easily complicated. It is well known that such a state is the onset of AIDS and induces malignant tumors such as Kaposi's sarcoma and becomes severe.

Currently, various preventive and therapeutic treatments for AIDS are tried as follows: for example, (1) inhibition of HIV proliferation by administration of reverse transcriptase inhibitors and protease inhibitors, and (2) prevention or alleviation of opportunistic infections by administration of an immunostimulant, etc.

HIV mainly infects helper T cells which play a key role in the immune system. Since 1985, it has been known that in this process HIV utilizes a membrane protein CD4 that is expressed on the membrane of T cells (Cell, 52, 631 (1985)). CD4 molecule consists of 433 amino acid residues and is expressed in macrophages, some of B cells, vascular endothelial cells, Langerhans cells in skin tissues, dendritic cells located in lymphatic tissues, glia cells of central nervous system and the like in addition to mature helper T cells. However, as it becomes obvious that HIV infection cannot be established with only CD4 molecule, the possible presence of some factor that is responsible for infection of cell with HIV, other than CD4 molecule, has been suggested.

In 1996, a cell membrane protein called Fusin has been identified as a factor responsible for HIV infection other than a CD4 molecule (Science, 272, 872 (1996)). This Fusin molecule has been demonstrated to be a receptor for SDF-1, namely, CXCR4. In addition, it has been shown that SDF-1 specifically inhibits infection of T cell-directed (X4) HIV in vitro (Nature, 382, 829 (1996), Nature, 382, 833 (1996)). This may be considered that SDF-1 binds to CXCR4 prior to HIV, thereby taking away a scaffold for infecting a cell from HIV resulting in inhibition of HIV infection.

Also, at the same period, there has been found that another chemokine receptor CCR5, that is a receptor for RANTES, MIP-1α, and MIP-1β, is utilized at infection of macrophage-directed (R5) HIV (Science, 272, 1955 (1996)).

Accordingly, those which can compete with HIV for CXCR4 and CCR5 or those which bind to a HIV virus and prevent for said virus from binding to CXCR4 and CCR5 may be a HIV infection inhibitor. In addition, there is a case where a low molecular weight compound discovered as a HIV infection inhibitor was showed to be indeed an antagonist of CXCR4 (Nature Medicine, 4, 72 (1998)).

As described above, compounds having an antagonistic activity against CXCR4 is effective, such as, for prevention and/or treatment of inflammatory and immune diseases, allergic diseases, infections, particularly HIV infection, and diseases associated with the infection, psychoneurotic diseases, cerebral diseases, cardiovascular diseases, metabolic diseases, cancerous diseases and the like. Also, the compounds are useful for cell medical treatment and regeneration therapy.

Heretofore, some compounds having an antagonistic activity against CXCR4 have been reported. For example, it is disclosed that a compound represented by formula (X):

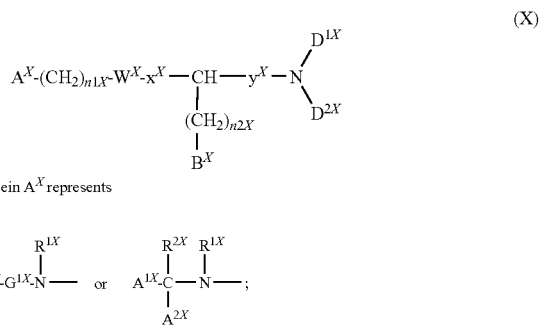

(wherein $A^X$ represents

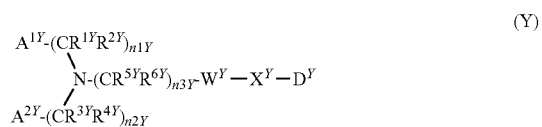

$A^{1X}$ and $A^{2X}$ each independently represents a hydrogen atom, an optionally substituted monocyclic or polycyclic heteroaromatic ring, or an optionally substituted monocyclic or polycyclic aromatic ring; GIX represents a single bond or $-CR^{2X}R^{3X}-$; $R^{1X}$, $R^{2X}$ and $R^{3X}$ represent an optionally substituted alkyl group having 1 to 6 carbon atom(s), etc.; $W^X$ represents an optionally substituted alkylene group having 1 to 7 carbon atom(s), an optionally substituted monocyclic or polycyclic heteroaromatic ring, an optionally substituted monocyclic or polycyclic aromatic ring, etc.; $x^X$ represents $-z^{1X}-CO-z^{2X}-$; $z^{1X}$ and $z^{2X}$ each independently represents a single bond, $NR^{13X}$, etc.; $y^X$ represents $-CO-$; $D^{1X}$ and $D^{2X}$ each independently represents a hydrogen atom or $-G^{2X}-R^{4X}$; $G^{2X}$ represents an optionally substituted alkylene group having 1 to 15 carbon atom(s), etc.; $R^{4X}$ represents a hydrogen atom, an optionally substituted monocyclic or polycyclic heteroaromatic ring, or an optionally substituted monocyclic or polycyclic aromatic ring; n2X represents 0 to 4; n1X represents 0 to 3; and $B^X$ represents $-NR^{6X}R^{7X}$, and only required portions were extracted with respect to definition of each group), or a pharmaceutically acceptable salt has an antagonistic activity against CXCR4 (see WO2003/029218 pamphlet).

Also, it is disclosed that a compound represented by formula (Y):

$$A^{1Y}-(CR^{1Y}R^{2Y})_{n1Y} \diagdown$$
$$N-(CR^{5Y}R^{6Y})_{n3Y}-W^Y-X^Y-D^Y$$
$$A^{2Y}-(CR^{3Y}R^{4Y})_{n2Y} \diagup$$

(wherein n1Y, n2Y and n3Y represent 0 to 3; $R^{1Y}$, $R^{2Y}$, $R^{3Y}$, $R^{4Y}$, $R^{5Y}$ and $R^{6Y}$ each independently represents a hydrogen atom, or an optionally substituted alkyl group having 1 to 15 carbon atom(s), etc.; $A^{1Y}$ and $A^{2Y}$ each independently represents an optionally substituted monocyclic or polycyclic heteroaromatic ring, etc.; $W^Y$ represents an optionally substituted alkylene group having 1 to 15 carbon atom(s), etc.; $X^Y$ represents O, CH$_2$, NR$^{11Y}$, etc.; D$^Y$ represents -Q$^Y$-Y$^Y$—B$^Y$; Q$^Y$ represents a single bond or —CO— when X is NR$^{11Y}$, etc.; Y$^Y$ represents —(CR$^{18Y}$R$^{19Y}$)$_{m3Y}$—, etc.; R$^{18Y}$ and R$^{19Y}$ each independently represents a hydrogen atom, or an optionally substituted alkyl group having 1 to 15 carbon atom(s), etc.; m3Y represents 0 to 6, etc.; B$^Y$ represents —NR$^{25Y}$R$^{26Y}$; and R$^{25Y}$ and R$^{26Y}$ represent a hydrogen atom, an optionally substituted alkyl group having 1 to 15 carbon atom(s) when X$^Y$ is not CH$_2$, etc., and only required portions were extracted with respect to definition of each group), or a pharmaceutically acceptable salt or a prodrug thereof has an antagonistic activity against CXCR4 (see WO2004/024697 pamphlet).

Furthermore, it is disclosed that a compound represented by general formula (Z):

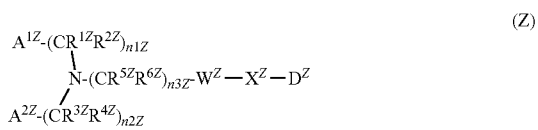

(wherein n1Z, n2Z and n3Z represent 0 to 3; R$^{1Z}$, R$^{2Z}$, R$^{3Z}$, R$^{4Z}$, R$^{5Z}$ and R$^{6Z}$ each independently represents a hydrogen atom, an optionally substituted alkyl group having 1 to 15 carbon atom(s), etc., and R$^{5Z}$ and R$^{6Z}$ may form a carbonyl group together with a carbon atom; A$^{1Z}$ and A$^{2Z}$ each independently represents an optionally substituted monocyclic or polycyclic heteroaromatic ring, etc.; W$^Z$ represents an optionally substituted benzene ring, etc.; XZ represents O, CH$_2$, or NR$^{11Z}$, etc.; D$^Z$ represents -Q$^Z$-Y$^Z$—B$^Z$; Q$^Z$ represents a single bond, —CO—, —CONH—, NR$^{12Z}$, etc. when X$^Z$ is CH$_2$; Y$^Z$ represents —(CR$^{18Z}$R$^{19Z}$)$_{m3Z}$—, etc.; R$^{18Z}$ and R$^{19Z}$ each independently represents a hydrogen atom, or an optionally substituted alkyl group having 1 to 15 carbon atom(s), etc.; m3Z represents 0 to 6; B$^Z$ represents —NR$^{25Z}$R$^{26Z}$; and R$^{25Z}$ and R$^{26Z}$ represent a hydrogen atom, or an optionally substituted alkyl group having 1 to 15 carbon atom(s), etc. when X$^Z$ is not CH$_2$, and only required portions were extracted with respect to definition of each group), or a pharmaceutically acceptable salt or a prodrug thereof has an antagonistic activity against CXCR4 (see WO2005/085209 pamphlet).

| Patent Literature 1 | WO2003/029218 pamphlet |
| Patent Literature 2 | WO2004/024697 pamphlet |
| Patent Literature 3 | WO2005/085209 pamphlet |

DISCLOSURE OF THE INVENTION

Problems to be Solved by the Invention

It is earnestly desired to develop an antagonist of CXCR4, which is useful as a preventive and/or therapeutic agent for inflammatory and immune diseases (for example, rheumatoid arthritis, arthritis, systemic erythematosus, retinopathy, macular degeneration, pulmonary fibrosis, rejection of transplanted organ, etc.), allergic diseases, infections (for example, human immunodeficiency virus infection, acquired immunodeficiency syndrome, etc.), cancerous diseases (for example, cancer, cancer metastasis, etc.), cardiac/vascular diseases (for example, arteriosclerosis, myocardial infarction, stenocardia, cerebral infarction, chronic arterial occlusive disease, etc.), or an agent for regeneration therapy, and is also safe with less side effects.

The present invention relates to

[1] A compound represented by formula (I):

wherein A$^1$ and A$^2$ each independently represents a group having a basic group;

B$^1$ and B$^2$ each independently represents a bond or a spacer having a main chain of 1 to 4 atom(s);

E represents a spacer having a main chain of 1 to 10 atom(s);

L represents a bond or a spacer having a main chain of 1 to 4 atom(s);

J represents (1) an aliphatic hydrocarbon group which is substituted with a group having a basic group, and also may have a substituent(s), (2) a monocyclic or condensed cyclic group which is substituted with a group having a basic group, and also may have a substituent(s), (3) a spiro-bound cyclic group which may be substituted with a group having a basic group, and also may have a substituent(s), or (4) a bridged cyclic group which may be substituted with a group having a basic group, and also may have a substituent(s);

G represents a bond, a carbon atom which may have a substituent(s), an oxygen atom, a nitrogen atom which may have a substituent(s), an optionally oxidized sulfur atom, or -carbon atom which may have a substituent(s)-nitrogen atom which may have a substituent(s)-;

wherein when J represents (1) or (2), G represents a bond, a carbonyl group, an oxygen atom, a nitrogen atom which may have a substituent(s) or an optionally oxidized sulfur atom, or B$^1$ represents a spacer having a main chain of 1 to 4 atom(s) composed of 1 to 4 group(s) selected optionally from —O—, —S—, —CO—, —SO—, —SO$_2$— and a divalent nitrogen atom which may have a substituent(s), a salt thereof, or an N-oxide thereof, or a solvate thereof, or a prodrug thereof;

[2] The compound according to the above [1], wherein A$^1$ and A$^2$ each independently represents a nitrogen-containing heterocyclic ring which may have a substituent(s), a salt thereof, or an N-oxide thereof, or a solvate thereof, or a prodrug thereof;

[3] The compound according to the above [2], wherein the nitrogen-containing heterocyclic ring is an imidazole ring, a benzimidazole ring, or a pyridine ring, a salt thereof, or an N-oxide thereof, or a solvate thereof, or a prodrug thereof;

[4] The compound according to the above [1], wherein the spacers having a main chain of 1 to 4 atom(s) represented by B$^1$ and B$^2$ each independently represents —CO—, —SO$_2$—, or —CH$_2$—, a salt thereof, or an N-oxide thereof, or a solvate thereof, or a prodrug thereof;

[5] The compound according to the above [1], wherein G is —CO—, —SO$_2$—, or —CH$_2$—, a salt thereof, or an N-oxide thereof, or a solvate thereof, or a prodrug thereof;

[6] The compound according to the above [1], wherein E is a divalent 3- to 8-membered monocyclic cyclic group which may have a substituent(s) or a divalent 9- to 10-membered condensed cyclic group which may have a substituent(s), a salt thereof, or an N-oxide thereof, or a solvate thereof, or a prodrug thereof;

[7] The compound according to the above [6], wherein the 3- to 8-membered monocyclic cyclic ring is a benzene ring, a salt thereof, or an N-oxide thereof, or a solvate thereof, or a prodrug thereof;

[8] The compound according to the above [1], wherein L is —CH$_2$—, —CO—, —CONH—, or —CH$_2$—NH— wherein a nitrogen atom is bonded to J in —CONH— and —CH$_2$—NH—, a salt thereof, or an N-oxide thereof, or a solvate thereof, or a prodrug thereof;

[9] The compound according to the above [1], which is 2-(4-{[bis(1H-imidazol-2-ylmethyl)amino]methyl}benzyl)-8-(1-ethylpropyl)-2,8-diazaspiro[4.5]decan-3-one, 2-(4-{[bis(1H-imidazol-2-ylmethyl)amino]methyl}benzyl)-8-(1-ethylpropyl)-2,8-diazaspiro[4.5]decan-1-one, or 2-(4-{[bis(1H-imidazol-2-ylmethyl)amino]methyl}benzyl)-9-(1-ethylpropyl)-2,9-diazaspiro[5.5]undecan-1-one, a salt thereof, or an N-oxide thereof, or a solvate thereof, or a prodrug thereof;

[10] The compound according to the above [1], wherein formula (I) is formula (I-1):

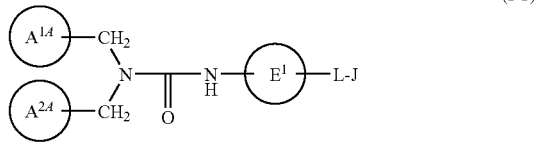

(I-1)

wherein ring $A^{1A}$ and ring $A^{2A}$ each independently represents a nitrogen-containing heterocyclic ring which may have a substituent(s), ring $E^1$ represents a divalent 3- to 8-membered monocyclic cyclic group which may have a substituent(s) or a divalent 9- to 10-membered condensed cyclic group which may have a substituent(s), and other symbols are as defined in the above [1], a salt thereof, or an N-oxide thereof, or a solvate thereof, or a prodrug thereof;

[11] The compound according to the above [1], wherein formula (I) is formula (I-2):

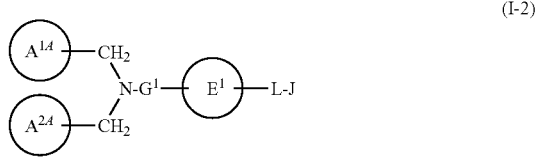

(I-2)

wherein $G^1$ represents —CO—, —SO$_2$—, or —CH$_2$—, other symbols are as defined in the above [1] or the above [10], a salt thereof, or an N-oxide thereof, or a solvate thereof, or a prodrug thereof;

[12] The compound according to the above [11], wherein $G^1$ is —SO$_2$—, a salt thereof, or an N-oxide thereof, or a solvate thereof, or a prodrug thereof;

[13] The compound according to the above [1], wherein formula (I) is formula (I-3):

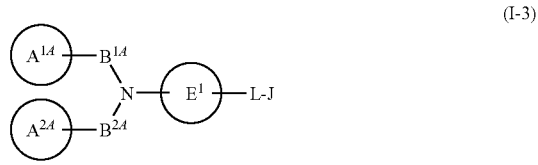

(I-3)

wherein $B^{1A}$ and $B^{2A}$ each independently represents —CO—, —SO$_2$—, or —CH$_2$—, and other symbols are as defined in the above [1] or the above [10], a salt thereof, or an N-oxide thereof, or a solvate thereof, or a prodrug thereof;

[14] The compound according to the above [11], wherein

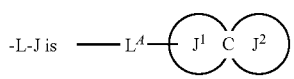

in the group, $L^A$ represents (a)—an aliphatic hydrocarbon group having 1 to 3 carbon atom(s) which may have a substituent(s)—a nitrogen atom which may have a substituent(s)—, or (b) a divalent aliphatic hydrocarbon group having 1 to 4 carbon atom(s) which may have a substituent(s), when $L^A$ represents (a)—an aliphatic hydrocarbon group having 1 to 3 carbon atom(s) which may have a substituent(s)—a nitrogen atom which may have a substituent(s)—, ring $J^1$ represents (i) a C3-10 monocyclic or bicyclic carbocyclic ring, or (ii) a 3- to 10-membered monocyclic or bicyclic heterocyclic ring composed of a carbon atom(s), an oxygen atom(s) and/or an optionally oxidized sulfur atom(s), when $L^A$ is (b) a divalent aliphatic hydrocarbon group having 1 to 4 carbon atom(s) which may have a substituent(s), ring $J^1$ represents a 3- to 10-membered monocyclic or bicyclic heterocyclic ring which has at least one nitrogen atom, and also may have an oxygen atom(s) and/or an optionally oxidized sulfur atom(s), ring $J^2$ represents (i) a C3-10 monocyclic or bicyclic carbocyclic ring which is substituted with a group having a basic group, (ii) a 3- to 10-membered monocyclic or bicyclic heterocyclic ring composed of a carbon atom(s), an oxygen atom(s) and/or an optionally oxidized sulfur atom(s), which is substituted with a group having a basic group, or (iii) a 3- to 10-membered monocyclic or bicyclic heterocyclic ring which has at least one nitrogen atom and also may have an oxygen atom(s) and/or an optionally oxidized sulfur atom(s), and which may be substituted with a group having a basic group, ring $J^1$ and ring $J^2$ may have 1 to 8 substituent(s) on the substitutable position, and when two or more substituents are present, plural substituents may be the same or different, wherein a nitrogen atom which may have a substituent(s) in $L^{A1}$ is bonded to ring $J^{1a}$, a salt thereof, or an N-oxide thereof, or a solvate thereof, or a prodrug thereof;

[15] The compound according to the above [14], wherein $L^A$ is —CO— or —CH$_2$—, a salt thereof, or an N-oxide thereof, or a solvate thereof, or a prodrug thereof;

[16] The compound according to the above [14], wherein
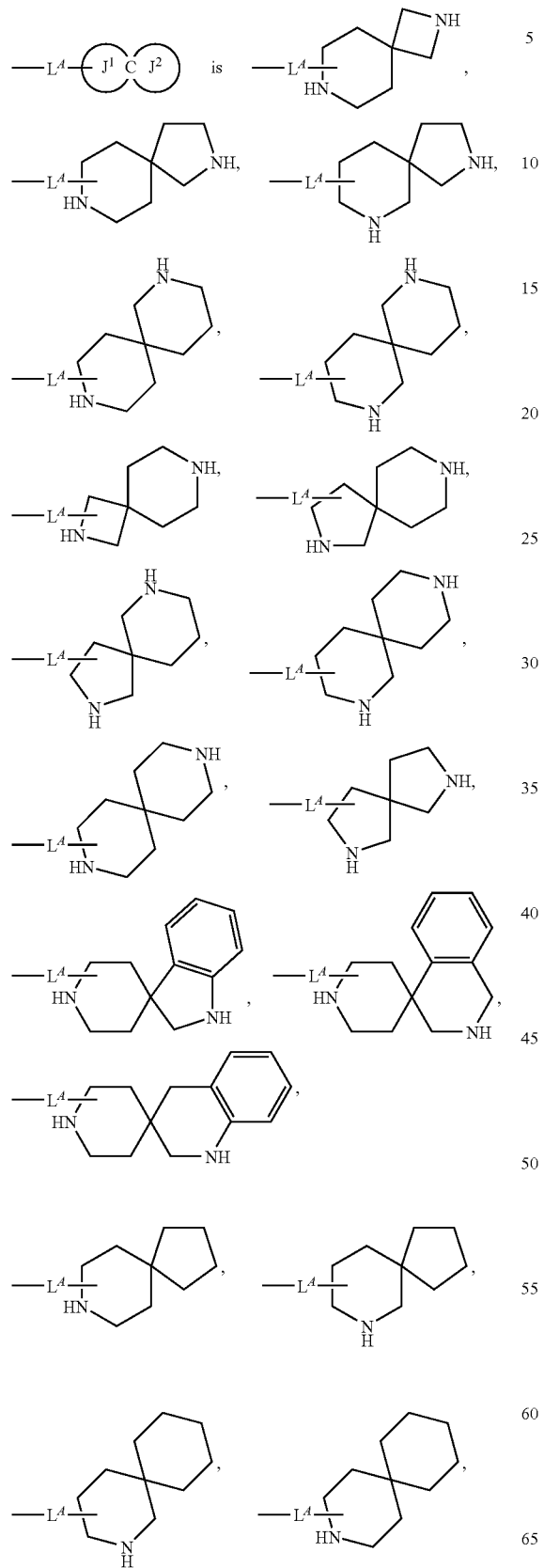
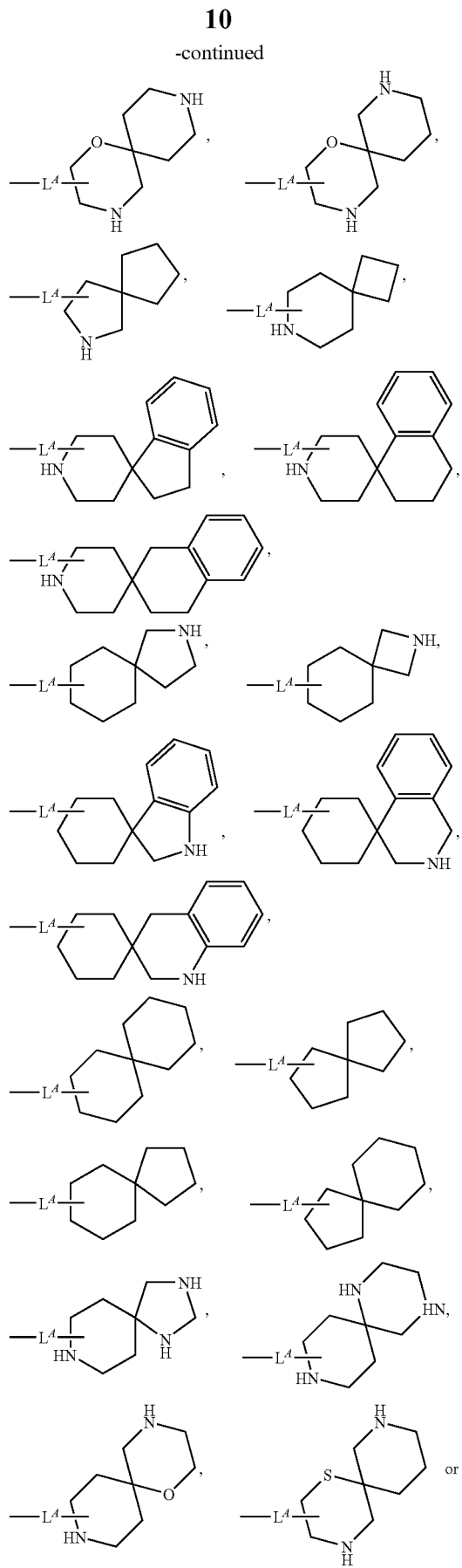

-continued

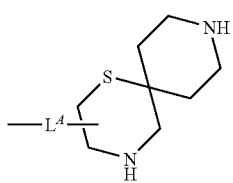

wherein $L^A$ may be bonded to a nitrogen atom of —NH—, and the nitrogen atom of —NH— may have a substituent(s), a salt thereof, or an N-oxide thereof, or a solvate thereof, or a prodrug thereof;

[17] The compound according to the above [14], wherein

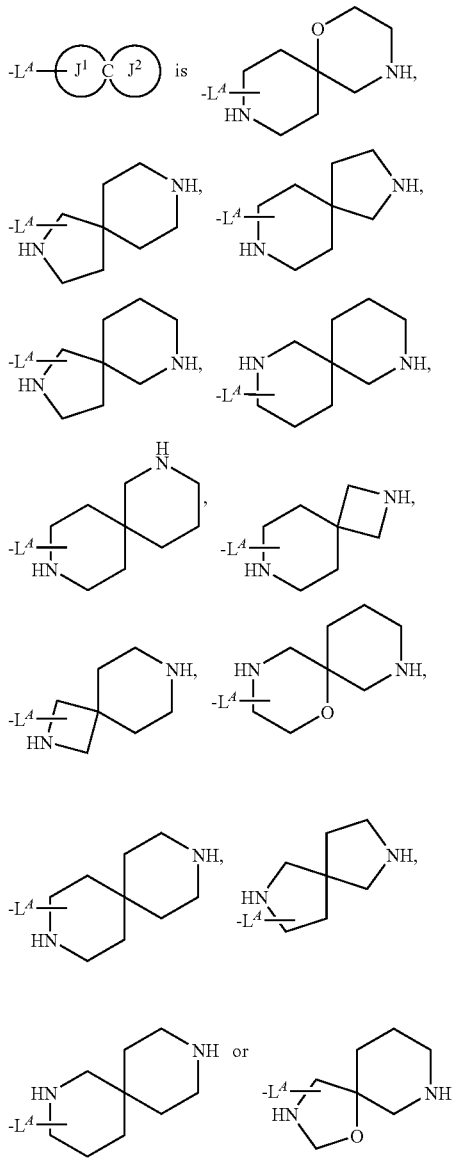

wherein $L^A$ may be bonded to a nitrogen atom of —NH—, and the nitrogen atom of —NH— may have a substituent(s), a salt thereof, or an N-oxide thereof, or a solvate thereof, or a prodrug thereof;

[18] The compound according to the above [11], wherein formula (I) is formula (I-2-a):

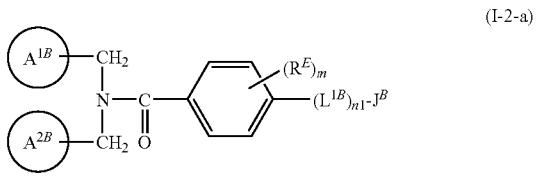

(I-2-a)

wherein ring $A^{1B}$ and ring $A^{2B}$ represent an imidazole ring which may have a substituent(s), a benzimidazole ring which may have a substituent(s), or a pyridine ring which may have a substituent(s), $R^E$ represents a halogen atom or an aliphatic hydrocarbon group, m represents an integer of 0 or 1 to 2, $L^{1B}$ represents —CO— or —CH$_2$—, n1 represents an integer of 1 to 2 and, when n1 is 2, two $L^{1B}$(s) may be the same or different, and $J^B$ represents:

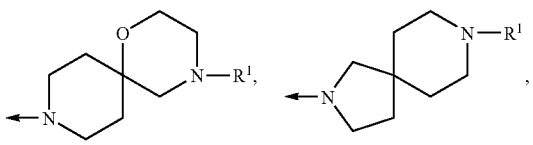

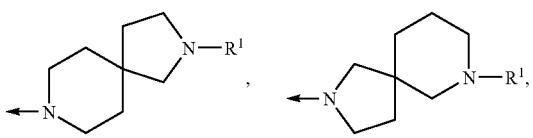

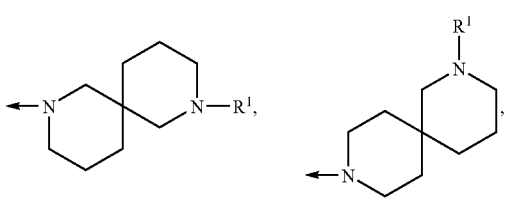

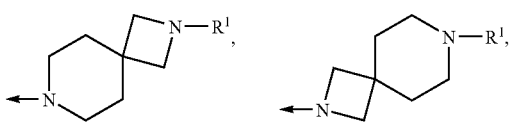

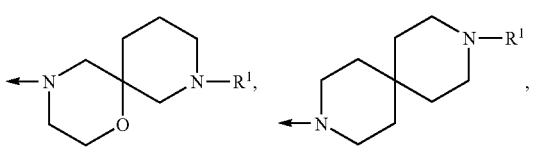

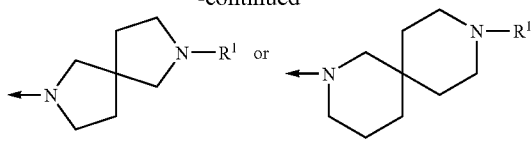

in the group, the arrow is bonded with $L^{1B}$, and $R^1$ represents a hydrogen atom or a substituent, formula (I-2-b):

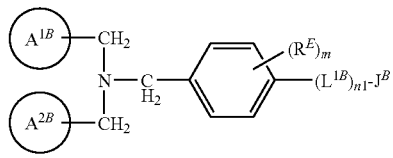

(I-2-b)

wherein all symbols are as defined above, or formula (I-2-c):

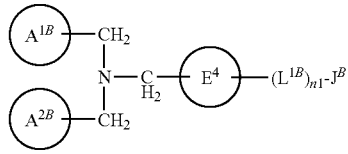

(I-2-c)

wherein ring $E^4$ represents a pyrrolidine ring which may be substituted by an aliphatic hydrocarbon group, or a piperidine ring which may be substituted by an aliphatic hydrocarbon group, and other symbols are as defined above, a salt thereof, or an N-oxide thereof, or a solvate thereof, or a prodrug thereof;

[19] The compound according to the above [18], wherein the substituent of ring $A^{1B}$ and ring $A^{2B}$ is absent or a C1-8 alkyl group, a salt thereof, or an N-oxide thereof, or a solvate thereof, or a prodrug thereof;

[20] The compound according to the above [18], wherein $R^1$ is a C4-7 monocyclic carbocyclic ring or a C1-8 alkyl group, a salt thereof, or an N-oxide thereof, or a solvate thereof, or a prodrug thereof;

[21] The compound according to the above [10], [11] or [13], wherein

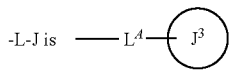

in the group, $L^A$ is as defined in the above [14], (a) when $L^A$ is—an aliphatic hydrocarbon group having 1 to 3 carbon atom(s) which may have a substituent(s)—a nitrogen atom which may have a substituent(s)—, ring $J^3$ represents (i) a bridged carbocyclic ring substituted with a group having a basic group, or (ii) a bridged heterocyclic ring composed of a carbon atom(s), an oxygen atom(s) and/or an optionally oxidized sulfur atom(s), which is substituted with a group having a basic group, (b) when $L^A$ is a divalent aliphatic hydrocarbon group having 1 to 4 carbon atom(s) which may have a substituent(s), ring $J^3$ represents a bridged heterocyclic ring which has at least one nitrogen atom which may be substituted with a group having a basic group, and also may have an oxygen atom(s) and/or an optionally oxidized sulfur atom(s), and ring $J^3$ may have 1 to 8 substituent(s) on the substitutable position, and when two or more substituents are present, plural substituents may be the same or different, wherein a nitrogen atom which may have a substituent(s) in $L^A$ is bonded to ring $J^{1a}$, a salt thereof, or an N-oxide thereof, or a solvate thereof, or a prodrug thereof;

[22] The compound according to the above [21], wherein the bridged carbocyclic ring is:

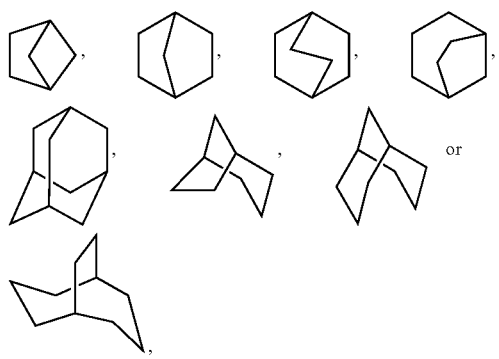

a salt thereof, or an N-oxide thereof, or a solvate thereof, or a prodrug thereof;

[23] The compound according to the above [21], wherein the bridged heterocyclic ring which has at least one nitrogen atom, and also may have an oxygen atom(s) and/or an optionally oxidized sulfur atom(s) is:

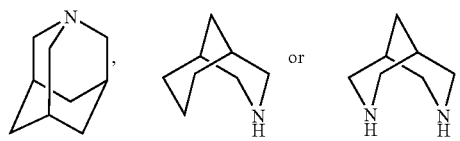

in the group, a nitrogen atom of —NH— may have a substituent(s), a salt thereof, or an N-oxide thereof, or a solvate thereof, or a prodrug thereof;

[24] The compound according to the above [10], [11] or [13], wherein

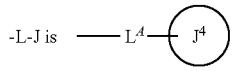

in the group, $L^A$ is as defined in the above [14], (a) when $L^A$ is -(an aliphatic hydrocarbon group having 1 to 3 carbon atom(s) which may have a substituent(s))-(a nitrogen atom which may have a substituent(s))-, ring $J^4$ represents (i) a C3-15 monocyclic or condensed carbocyclic ring substituted with a group having a basic group, or (ii) a 3- to 15-membered monocyclic or condensed heterocyclic ring composed of a carbon atom(s), an oxygen atom(s) and/or an optionally oxidized sulfur atom(s), which is substituted with a group having a basic group, (b) when $L^A$ is a divalent aliphatic hydrocarbon group having 1 to 4 carbon atom(s) which may have a substituent(s), ring $J^4$ represents (iii) a 3- to 15-membered monocyclic or condensed heterocyclic ring which has at least one nitrogen atom which may be substituted with a group having a basic group, and also may have an oxygen atom(s) and/or an optionally oxidized sulfur atom(s), and ring $J^4$ may have 1 to 8 substituent(s) on the substitutable position, and when two or more substituents are present, plural substituents may be the same or different, wherein a nitrogen atom which may have a substituent(s) in $L^A$ is bonded to ring $J^4$, a salt thereof, or an N-oxide thereof, or a solvate thereof, or a prodrug thereof;

[25] The compound according to the above [24], wherein the C3-15 monocyclic or condensed carbocyclic ring is:

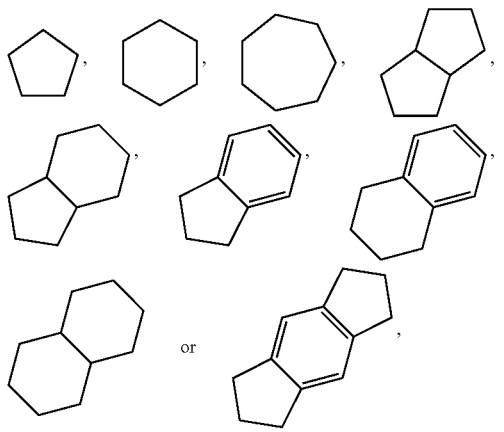

a salt thereof, or an N-oxide thereof, or a solvate thereof, or a prodrug thereof;

[26] The compound according to the above [25], wherein the C3-15 monocyclic or condensed carbocyclic ring is a cyclohexyl group, a salt thereof, or an N-oxide thereof, or a solvate thereof, or a prodrug thereof;

[27] The compound according to the above [1], wherein formula (I) is formula (I-4)

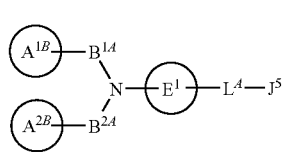

(I-4)

wherein ring $A^{1B}$ and ring $A^{2B}$ are as defined in the above [18], $B^{1A}$ and $B^{2A}$ are as defined in the above [13], ring $E^1$ is as defined in the above [13], $L^A$ is as defined in the above [14], $J^5$ represents a spiro-bound cyclic group which may be substituted with a group having a basic group, and also may have a substituent(s) or a bridged cyclic group which may be substituted with a group having a basic group, and also may have a substituent(s), wherein a nitrogen atom which may have a substituent(s) in $L^A$ is bonded to $J^5$, a salt thereof, or an N-oxide thereof, or a solvate thereof, or a prodrug thereof;

[28] The compound according to the above [27], wherein -$L^A$-$J^5$ is

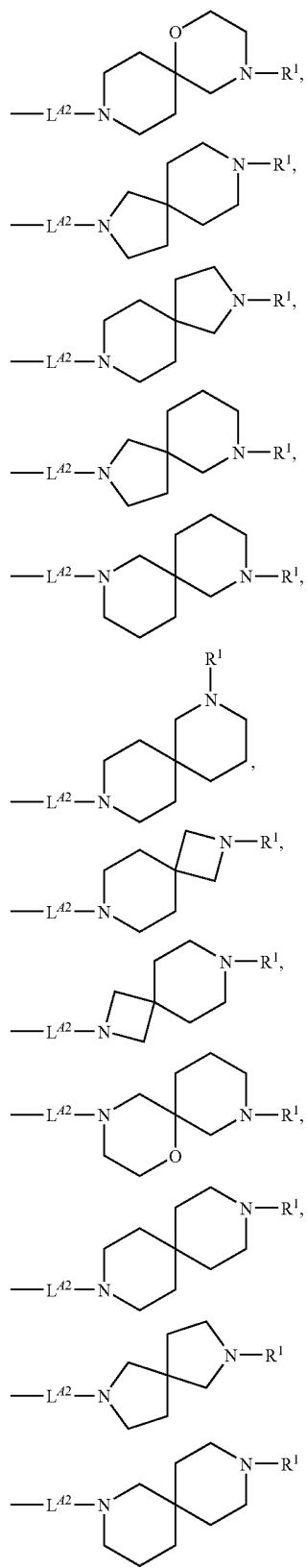

in the group, L$^{A2}$ represents a divalent aliphatic hydrocarbon group having 1 to 4 carbon atom(s) which may have a substituent(s), R$^1$ is as defined in the above [18], a salt thereof, or an N-oxide thereof, or a solvate thereof, or a prodrug thereof;

[29] The compound according to the above [28], wherein R$^1$ is a cyclic group which may have a substituent(s) or an aliphatic hydrocarbon group substituted with a cyclic group which may have a substituent(s), a salt thereof, or an N-oxide thereof, or a solvate thereof, or a prodrug thereof;

[30] The compound according to the above [27], wherein ring E$^1$ is a divalent 3- to 8-membered monocyclic cyclic group which may have a substituent(s), a salt thereof, or an N-oxide thereof, or a solvate thereof, or a prodrug thereof;

[31] The compound according to the above [1], wherein formula (I) is formula (I-4-a):

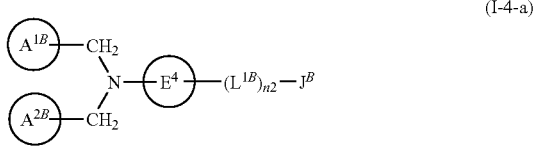

(I-4-a)

wherein n2 represents an integer of 2 to 4, and plural L$^{1B}$(s) may be the same or different, and other symbols are as defined in the above [18], a salt thereof, or an N-oxide thereof, or a solvate thereof, or a prodrug thereof;

[32] The compound according to the above [31], wherein the substituent of ring A$^{1B}$ and ring A$^{2B}$ is absent or a C1-8 alkyl group, a salt thereof, or an N-oxide thereof, or a solvate thereof, or a prodrug thereof;

[33] The compound according to the above [31], wherein R$^1$ is a C4-7 monocyclic carbocyclic ring or a C1-8 alkyl group, a salt thereof, or an N-oxide thereof, or a solvate thereof, or a prodrug thereof;

[34] The compound according to the above [1], wherein the compound represented by formula (I) is:

N'-({1-[(1-cycloheptyl-4-piperidinyl)methyl]-4-piperidinyl}methyl)-N,N-bis(1H-imidazol-2-ylmethyl) urea, 4-[({4-[cycloheptyl(propyl)amino]cyclohexyl}amino)methyl]-N,N-bis(1H-imidazol-2-ylmethyl)benzamide, 4-{[8-(2,2-dimethylpropyl)-2,8-diazaspiro[4.5]dec-2-yl]methyl}-N,N-bis(1H-imidazol-2-ylmethyl)benzamide, 4-{[(1-cycloheptyl-4-piperidinyl)amino]methyl}-N,N-bis(1H-imidazol-2-ylmethyl)benzamide, 1-(1H-imidazol-2-yl)-N-(1H-imidazol-2-ylmethyl)-N-(4-{[8-(2-thienylmethyl)-2,8-diazaspiro[4.5]dec-2-yl]methyl}benzyl)methanamine, 1-(1H-imidazol-2-yl)-N-(1H-imidazol-2-ylmethyl)-N-[4-({8-[(3-methyl-2-thienyl)methyl]-2,8-diazaspiro[4.5]dec-2-yl}methyl)benzyl]methanamine, 4-[(8-cyclohexyl-2,8-diazaspiro[4.5]dec-2-yl)methyl]-N,N-bis(1H-imidazol-2-ylmethyl)-3-methoxybenzamide, N'-{trans-4-[(8-cyclohexyl-2,8-diazaspiro[4.5]dec-2-yl)methyl]cyclohexyl}-N,N-bis(1H-imidazol-2-ylmethyl)urea, 4-({[2-(1-cycloheptyl-4-piperidinylidene)ethyl]amino}methyl)-N,N-bis(1H-imidazol-2-ylmethyl)benzamide, N,N-bis(1H-imidazol-2-ylmethyl)-4-({[trans-4-(2,3,6,7-tetrahydro-1H-azepin-1-yl)cyclohexyl]amino}methyl)benzamide, N,N-bis(1H-imidazol-2-ylmethyl)-5-{8-[(3-methyl-2-thienyl)methyl]-2,8-diazaspiro[4.5]dec-2-yl}-1-pentanamine, N'-[4-(8-cyclohexyl-2,8-diazaspiro[4.5]dec-2-yl)cyclohexyl]-N,N-bis(1H-imidazol-2-ylmethyl)urea, 1-(1H-imidazol-2-yl)-N-(1H-imidazol-2-ylmethyl)-N-(4-{[7-(2-thienylmethyl)-2,7-diazaspiro[4.4]non-2-yl]methyl}benzyl)methanamine, 1-(1H-imidazol-2-yl)-N-(1H-imidazol-2-ylmethyl)-N-[4-({7-[(3-methyl-2-thienyl)methyl]-2,7-diazaspiro[4.4]non-2-yl}methyl)benzyl]methanamine, 1-(1H-imidazol-2-yl)-N-(1H-imidazol-2-ylmethyl)-N-{4-[(8-isobutyl-2,8-diazaspiro[4.5]dec-2-yl)carbonyl]benzyl}methanamine, 2-{[{4-[(8-cyclohexyl-2,8-diazaspiro[4.5]dec-2-yl)methyl]benzyl}(1H-imidazol-2-ylmethyl)amino]methyl}-3-pyridinol, 1-{4-[(8-cyclohexyl-2,8-diazaspiro[4.5]dec-2-yl)methyl]phenyl}-N-(1H-imidazol-2-ylmethyl)-N-[(1-methyl-1H-imidazol-2-yl)methyl]methanamine, 1-(4-{[8-(2-ethylbutyl)-2,8-diazaspiro[4.5]dec-2-yl]carbonyl}phenyl)-N,N-bis(1H-imidazol-2-ylmethyl)methanamine, N,N-bis(1H-imidazol-2-ylmethyl)-4-{[8-(1-propylbutyl)-2,8-diazaspiro[4.5]dec-2-yl]methyl}benzamide, 1-(4-{[8-(1-ethylpropyl)-2,8-diazaspiro[4.5]dec-2-yl]carbonyl}phenyl)-N,N-bis(1H-imidazol-2-ylmethyl)methanamine, 1-(1H-imidazol-2-yl)-N-(1H-imidazol-2-ylmethyl)-N-{4-[(9-isobutyl-1-oxa-4,9-diazaspiro[5.5]undec-4-yl)carbonyl]benzyl}methanamine, 1-{4-[(9-cyclohexyl-1-oxa-4,9-diazaspiro[5.5]undec-4-yl)carbonyl]phenyl}-N,N-bis(1H-imidazol-2-ylmethyl)methanamine, 4-{[9-(2-ethylbutyl)-3,9-diazaspiro[5.5]undec-3-yl]methyl}-N,N-bis(1H-imidazol-2-ylmethyl)benzamide, 1-(1H-imidazol-2-yl)-N-{4-[(9-isobutyl-1-oxa-4,9-diazaspiro[5.5]undec-4-yl)carbonyl]benzyl}-N-[(1-methyl-1H-imidazol-2-yl)methyl]methanamine, 1-{4-[(8-cyclohexyl-2,8-diazaspiro[4.5]dec-2-yl)methyl]phenyl}-N-[(1-ethyl-1H-imidazol-2-yl)methyl]-N-(1H-imidazol-2-ylmethyl)methanamine, 1-(4-{[9-(2-ethylbutyl)-2,9-diazaspiro[5.5]undec-2-yl]carbonyl}phenyl)-N,N-bis(1H-imidazol-2-ylmethyl)methanamine, 1-{4-[(8-cyclohexyl-2,8-diazaspiro[4.5]dec-2-yl)methyl]phenyl}-N-(1H-imidazol-2-ylmethyl)-N-[(1-isopropyl-1H-imidazol-2-yl)methyl]methanamine, 1-{4-[(8-cyclohexyl-2,8-diazaspiro[4.5]dec-2-yl)methyl]phenyl}-N-(1H-imidazol-2-ylmethyl)-N-[(1-isobutyl-1H-imidazol-2-yl)methyl]methanamine, 1-{4-[(8-cyclohexyl-2,8-diazaspiro[4.5]dec-2-yl)methyl]phenyl}-N,N-bis[(1-methyl-1H-imidazol-2-yl)methyl]methanamine, 1-{4-[(8-cyclohexyl-2,8-diazaspiro[4.5]dec-2-yl)methyl]phenyl}-N-(1H-imidazol—2-ylmethyl)-N-(2-pyridinylmethyl)methanamine, 1-{4-[(8-cyclohexyl-2,8-diazaspiro[4.5]dec-2-yl)methyl]phenyl}-N-(1H-imidazol-2-ylmethyl)-N-[(3-methyl-2-pyridinyl)methyl]methanamine, N,N-bis(1H-imidazol-2-ylmethyl)-4-({[trans-4-(2,3,6,7-tetrahydro-1H-azepin-1-yl)cyclohexyl]amino}methyl)benzenesulfonamide, or 1-(1H-imidazol-2-yl)-N-(1H-imidazol-2-ylmethyl)-N-[4-({7-[(3-methyl-2-thienyl)methyl]-2,7-diazaspiro[3.5]non-2-yl}methyl)benzyl]methanamine, a salt thereof, or an N-oxide thereof, or a solvate thereof, or a prodrug thereof;

[35] The compound according to the above [1], wherein the compound represented by formula (I) is trans-4-[(8-cyclohexyl-2,8-diazaspiro[4.5]dec-2-yl)methyl]-N,N-bis(1H-imidazol-2-ylmethyl)cyclohexanamine or trans-4-[(9-cyclohexyl-3,9-diazaspiro[5.5]undec-3-yl)methyl]-N,N-bis(1H-imidazol-2-ylmethyl)cyclohexanamine, a salt thereof, or an N-oxide thereof, or a solvate thereof, or a prodrug thereof;

[36] The compound according to the above [1], wherein the compound represented by formula (I) is:
1-{1-[2-(8-cyclohexyl-2,8-diazaspiro[4.5]dec-2-yl)-2-oxoethyl]-4-piperidinyl}-N,N-bis(1H-imidazol-2-ylmethyl)methanamine,
2-{4-[(8-cyclohexyl-2,8-diazaspiro[4.5]dec-2-yl)carbonyl]phenyl}-N,N-bis(1H-imidazol-2-ylmethyl)ethanamine,
1-(4-{[9-(1-ethylpropyl)-1-oxa-4,9-diazaspiro[5.5]undec-4-yl]carbonyl}phenyl)-N-(1H-imidazol-2-ylmethyl)-N-[(1-methyl-1H-imidazol-2-yl)methyl]methanamine,
1-(4-{[9-(1-ethylpropyl)-1-oxa-4,9-diazaspiro[5.5]undec-4-yl]carbonyl}phenyl)-N,N-bis[(1-methyl-1H-imidazol-2-yl)methyl]methanamine,
1-(4-{[8-(1-ethylpropyl)-2,8-diazaspiro[4.5]dec-2-yl]carbonyl}phenyl)-N-(1H-imidazol-2-ylmethyl)-N-[(1-isobutyl-1H-imidazol-2-yl)methyl]methanamine,
4-{[8-(1-ethylpropyl)-2,8-diazaspiro[4.5]dec-2-yl]methyl}-N-(1H-imidazol-2-ylmethyl)-N-[(1-isobutyl-1H-imidazol-2-yl)methyl]benzamide,
1-(4-{2-[8-(1-ethylpropyl)-2,8-diazaspiro[4.5]dec-2-yl]-2-oxoethyl}phenyl)-N,N-bis(1H-imidazol-2-ylmethyl)methanamine,
4-{[2-(1-ethylpropyl)-2,8-diazaspiro[4.5]dec-8-yl]methyl}-N,N-bis(1H-imidazol-2-ylmethyl)benzamide,
4-{[4-(1-ethylpropyl)-1-oxa-4,9-diazaspiro[5.5]undec-9-yl]methyl}-N,N-bis(1H-imidazol-2-ylmethyl)benzamide, or
2-(2-{[{4-[(8-cyclohexyl-2,8-diazaspiro[4.5]dec-2-yl)methyl]benzyl}(1H-imidazol-2-ylmethyl)amino]methyl}-1H-imidazol-1-yl)-N,N-dimethylacetamide,
a salt thereof, or an N-oxide thereof, or a solvate thereof, or a prodrug thereof;

[37] The compound according to the above [1], wherein the compound represented by formula (I) is:
1-[3-(8-cyclohexyl-2,8-diazaspiro[4.5]dec-2-yl)-3-oxopropyl]-N,N-bis(1H-imidazol-2-ylmethyl)-4-piperidinamine,
1-[3-(8-cyclohexyl-2,8-diazaspiro[4.5]dec-2-yl)-3-oxopropanoyl]-N,N-bis(1H-imidazol-2-ylmethyl)-4-piperidinamine,
1-{3-[8-(1-ethylpropyl)-2,8-diazaspiro[4.5]dec-2-yl]-3-oxopropanoyl}-N,N-bis(1H-imidazol-2-ylmethyl)-4-piperidinamine,
1-[3-(8-cyclohexyl-2,8-diazaspiro[4.5]dec-2-yl)-3-oxopropanoyl]-N,N-bis(1H-imidazol-2-ylmethyl)-3-pyrrolidinamine, or
1-[3-(8-benzyl-2,8-diazaspiro[4.5]dec-2-yl)-3-oxopropanoyl]-N,N-bis(1H-imidazol-2-ylmethyl)-4-piperidinamine,
a salt thereof, or an N-oxide thereof, or a solvate thereof, or a prodrug thereof;

[38] A pharmaceutical composition comprising the compound represented by formula (I) according to the above [1], a salt thereof, or an N-oxide thereof, or a solvate thereof, or a prodrug thereof;

[39] The pharmaceutical composition according to the above [38], which is a CXCR4 antagonist;

[40] The pharmaceutical composition according to the above [39], which is a preventive and/or therapeutic agent of CXCR4-mediated diseases, or an agent for regeneration therapy;

[41] The pharmaceutical composition according to the above [40], wherein the CXCR4-mediated disease is asthma, human immunodeficiency virus infection, acquired immunodeficiency syndrome, cancer, cancer metastasis, rheumatoid arthritis, arthritis, retinopathy, macular degeneration, pulmonary fibrosis, ischemic diseases, systemic erythematosus or transplanted organ rejection, or the agent for regeneration therapy is an agent for recruitment of hemopoietic stem cells to peripheral blood, or an agent for a transplantation medical treatment;

[42] The pharmaceutical composition according to the above [40], wherein the CXCR4-mediated diseases is human immunodeficiency virus infection;

[43] The pharmaceutical composition according to the above [39], which is a preventive and/or therapeutic agent of cancerous diseases;

[44] A pharmaceutical composition comprising the compound represented by formula (I) according to the above [1], a salt thereof, an N-oxide thereof or a solvate thereof, or a prodrug thereof, and one or more kinds selected from reverse transcriptase inhibitor, protease inhibitor, CCR2 antagonist, CCR3 antagonist, CCR4 antagonist, CCR5 antagonist, CXCR4 antagonist, HIV integrase inhibitor, fusion inhibitor, CD4 antagonist, antibody against surface antigen of HIV, Short Interfering RNA targeting a HIV-related factor, and vaccine of HIV;

[45] A method for antagonizing CXCR4 in a mammal, comprising administering an effective dosage of the compound represented by formula (I) according to the above [1], a salt thereof, an N-oxide thereof or a solvate thereof, or a prodrug thereof to the mammal;

[46] A method of prevention and/or treatment for CXCR4-mediated diseases in a mammal, comprising administering an effective dosage of the compound represented by formula (I) according to the above [1], a salt thereof, an N-oxide thereof or a solvate thereof, or a prodrug thereof to the mammal;

[47] Use of the compound represented by formula (I) according to the above [1], a salt thereof, an N-oxide thereof or a solvate thereof or a prodrug thereof for production of a CXCR4 antagonist;

[48] Use of the compound represented by formula (I) according to the above [1], a salt thereof, an N-oxide thereof or a solvate thereof or a prodrug thereof for production of a preventive and/or therapeutic agent for CXCR4-mediated diseases; and

[49] The method for producing a compound represented by formula (I), a salt thereof, an N-oxide thereof or a solvate thereof, or a prodrug thereof.

Effect of the Invention

The compound of the present invention has an antagonistic activity against CXCR4 and is therefore useful as a preventive and/or therapeutic agent for diseased mediated by CXCR4, namely, CXCR4-mediated diseases. Furthermore, the compound of the present invention is also useful as a preventive and/or therapeutic agent for cancerous diseases or infections.

BEST MODE FOR CARRYING OUT THE INVENTION

In the present specification, "bond" means to directly bind without mediating the other atom therebetween.

In the present specification, "cyclic group" includes, for example, a monocyclic or condensed cyclic group, a bridged cyclic group, a spiro-bound cyclic group and the like. The "monocyclic or condensed cyclic group" herein includes, for example, a monocyclic or condensed carbocyclic ring, a monocyclic or condensed heterocyclic ring and the like. The "monocyclic or condensed carbocyclic ring" includes a C3-15 monocyclic or condensed carbocyclic ring.

The "C3-15 monocyclic or condensed carbocyclic ring" includes a C3-15 monocyclic or condensed unsaturated carbocyclic ring, or partially or completely saturated one thereof. Examples of the "C3-15 monocyclic or condensed unsaturated carbocyclic ring, or partially or completely saturated one thereof" include, for example, cyclopropane, cyclobutane, cyclopentane, cyclohexane, cycloheptane, cyclooctane, cyclononane, cyclodecane, cycloundecane, cyclododecane, cyclotridecane, cyclotetradecane, cyclopentadecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indane, naphthalene, dihydronaphthalene, tetrahydronaphthalene, perhydronaphthalene, heptalene, perhydroheptalene, biphenylene, as-indacene, s-indacene, acenaphthylene, acenaphthene, fluorene, phenalene, phenanthrene, anthracene, and 1,2,3,5,6,7-hexahydro-s-indacene rings. Among these, examples of the "C3-15 monocyclic or condensed aromatic carbocyclic ring" include benzene, azulene, naphthalene, phenanthrene, anthracene rings and the like.

The "monocyclic or condensed heterocyclic ring" includes, for example, a 3- to 15-membered monocyclic or condensed heterocyclic ring having, as a hetero atom, 1 to 4 nitrogen atom(s), 1 to 2 oxygen atom(s) and/or 1 to 2 sulfur atom(s). Examples of the "3- to 15-membered monocyclic or condensed heterocyclic ring having, as a hetero atom, 1 to 4 nitrogen atom(s), 1 to 2 oxygen atom(s) and/or 1 to 2 sulfur atom(s)" include a 3- to 15-membered monocyclic or condensed unsaturated heterocyclic ring having, as a hetero atom, 1 to 4 nitrogen atom(s), 1 to 2 oxygen atom(s) and/or 1 to 2 sulfur atom(s), or partially or completely saturated one thereof. Examples of the "3- to 15-membered monocyclic or condensed unsaturated heterocyclic ring having, as a hetero atom, 1 to 4 nitrogen atom(s), 1 to 2 oxygen atom(s) and/or 1 to 2 sulfur atom(s), or partially or completely saturated one thereof" include, for example, pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzoxepine, benzoxazepine, benzoxadiazepine, benzothiepine, benzothiazepine, benzothiadiazepine, benzoazepine, benzodiazepine, benzofurazan, benzothiadiazole, benzotriazole, carbazole, β-carboline, acridine, phenazine, dibenzofuran, xanthene, dibenzothiophene, phenothiazine, phenoxazine, phenoxathiin, thianthrene, phenanthridine, phenanthroline, perimidine, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydro benzoazepin, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenzothiophene, dioxolane, dioxane, dithiolane, dithiane, dioxaindane, benzodioxane, chroman, benzodithiolane, benzodithiane, 6,7-dihydro-5H-cyclopenta[b]pyrazine, 5H-cyclopenta[b]pyrazine, imidazo[2,1-b][1,3]thiazole, pyrido[2,3-b]pyrazine, pyrido[3,4-b]pyrazine, [1,3]thiazolo[4,5-b]pyrazine, thieno[2,3-b]pyrazine, 3,4-dihydro-2H-pyrazino[2,3-b][1,4]oxazine, 6,7-dihydro-5H-cyclopenta[b]pyrazine, imidazo[1,2-a]pyrazine, 6,7-dihydro-5H-cyclopenta[b]pyridine, furo[3,2-b]pyridine, pyrido[2,3-d]pyrimidine, 2,3-dihydro-1H-pyrrolo[2,3-b]pyridine, 5,6,7,8-tetrahydro-1,6-naphthylidine, 6,7,8,9-tetrahydro-5H-pyrido[2,3-d]azepine, 3,4-dihydro-2H-pyrano[3,2-c]pyridine, 2,3-dihydrofuro[3,2-c]pyridine, hexahydro-1H-pyrrolidine, octahydrocyclopenta[c]pyrrole, octahydrocyclopenta[b]pyrrole, octahydropyrrolo[3,2-b]pyrrole, octahydropyrrolo[3,4-c]pyrrole, hexahydro-2H-furo[3,2-b]pyrrole, hexahydro-2H-thieno[3,2-b]pyrrole, decahydroquinoline, decahydro-2,6-naphthylidine, octahydro-2H-quinolidine, octahydro-1H-pyrido[1,2-c]pyrimidine, octahydro-2H-1,4-benzooxazine, decahydro-1,5-naphthylidine, octahydro-1H-pyrrolo[3,4-b]pyridine, octahydro-1H-pyrrolo[3,4-c]pyridine rings and the like. Among these, examples of the "3- to 15-membered monocyclic or condensed heterocyclic ring having, as a hetero atom, 1 to 4 nitrogen atom(s), 1 to 2 oxygen atom(s) and/or 1 to 2 sulfur atom(s)" include pyrrole, imidazole, triazole, tetrazole, pyrazole, pyridine, pyrazine, pyrimidine, pyridazine, furan, thiophene, oxazole, isoxazole, thiazole, isothiazole, furazan, oxadiazole, thiadiazole, indole, isoindole, benzofuran, isobenzofuran, benzothiophene, isobenzothiophene, indazole, quinoline, isoquinoline, purine, phthalazine, pteridine, naphthylidine, quinoxaline, quinazoline, cinnoline, benzoxazole, benzothiazole, benzimidazole, benzofurazan, benzothiadiazole, benzotriazole, carbazole, β-carboline, acridine, phenazine, dibenzofuran, dibenzothiophene, phenanthridine, phenanthroline, perimidine rings and the like.

The "bridged cyclic group" includes a bridged carbocyclic ring and a bridged heterocyclic ring. The "bridged carbocyclic ring" includes, for example, a C4-15 bridged carbocyclic ring. Examples of the "C4-15 bridged carbocyclic ring" include bicyclo[2.2.1]heptane, bicyclo[2.2.1]hept-2-ene, bicyclo[3.1.1]heptane, bicyclo[3.1.1]hept-2-ene, bicyclo[3.2.1]octane, bicyclo[2.2.2]octane, bicyclo[2.2.2]oct-2-ene, adamantane, noradamantane, bicyclo[2.1.1]hexane, bicyclo[3.3.1]nonane, bicyclo[3.2.1]octane, bicyclo[3.3.2]decane ring and the like.

Examples of the "bridged heterocyclic ring" include, for example, a heterocyclic bridged ring having, as a hetero atom, 1 to 4 nitrogen atom(s), 1 to 2 oxygen atom(s) and/or 1 to 2 sulfur atom(s). Examples of the "heterocyclic bridged ring having, as a hetero atom, 1 to 4 nitrogen atom(s), 1 to 2 oxygen atom(s) and/or 1 to 2 sulfur atom(s)" include, for example, a "4- to 15-membered heterocyclic bridged ring having, as a hetero atom, 1 to 4 nitrogen atom(s), 1 to 2 oxygen atom(s) and/or 1 to 2 sulfur atom(s)". Examples of the "4- to 15-membered heterocyclic bridged ring having, as a hetero atom, 1 to 4 nitrogen atom(s), 1 to 2 oxygen atom(s) and/or 1 to 2 sulfur atom(s)" include azabicyclo[2.2.1]heptane, oxabicyclo[2.2.1]heptane, azabicyclo[3.1.1]heptane, azabicyclo[3.2.1]octane, oxabicyclo[3.2.1]octane, azabicyclo[2.2.2]octane, diazabicyclo[2.2.2]octane, 1-azatricyclo[3.3.1.1$^{3,7}$]decane, 3-azabicyclo[3.3.1]nonane, and 3,7-diazabicyclo[3.3.1]nonane rings and the like.

The "spiro-bound cyclic group" includes a spiro-bound carbocyclic ring and a spiro-bound heterocyclic ring. Examples of the "spiro-bound carbocyclic ring" include spiro[4.4]nonane, spiro[4.5]decane, spiro[5.5]undecane, spiro[3.4]octane, spiro[3.5]nonane rings and the like.

The "spiro-bound heterocyclic ring" includes a spiro-bound heterocyclic ring having, as a hetero atom, 1 to 4 nitrogen atom(s), 1 to 2 oxygen atom(s) and/or 1 to 2 sulfur atom(s). The "spiro-bound heterocyclic ring having, as a hetero atom, 1 to 4 nitrogen atom(s), 1 to 2 oxygen atom(s) and/or 1 to 2 sulfur atom(s)" include a 7- to 15-membered spiro-bound heterocyclic ring having, as a hetero atom, 1 to 4 nitrogen atom(s), 1 to 2 oxygen atom(s) and/or 1 to 2 sulfur atom(s). Examples of the "7- to 15-membered spiro-bound heterocyclic ring having, as a hetero atom, 1 to 4 nitrogen atom(s), 1 to 2 oxygen atom(s) and/or 1 to 2 sulfur atom(s)" herein include azaspiro[4.4]nonane, oxazaspiro[4.4]nonane, dioxaspiro[4.4]nonane, azaspiro[4.5]decane, thiaspiro[4.5]decane, dithiaspiro[4.5]decane, dioxaspiro[4.5]decane, oxazaspiro[4.5]decane, azaspiro[5.5]undecane, oxaspiro[5.5]undecane, dioxaspiro[5.5]undecane, 2,7-diazaspiro[3.5]nonane, 2,8-diazaspiro[4.5]decane, 2,7-diazaspiro[4.5]decane, 2,9-diazaspiro[5.5]undecane, 2,8-diazaspiro[5.5]undecane, 3,9-diazaspiro[5.5]undecane, 2,7-diazaspiro[4.4]nonane, 1,2-dihydrospiro[indole-3,4'-piperidine], 2,3-dihydro-1H-spiro[isoquinoline-4,4'-piperidine], 1',4'-dihydro-2'H-spiro[piperidine-4,3'-quinoline], 2',3'-dihydro-1'H-spiro[piperidine-4,4'-quinoline], 8-azaspiro[4.5]decane, 7-azaspiro[4.5]decane, 3-azaspiro[5.5]undecane, 2-azaspiro[5.5]undecane, 1-oxa-4,8-diazaspiro[5.5]undecane, 1-oxa-4,9-diazaspiro[5.5]undecane, 3,4-dihydrospiro[chromene-2,4'-piperidine], 2-azaspiro[4.4]nonane, 7-azaspiro[3.5]nonane, 2,3-dihydrospiro[indene-1,4'-piperidine], 3,4-dihydro-2H-spiro[naphthalene-1,4'-piperidine], 3,4-dihydro-1H-spiro[naphthalene-2,4'-piperidine], 2-azaspiro[4.5]decane, 2-azaspiro[3.5]nonane, 1',2'-dihydrospiro[cyclohexane-1,3'-indole], 2',3'-dihydro-1'H-spiro[cyclohexane-1,4'-isoquinoline], 1',4'-dihydro-2'H-spiro[cyclohexane-1,3'-quinoline], 1,6-diazaspiro[3.4]octane, 1,5-diazaspiro[3.4]octane, 1,7-diazaspiro[3.5]nonane, 1,6-diazaspiro[3.5]nonane, 1,5-diazaspiro[3.5]nonane, 1,7-diazaspiro[4.4]nonane, 1,6-diazaspiro[4.4]nonane, 1,8-diazaspiro[4.5]decane, 1,7-diazaspiro[4.5]decane, 2,6-diazaspiro[3.4]octane, 1,6-diazaspiro[4.5]decane, 2,6-diazaspiro[3.5]nonane, 1,9-diazaspiro[5.5]undecane, 1,8-diazaspiro[5.5]undecane, 6-azaspiro[3.5]nonane, 6-azaspiro[3.4]octane, 2-azaspiro[3.4]octane, 1,7-diazaspiro[5.5]undecane, 1,4,9-triazaspiro[5.5]undecane, 1,3,8-triazaspiro[4.5]decane, 1-thia-4,9-diazaspiro[5.5]undecane, 1-thia-4,8-diazaspiro[5.5]undecane rings and the like.

In the present specification, "aliphatic hydrocarbon group" includes, for example, "linear or branched aliphatic hydrocarbon group". Examples of the "linear or branched aliphatic hydrocarbon group" include "aliphatic hydrocarbon group having 1 to 8 carbon atom(s)", and examples of "aliphatic hydrocarbon group having 1 to 8 carbon atom(s)" include C1-8 alkyl group, C2-8 alkenyl group, and C2-8 alkynyl group.

Examples of the C1-8 alkyl group include methyl, ethyl, propyl, butyl, pentyl, hexyl, heptyl, and octyl groups, and isomer groups thereof.

Examples of the C2-8 alkenyl group include vinyl, propenyl, butenyl, pentenyl, hexenyl, heptenyl, octenyl, butadienyl, pentadienyl, hexadienyl, heptadienyl, octadienyl, hexatrienyl, heptatrienyl, and octatrienyl groups, and isomer groups thereof.

Examples of the C2-8 alkynyl group include ethynyl, propynyl, butynyl, pentynyl, hexynyl, heptynyl, octynyl, butadiynyl, pentadiynyl, hexadiynyl, heptadiynyl, octadiynyl, hexatriynyl, heptatriynyl, and octatriynyl groups, and isomer groups thereof.

In the present specification, "group having a basic group" represented by $A^1$ and $A^2$ is not specifically limited as long as it has a basic group. Examples thereof include (1) basic group, (2) aliphatic hydrocarbon group which is substituted with a basic group, and also may have a substituent(s), and (3) cyclic group which is substituted with a basic group, and also may have a substituent(s).

The "aliphatic hydrocarbon group" in the "aliphatic hydrocarbon group which is substituted with a basic group, and also may have a substituent(s)" has the same meaning as in the above aliphatic hydrocarbon group.

The "cyclic group" in the "cyclic group which is substituted with a basic group, and also may have a substituent(s)" has the same meaning as in the above cyclic group.

The "substituent" in the "aliphatic hydrocarbon group which is substituted with a basic group, and also may have a substituent(s)" or the "cyclic group which is substituted with a basic group, and also may have a substituent(s)" is not specifically limited as long as it is a substituent. Examples thereof include the following substituents defined as T.

Examples of T include:
(1) aliphatic hydrocarbon group,
(2) C1-8 alkylidene group (for example, methylidene, ethylidene, propylidene, butylidene, pentylidene, hexylidene, heptylidene, or octylidene group, and isomer thereof, etc.),
(3) cyclic group, (4) aliphatic hydrocarbon group substituted with a cyclic group (for example, cyclopropyl methyl, cyclopentyl methyl, cyclohexyl methyl, phenylmethyl, naphthylmethyl, pyridinylmethyl, cyclopropylethyl, cyclopentylethyl, cyclohexylethyl, phenylethyl, naphthylethyl, pyridinylethyl, cyclopropylpropyl, cyclopentylpropyl, cyclohexylpropyl, phenylmethyl, phenylpropyl, naphthylpropyl, pyridinylpropyl, etc.), (5) hydroxyl group, (6) —O-aliphatic hydrocarbon group (for example, methoxy, ethoxy, propoxy, isopropoxy, butoxy, isobutoxy, tert-butoxy, pentoxy, hexyloxy, heptyloxy, octyloxy, propenyloxy, butenyloxy, pentenyloxy, hexenyloxy, propynyloxy, butynyloxy, pentynyloxy, hexynyloxy, etc.), (7) —O-cyclic group (for example, cyclopropyloxy, cyclopentyloxy, cyclohexyloxy, phenoxy, naphthyloxy, pyridinyloxy, etc.), (8) —O-aliphatic hydrocarbon-cyclic group (for example, cyclopentylmethoxy, cyclohexylmethoxy, phenylmethoxy, etc.), (9) mercapto group,

(10) —S-aliphatic hydrocarbon group (for example, methylthio, ethylthio, propylthio, isopropylthio, butylthio, isobutylthio, tert-butylthio, pentylthio, hexylthio, heptylthio, octylthio, propenylthio, butenylthio, pentenylthio, hexenylthio, propynylthio, butynylthio, pentynylthio, hexynylthio, etc.),

(11) —S-cyclic group (for example, cyclopropylthio, cyclopentylthio, cyclohexylthio, phenylthio, naphthylthio, pyridinylthio, etc.),

(12) —S-aliphatic hydrocarbon-cyclic group (for example, cyclopentylmethylthio, cyclohexylmethylthio, phenylmethylthio, etc.),

(13) —S(O)-aliphatic hydrocarbon group (for example, methylsulfinyl, ethylsulfinyl, propylsulfinyl, isopropylsulfinyl, butylsulfinyl, isobutylsulfinyl, tert-butylsulfinyl, pentylsulfinyl, hexylsulfinyl, heptylsulfinyl, octylsulfinyl, propenylsulfinyl, butenylsulfinyl, pentenylsulfinyl, hexenylsulfinyl, propynylsulfinyl, butynylsulfinyl, pentynylsulfinyl, hexynylsulfinyl, etc.),

(14) —S(O)-cyclic group (for example, cyclopropylsulfinyl, cyclopentylsulfinyl, cyclohexylsulfinyl, phenylsulfinyl, naphthylsulfinyl, pyridinylsulfinyl, etc.),

(15) —S(O)-aliphatic hydrocarbon-cyclic group (for example, cyclopentylmethylsulfinyl, cyclohexylmethylsulfinyl, phenylmethylsulfinyl, etc.),

(16) —$SO_2$-aliphatic hydrocarbon group (for example, methylsulfonyl, ethylsulfonyl, propylsulfonyl, isopropylsulfonyl, butylsulfonyl, isobutylsulfonyl, tert-butylsulfonyl, pentylsulfonyl, hexylsulfonyl, heptylsulfonyl, octylsulfonyl, propenylsulfonyl, butenylsulfonyl, pentenylsulfonyl, hexenylsulfonyl, propynylsulfonyl, butynylsulfonyl, pentynylsulfonyl, hexynylsulfonyl, etc.),

(17) —$SO_2$-cyclic group (for example, cyclopropylsulfonyl, cyclopentylsulfonyl, cyclohexylsulfonyl, phenylsulfonyl, naphthylsulfonyl, pyridinylsulfonyl, etc.),

(18) —$SO_2$-aliphatic hydrocarbon-cyclic group (for example, cyclopentylmethylsulfonyl, cyclohexylmethylsulfonyl, phenylmethylsulfonyl, etc.),

(19) —O—CO-aliphatic hydrocarbon group (for example, methanoyloxy, ethanoyloxy, propanoyloxy, isopropanoyloxy, butanoyloxy, isobutanoyloxy, tert-butanoyloxy, pentanoyloxy, hexanoyloxy, heptanoyloxy, octanoyloxy, propenoyloxy, butenoyloxy, pentenoyloxy, hexenoyloxy, propynoyloxy, butynoyloxy, pentynoyloxy, hexynoyloxy, etc.),

(20) —O—CO-cyclic group (for example, cyclopropylcarbonyloxy, cyclopentyl carbonyloxy, cyclohexyl carbonyloxy, phenyl carbonyloxy, naphthylcarbonyloxy, pyridinylcarbonyloxy, etc.),

(21) —O—CO-aliphatic hydrocarbon-cyclic group (for example, cyclopentylmethanoyloxy, cyclohexylmethanoyloxy, phenylmethanoyloxy, etc.),

(22) —CO-aliphatic hydrocarbon group (for example, methanoyl, ethanoyl, propanoyl, isopropanoyl, butanoyl, isobutanoyl, tert-butanoyl, pentanoyl, hexanoyl, heptanoyl, octanoyl, propenoyl, butenoyl, pentenoyl, hexenoyl, propynoyl, butynoyl, pentynoyl, hexynoyl, etc.),

(23) —CO-cyclic group (for example, cyclopropylcarbonyl, cyclopentylcarbonyl, cyclohexylcarbonyl, phenylcarbonyl, naphthylcarbonyl, pyridinylcarbonyl, etc.),

(24) —CO-aliphatic hydrocarbon-cyclic group (for example, cyclopentylmethanoyl, cyclohexylmethanoyl, phenylmethanoyl, etc.),

(25) oxo group,

(26) thioxo group,

(27) sulfino group,

(28) sulfo group,

(29) amino group,

(30) mono- or di-substituted amino group ("substituent" in "mono- or di-substituted amino group" herein includes, for example, (1) aliphatic hydrocarbon group, (2) cyclic group, and (3) aliphatic hydrocarbon group substituted with a cyclic group. Examples of "mono- or di-substituted amino group" include methylamino, ethylamino, propylamino, isopropylamino, butylamino, isobutylamino, tert-butylamino, pentylamino, hexylamino, heptylamino, octylamino, dimethylamino, diethylamino, dipropylamino, dibutylamino, dipentylamino, dihexylamino, diheptylamino, dioctylamino, N-methyl-N-ethylamino, cyclopropylamino, cyclopentylamino, cyclohexylamino, phenylamino, diphenylamino, dibenzylamino, N-phenyl-N-methylamino, N-phenyl-N-ethylamino, N-benzyl-N-methylamino, N-benzyl-N-ethylamino, N-cyclohexyl-N-propylamino, etc.),

(31) sulfamoyl group,

(32) mono- or di-substituted sulfamoyl group ("substituent" in "mono- or di-substituted sulfamoyl group" include, for example, (1) aliphatic hydrocarbon group, (2) cyclic group, and (3) aliphatic hydrocarbon group substituted with a cyclic group. Examples of "mono- or di-substituted sulfamoyl group" include N-methylsulfamoyl, N-ethylsulfamoyl, N-propylsulfamoyl, N-isopropylsulfamoyl, N-butylsulfamoyl, N-isobutylsulfamoyl, N-(tert-butyl)sulfamoyl, N-pentylsulfamoyl, N-hexylsulfamoyl, N-heptylsulfamoyl, N-octylsulfamoyl, N,N-dimethylsulfamoyl, N,N-diethylsulfamoyl, N,N-dipropylsulfamoyl, N,N-dibutylsulfamoyl, N,N-dipentylsulfamoyl, N,N-dihexylsulfamoyl, N-methyl-N-ethylsulfamoyl, N-cyclopropylsulfamoyl, N-cyclopentylsulfamoyl, N-cyclohexylsulfamoyl, N-phenylsulfamoyl, N,N-diphenylsulfamoyl, N,N-dibenzylsulfamoyl, N-phenyl-N-methylsulfamoyl, N-phenyl-N-ethylsulfamoyl, N-benzyl-N-methylsulfamoyl, N-benzyl-N-ethylsulfamoyl, N-cyclohexyl-N-propylsulfamoyl, etc.),

(33) carboxyl group,

(34) —COO-aliphatic hydrocarbon group (for example, methoxycarbonyl, ethoxycarbonyl, propoxycarbonyl, isopropoxycarbonyl, butoxycarbonyl, isobutoxycarbonyl, tert-butoxycarbonyl, pentoxycarbonyl, hexyloxycarbonyl, heptyloxycarbonyl, octyloxycarbonyl, propenyloxycarbonyl, butenyloxycarbonyl, pentenyloxycarbonyl, hexenyloxycarbonyl, propynyloxycarbonyl, butynyloxycarbonyl, pentynyloxycarbonyl, hexynyloxycarbonyl, etc.),

(35) —COO-cyclic group (for example, cyclopropyloxycarbonyl, cyclopentyloxycarbonyl, cyclohexyloxycarbonyl, phenoxycarbonyl, naphthyloxycarbonyl, pyridinyloxycarbonyl, etc.),
(36) —COO-aliphatic hydrocarbon-cyclic group (for example, cyclopentyl methoxycarbonyl, cyclohexylmethoxycarbonyl, phenyl methoxycarbonyl, etc.),
(37) carbamoyl group,
(38) mono- or di-substituted carbamoyl group ("substituent" in "mono- or di-substituted carbamoyl group" herein includes, for example, (1) aliphatic hydrocarbon group, (2) cyclic group, and (3) aliphatic hydrocarbon group substituted with a cyclic group. Examples of "mono- or di-substituted carbamoyl group" include N-methylcarbamoyl, N-ethylcarbamoyl, N-propylcarbamoyl, N-isopropylcarbamoyl, N-butylcarbamoyl, N-isobutylcarbamoyl, N-(tert-butyl)carbamoyl, N-pentylcarbamoyl, N-hexylcarbamoyl, N-heptylcarbamoyl, N-octylcarbamoyl, N-cyclopropylcarbamoyl, N-cyclopentylcarbamoyl, N-cyclohexylcarbamoyl, N-phenylcarbamoyl, N,N-dimethylcarbamoyl, N,N-diethylcarbamoyl, N,N-dipropylcarbamoyl, N,N-dibutylcarbamoyl, N,N-dipentylcarbamoyl, N,N-dihexylcarbamoyl, N-methyl-N-ethylcarbamoyl, N,N-diphenylcarbamoyl, N,N-dibenzylcarbamoyl, N-phenyl-N-methylcarbamoyl, N-phenyl-N-ethylcarbamoyl, N-benzyl-N-methylcarbamoyl, N-benzyl-N-ethylcarbamoyl, etc.),
(39) —NH—CO-aliphatic hydrocarbon group (for example, methanoylamino, ethanoylamino, propanoylamino, isopropanoylamino, butanoylamino, isobutanoylamino, tert-butanoylamino, pentanoylamino, hexanoylamino, heptanoylamino, octanoylamino, propenoylamino, butenoylamino, pentenoylamino, hexenoylamino, propynoylamino, butynoylamino, pentynoylamino, hexynoylamino, etc.),
(40) —NH—CO-cyclic group (for example, cyclopropylcarbonylamino, cyclopentylcarbonylamino, cyclohexylcarbonylamino, phenylcarbonylamino, naphthylcarbonylamino, pyridinylcarbonylamino, etc.),
(41) —NH—CO-aliphatic hydrocarbon-cyclic group (for example, cyclopentylmethanoylamino, cyclohexylmethanoylamino, phenylmethanoylamino, etc.),
(42) —NH—SO$_2$-aliphatic hydrocarbon group (for example, methylsulfonylamino, ethylsulfonylamino, propylsulfonylamino, isopropylsulfonylamino, butylsulfonylamino, isobutylsulfonylamino, tert-butylsulfonylamino, pentylsulfonylamino, hexylsulfonylamino, heptylsulfonylamino, octylsulfonylamino, propenylsulfonylamino, butenylsulfonylamino, pentenylsulfonylamino, hexenylsulfonylamino, propynylsulfonylamino, butynylsulfonylamino, pentynylsulfonylamino, hexynylsulfonyl, etc.),
(43) —NH—SO$_2$-cyclic group (for example, cyclopropylsulfonylamino, cyclopentylsulfonylamino, cyclohexylsulfonylamino, phenylsulfonylamino, naphthylsulfonylamino, pyridinylsulfonyl, etc.),
(44) —NH—SO$_2$-aliphatic hydrocarbon-cyclic group (for example, cyclopentylmethylsulfonylamino, cyclohexylmethylsulfonylamino, phenylmethylsulfonyl, etc.),
(45) cyano group,
(46) hydrazino group,
(47) nitro group,
(48) nitroso group,
(49) imino group,
(50) mono-substituted imino group ("substituent" in the mono-substituted imino group includes, for example, (1) aliphatic hydrocarbon group, (2) cyclic group, (3) aliphatic hydrocarbon group substituted with a cyclic group, (4) hydroxyl group, (5) —O-aliphatic hydrocarbon group, (6) —O-cyclic group, and (7) —O-aliphatic hydrocarbon-cyclic group. Examples of "mono-substituted imino group" include methylimino, ethylimino, propylimino, isopropylimino, butylimino, isobutylimino, (tert-butyl)imino, pentylimino, hexylimino, heptylimino, octylimino, cyclopropylimino, cyclopentylimino, cyclohexylimino, phenylimino, benzylimino, hydroxyimino, ethoxyimino, propoxyimino, isopropoxyimino, butoxyimino, cyclopentoxyimino, cyclohexyloxyimino, phenoxyimino, benzyloxyimino, etc.),
(51) halogen atom (for example, fluorine atom, chlorine atom, bromine atom, iodine atom, etc.),
(52) methyl group substituted with 1 to 3 halogen atom(s) (for example, fluoromethyl, difluoromethyl, trifluoromethyl, trichloromethyl, etc.), and
(53) methoxy group substituted with 1 to 3 halogen atom(s) (for example, fluoromethoxy, difluoromethoxy, trifluoromethoxy, trichloromethoxy, etc.). These optional substituents may be substituted on the optional substitutable position in optional substitutable number. The number of substituents is preferably from 1 to 8, and more preferably from 1 to 5. The "aliphatic hydrocarbon group" and the "cyclic group" in T are as defined above. Also, "-aliphatic hydrocarbon-" means a divalent aliphatic hydrocarbon group and includes, for example, a divalent group in which one optional hydrogen atom is further removed from the "aliphatic hydrocarbon group".

The "basic group" of "(1) basic group", "(2) aliphatic hydrocarbon group which is substituted with a basic group, and also may have a substituent(s)", and "(3) cyclic group which is substituted with a basic group, and also may have a substituent(s)" defined as the "group having a basic group" is not specifically limited as long as it has a basic nitrogen atom. Examples thereof include (a) amino group, (b) amidino group, (c) guanidino group, (d) hydrazino group, (e) mono- or di-substituted amino group, (f) mono-, di- or tri-substituted amidino group, (g) mono-, di-, tri- or tetra-substituted guanidino group, (h) mono-, di- or tri-substituted hydrazino group, and (i) nitrogen-containing heterocyclic ring which may have a substituent(s). Examples of the "substituent" in the "mono- or di-substituted amino group" herein include (1) aliphatic hydrocarbon group (which is as defined above), (2) cyclic group (which is as defined above), (3) aliphatic hydrocarbon group substituted with a cyclic group (aliphatic hydrocarbon and cyclic group are as defined above), (4) cyclic group substituted with a substituent(s) (substituent has the same meaning as in T, and cyclic group is as defined above), (5) aliphatic hydrocarbon group substituted with a substituent(s) (substituent has the same meaning as in T, and aliphatic hydrocarbon is as defined above), (6) aliphatic hydrocarbon group substituted with a cyclic group substituted with a substituent(s) (substituent has the same meaning as in T, and aliphatic hydrocarbon and cyclic groups are as defined above), and (7) substituent exemplified as the above T other than the above (1) to (6). These optional substituents may be substituted on the optional substitutable position in optional substitutable number. The number of substituents is preferably from 1 to 8, and more preferably from 1 to 5. Examples thereof include methylamino, ethylamino, propylamino, isopropylamino, butylamino, isobutylamino, tert-butylamino, pentylamino, hexylamino, heptylamino, octylamino, dimethylamino, diethylamino, dipropylamino, dibutylamino, dipentylamino, dihexylamino, diheptylamino, dioctylamino, N-methyl-N-ethylamino, cyclopropylamino, cyclopentylamino, cyclohexylamino, phenylamino, diphenylamino, dibenzylamino, N-phenyl-N-methylamino, N-phenyl-N-ethylamino, N-benzyl-N-methylamino, N-benzyl-N-ethylamino, N-benzyl-N-cyclohexylamino, N-cyclohexyl-N-propylamino, N-cyclohexyl-N-(3-hydroxypropyl)amino, N-(4-hydroxycyclohexyl)-N-propylamino, N-(4-hydroxycyclohexyl)-N-(3-hydroxypropyl)amino, N-(4-hydroxycyclohexyl)methyl-N-propylamino, N-cyclohexyl-N-acetylamino, N-(3-methoxypropyl)-N-propylamino, N-(2-carboxyethyl)-N-propylamino, N-(2-ethylpropyl)-N-propylamino, N-cyclohexyl-N-(methylsulfonyl)amino, N-(tetrahydropyran-4-yl)-N-propylamino, and N-(indan-2-yl)-N-propylamino.

Examples of the "substituent" in the "mono-, di- or tri-substituted amidino group" include (1) aliphatic hydrocarbon group (which is as defined above), (2) cyclic group (which is as defined above), (3) aliphatic hydrocarbon group substituted with a cyclic group (aliphatic hydrocarbon and cyclic groups are as defined above). Examples of the "mono-, di- or tri-substituted amidino group" include methylamidino, ethylamidino, propylamidino, isopropylamidino, butylamidino, isobutylamidino, tert-butylamidino, pentylamidino, hexylamidino, heptylamidino, octylamidino, N,N-dimethylamidino, N,N'-dimethylamidino, N,N,N'-trimethylamidino, N,N-diethylamidino, N,N'-diethylamidino, N,N,N'-triethylamidino, N,N-dipropylamidino, N,N'-dipropylamidino, N,N,N'-tripropylamidino, N,N-dibutylamidino, N,N'-dibutylamidino, N,N,N'-tributylamidino, N,N-dipentylamidino, N,N'-dipentylamidino, N,N,N'-tripentylamidino, N,N-dihexylamidino, N,N'-dihexylamidino, N,N,N'-trihexylamidino, N,N-diheptylamidino, N,N'-diheptylamidino, N,N,N'-triheptylamidino, N,N-dioctylamidino, N,N'-dioctylamidino, N,N,N'-trioctylamidino, N-methyl-N-ethylamidino, N-methyl-N'-ethylamidino, cyclopropylamidino, cyclopentylamidino, cyclohexylamidino, phenylamidino, N,N-diphenylamidino, N,N'-diphenylamidino, N,N,N'-triphenylamidino, N,N-dibenzylamidino, N,N'-dibenzylamidino, N,N,N'-tribenzylamidino, N-phenyl-N'-methylamidino, N-phenyl-N'-ethylamidino, N-benzyl-N-methylamidino, N-benzyl-N-ethylamidino and the like.

Examples of the "substituent" in the "mono-, di-, tri- or tetra-substituted guanidino group" include (1) aliphatic hydrocarbon group (which is as defined above), (2) cyclic group (which is as defined above), and (3) aliphatic hydrocarbon group substituted with a cyclic group (aliphatic hydrocarbon and cyclic groups are as defined above). Examples of the "mono-, di-, tri- or tetra-substituted guanidino group" include, for example, methylguanidino, ethylguanidino, propylguanidino, isopropylguanidino, butylguanidino, isobutylguanidino, tert-butylguanidino, pentylguanidino, hexylguanidino, heptylguanidino, octylguanidino, N,N-dimethylguanidino, N,N'-dimethylguanidino, N,N,N'-trimethylguanidino, N,N,N',N"-tetramethylguanidino, N,N-diethylguanidino, N,N'-diethylguanidino, N,N,N'-triethylguanidino, N,N,N',N"-tetraethylguanidino, N,N-dipropylguanidino, N,N'-dipropylguanidino, N,N,N'-tripropylguanidino, N,N,N',N"-tetrapropylguanidino, N,N-dibutylguanidino, N,N'-dibutylguanidino, N,N,N'-tributylguanidino, N,N,N',N"-tetrabutylguanidino, N,N-dipentylguanidino, N,N'-dipentylguanidino, N,N,N'-tripentylguanidino, N,N,N',N"-tetrapentylguanidino, N,N-dihexylguanidino, N,N'-dihexylguanidino, N,N,N'-trihexylguanidino, N,N,N',N"-tetrahexylguanidino, N,N-diheptylguanidino, N,N'-diheptylguanidino, N,N,N'-triheptylguanidino, N,N,N',N"-tetraheptylguanidino, N,N-dioctylguanidino, N,N'-dioctylguanidino, N,N,N'-trioctylguanidino, N,N,N',N"-tetraoctylguanidino, N-methyl-N-ethylguanidino, N-methyl-N'-ethylguanidino, cyclopropylguanidino, cyclopentylguanidino, cyclohexylguanidino, phenylguanidino, N,N-diphenylguanidino, N,N'-diphenylguanidino, N,N,N'-triphenylguanidino, N,N,N',N"-tetraphenylguanidino, N,N-dibenzylguanidino, N,N'-dibenzylguanidino, N,N,N'-tribenzylguanidino, N,N,N',N"-tetrabenzylguanidino, N-phenyl-N'-methylguanidino, N-phenyl-N'-ethylguanidino, N-benzyl-N-methylguanidino, N-benzyl-N-ethylguanidino and the like.

Examples of the "substituent" in the "mono-, di- or tri-substituted hydrazino group" include (1) aliphatic hydrocarbon group (which is as defined above), (2) cyclic group (which is as defined above), and (3) aliphatic hydrocarbon group substituted with a cyclic group (aliphatic hydrocarbon and cyclic groups are as defined above). Examples of the "mono-, di- or tri-substituted hydrazino group" include, for example, methylhydrazino, ethylhydrazino, propylhydrazino, isopropylhydrazino, butylhydrazino, isobutylhydrazino, tert-butylhydrazino, pentylhydrazino, hexylhydrazino, heptylhydrazino, octylhydrazino, N,N-dimethylhydrazino, N,N'-dimethylhydrazino, N,N,N'-trimethylhydrazino, N,N-diethylhydrazino, N,N'-diethylhydrazino, N,N,N'-triethylhydrazino, N,N-dipropylhydrazino, N,N'-dipropylhydrazino, N,N,N'-tripropylhydrazino, N,N-dibutylhydrazino, N,N'-dibutylhydrazino, N,N,N'-tributylhydrazino, N,N-dipentylhydrazino, N,N'-dipentylhydrazino, N,N,N'-tripentylhydrazino, N,N-dihexylhydrazino, N,N'-dihexylhydrazino, N,N,N'-trihexylhydrazino, N,N-diheptylhydrazino, N,N'-diheptylhydrazino, N,N,N'-triheptylhydrazino, N,N-dioctylhydrazino, N,N'-dioctylhydrazino, N,N,N'-trioctylhydrazino, N-methyl-N-ethylhydrazino, N-methyl-N'-ethylhydrazino, cyclopropylhydrazino, cyclopentylhydrazino, cyclohexylhydrazino, phenylhydrazino, N,N-diphenylhydrazino, N,N'-diphenylhydrazino, N,N,N'-triphenylhydrazino, N,N-dibenzylhydrazino, N,N'-dibenzylhydrazino, N,N,N'-tribenzylhydrazino, N-phenyl-N'-methylhydrazino, N-phenyl-N'-ethylhydrazino, N-benzyl-N-methylhydrazino, N-benzyl-N-ethylhydrazino and the like.

The "nitrogen-containing heterocyclic ring" in the "nitrogen-containing heterocyclic ring which may have a substituent(s)" include, for example, a heterocyclic ring which is a 3- to 11-membered monocyclic or bicyclic heterocyclic ring having, as a hetero atom, at least one nitrogen atom, and also may have an oxygen atom(s) and/or an optionally oxidized sulfur atom(s) and has basicity and the like. Example of the "heterocyclic ring which is a 3- to 1'-membered monocyclic or bicyclic heterocyclic ring having, as a hetero atom, at least one nitrogen atom, and also may have an oxygen atom(s) and/or an optionally oxidized sulfur atom(s) and has basicity" herein, include pyrrole, imidazole, triazole, pyrazole, pyridine, pyrazine, pyrimidine, pyridazine, azepine, diazepine, oxazole, thiazole, isoxazole, isothiazole, indole, isoindole, quinoline, isoquinoline, benzoxazole, benzothiazole, benzimidazole, aziridine, azetidine, pyrrolidine, piperidine, piperazine, morpholine, thiomorpholine, perhydroazepine, perhydrodiazepine, indoline, isoindoline, quinazoline, tetrahydroquinoline, perhydroquinoline, tetrahydroisoquinoline, perhydroisoquinoline, tetrahydronaphthyridine, quinoxaline, tetrahydroquinoxaline, dihydrobenzimidazole, perhydrobenzimidazole, carbazole, tetrahydrocarbazole, azabicyclo[3.2.1]octane, quinuclidine, 2,8-diazaspiro[4.5]decane, 1,4,9-triazaspiro[5.5]undecane, 3,9-diazaspiro[5.5]undecane, 2,9-diazaspiro[5.5]undecane, 1,6-diazaspiro[3.4]octane, 1,5-diazaspiro[3.4]octane, 1,7-diazaspiro[3.5]nonane, 1,6-diazaspiro[3.5]nonane, 1,5-diazaspiro[3.5]nonane, 1,7-diazaspiro[4.4]nonane, 1,6-diazaspiro[4.4]nonane, 1,8-diazaspiro[4.5]decane, 1,7-diazaspiro[4.5]decane, 2,6-diazaspiro[3.4]octane, 1,6-diazaspiro[4.5]decane, 2,6-diazaspiro[3.5]nonane, 1,9-diazaspiro[5.5]

undecane, 1,8-diazaspiro[5.5]undecane, 6-azaspiro[3.5]nonane, 6-azaspiro[3.4]octane, 2-azaspiro[3.4]octane, 1,7-diazaspiro[5.5]undecane, 1,4,9-triazaspiro[5.5]undecane, 1,3,8-triazaspiro[4.5]decane, 1-thia-4,9-diazaspiro[5.5]undecane, 1-thia-4,8-diazaspiro[5.5]undecane ring and the like.

The "substituent" in the "nitrogen-containing heterocyclic ring which may have a substituent(s)" includes, other than those exemplified as for the above T, (a) aliphatic hydrocarbon group substituted with 1 to 5 substituent(s) selected from those exemplified in (5) to (26), (29) to (32) and (37) to (53) of the above T (aliphatic hydrocarbon is as defined above), (b) cyclic group substituted with 1 to 5 substituent(s) selected from those exemplified in (5) to (26), (29) to (32) and (37) to (53) of the above T (cyclic group is as defined above), (c) aliphatic hydrocarbon group substituted with "cyclic group substituted with 1 to 5 substituent(s) selected from those exemplified in (5) to (26), (29) to (32) and (37) to (53) of the above T" (aliphatic hydrocarbon is as defined above). These optional substituents may be substituted on the optional substitutable position in optional substitutable number. The number of substituents is preferably from 1 to 8, and more preferably from 1 to 5.

In the present specification, the "nitrogen-containing heterocyclic ring which may have a substituent(s)" represented by ring $A^{1A}$ and ring $A^{2A}$ has the same meaning as in the "nitrogen-containing heterocyclic ring which may have a substituent(s)" defined in the above ring $A^1$ and ring $A^2$.

In the present specification, examples of the "substituent" of "an imidazole ring which may have a substituent(s), a benzimidazole ring which may have a substituent(s), or a pyridine ring which may have a substituent(s)" represented by ring $A^{1B}$ and ring $A^{2B}$ has the same meaning as the "substituent" of the "nitrogen-containing heterocyclic ring which may have a substituent(s)" defined in the above ring $A^1$ and ring $A^2$.

In the present specification, "spacer having a main chain of 1 to 4 atom(s)" represented by $B^1$ and $B^2$ mean the space wherein 1 to 4 atom(s) of the main chain are arranged in a line. "Number of atoms of main chain" is counted so that the number of atoms of the main chain is minimized. For example, it is counted that the number of atoms of 1,2-cyclopentylene is 2 and the number of atoms of 1,3-cyclopentylene is 3. Examples of the "spacer having a main chain of 1 to 4 atom(s)" include divalent group composed of 1 to 4 group(s) selected optionally from —O—, —S—, —CO—, —SO—, —SO$_2$—, divalent nitrogen atom which may have a substituent, divalent aliphatic hydrocarbon group having 1 to 4 carbon atom(s) which may have a substituent(s), and divalent 3- to 8-membered monocyclic cyclic group which may have a substituent(s), wherein 1 to 4 atom(s) of the main chain are arranged in a line.

The "divalent nitrogen atom which may have a substituent" represents, in addition to —NH—, those wherein hydrogen atom in the "—NH-" group are optionally substituted with (1) aliphatic hydrocarbon group, (2) cyclic group, (3) aliphatic hydrocarbon group substituted with a cyclic group, (4) hydroxyl group, (5) —O-aliphatic hydrocarbon group, (6) —O-cyclic group, (7) —O-aliphatic hydrocarbon-cyclic group, (8) —SO$_2$-aliphatic hydrocarbon group, (9) —SO$_2$-cyclic group, (10) —SO$_2$-aliphatic hydrocarbon-cyclic group, (11) —CO-aliphatic hydrocarbon, (12) —CO-cyclic group, (13) —CO-aliphatic hydrocarbon-cyclic group, (14) carboxyl group, (15) —COO-aliphatic hydrocarbon, (16) —COO-cyclic group, or (17) —COO-aliphatic hydrocarbon-cyclic group, among the substituents exemplified as for the above-described T.

Furthermore, the "substituent" in the "divalent nitrogen atom which may have a substituent" represents those wherein hydrogen atom in the "—NH-" group are optionally substituted with (a) aliphatic hydrocarbon group substituted with 1 to 5 substituent(s) selected from those exemplified in (5) to (53) of the above T, (b) cyclic group substituted with 1 to 5 substituent(s) selected from those exemplified in (5) to (53) of the above T, (c) cyclic group substituted with "aliphatic hydrocarbon group substituted with 1 to 5 substituent(s) selected from those exemplified in (5) to (53) of the above T", or (d) aliphatic hydrocarbon group substituted with "a cyclic group substituted with 1 to 5 substituent(s) selected from those exemplified in (5) to (53) of the above T". The "aliphatic hydrocarbon group", the "cyclic group" and the "-aliphatic hydrocarbon-" are as defined above.

Examples of the "divalent aliphatic hydrocarbon group having 1 to 4 carbon atom(s)" in the "divalent aliphatic hydrocarbon group having 1 to 4 carbon atom(s) which may have a substituent(s)" include C1-4 alkylene group (for example, —CH$_2$—, —(CH$_2$)$_2$—, —(CH$_2$)$_3$—, —(CH$_2$)$_4$—, etc.), C2-4 alkenylene group (for example, —CH=CH—, —CH$_2$—CH=CH—, —CH=CH—CH$_2$—, —(CH$_2$)$_2$—CH=CH—, —CH=CH—(CH$_2$)$_2$—, —CH$_2$—CH=CH—CH$_2$—, etc.), and C2-4 alkynylene group (for example, —C≡C—, —CH$_2$—C≡C—, —C≡C—, —CH$_2$—, —(CH$_2$)$_2$—C≡C—, —C≡C—(CH$_2$)$_2$—, —CH$_2$—C≡C—CH$_2$—, etc.). Examples of the "substituent" in the "divalent aliphatic hydrocarbon group having 1 to 4 carbon atom(s) which may have a substituent(s)" include those exemplified as for the above-described T, and these optional substituents may be substituted on the substitutable position and the number of substituents is from 1 to 5, and preferably from 1 to 2.

Examples of the "divalent 3- to 8-membered monocyclic cyclic group" in the "divalent 3- to 8-membered monocyclic cyclic group which may have a substituent(s)" include divalent group which can be obtained by eliminating optional two hydrogen atoms from the "C3-8 monocyclic cyclic group". The two hydrogen atoms may be the ones which bonds the same carbon atom or which bonds different carbon atoms, the latter is preferable. Examples of the "C3-8 monocyclic cyclic group" herein include "C3-8 monocyclic carbocyclic ring" and "3- to 8-membered monocyclic heterocyclic ring". The "C3-8 monocyclic carbocyclic ring" includes C3-8 monocyclic unsaturated carbocyclic ring, and partially or completely saturated one thereof. Examples of the "C3-8 monocyclic unsaturated carbocyclic ring, and partially or completely saturated one thereof" include cyclopropane, cyclobutane, cyclopentane, cyclohexane, cycloheptane, cyclooctane, cyclopentene, cyclohexene, cycloheptene, cyclooctene, cyclopentadiene, cyclohexadiene, cycloheptadiene, cyclooctadiene, and benzene rings. Among these, the "C3-8 monocyclic aromatic carbocyclic ring" includes, for example, benzene ring.

Examples of the "3- to 8-membered monocyclic heterocyclic ring" include "3- to 8-membered monocyclic heterocyclic ring having, as a hetero atom, 1 to 4 nitrogen atom(s), 1 to 2 oxygen atom(s) and/or 1 to 2 sulfur atom(s)". The 3- to 8-membered monocyclic heterocyclic ring having, as a hetero atom, 1 to 4 nitrogen atom(s), 1 to 2 oxygen atom(s) and/or 1 to 2 sulfur atom(s)" herein includes 3- to 8-membered monocyclic unsaturated heterocyclic ring having, as a hetero atom, 1 to 4 nitrogen atom(s), 1 to 2 oxygen atom(s) and/or 1 to 2 sulfur atom(s), and partially or completely saturated one thereof. Examples of the "3- to 8-membered monocyclic unsaturated heterocyclic ring having, as a hetero atom, 1 to 4 nitrogen atom(s), 1 to 2 oxygen atom(s) and/or 1 to 2 sulfur atom(s), and partially or completely saturated one thereof" include pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, aziridine, azetidine, pyrroline, pyrrolidine, imidazoline, imidazolidine, triazoline, triazolysine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, dioxolane, dioxane, dithiolane, dithiane rings and the like. Among these, examples of the "3- to 8-membered monocyclic aromatic heterocyclic ring having, as a hetero atom, 1 to 4 nitrogen atom(s), 1 to 2 oxygen atom(s) and/or 1 to 2 sulfur atom(s)" include pyrrole, imidazole, triazole, tetrazole, pyrazole, pyridine, pyrazine, pyrimidine, pyridazine, furan, thiophene, oxazole, isoxazole, thiazole, isothiazole, furazan, oxadiazole, thiadiazole rings and the like.

Examples of the "3- to 8-membered monocyclic cyclic group" in the "divalent 3- to 8-membered monocyclic cyclic group which may have a substituent(s)" include, for example, cyclohexylene, phenylene, pyrrolidine-diyl, piperidine-diyl. Examples of the "substituent" in the "divalent 3- to 8-membered monocyclic cyclic group which may have a substituent(s)" include, for example, those exemplified as the above T. These optional substituents may be substituted on the optional substitutable position in optional substitutable number. The number of substituents is preferably from 1 to 8, and more preferably from 1 to 5.

In the present specification, "spacer having a main chain of 1 to 10 atom(s)" represented by E means the space wherein 1 to 10 atom(s) of the main chain are arranged in a line. "Number of atoms of main chain" is counted so that the number of atoms of the main chain is minimized. For example, it is counted that the number of atoms of

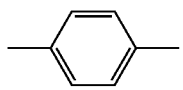

is 4, the number of atoms of

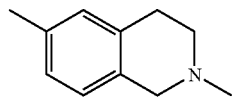

is 6 and the number of atoms of

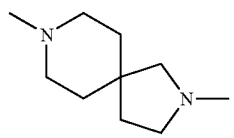

is 6.

Examples of the "spacer having a main chain of 1 to 10 atom(s)" include divalent group composed of 1 to 10 group(s) selected optionally from —O—, —S—, —CO—, —SO—, —SO$_2$—, divalent nitrogen atom which may have a substituent, divalent aliphatic hydrocarbon group having 1 to 10 carbon atom(s) which may have a substituent(s), and divalent 3- to 15-membered monocyclic cyclic group which may have a substituent(s), wherein 1 to 10 atom(s) of the main chain are arranged in a line. The "divalent nitrogen atom which may have a substituent" is as defined above. Examples of the "divalent aliphatic hydrocarbon group having 1 to 10 carbon atom(s)" in the "divalent aliphatic hydrocarbon group having 1 to 10 carbon atom(s) which may have a substituent(s)" include C1-10 alkylene group (methylene, ethylene, trimethylene, tetramethylene, pentamethylene, hexamethylene, heptamethylene, octamethylene, nonamethylene, decamethylene group, and isomers thereof), C2-10 alkenylene group (ethenylene, propenylene, butenylene, pentenylene, hexenylene, heptenylene, octenylene, nonenylene, decenylene group, and isomers thereof), and C2-10 alkynylene group (ethynylene, propynylene, butynylene, pentynylene, hexynylene, heptynylene, octynylene, nonynylene, decynylene group, and isomers thereof). Examples of the "substituent" in the "divalent aliphatic hydrocarbon group having 1 to 10 carbon atom(s) which may have a substituent(s)" include those exemplified as for T, and these optional substituents may be substituted on the substitutable position and the number of substituents is from 1 to 5, and preferably from 1 to 2.

The "divalent 3- to 15-membered cyclic group" in the "divalent 3- to 15-membered cyclic group which may have a substituent(s)" includes, for example, a divalent group which can be obtained by eliminating optional two hydrogen atoms from the "divalent 3- to 15-membered cyclic group". The "divalent 3- to 15-membered cyclic group" herein includes, for example, a C3-15 monocyclic or condensed carbocyclic ring defined above, a C4-15 bridged ring, or a C7-15 spirobound carbocyclic ring, a 3- to 15-membered monocyclic or condensed heterocyclic ring having, as a hetero atom, 1 to 4 nitrogen atom(s), 1 to 2 oxygen atom(s) and/or 1 to 2 sulfur atom(s), a 4- to 15-membered bridged heterocyclic ring having, as a hetero atom, 1 to 4 nitrogen atom(s), 1 to 2 oxygen atom(s) and/or 1 to 2 sulfur atom(s), and a 7- to 15-membered spiro-bound heterocyclic ring having, as a hetero atom, 1 to 4 nitrogen atom(s), 1 to 2 oxygen atom(s) and/or 1 to 2 sulfur atom(s). Examples of the "substituent" in the "divalent 3- to 15-membered cyclic group which may have a substituent(s)" include those exemplified as for T, and these optional substituents may be substituted on the substitutable position and the number of substituents may be from 1 to 5, and preferably from 1 to 2.

In the present specification, the "divalent 3- to 8-membered monocyclic group which may have a substituent(s)" represented by E has the same meaning as the "divalent 3- to 8-membered monocyclic group which may have a substituent(s)" defined in $B^1$ and $B^2$.

In the present specification, the "divalent 9- to 10-membered condensed cyclic ring which may have a substituent(s)" in the "divalent 9- to 10-membered condensed cyclic group" represented by E includes, for example, the divalent group which can be obtained by eliminating optional two hydrogen atoms from the "9- to 10-membered condensed cyclic ring". The "9- to 10-membered condensed cyclic group" herein includes a "9- to 10-membered condensed carbocyclic ring" and a "9- to 10-membered condensed heterocyclic ring". The "9- to 10-membered condensed carbocyclic ring" includes a 9- to 10-membered condensed unsaturated carbocyclic ring, and partially or completely saturated one thereof. Examples of the "9- to 10-membered condensed unsaturated carbocyclic ring, and partially or completely saturated one thereof" include, for example, azulene, naphthalene, perhydroazulene, indene, perhydroindene, indan, dihydronaphthalene, teterahydronaphthalene, and perhydronaphthalene ring. The "9- to 10-membered condensed heterocyclic ring" includes a 9- to 10-membered condensed unsaturated heterocyclic ring having, as a hetero atom, 1 to 4 nitrogen atom(s), 1 to 2 oxygen atom(s) and/or 1 to 2 sulfur atom(s), and partially or completely saturated one thereof. Examples of the "9- to 10-membered condensed unsaturated heterocyclic ring having, as a hetero atom, 1 to 4 nitrogen atom(s), 1 to 2 oxygen atom(s) and/or 1 to 2 sulfur atom(s), and partially or completely saturated one thereof" include, for example, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzofurazan, benzothiadiazole, benzotriazole, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, and perhydrobenzimidazole ring.

Examples of the "substituent" in the "divalent 9- to 10-membered condensed heterocyclic ring which may have a substituent(s)" represented by E include those exemplified as for T, and these optional substituents may be substituted on the substitutable position and the number of substituents may be from 1 to 5, and preferably from 1 to 2.

In the present specification, the "divalent 3- to 8-membered condensed cyclic group which may have a substituent(s)" represented by ring $E^1$ has the same meaning as the "divalent 3- to 8-membered monocyclic cyclic group which may have a substituent(s)" in $B^1$ and $B^2$. The "divalent 9- to 10-membered condensed cyclic group which may have a substituent(s)" represented by ring $E^1$ has the same meaning as the "divalent 9- to 10-membered condensed cyclic group which may have a substituent(s)" in E.

In the present specification, the "aliphatic hydrocarbon group" in the "pyrrolidine ring which may be substituted by an aliphatic hydrocarbon group or a piperidine ring which may be substituted by an aliphatic hydrocarbon group" represented by ring $E^4$ has the same meaning as the above "aliphatic hydrocarbon group".

In the present specification, the "spacer having a main chain of 1 to 4 atom(s)" represented by L has the same meaning as the "spacer having a main chain of 1 to 4 atom(s)" defined in $B^1$ and $B^2$.

In the present specification, the "group having a basic group" in the "aliphatic hydrocarbon group which is substituted with a group having a basic group, and also may have a substituent(s)", the "monocyclic or condensed cyclic group which is substituted with a group having a basic group, and also may have a substituent(s)", the "spiro-bound cyclic group which may be substituted with a group having a basic group, and also may have a substituent(s)", and the "bridged cyclic group which may be substituted with a group having a basic group, and also may have a substituent(s)" represented by J has the same meaning as the above "group having a basic group" defined in $A^1$ and $A^2$. The "aliphatic hydrocarbon group" in the "aliphatic hydrocarbon group which is substituted with a group having a basic group, and also may have a substituent(s)" herein has the same meaning as the "aliphatic hydrocarbon group". The "monocyclic or condensed cyclic group" in the "monocyclic or condensed cyclic group which is substituted with a group having a basic group, and also may have a substituent(s)" has the same meaning as the "monocyclic or condensed cyclic group" in the above "cyclic group". The "spiro-bound cyclic group" in the "spiro-bound cyclic group which may be substituted with a group having a basic group, and also may have a substituent(s)" has the same meaning as the "spiro-bound cyclic group" in the above "cyclic group". The "bridged cyclic group" of the "bridged cyclic group which may be substituted with a group having a basic group, and also may have a substituent(s)" has the same meaning as the "bridged cyclic group" in the "cyclic group". The "substituent" herein is not specifically limited. Examples thereof include (1) an aliphatic hydrocarbon group which may have a substituent(s), (2) a cyclic group which may have a substituent(s), (3) an aliphatic hydrocarbon group substituted by a cyclic group which may have a substituent(s) and (4) substituent exemplified as the above T other than the above. The "aliphatic hydrocarbon group" and the "cyclic group" herein the "aliphatic hydrocarbon group which may have a substituent(s)", the "cyclic group which may have a substituent(s)" and the "aliphatic hydrocarbon group substituted by a cyclic group which may have a substituent(s)" have the same meaning as described above. The "substituent" in the above (1) to (3) includes those exemplified as for T, and these optional substituents may be substituted on the substitutable position and the number of substituents may be from 1 to 5.

In the present specification, ring $J^1$ and ring $J^2$ represent a ring which forms a spiro-bound cyclic group.

In the present specification, the "C3-10 monocyclic or bicyclic carbocyclic ring" represented by ring $J^1$ includes a C3-10 monocyclic or bicyclic unsaturated carbocyclic ring, and partially or completely saturated one thereof. Examples thereof include, for example, benzene, azulene, naphthalene, cyclopropane, cyclobutane, cyclopentane, cyclohexane, cycloheptane, cyclooctane, cyclononane, cyclodecane, cyclohexene, cycloheptene, cyclooctene, cyclopentadiene, cyclohexadiene, cycloheptadiene, cyclooctadiene, pentalene, perhydropentalene, perhydroazulene, indene, perhydroindene, indane, dihydronaphthalene, tetrahydronaphthalene, perhydronaphthalene, heptalene, perhydroheptalene and the like.

In the present specification, the "3- to 10-membered monocyclic or bicyclic heterocyclic ring composed of a carbon atom(s), an oxygen atom(s) and/or an optionally oxidized sulfur atom(s)" represented by ring $J^1$ includes a 3- to 10-membered monocyclic or bicyclic unsaturated heterocyclic ring composed of a carbon atom(s), an oxygen atom(s) and/or an optionally oxidized sulfur atom(s), and partially or completely saturated one thereof. Examples thereof include, for example, furan, pyran, oxepine, thiophene, thiopyran, thiepine, benzofuran, isobenzofuran, benzothiophene, isobenzothiophene, dithianaphthalene, chromene, benzoxepine, benzothiepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, oxathiane, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, benzoxathiane, benzodioxepane, dioxolane, dioxane, dithiolane, dithiane, dioxaindane, benzodioxane, chroman, benzodithiolane, benzodithiane and the like.

In the present specification, the "3- to 10-membered monocyclic or bicyclic heterocyclic ring which has at least one nitrogen atom and also may have an oxygen atom(s) or an optionally oxidized sulfur atom(s)" represented by ring $J^1$ includes a 3- to 10-membered monocyclic or bicyclic unsaturated heterocyclic ring which has at least one nitrogen atom and also may have an oxygen atom(s) or an optionally oxidized sulfur atom(s), and partially or completely saturated one thereof. Examples thereof include, for example, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, indoline, isoindoline, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, pyrrole, imidazole, triazole, tetrazole, pyrazole, pyridine, pyrazine, pyrimidine, pyridazine, azepine, diazepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, indazole, quinoline, isoquinoline, quinolizine, purine, phthalazine, pteridine, naphthyridine, quinoxaline, quinazoline, cinnoline, benzoxazole, benzothiazole, benzimidazole, benzoxazepine, benzoxadiazepine, benzothiepine, benzothiazepine, benzothiadiazepine, benzoazepine, benzodiazepine, benzofurazan, benzothiadiazole, benzotriazole and the like.

The "C3-10 monocyclic or bicyclic carbocyclic ring", "3- to 10-membered monocyclic or bicyclic heterocyclic ring composed of a carbon atom(s), an oxygen atom(s) and/or an optionally oxidized sulfur atom(s)", or "3- to 10-membered monocyclic or bicyclic heterocyclic ring which has at least one nitrogen atom and also may have an oxygen atom(s) or an optionally oxidized sulfur atom(s)" in the "C3-10 monocyclic or bicyclic carbocyclic ring, which is substituted with a group having a basic group", "3- to 10-membered monocyclic or bicyclic heterocyclic ring composed of a carbon atom(s), an oxygen atom(s) and/or an optionally oxidized sulfur atom(s), which is substituted with a group having a basic group", or "3- to 10-membered monocyclic or bicyclic heterocyclic ring which has at least one nitrogen atom and also may have an oxygen atom(s) or an optionally oxidized sulfur atom(s), and also which may be substituted with a group having a basic group" represented by ring $J^2$ is as defined above. The "group having a basic group" here has the same meaning as the "group having a basic group" defined in $A^1$ and $A^2$.

In the present specification, the "bridged carbocyclic ring" in the "bridged carbocyclic ring substituted with a group having a basic group" represented by ring $J^3$ has the same meaning as in the above-described "bridged carbocyclic ring" in the "cyclic group".

In the present specification, examples of the "bridged heterocyclic ring composed of a carbon atom(s), an oxygen atom(s) and/or an optionally oxidized sulfur atom(s)" of the "bridged heterocyclic ring composed of a carbon atom(s), an oxygen atom(s) and/or an optionally oxidized sulfur atom(s), which is substituted with a group having a basic group" represented by ring $J^3$ include, for example, oxabicyclo[2.2.1]heptane oxabicyclo[3.2.1]octane and the like.

In the present specification, examples of the "bridged heterocyclic ring which has at least one nitrogen atom and also may have an oxygen atom(s) and/or an optionally oxidized sulfur atom(s)" of the "bridged heterocyclic ring which has at least one nitrogen atom and also may have an oxygen atom(s) and/or an optionally oxidized, which may be substituted with a group having a basic group" represented by ring $J^3$ include, for example, azabicyclo[2.2.1]heptane, oxabicyclo[2.2.1]heptane, azabicyclo[3.1.1]heptane, azabicyclo[3.2.1]octane, oxabicyclo[3.2.1]octane, azabicyclo[2.2.2]octane, diazabicyclo[2.2.2]octane, 1-azatricyclo[3.3.1.1$^{3,7}$]decane, 3-azabicyclo[3.3.1]nonane, 3,7-diazabicyclo[3.3.1]nonane and the like.

The "group having a basic group" in ring $J^3$ has the same meaning as in the "group having a basic group" in the above-described $A^1$ and $A^2$.

In the present specification, the "C3-15 monocyclic or condensed carbocyclic ring" in the "C3-15 monocyclic or condensed carbocyclic ring substituted with a group having a basic group" represented by ring $J^4$ has the same meaning as in the "C3-15 monocyclic or condensed unsaturated carbocyclic ring, and partially or completely saturated one thereof" in the "cyclic group".

In the present specification, the "3- to 15-membered monocyclic or condensed heterocyclic ring" of the "3- to 15-membered monocyclic or condensed heterocyclic ring composed of a carbon atom(s), an oxygen atom(s) and/or an optionally oxidized sulfur atom(s), which is substituted with a group having a basic group" represented by ring $J^4$ includes a 3- to 15-membered monocyclic or condensed unsaturated heterocyclic ring composed of a carbon atom(s), an oxygen atom(s) and/or an optionally oxidized sulfur atom(s), and partially or completely saturated one thereof. Examples thereof include, for example, furan, pyran, oxepine, thiophene, thiopyran, thiepine, benzofuran, isobenzofuran, benzothiophene, isobenzothiophene, dithianaphthalene, chromene, benzoxepine, benzothiepine, dibenzofuran, xanthene, dibenzothiophene, phenoxathiin, thianthrene, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, oxathiane, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, benzoxathiane, benzodioxepane, dihydrodibenzofuran, dihydrodibenzothiophene, tetrahydrodibenzofuran, tetrahydrodibenzothiophene, perhydrodibenzofuran, perhydrodibenzothiophene, dioxolane, dioxane, dithiolane, dithiane, dioxaindane, benzodioxane, chroman, benzodithiolane, benzodithiane and the like.

In the present specification, the "3- to 15-membered monocyclic or condensed heterocyclic ring which has at least one nitrogen atom and also may have an oxygen atom(s) and/or an optionally oxidized sulfur atom(s)" of the "3- to 15-membered monocyclic or condensed heterocyclic ring which has at least one nitrogen atom and also may have an oxygen atom(s) and/or an optionally oxidized sulfur atom(s), which may be substituted with a group having a basic group" represented by ring $J^4$ includes a monocyclic or condensed 3- to 15-membered unsaturated heterocyclic ring which has at least one nitrogen atom and also may have an oxygen atom(s) and/or an optionally oxidized sulfur atom(s), and partially or completely saturated one thereof. Examples thereof include, for example, pyrrole, imidazole, triazole, tetrazole, pyrazole, pyridine, pyrazine, pyrimidine, pyridazine, azepin, diazepin, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepin, indole, isoindole, indolizine, indazole, quinoline, isoquinoline, quinolizine, purine, phthalazine, pteridine, naphthyridine, quinoxaline, quinazoline, cinnoline, benzoxazole, benzothiazole, benzimidazole, benzoxazepine, benzoxadiazepine, benzothiazepin, benzothiadiazepine, benzoxazepine, benzodiazepine, benzofurazan, benzothiadiazole, benzotriazole, carbazole, β-carboline, acridine, phenazine, phenothiazine, phenoxazine, phenanthridine, phenanthroline, perimidine, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, indoline, isoindoline, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, dihydrobenzoxazepine, tetrahydrobenzoxazepine, dihydrocarbazole, tetrahydrocarbazole, perhydrocarbazole, dihydroacridine, tetrahydroacridine, perhydroacridine, hexahydro-1H-pyrrolidine, octahydrocyclopenta[c]pyrrole, octahydrocyclopenta[b]pyrrole, octahydropyrrolo[3,2-b]pyrrole, octahydropyrrolo[3,4-c]pyrrole, hexahydro-2H-furo[3,2-b]pyrrole, hexahydro-2H-thieno[3,2-b]pyrrole, decahydroquinoline, decahydro-2,6-naphthylidine, octahydro-2H-quinolidine, octahydro-1H-pyrido[1,2-c]pyrimidine, octahydro-2H-1,4-benzooxazine, decahydro-1,5-naphthylidine, octahydro-1H-pyrrolo[3,4-b]pyridine, octahydro-1H-pyrrolo[3,4-c]pyridine and the like.

The "group having a basic group" in ring $J^4$ has the same meaning as in the "group having a basic group" in the above-described $A^1$ and $A^2$.

In the present specification,

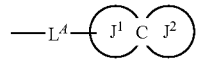

represents

(in the group, $L^{A1}$ represents -(an aliphatic hydrocarbon group having 1 to 3 carbon atom(s) which may have a substituent(s))-(a nitrogen atom which may have a substituent(s))-, ring $J^{1a}$ and ring $J^{2a}$ each independently represents (i) a C3-10 monocyclic or bicyclic carbocyclic ring, or (ii) a 3- to 10-membered monocyclic or bicyclic heterocyclic ring composed of a carbon atom(s), an oxygen atom(s) and/or an optionally oxidized sulfur atom(s), $R^A$ represents a group having a basic group, ring $J^{1a}$ and ring $J^{2a}$ may have, in addition to $R^A$, 1 to 8 substituent(s) on the substitutable position, and when two or more substituents are present, plural substituents may be the same or different, wherein a nitrogen atom which may have a substituent(s)) in $L^{A1}$ is bonded to ring $J^{1a}$,

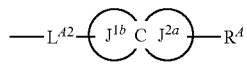

(in the group, $L^{A2}$ is as define above, ring $J_{1b}$ represents a 3- to 10-membered monocyclic or bicyclic heterocyclic ring which has at least one nitrogen atom and also may have an oxygen atom(s) and/or an optionally oxidized sulfur atom(s), ring $J^{1b}$ may have 1 to 8 substituent(s) on the substitutable position, and when two or more substituents are present, plural substituents may be the same or different, and other symbols are as defined above),

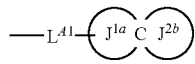

(in the group, ring $J^{2b}$ represents a 3- to 10-membered monocyclic or bicyclic heterocyclic ring which has at least one nitrogen atom and also may have an oxygen atom(s) or an optionally oxidized sulfur atom(s), and which may be substituted with a group having a basic group, ring $J^{2b}$ may have 1 to 8 substituent(s) on the substitutable position, and when two or more substituents are present, plural substituents may be the same or different, and other symbols are as defined above), or

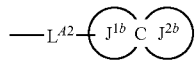

(in the group, all symbols are as defined above).

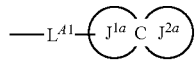

includes, for example,

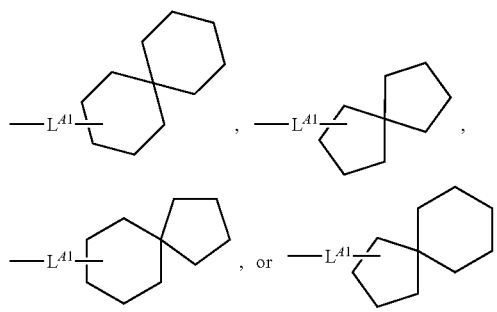

(in the group, all symbols are as defined above).

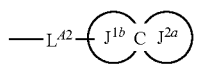

Includes, for example,

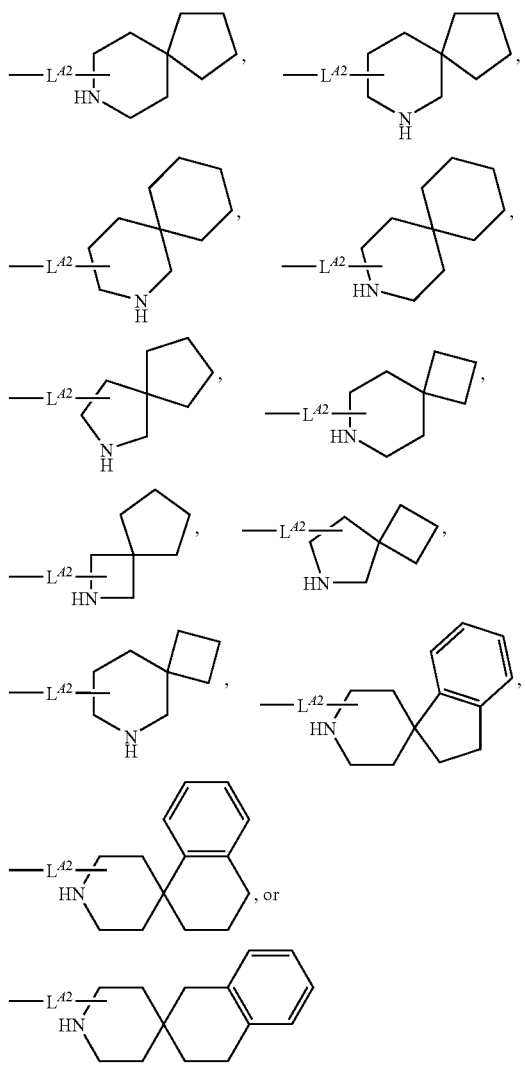

(in the group, all symbols are as defined above, provided that $L^{A2}$ may be a substituent of a nitrogen atom of —NH—),

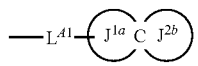

Includes, for example,

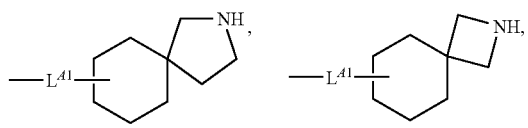

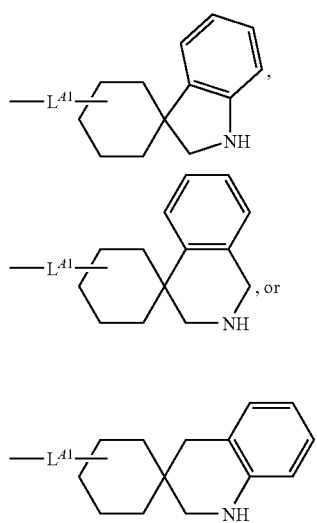
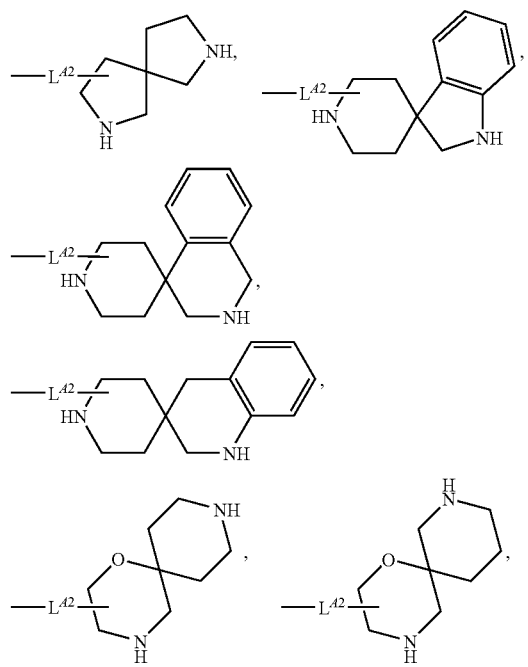
(in the group, all symbols are as defined above, provided that a nitrogen atom of —NH— may have a substituent), and
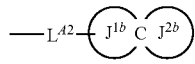
Includes, for example,
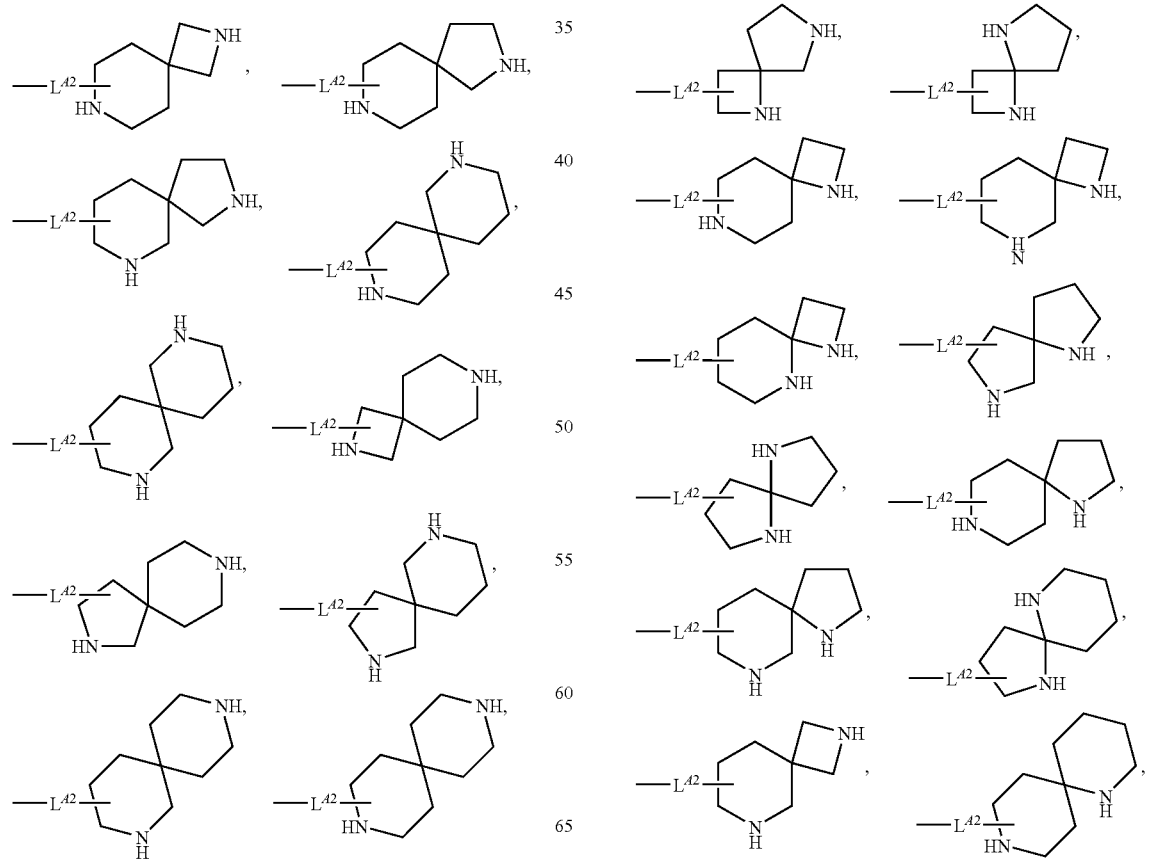

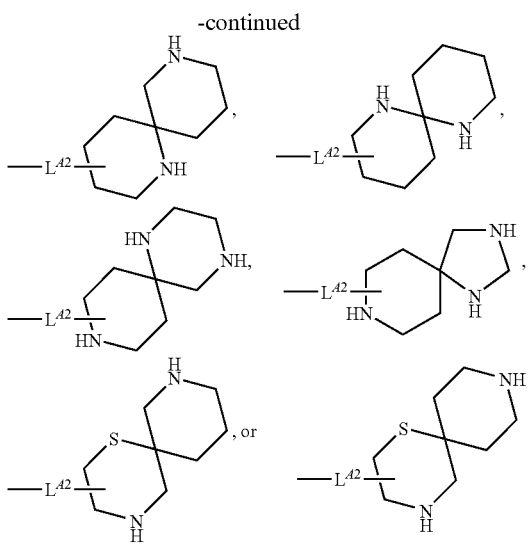

(in the group, all symbols are as defined above, provided that $L^{42}$ may be a substituent of a nitrogen atom of —NH—, and a nitrogen atom of —NH— may have a substituent).

In the present specification, "-(nitrogen atom which may have a substituent)-" in "-(aliphatic hydrocarbon group having 1 to 3 carbon atom(s) which may have a substituent(s))-(nitrogen atom which may have a substituent)-" represented by $L^A$ and $L^{A1}$ has the same meaning as in the "divalent nitrogen atom which may have a substituent". Examples of the "aliphatic hydrocarbon group having 1 to 3 carbon atom(s)" in the "aliphatic hydrocarbon group having 1 to 3 carbon atom(s) which may have a substituent(s)" include C1 to 3 alkylene group (for example, methylene, ethylene, trimethylene, etc.), C2-3 alkenylene group (for example, ethenylene, propenylene, etc.), and C2-3 alkynylene group (for example, ethynylene, propynylene, etc.). Examples of the "substituent" in the "aliphatic hydrocarbon group having 1 to 3 carbon atom(s) which may have a substituent(s)" include those exemplified as for T, and these optional substituents may be substituted on the substitutable position and the number of substituents is from 1 to 3.

In the present specification, the "divalent aliphatic hydrocarbon group having 1 to 4 carbon atom(s) which may have a substituent(s)" represented by LA and $L^{A2}$ is as defined above.

In the present specification, the "(i) C3-10 monocyclic or bicyclic carbocyclic ring or (ii) 3- to 10-membered monocyclic or bicyclic heterocyclic ring composed of a carbon atom(s), an oxygen atom(s) and/or an optionally oxidized sulfur atom(s)" represented by ring $J^{1a}$ and ring $J^{2a}$ has the same meaning as in the "(i) C3-10 monocyclic or bicyclic carbocyclic ring or (ii) 3- to 10-membered monocyclic or bicyclic heterocyclic ring composed of a carbon atom(s), a oxygen atom(s) and/or an optionally oxidized sulfur atom(s)" in ring $J^1$.

In the present specification, the "3- to 10-membered monocyclic or bicyclic heterocyclic ring which has at least one nitrogen atom, and also may have an oxygen atom(s) and/or an optionally oxidized sulfur atom(s)" represented by ring $J^{1b}$ has the same meaning as in the "3- to 10-membered monocyclic or bicyclic heterocyclic ring which has at least one nitrogen atom and also may have an oxygen atom(s) and/or an optionally oxidized sulfur atom(s)" in ring $J^1$.

In the present specification, "3- to 10-membered monocyclic or bicyclic heterocyclic ring which has at least one nitrogen atom and also may have an oxygen atom(s) or an optionally oxidized sulfur atom(s)" represented by ring $J^{2b}$ has the same meaning as in the "3- to 10-membered monocyclic or bicyclic heterocyclic ring which has at least one nitrogen atom and also may have an oxygen atom(s) or an optionally oxidized sulfur atom(s), and which may be substituted with a group having a basic group" in ring $J^2$.

In the present specification, the "group having a basic group" of $R^4$ has the same meaning as in the "group having a basic group" in $A^1$ and $A^2$.

In the present specification, the "spiro-bound cyclic group which may be substituted with a group having a basic group, and also may have a substituent(s)" and the "bridged cyclic group which may be substituted with a group having a basic group, and also may have a substituent(s)" of $J^5$ have the same meaning as the "spirocyclic group which may be substituted with a group having a basic group, and also may have a substituent(s)" and the "bridged cyclic group which may be substituted with a group having a basic group, and also may have a substituent(s)" in the above-described J.

In the present specification, the "substituent" of the "may have 1 to 8 substituent(s) on the substitutable position" of ring $J^1$, ring $J^2$, ring $J^3$, ring $J^4$, ring $J^{1a}$, ring $J^{1b}$, ring $J^{2a}$ and ring $J^{2b}$ is not specifically limited. Examples thereof include those exemplified as for T, and these optional substituents may be substituted on the substitutable position and the number of substituents is preferably from 1 to 8, and more preferably from 1 to 5. When ring $J^2$, ring $J^3$, ring $J^4$ and ring $J^{2b}$ are substituted with a group having a basic group, these optional substituents may be substituted on the substitutable position and the number of substituents is, in addition to a group having a basic group, preferably from 1 to 8, and more preferably from 1 to 4.

In the present specification, the "carbon atom which may have a substituent(s)" represented by G represents, in addition to —CH$_2$—, those wherein two hydrogen atoms in the "—CH$_2$-" group are, each independently, optionally substituted with an aliphatic hydrocarbon group, an aliphatic hydrocarbon group substituted with a cyclic group, a hydroxyl group, an —O-aliphatic hydrocarbon group, a mercapto group, a —S-aliphatic hydrocarbon group, a —S(O)-aliphatic hydrocarbon-cyclic group, a —SO$_2$-aliphatic hydrocarbon group, a —CO-aliphatic hydrocarbon group, a carboxyl group, a —COO-aliphatic hydrocarbon group, a cyano group, a nitro group, a halogen atom, a methyl group which is substituted with 1 to 3 halogen atom(s), or a methoxy group which is substituted with 1 to 3 halogen atom(s). These substituents exemplified herein are the same meaning as the substituents exemplified in the above described T.

In the present specification, the "nitrogen atom which may have a substituent(s)" represented by G represents, in addition to —NH—, those wherein a hydrogen atom in the "—NH-" group are optionally substituted with an aliphatic hydrocarbon group, an aliphatic hydrocarbon group substituted with a cyclic group, an —O-aliphatic hydrocarbon group, a —SO$_2$-aliphatic hydrocarbon group, a —CO-aliphatic hydrocarbon group, a —COO-aliphatic hydrocarbon group, a nitro group, or a methyl group which is substituted with 1 to 3 halogen atom(s). These substituents exemplified herein are the same meaning as the substituents exemplified in the above described T.

In the present specification, "(carbon atom which may have a substituent(s))" of "-(carbon atom which may have a substituent(s))-(nitrogen atom which may have a substituent(s))-" represented by G has the same meaning as the "carbon atom which may have a substituent(s)". The "(nitrogen atom which may have a substituent(s))" of "-(carbon atom which may have a substituent(s))-(nitrogen atom which may have a substituent(s))-" has the same meaning as the "nitrogen atom which may have a substituent(s)".

In the present specification, the "optionally oxidized sulfur atom" means —S—, —SO— and —SO$_2$—.

In the present specification, "substituent" represented by R$^1$ is not specifically limited. Examples thereof include (1) an aliphatic hydrocarbon group which may have a substituent(s), (2) a cyclic group which may have a substituent(s), (3) an aliphatic hydrocarbon group substituted by a cyclic group which may have a substituent(s), and (4) substituent exemplified as the above T other than the above (1) to (3). The "aliphatic hydrocarbon group" and the "cyclic group" herein the "aliphatic hydrocarbon group which may have a substituent(s)", the "cyclic group which may have a substituent(s)" and the "aliphatic hydrocarbon group substituted by a cyclic group which may have a substituent(s)" have the same meaning as described above. The "substituent" in (1) to (3) includes those exemplified as for T, and these optional substituents may be substituted on the substitutable position and the number of substituents may be from 1 to 5.

In the present specification, the "C4-7 monocyclic carbocyclic ring" represented by R$^1$ include cyclobutane, cyclopentane, cyclohexane, cycloheptane, benzene ring and the like.

In the present specification, the "C1-8 alkyl group" represented by R$^1$ is as defined above.

In the present specification, the "halogen atom" and the aliphatic hydrocarbon group" represented by R$^E$ are as defined above.

The present invention further relates to:

[50] the compound according to the above-described [1], wherein J is a spiro-bound cyclic group which may be substituted with a group having a basic group, and also may have a substituent(s), or a bridged cyclic group which may be substituted with a group having a basic group, and also may have a substituent(s);

[51] the compound according to the above-described [50], wherein J is a spiro-bound heterocyclic ring or a bridged heterocyclic ring which has at least one nitrogen atom, and also may have an oxygen atom(s) and/or an optionally oxidized sulfur atom(s), which may be substituted with a group having a basic group;

[52] the compound according to the above-described [50], wherein J is a spiro-bound carbocyclic ring or bridged carbocyclic ring which is substituted with a group having a basic group, and also may have a substituent(s);

[53] the compound according to the above-described [51], wherein the spiro-bound heterocyclic ring or bridged heterocyclic ring which have at least one nitrogen atom, and also may have an oxygen atom(s) and/or an optionally oxidized sulfur atom(s) is:

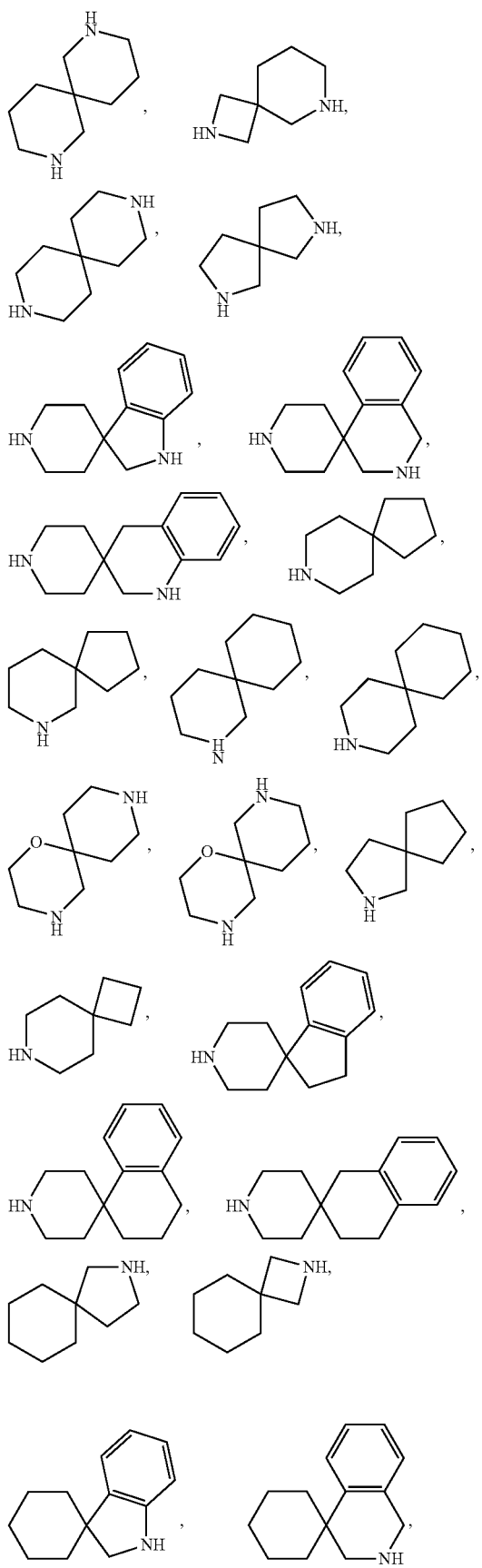

-continued

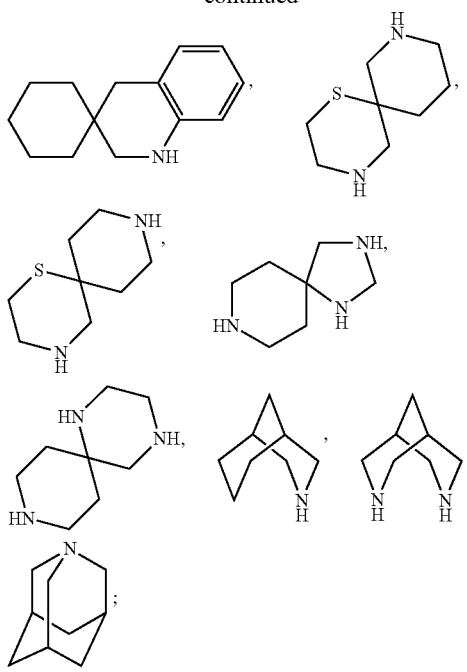

[54] the compound according to the above-described [51], wherein the spiro-bound heterocyclic ring is (i) a monocyclic cyclic ring composed of at least one nitrogen atom and carbon atom and/or (ii) a 7- to 15-membered spiro-bound bicyclic heterocyclic ring which consists of a monocyclic cyclic ring composed of at least one nitrogen atom, one oxygen atom and carbon atoms;

[55] The compound according to the above-described [54], wherein the 7- to 15-membered spiro-bound bicyclic heterocyclic ring is:

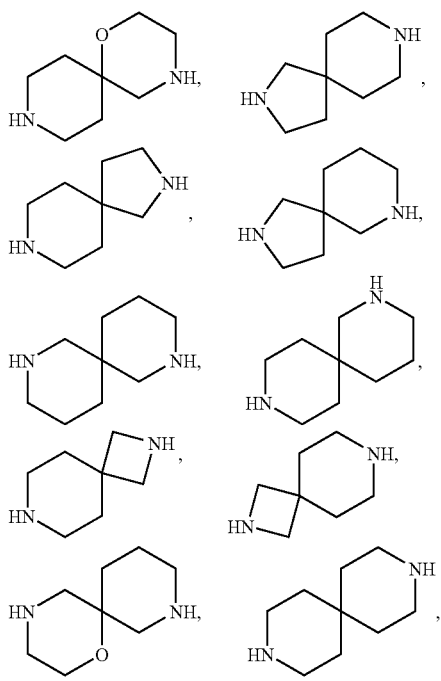

-continued

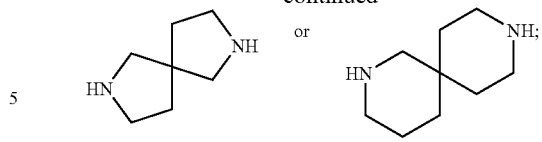

and

[56] the compound according to the above-described [52], wherein the spiro-bound carbocyclic ring or bridged carbocyclic ring is:

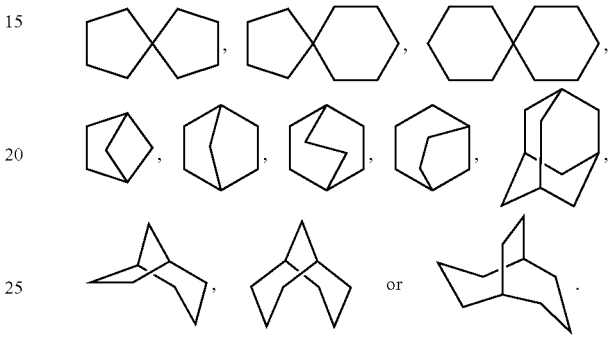

In the present specification, the "spiro-bound heterocyclic ring or bridged heterocyclic ring which has at least one nitrogen atom, and also may have an oxygen atom(s) and/or an optionally oxidized sulfur atom(s)" in the "spiro-bound heterocyclic ring or bridged heterocyclic ring which has at least one nitrogen atom and also may have an oxygen atom(s) and/or an optionally oxidized sulfur atom(s), which may be substituted with a group having a basic group and also may have a substituent(s)" represented by J includes spiro-bound heterocyclic ring which has at least one nitrogen atom and may also have an oxygen atom(s) and/or an optionally oxidized sulfur atom(s), and bridged heterocyclic ring which has at least one nitrogen atom, and also may have an oxygen atom(s) and/or an optionally oxidized sulfur atom(s). Examples of the "spiro-bound heterocyclic ring which has at least one nitrogen atom and also may have an oxygen atom(s) and/or an optionally oxidized sulfur atom(s)" include, for example, azaspiro[4.4]nonane, oxazaspiro[4.4]nonane, azaspiro[4.5]decane, oxazaspiro[4.5]decane, azaspiro[5.5]undecane, 2,7-diazaspiro[3.5]nonane, 2,8-diazaspiro[4.5]decane, 2,7-diazaspiro[4.5]decane-2,9-diazaspiro[5.5]undecane, 2,8-diazaspiro[5.5]undecane, 3,9-diazaspiro[5.5]undecane, 2,7-diazaspiro[4.4]nonane, 1,2-dihydrospiro[indole-3,4'-piperidine], 2,3-dihydro-1H-spiro[isoquinoline-4,4'-piperidine], 1',4'-dihydro-2'H-spiro[piperidine-4,3'-quinoline], 2',3'-dihydro-1'H-spiro[piperidine-4,4'-quinoline], 8-azaspiro[4.5]decane, 8-azaspiro[4.5]decane, 7-azaspiro[4.5]decane, 3-azaspiro[5.5]undecane, 2-azaspiro[5.5]undecane, 1-oxa-4,8-diazaspiro[5.5]undecane, 1-oxa-4,9-diazaspiro[5.5]undecane, 3,4-dihydrospiro[chromene-2,4'-piperidine], 2-azaspiro[4.4]nonane, 7-azaspiro[3.5]nonane, 2,3-dihydrospiro[indene-1,4'-piperidine], 3,4-dihydro-2H-spiro[naphthalene-1,4'-piperidine], 3,4-dihydro-1H-spiro[naphthalene-2,4'-piperidine], 2-azaspiro[4.5]decane, 2-azaspiro[3.5]nonane, 1',2'-dihydrospiro[cyclohexane-1,3'-indole], 2',3'-dihydro-1'H-spiro[cyclohexane-1,4'-isoquinoline], 1',4'-dihydro-2'H-spiro[cyclohexane-1,3'-quinoline], 1,6-diazaspiro[3.4]octane, 1,5-diazaspiro[3.4]octane, 1,7-diazaspiro[3.5]nonane, 1,6- diazaspiro[3.5]nonane, 1,5-diazaspiro[3.5]nonane, 1,7-diazaspiro[4.4]nonane, 1,6-diazaspiro[4.4]nonane, 1,8-diazaspiro[4.5]decane, 1,7-diazaspiro[4.5]decane, 2,6-diazaspiro[3.4]octane, 1,6-diazaspiro[4.5]decane, 2,6-diazaspiro[3.5]nonane, 1,9-diazaspiro[5.5]undecane, 1,8-diazaspiro[5.5]undecane, 6-azaspiro[3.5]nonane, 6-azaspiro[3.4]octane, 2-azaspiro[3.4]octane, 1,7-diazaspiro[5.5]undecane, 1,4,9-triazaspiro[5.5]undecane, 1,3,8-triazaspiro[4.5]decane, 1-thia-4,9-diazaspiro[5.5]undecane, 1-thia-4,8-diazaspiro[5.5]undecane and the like. Examples of the "bridged heterocyclic ring which has at least one nitrogen atom, and also may have an oxygen atom and/or a sulfur atom include, for example, azabicyclo[2.2.1]heptane, azabicyclo[3.1.1]heptane, azabicyclo[3.2.1]octane, azabicyclo[2.2.2]octane, diazabicyclo[2.2.2]octane, 1-azatricyclo[3.3.1.1$^{3,7}$]decane, 3-azabicyclo[3.3.1]nonane, 3,7-diazabicyclo[3.3.1]nonane and the like.

In the present specification, the "7- to 15-membered bicyclic spiro-bound heterocyclic ring wherein a ring comprising the spiro-bound heterocyclic ring is (i) a monocyclic cyclic ring composed of at least one nitrogen atom and carbon atoms, and/or (ii) a monocyclic cyclic ring composed of at least one nitrogen atom, one oxygen atom and carbon atoms" represented by J includes (1) 7- to 15-membered bicyclic spiro-bound heterocyclic ring which consists of two spiro-bound (a) 4- to 8-membered monocyclic cyclic rings composed of at least one nitrogen atom and carbon atoms, (2) 7- to 15-membered bicyclic spiro-bound heterocyclic ring which consists of spiro-bound (a) 4- to 8-membered monocyclic cyclic ring composed of at least one nitrogen atom and carbon atoms, and (b) 4- to 8-membered monocyclic cyclic ring composed of at least one nitrogen atom, one oxygen atom and carbon atoms, and (3) 7- to 15-membered bicyclic spiro-bound heterocyclic ring which consists of two spiro-bound (b) monocyclic cyclic rings composed of at least one nitrogen atom, one oxygen atom and carbon atoms "(1) 7- to 15-membered bicyclic spiro-bound heterocyclic ring wherein a ring comprising the spiro-bound heterocyclic ring is two (a) 4- to 8-membered monocyclic cyclic rings composed of at least one nitrogen atom and carbon atoms" means that two rings selected optionally from "(a) 4- to 8-membered monocyclic cyclic ring composed of at least one nitrogen atom and carbon atoms" share one carbon atom. The shared carbon atom may be any carbon atom as long as it is a carbon atom constituting the monocyclic cyclic ring.

"(2) 7- to 15-membered bicyclic spiro-bound heterocyclic ring which consists of spiro-bound (a) 4- to 8-membered monocyclic cyclic ring composed of at least one nitrogen atom and carbon atoms, and (b) 4- to 8-membered monocyclic cyclic ring composed of at least one nitrogen atom, one oxygen atom and carbon atoms" means that one ring selected optionally from "(a) 4- to 8-membered monocyclic cyclic ring composed of at least one nitrogen atom and carbon atoms" and one ring selected optionally from "(b) 4- to 8-membered monocyclic cyclic ring composed of at least one nitrogen atom, one oxygen atom and carbon atoms" share one carbon atom. The shared carbon atom may be any carbon atom as long as it is a carbon atom constituting the monocyclic cyclic ring.

"(3) 7- to 15-membered bicyclic spiro-bound heterocyclic ring which consists of two spiro-bound (b) monocyclic cyclic rings composed of at least one nitrogen atom, one oxygen atom and carbon atoms" means that two rings selected optionally from "(b) monocyclic cyclic ring composed of at least one nitrogen atom, one oxygen atom and carbon atoms" shares one carbon atom. The shared carbon atom may be any carbon atom as long as it is a carbon atom constituting the monocyclic cyclic ring.

In addition, examples of the "(a) 4- to 8-membered monocyclic cyclic ring composed of at least one nitrogen atom and carbon atoms" include, for example, azetidine, pyrrolidine, piperidine, piperazine, azepane, 1,4-diazepane, azocane, 1,4-diazocane, 1,5-diazocane, and the like; and examples of the "(b) 4- to 8-membered monocyclic cyclic ring composed of at least one nitrogen atom, one oxygen atom and carbon atoms" include, for example, 1,4-oxazepane, 1,4-oxazocane, 1,5-oxazocane, morpholine and the like.

Examples of the above described "(1) 7- to 15-membered bicyclic spiro-bound heterocyclic ring which consists of two spiro-bound (a) 4- to 8-membered monocyclic cyclic rings composed of at least one nitrogen atom and carbon atoms" represented by J, include, for example, 2,7-diazaspiro[3.5]nonane, 2,8-diazaspiro[4.5]decane, 2,7-diazaspiro[4.5]decane, 2,9-diazaspiro[5.5]undecane, 2,8-diazaspiro[5.5]undecane, 2,6-diazaspiro[3.5]nonane, 3,9-diazaspiro[5.5]undecane, 2,7-diazaspiro[4.4]nonane, 1,3,8-triazaspiro[4.5]decane, 1,4,9-triazaspiro[5.5]undecane and the like.

Examples of the above described "(2) 7- to 15-membered bicyclic spiro-bound heterocyclic ring which consists of spiro-bound (a) 4- to 8-membered monocyclic cyclic ring composed of at least one nitrogen atom and carbon atoms, and (b) 4- to 8-membered monocyclic cyclic ring composed of at least one nitrogen atom, one oxygen atom and carbon atoms" represented by J, include 1-oxa-4,9-diazaspiro[5.5]undecane, 1-oxa-4,8-diazaspiro[5.5]undecane and the like.

Examples of the above described "(3) 7- to 15-membered bicyclic spiro-bound heterocyclic ring which consists of two spiro-bound (b) monocyclic cyclic rings composed of at least one nitrogen atom, one oxygen atom and carbon atoms" represented by J, include 2,9-dioxa-5,12-diazaspiro[6.6]tridecane and the like.

In the present invention, all isomers are included unless otherwise specified. For example, alkyl group, alkenyl group, alkynyl group, alkylene group, alkenylene group, alkynylene group, alkylidene group and the like include those which are linear and branched. Furthermore, all of isomers (E-, Z-, cis-, and trans-isomers) on the double bond, ring and condensed ring, isomers (R-isomer, S-isomer, α,β configuration, enantiomer, and diastereomer) due to the presence of asymmetric carbon, optically active substances with optical rotation (D-, L-, d-, and I-compounds), polar compounds (high polar compound and low polar compound) generated by chromatographic separation, equilibrium compounds, rotational isomers, mixtures in an optional mixing ratio and racemic mixtures are included in the present invention.

In the present invention, as is apparent to those skilled in the art, the symbol ⫼ represents that it is bonded to the other side of the page (namely, α configuration), the symbol ⟋ represents that it is bonded to this side of the page (namely, β configuration), the symbol ⟋ represents that it is a mixture of the α configuration and the β configuration, and ⫼ represents that it is bonded to the other side of the page (namely, α configuration) or this side of the page (namely, β configuration) with the proviso that its absolute configuration is not determined.

[Salts]

Salts of the compound represented by formula (I) include all of nontoxic salts and pharmaceutically acceptable salts. The pharmaceutically acceptable salt is preferably a water soluble salt which shows less toxicity. Examples of the suitable salt of the compound represented by formula (I) include salts of alkali metal (potassium, sodium, lithium, etc.), salts of alkali earth metal (calcium, magnesium, etc.), ammonium salts (tetramethylammonium salt, tetrabutylammonium salt, etc.), salts of organic amine (triethylamine, methylamine, dimethylamine, cyclopentylamine, benzylamine, phenethylamine, piperidine, monoethanolamine, diethanolamine, tris (hydroxymethyl)methylamine, lysine, arginine, N-methyl-D-glucamine, etc.), acid addition salts [inorganic acid salts (hydrochloride, hydrobromide, hydroiodide, sulfate, phosphate, nitrate, etc.), and organic acid salts (acetate, trifluoroacetate, lactate, tartrate, oxalate, fumarate, maleate, benzoate, citrate, methanesulfonate, ethanesulfonate, benzenesulfonate, toluenesulfonate, isethionate, glucuronate, gluconate, etc.)] and the like.

Furthermore, salts include quaternary ammonium salts. The quaternary ammonium salt is obtained by quaternizing a nitrogen atom of the compound represented by formula (I) with a $R^0$ group ($R^0$ group represents a C1-8 alkyl group, or a C1-8 alkyl group substituted with a phenyl group).

Also, salts include N-oxide. The compound of the present invention can be converted into N-oxide by an optional method. N-oxide is obtained by oxidizing a nitrogen atom of the compound represented by formula (I).

Examples of suitable solvate of the compound represented by formula (I) include solvates such as water, alcoholic solvent (for example, methanol, ethanol, etc.) and the like. The solvate is preferably nontoxic and water soluble. The solvate of the compound of the present invention also includes solvates of alkali (earth) metal salts, ammonium salts, salts of organic amine, and acid addition salts of the compound of the present invention.

The compound of the present invention can be converted into the above salts and solvates by a known method.

[Prodrugs]

A prodrug of the compound represented by formula (I) means a compound which is converted into the compound represented by formula (I) in the living body by the reaction with an enzyme, gastric acid or the like. Examples of the prodrug of the compound represented by formula (I) include compound wherein an amino group is acylated, alkylated, or phosphorylated (for example, compound wherein an amino group of the compound represented by formula (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, acetoxymethylated, tert-butylated, etc.) when the compound represented by formula (I) has an amino group; compound wherein a hydroxyl group is acylated, alkylated, phosphorylated, boricated or the like (for example, compound wherein a hydroxyl group of the compound represented by formula (I) is acetylated, palmitoylated, propanoylated, pivaloylated, succinylated, fumarylated, alanylated, dimethylaminomethylcarbonylated, etc.) when the compound represented by formula (I) has a hydroxyl group; and compound wherein a carboxy group is esterificated, amidated or the like (for example, compound wherein a carboxy group of the compound represented by formula (I) is ethylesterificated, phenylesterificated, carboxymethylesterificated, dimethylaminomethylesterificated, pivaloyloxymethylesterificated, ethoxycarbonyloxyethylesterificated, phthalidylesterificated, (5-methyl-2-oxo-1,3-dioxolen-4-yl)methylesterificated, cyclohexyloxycarbonylethylesterificated, methylamidated, etc.) when the compound represented by formula (I) has a carboxy group. These compounds can be prepared by a per se known method. The prodrug of the compound represented by formula (I) may be either of a hydrate and a non-hydrate. Also, the prodrug of the compound represented by formula (I) may be converted into the compound represented by formula (I) under physiological conditions described in "Development of Drug" published in 1990 by Hirokawa Shoten, Vol. 7, "Molecular Design", pp. 163-198. Furthermore, the compound represented by formula (I) may be labelled with isotope (for example, $^3$H, $^{14}$C, $^{35}$S, $^{125}$I, etc.) and the like.

The compound represented by formula (I) of the present invention, a salt thereof, a solvate thereof, or a prodrug thereof (hereinafter abbreviated to a compound of the present invention, sometimes) is a compound which is excellent in solubility and oral absorption and maintain its pharmacological activity for a long period of time, and is also less likely to be inhibited by a drug metabolizing enzyme and has low toxicity. These properties are most important physical, chemical and pharmacological properties required when preparations are developed, and the inventive compound satisfies these conditions and is expected to be useful for developing extremely excellent (see The Merck Manual of Diagnosis and Therapy (17th Ed.), Merck & Co.).

The fact that the compound of the present invention is useful as a drug can be evaluated by methods described in various tests and biological examples described hereinafter, and methods which can be carried out by appropriately improving the above methods. The fact that the compound of the present invention is kinetically excellent in length of half-life in blood, stability in alimentary canal, oral absorption and bioavailability can be easily evaluated by a known method, for example, a method described in "Drug Bioavailability (Science of Evaluation and Improvement)", Gendai Iryo-sha, published on Jul. 6, 1998.

In the formula (I) of the present invention, any of each definition by $A^1$, $A^2$, $B^1$, $B^2$, G, E, L, and J is preferred. In the following, preferable groups will be listed. The symbols used herein have the same meaning as described above.

In the present specification, the "group having a basic group" represented by $A^1$ and $A^2$ is preferably, for example, a "nitrogen-containing heterocyclic ring which may have a substituent(s)". The "nitrogen-containing heterocyclic ring" in the "nitrogen-containing heterocyclic ring which may have a substituent(s)" here is preferably, for example, imidazole, benzimidazole and pyridine, and the "substituent" is preferably, for example, absent, an aliphatic hydrocarbon group, or an aliphatic hydrocarbon group substituted by 1 to 5 substituents selected from (5) to (26), (29) to (32) and (37) to (53) in the above T, more preferably, for example, absent, a C1-4 alkyl group, or an aliphatic hydrocarbon group substituted by an oxo group and a mono- or di-substituted amino group, and still more preferably, for example, absent, methyl, or a dimethylacetamide group. $A^1$ and $A^2$ are preferably, for example, 1H-imidazol-2-yl, 1-methyl-1H-imidazol-2-yl, and 2-(1H-imidazol-1-yl)-N,N-dimethylacetamide.

In the present specification, the "nitrogen-containing heterocyclic ring" in the "nitrogen-containing heterocyclic ring which may have a substituent(s)" represented by ring $A^{1A}$ and ring $A^{2A}$ is preferably, for example, imidazole, benzimidazole, or pyridine. Provided that ring $A^1$ and ring $A^2$ may be the same or different. The "substituent" in the "nitrogen-containing heterocyclic ring which may have a substituent(s)" represented by ring $A^{1A}$ and ring $A^{2A}$ is preferably, for example, absent, aliphatic hydrocarbon group, or an aliphatic hydrocarbon group substituted by 1 to 5 substituent(s) selected from (5) to (26), (29) to (32) and (37) to (53) in the above T, more preferably, for example, absent, a C1-4 alkyl group (for example, methyl, ethyl, propyl, isopropyl, butyl, sec-butyl, or tert-butyl group), an aliphatic hydrocarbon group substituted by an oxo group and a mono- or di-substituted amino group, and still more preferably, for example, absent, methyl, or a dimethylacetamide group. Ring $A^{1A}$ and ring $A^{2A}$ are preferably, for example, 1H-imidazol-2-yl, 1-methyl-1H-imidazol-2-yl, 2-(1H-imidazol-1-yl)-N,N-dimethylacetamide, 1-isobutyl-1H-imidazol-2-yl, and 3-methyl-2-pyridinyl, and more preferably, for example, 1H-imidazol-2-yl or 1-methyl-1H-imidazol-2-yl.

In the present specification, the "substituent" of "imidazole which may have a substituent(s), benzimidazole which may have a substituent(s), or pyridine which may have a substituent(s)" represented by ring $A^{1B}$ and ring $A^{2B}$ is preferably, for example, absent, an aliphatic hydrocarbon group, or an aliphatic hydrocarbon group substituted by an oxo group and a mono- or di-substituted amino group and more preferably, for example, absent, a C1-4 alkyl group or N,N-dimethylacetamide.

In the present specification, $B^1$ and $B^2$ each is preferably, for example, a spacer having a main chain of 1 atom and more preferably a methylene group ($-CH_2-$) which may have a substituent(s). The "substituent" herein is preferably absent or a methyl group and more preferably absent. $B^1$ and $B^2$ may be the same or different.

In the present specification, $B^{1A}$ and $B^{2A}$ each is preferably, for example, $-CO-$, or $-CH_2-$. $B^{1A}$ and $B^{2A}$ are more preferably, for example, $-CH_2-$.

In the present specification, G is preferably, for example, bond, a carbon atom which may have a substituent(s), an optionally oxidized sulfur atom, or -(carbon atom which may have a substituent(s))-(nitrogen atom which may have a substituent(s)). The "substituent" here is preferably, for example, absent, a methyl group, or an oxo group, and more preferably absent. G is more preferably bond, $-CO-$, $-SO_2-$, $-CH_2-$, or $-CONH-$. G is still more preferably, for example, bond, $-CO-$, or $-CH_2-$.

In the present specification, $G^1$ is, for example, preferably $-CO-$, $-CH_2-$, or the like.

In the present specification, E is preferably, for example, a divalent aliphatic hydrocarbon group having 1 to 4 carbon atom(s) which may have a substituent(s), a divalent 3- to 8-membered monocyclic cyclic group which may have a substituent(s), or a divalent 9- to 10-membered condensed cyclic group which may have a substituent(s), more preferably, a divalent 3- to 8-membered monocyclic cyclic group which may have a substituent(s), or a divalent 9- to 10-membered condensed cyclic group which may have a substituent(s). The "divalent 3- to 8-membered monocyclic cyclic group which may have a substituent(s)" has the same meaning as in the above $B^1$. The "3- to 8-membered monocyclic cyclic ring" here is preferably, a C5-7 monocyclic carbocyclic ring (those having 5 to 7 carbon atoms are selected from the above C3-8 monocyclic carbocyclic ring), a 5- to 7-membered monocyclic heterocyclic ring (those having 5- to 7-membered ring are selected from the above 3- to 8-membered monocyclic heterocyclic ring), still more preferably, for example, a cyclopentane, cyclohexane, cycloheptane, cyclohexene, cyclohexadiene, benzene, pyridine, pyrazine, pyrimidine, pyridazine, piperidine, or piperazine ring, and particularly preferably, a benzene or cyclohexane ring. The "9- to 10-membered condensed cyclic group" in the "divalent 9- to 10-membered condensed cyclic group which may have a substituent(s)" is preferably a 9- to 10-membered condensed heterocyclic ring, more preferably, for example, a tetrahydroisoquinoline ring. The "substituent" in the "divalent 3- to 8-membered monocyclic cyclic group which may have a substituent(s)" and the "divalent 9- to 10-membered condensed cyclic group which may have a substituent(s)" is preferably, for example, absent, a halogen atom, or an aliphatic hydrocarbon group. The "aliphatic hydrocarbon group" herein has the same meaning as described above.

The "divalent 3- to 8-membered monocyclic cyclic group which may have a substituent(s)" is preferably, for example, 1,4-phenylene, 1,4-cyclohexylene, 1,3-pyrrolidinediyl, or 1,4-piperidinediyl.

In the present specification, ring $E^1$ is preferably, for example, a divalent 3- to 8-membered monocyclic cyclic group which may have a substituent(s). The "monocyclic cyclic ring" here is preferably, for example, cyclopentane, cyclohexane, benzene, pyrrolidine, or piperidine ring. The "substituent" here is preferably, absent, an aliphatic hydrocarbon group, or a halogen atom. Ring $E^1$ is preferably, for example, 1,4-phenylene, 1,4-cyclohexylene, 1,3-pyrrolidinediyl, or 1,4-piperidinediyl.

In the present specification, m is preferably, for example, 0 or 1.

In the present specification, L is preferably, for example, a spacer having a main chain of 1 to 2 atom(s). The "spacer having a main chain of 1 to 2 atom(s)" here is preferably a divalent group composed of 1 to 2 group(s) selected optionally from $-O-$, $-S-$, $-CO-$, $-SO-$, $-SO_2-$, divalent nitrogen atom which may have a substituent(s), and a divalent aliphatic hydrocarbon group (methylene) having one carbon atom which may have a substituent(s), wherein 1 to 2 atom(s) of the main chain are arranged in a line, more preferably, for example, $-CH_2-$, $-O-CH_2-$, $-S-CH_2-$, $-NH-CH_2-$, $-CH_2-CH_2-$, $-CH=CH-$, $-C\equiv C-$, $-CH_2-O-$, $-CH_2-S-$, $-CH_2-NH-$, $-CONH-$, $-SO_2-NH-$, $-NH-CO-$, or $-NH-SO_2-$, and particularly preferably, for example, $-CH_2-$, $-CONH-$, $-CH_2-NH-$, $-O-CH_2-$, $-S-CH_2-$, or $-CH_2-CH_2-$ (J is bonded to the right side). Also, a bond is also preferred. The "substituent" of the divalent nitrogen atom which may have a substituent(s)" here is preferably, absent, an aliphatic hydrocarbon group, an aliphatic hydrocarbon group substituted by a carboxyl group, an aliphatic hydrocarbon group substituted by a "$-COO$-aliphatic hydrocarbon group", an aliphatic hydrocarbon group substituted by a hydroxyl group, an aliphatic hydrocarbon group, or a $-CO$-cyclic group. The "substituent" of the divalent aliphatic hydrocarbon group having one carbon atom which may have a substituent(s)" is preferably, for example, absent, a methyl group, or an oxo group, more preferably absent.

In the present specification, $L^A$ is preferably, for example, a divalent aliphatic hydrocarbon group having 1 to 4 carbon atom(s) which may have a substituent(s).

In the present specification, $L^{A2}$ is preferably, for example, $-(L^{1B})_{n1}-$ (in the group, all symbols are as defined above).

In the present specification, J is preferably an aliphatic hydrocarbon group which is substituted by a basic group, and also may have a substituent(s), a cyclic group which is substituted by an aliphatic hydrocarbon group substituted by a basic group, and also may have a substituent(s), or an aliphatic hydrocarbon group which is substituted by a cyclic group substituted by a basic group, and also may have a substituent(s). The "basic group" here is preferably, for example, a mono- or di-substituted amino group, or a nitrogen-containing heterocyclic ring which may have a substituent(s). The "mono- or di-substituted amino group" here is preferably a di-substituted amino group, more preferably, for example, dimethylamino, diethylamino, dipropylamino, dibutylamino, or N-cyclohexyl-N-propylamino, and particularly preferably, dipropylamino or N-cyclohexyl-N-propylamino. The "nitrogen-containing heterocyclic ring which may have a substituent(s)" here is preferably, absent, or a nitrogen-containing heterocyclic ring substituted by a C1-8 alkyl group or oxo group, and preferred "nitrogen-containing heterocyclic ring" includes for example, pyrrolidine, piperidine, morpholine, thiomorpholine, perhydrodiazepine, tetrahydroisoquinoline, 2,8-diazaspiro[4.5]decane, 1,4,9-triazaspiro[5.5]undecane, 3,9-diazaspiro[5.5]undecane, or 2,9-diazaspiro[5.5]undecane ring.

The "aliphatic hydrocarbon group" in the "aliphatic hydrocarbon group which is substituted by a basic group, and also may have a substituent(s)" or "aliphatic hydrocarbon group which is substituted by a cyclic group substituted by a basic group, and also which may have a substituent(s)" is preferably, for example, a C1-8 alkyl group or a C2-8 alkenyl group, more preferably, for example, methyl, ethyl, propyl, butyl, pentyl, or hexyl. The "cyclic group" in the" cyclic group which is substituted by an aliphatic hydrocarbon group substituted by a basic group, and also may have a substituent(s)" is preferably, for example, a C5-7 monocyclic carbocyclic ring (those having 5 to 7 carbon atoms are selected from the above C3-15 monocyclic or condensed carbocyclic ring), a 5- to 7-membered monocyclic heterocyclic ring (those having a 5- to 7-membered ring are selected from the above 3- to 15-membered monocyclic or condensed heterocyclic ring), more preferably, for example, cyclopentane, cyclohexane, cyclohexene, cyclohexadiene, benzene, pyridine, pyrazine, tetrahydropyran, pyrimidine, pyridazine, piperidine, or piperazine ring. The "substituent" here is preferably, for example, absent, a halogen atom, a methyl group, a hydroxyl group, an amino group, or an oxo group, more preferably, absent.

Furthermore, J is preferably, a "cyclic group which is substituted by group having a basic group, and also may have a substituent(s)", a "spiro-bound cyclic group which may be substituted with a group having a basic group, and also may have a substituent(s)", or a "bridged cyclic group which may be substituted with a group having a basic group, and also may have a substituent(s)". The "cyclic group", "spiro-bound cyclic group", or "bridged cyclic group" here is preferably, (1) a spiro-bound cyclic group, (2) a bridged carbocyclic ring, (3) a bridged heterocyclic ring composed of a carbon atom(s), an oxygen atom(s) and/or an optionally oxidized sulfur atom(s), (4) a bridged heterocyclic ring which has at least one nitrogen atom, and also may have an oxygen atom(s) and/or an optionally oxidized sulfur atom(s), (5) a C3-15 monocyclic or condensed carbocyclic ring, (6) a 3- to 15-membered monocyclic or condensed heterocyclic ring composed of a carbon atom(s), an oxygen atom(s) and/or an optionally oxidized sulfur atom(s), or (7) a 3- to 15-membered monocyclic or condensed heterocyclic ring which has at least one nitrogen atom, and also composes of a carbon atom(s), an oxygen atom(s) and/or an optionally oxidized sulfur atom(s).

The "spiro-bound cyclic group" is preferably 2,7-diazaspiro[3.5]nonane, 2,8-diazaspiro[4.5]decane, 2,7-diazaspiro[4.5]decane, 2,9-diazaspiro[5.5]undecane, 2,8-diazaspiro[5.5]undecane, 3,9-diazaspiro[5.5]undecane, 2,7-diazaspiro[4.4]nonane, 1,2-dihydrospiro[indole-3,4'-piperidine], 2,3-dihydro-1H-spiro[isoquinoline-4,4'-piperidine], 1',4'-dihydro-2'H-spiro[piperidine-4,3'-quinoline], 2',3'-dihydro-1'H-spiro[piperidine-4,4'-quinoline], 8-azaspiro[4.5]decane, 8-azaspiro[4.5]decane, 7-azaspiro[4.5]decane, 3-azaspiro[5.5]undecane, 2-azaspiro[5.5]undecane, 1-oxa-4,8-diazaspiro[5.5]undecane, 1-oxa-4,9-diazaspiro[5.5]undecane, 3,4-dihydrospiro[chromene-2,4'-piperidine], 2-azaspiro[4.4]nonane, 7-azaspiro[3.5]nonane, 2,3-dihydrospiro[indene-1,4'-piperidine], 3,4-dihydro-2H-spiro[naphthalene-1,4'-piperidine], 3,4-dihydro-1H-spiro[naphthalene-2,4'-piperidine], 2-azaspiro[4.5]decane, 2-azaspiro[3.5]nonane, 1',2'-dihydrospiro[cyclohexane-1,3'-indole], 2',3'-dihydro-1'H-spiro[cyclohexane-1,4'-isoquinoline], 1',4'-dihydro-2'H-spiro[cyclohexane-1,3'-quinoline], 1,6-diazaspiro[3.4]octane, 1,5-diazaspiro[3.4]octane, 1,7-diazaspiro[3.5]nonane, 1,6-diazaspiro[3.5]nonane, 1,5-diazaspiro[3.5]nonane, 1,7-diazaspiro[4.4]nonane, 1,6-diazaspiro[4.4]nonane, 1,8-diazaspiro[4.5]decane, 1,7-diazaspiro[4.5]decane, 2,6-diazaspiro[3.4]octane, 1,6-diazaspiro[4.5]decane, 2,6-diazaspiro[3.5]nonane, 1,9-diazaspiro[5.5]undecane, 1,8-diazaspiro[5.5]undecane, 6-azaspiro[3.5]nonane, 6-azaspiro[3.4]octane, 2-azaspiro[3.4]octane, 1,7-diazaspiro[5.5]undecane, 1,4,9-triazaspiro[5.5]undecane, 1,3,8-triazaspiro[4.5]decane, 1-thia-4,9-diazaspiro[5.5]undecane, 1-thia-4,8-diazaspiro[5.5]undecane, spiro[4.4]nonane, spiro[4.5]decane, spiro[5.5]undecane, spiro[3.4]octane, or spiro[3.5]nonane. The "spiro-bound cyclic group" is more preferably 2,7-diazaspiro[3.5]nonane, 2,8-diazaspiro[4.5]decane, 2,7-diazaspiro[4.5]decane, 2,9-diazaspiro[5.5]undecane, 2,8-diazaspiro[5.5]undecane, 3,9-diazaspiro[5.5]undecane, 2,7-diazaspiro[4.4]nonane, 1,2-dihydrospiro[indole-3,4'-piperidine], 2,3-dihydro-1H-spiro[isoquinoline-4,4'-piperidine], 1',4'-dihydro-2'H-spiro[piperidine-4,3'-quinoline], 2',3'-dihydro-1'H-spiro[piperidine-4,4'-quinoline], 8-azaspiro[4.5]decane, 1-oxa-4,8-diazaspiro[5.5]undecane, 1-oxa-4,9-diazaspiro[5.5]undecane, 3,4-dihydrospiro[chromene-2,4'-piperidine], 1,6-diazaspiro[3.4]octane, 1,5-diazaspiro[3.4]octane, 1,7-diazaspiro[3.5]nonane, 1,6-diazaspiro[3.5]nonane, 1,5-diazaspiro[3.5]nonane, 1,7-diazaspiro[4.4]nonane, 1,6-diazaspiro[4.4]nonane, 1,8-diazaspiro[4.5]decane, 1,7-diazaspiro[4.5]decane, 2,6-diazaspiro[3.4]octane, 1,6-diazaspiro[4.5]decane, 2,6-diazaspiro[3.5]nonane, 1,9-diazaspiro[5.5]undecane, 1,8-diazaspiro[5.5]undecane, 1,7-diazaspiro[5.5]undecane, 1,4,9-triazaspiro[5.5]undecane, 1,3,8-triazaspiro[4.5]decane, 1-thia-4,9-diazaspiro[5.5]undecane, or 1-thia-4,8-diazaspiro[5.5]undecane. The "spiro-bound cyclic group" is particularly preferably 2,7-diazaspiro[4.5]decane, 2,8-diazaspiro[4.5]decane, 2,8-diazaspiro[5.5]undecane, 2,9-diazaspiro[5.5]undecane, 2,7-diazaspiro[3.5]nonane, or 1-oxa-4,9-diazaspiro[5.5]undecane. The most preferable "spiro-bound cyclic group" is a 2,8-diazaspiro[4.5]decane ring.

The "bridged carbocyclic ring" is preferably bicyclo[2.1.1]hexane, bicyclo[2.2.1]heptane, bicyclo[2.2.2]octane, bicyclo[3.2.1]octane, adamantane, bicyclo[3.3.1]nonane, bicyclo[3.2.1]octane, or bicyclo[3.3.2]decane.

The "bridged heterocyclic ring composed of a carbon atom(s), an oxygen atom(s) and/or an optionally oxidized sulfur atom(s)" is preferably oxabicyclo[2.2.1]heptane or oxabicyclo[3.2.1]octane.

The "bridged heterocyclic ring which has at least one nitrogen atom, and also may have an oxygen atom(s) and/or an optionally oxidized sulfur atom(s)" is preferably 1-azatricyclo[3.3.1.1$^{3,7}$]decane, 3-azabicyclo[3.3.1]nonane, or 3,7-diazabicyclo[3.3.1]nonane.

The "C3-15 monocyclic or condensed carbocyclic ring" is preferably cyclopropane, cyclobutane, cyclopentane, cyclohexane, cycloheptane, cyclooctane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indane, naphthalene, dihydronaphthalene, tetrahydronaphthalene, perhydronaphthalene, or 1,2,3,5,6,7-hexahydro-s-indacene. More preferably, it is cyclopentane, cyclohexane, or cyclooctane. Most preferably, it is cyclohexane.

The "3- to 15-membered monocyclic or condensed heterocyclic ring composed of a carbon atom, an oxygen atom and/or an optionally oxidized sulfur atom" is preferably a partially or completely saturated 3- to 15-membered monocyclic or condensed heterocyclic ring composed of a carbon atom(s), an oxygen atom(s) and/or an optionally oxidized sulfur atom(s).

The "3- to 15-membered monocyclic or condensed heterocyclic ring which has at least one nitrogen atom, and also composes of a carbon atom(s), an oxygen atom(s) and/or an optionally oxidized sulfur atom(s)" is preferably a partially or completely saturated 3- to 15-membered monocyclic or condensed heterocyclic ring which has at least one nitrogen atom, and also composes of a carbon atom(s), an oxygen atom(s) and/or an optionally oxidized sulfur atom(s).

The "7- to 15-membered spiro-bound bicyclic heterocyclic ring which consists of a monocyclic cyclic ring composed of (i) at least one nitrogen atom, and/or a monocyclic cyclic ring composed of (ii) at least one nitrogen atom, one oxygen atom and carbon atoms" among the "spiro-bound heterocyclic ring" is preferably is a monocyclic cyclic ring wherein the ring constituting the spiro-bound heterocyclic ring is a monocyclic cyclic ring composed of at least one nitrogen atom and a carbon atom and/or a 9- to 11-membered spiro-bound bicyclic heterocyclic ring composed of at least one nitrogen atom, one oxygen atom and carbon atoms.

The 9- to 11-membered spiro-bound bicyclic heterocyclic ring which consists of a monocycle composed of at least one nitrogen atom and a carbon atom and/or a monocyclic cyclic ring composed of at least one nitrogen atom, one oxygen atom and carbon atoms" is preferably, 2,7-diazaspiro[4.5]decane, 2,8-diazaspiro[4.5]decane, 2,8-diazaspiro[5.5]undecane, 2,9-diazaspiro[5.5]undecane, 2,7-diazaspiro[3.5]nonane, or 1-oxa-4,9-diazaspiro[5.5]undecane ring.

The "substituent" of "may have 1 to 8 substituent(s)" or "may have a subtituent(s)" of ring $J^1$, ring $J^2$, ring $J^3$, ring $J^4$, and $J^5$ is preferably, for example, an aliphatic hydrocarbon group, a cyclic group, or an aliphatic hydrocarbon group substituted by a cyclic group, more preferably a C1-8 aliphatic hydrocarbon group, or a C3-10 monocyclic or bicyclic carbocyclic ring. Absent is also preferred as the "substituent" of "optionally substituted by the substituent" of ring $J^1$.

The "substituent" of "optionally substituted by the substituent" of ring $J^2$ is preferably, for example, an aliphatic hydrocarbon group or a cyclic group, more preferably, for example, C1-8 alkyl group, cyclopentane, cyclohexane, cycloheptane, or benzene ring.

In the present specification, the "substituent" of "o may have 1 to 8 substituent(s) on the substitutable position" of ring $J^{1a}$, ring $J^{1b}$, and ring $J^{2a}$, is preferably, for example, absent, a halogen atom, or an aliphatic hydrocarbon group, and more preferably absent.

In the present specification, the "substituent" of "may have 1 to 8 substituent(s) on the substitutable position" of ring $J^{2b}$ is preferably, for example, C1-8 alkyl group, cyclopentane, cyclohexane, cycloheptane, or benzene ring.

The "group having a basic group" of "substituted with a group having a basic group" or "may be substituted with a group having a basic group" of ring $J^2$, ring $J^3$, ring $J^4$, and $J^5$ is preferably, for example, a mono- or di-substituted amino group, or a nitrogen-containing heterocyclic ring which may have a substituent(s). The "mono- or di-substituted amino group" here is preferably a di-substituted amino group, more preferably, for example, dimethylamino, diethylamino, dipropylamino, dibutylamino, or N-cyclohexyl-N-propylamino, and particularly preferably, dipropylamino or N-cyclohexyl-N-propylamino. The "nitrogen-containing heterocyclic ring which may have a substituent(s)" here is preferably a piperidine ring. The substituent of the "mono-substituted amino group" of the "mono- or di-substituted amino group" is preferably cyclohexane or cycloheptane ring.

In the present specification,

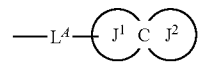

is preferably, $-(L^{B1})_{n1}-J^B$ (in the group, all symbols are as defined above).

In the present specification, $J^B$ is preferably, for example,

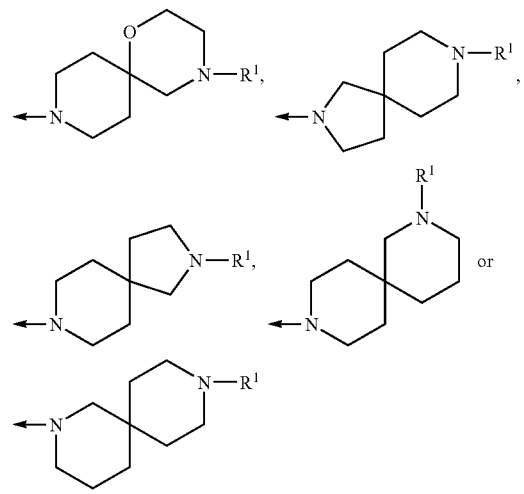

(in the group, the arrow is bonded to $L^{1B}$, and $R^1$ is as defined above).

In the present specification, a compound of formula (I) including a combination of preferable groups listed above is preferable.

In the present specification, the preferred compound includes compounds represented by formula (I-1):

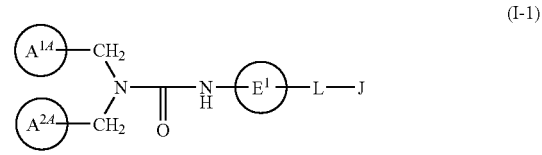

(I-1)

wherein all symbols are as defined above, formula (I-2):

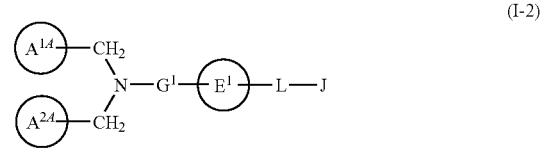

(I-2)

wherein all symbols are as defined above, formula (I-3):

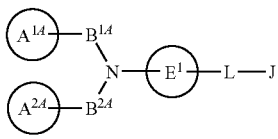
(I-3)

wherein all symbols are as defined above, and
formula (I-4):

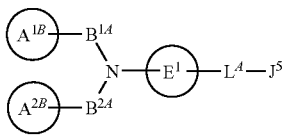
(I-4)

wherein all symbols are as defined above,
a salt thereof, or an N-oxide thereof, or a solvate thereof, or a prodrug thereof.

In the present specification, more preferred compound includes compounds represented by formula (I-5):

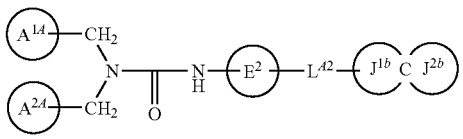
(I-5)

(wherein ring $E^2$ represents a monocyclic carbocyclic ring which may have a substituent(s), and other symbols are as defined above), formula (I-6):

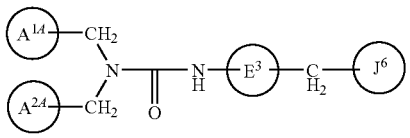
(I-6)

(wherein ring $E^3$ represents a divalent monocyclic heterocyclic ring which may have a substituent(s), ring $J^6$ represents a monocyclic or condensed heterocyclic ring which may have a substituent(s), and other symbols are as defined above), and formula (I-7):

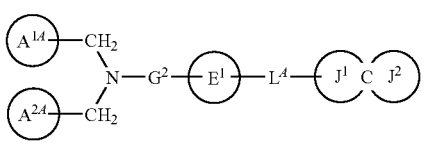
(I-7)

(wherein $G^2$ represents a bond or —CH$_2$—, and other symbols are as defined above), a salt thereof, or an N-oxide thereof, or a solvate thereof, or a prodrug thereof.

In the present invention, more preferred compounds are compounds represented by formula (I-2-a):

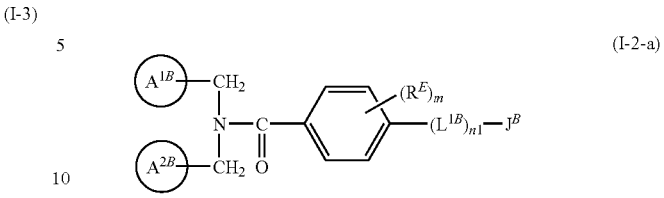
(I-2-a)

(wherein all symbols are as defined above),
formula (I-2-b)

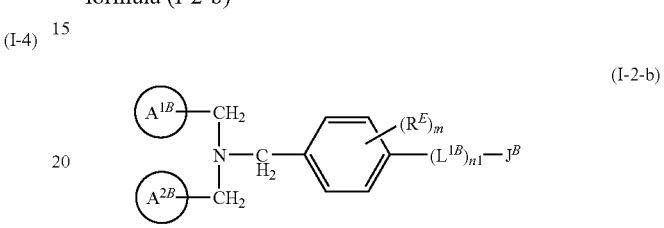
(I-2-b)

(wherein all symbols are as defined above),
formula (I-2-c):

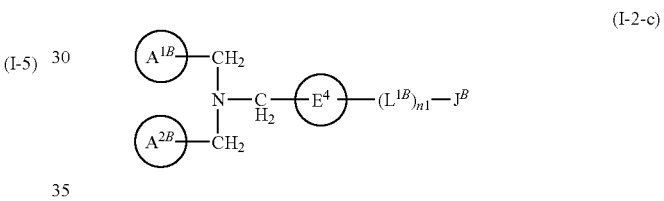
(I-2-c)

(wherein all symbols are as defined above) and
formula (I-4-a):

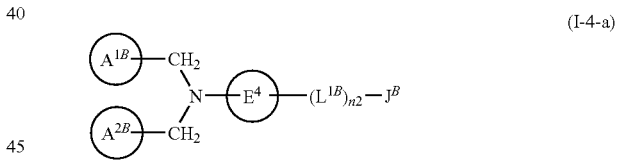
(I-4-a)

(wherein all symbols are as defined above),
a salt thereof, or an N-oxide thereof, or a solvate thereof, or a prodrug thereof.

In the present specification, the "monocyclic carbocyclic ring which may have a substituent(s)" represented by ring $E^2$ has the same meaning as those wherein the "3- to 8-membered monocyclic cyclic ring" is a "C3-8 monocyclic carbocyclic ring" among divalent groups which can be obtained by eliminating optional two hydrogen atoms from the "3- to 8-membered monocyclic cyclic ring" in the "divalent 3- to 8-membered monocyclic cyclic group which may have a substituent(s)". The "C3-8 monocyclic carbocyclic ring" here is preferably benzene or cyclohexane.

In the present specification, the "monocyclic carbocyclic ring which may have a substituent(s)" represented by ring $E^3$ has the same meaning as those wherein the "3- to 8-membered monocyclic cyclic ring" is a "3- to 8-membered monocyclic heterocyclic ring" among divalent groups which can be obtained by eliminating optional two hydrogen atoms from the "3- to 8-membered monocyclic cyclic ring" in the "divalent 3- to 8-membered monocyclic cyclic group which may have a substituent(s)". The "3- to 8-membered monocyclic heterocyclic ring" here is preferably piperidine.

In the present specification, the "substituent" of ring $E^2$ and ring $E^3$ is not specifically limited. Examples of the "substituent" include those exemplified as for T, and these optional substituents may be substituted on the substitutable position and the number of substituents may be from 1 to 6, and preferably from 1 to 3. The "substituent" of ring $E^2$ and ring $E^3$ is preferably, for example, absent, a halogen atom, or an aliphatic hydrocarbon group.

In the present specification, ring $E^2$ is preferably, for example, a cyclopentane which may have a substituent(s), a cyclohexane which may have a substituent(s), or a benzene ring which may have a substituent(s). The "substituent" here is preferably, for example, an aliphatic hydrocarbon group or a halogen atom.

In the present specification, ring $E^3$ is preferably, for example, pyrrolidine, piperidine, pyrrolidine substituted by a C1-4 alkyl group, or a piperidine ring substituted by a C1-4 alkyl group.

In the present specification, the "monocyclic or condensed heterocyclic ring" in the "monocyclic or condensed heterocyclic ring which may have a substituent" represented by ring $J^6$ has the same meaning as the "monocyclic or condensed heterocyclic ring". The "substituent" of ring $J^6$ is not specifically limited. Examples of the "substituent" include those exemplified as for T, and these optional substituents may be substituted on the substitutable position and the number of substituents may be from 1 to 8, and preferably from 1 to 5.

The substituent of ring $J^{2b}$ is preferably $R^1$.

$R^1$ is preferably, an aliphatic hydrocarbon group which may have a substituent(s), an aliphatic hydrocarbon group substituted by a cyclic group which may have a substituent(s), or a cyclic group which may have a substituent(s). The "aliphatic hydrocarbon group" of the "an aliphatic hydrocarbon group which may have a substituent(s)" and the "aliphatic hydrocarbon group substituted by a cyclic group which may have a substituent(s)" represented by $R^1$ is preferably, a C1-8 alkyl group, more preferably, for example, sec-butyl, tert-butyl, or pentyl. The "cyclic group" of the "cyclic group which may have a substituent(s)" represented by $R^1$ is preferably, a C3-15 monocyclic or condensed unsaturated carbocyclic ring, or a partially or completely saturated carbocyclic ring, more preferably a C3-8 monocyclic saturated carbocyclic ring, and particularly preferably a cyclopropane, cyclobutane, cyclopentane, cyclohexane, or cycloheptane ring. The "substituent" of the "aliphatic hydrocarbon group which may have a substituent(s)" is preferably a cyclopentane, cyclohexane, thiophene, or a benzene ring. The "cyclic group" of the "aliphatic hydrocarbon group substituted by a cyclic group which may have a substituent(s)" is preferably a thiophene ring.

Preferred compound of the present invention include compounds described in Examples, a salt thereof, or an N-oxide thereof, or a solvate thereof, or a prodrug thereof.

[Method for Producing Compound of the Present Invention]

The compound of the present invention represented by formula (I) can be prepared by appropriately improving a known method, for example, methods shown below, methods described in Examples, and a method described in Comprehensive Organic Transformations: A Guide to Functional Group Preparations, Second edition (written by Richard C. Larch, John Wiley & Sons Inc, 1999) and using improved methods in combination. In the following production methods, starting compounds may be used in the form of a salt. As the salt, those described as a salt of the above described formula (I) are used.

A compound wherein G represents —CO— among the compounds of the present invention represented by formula (I), namely, a compound represented by formula (I-A):

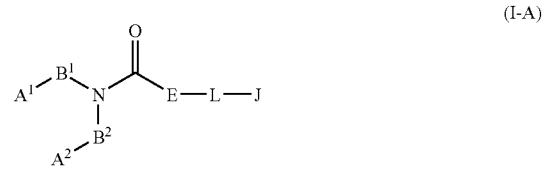

(wherein all symbols are as defined above) can be prepared by subjecting a compound represented by formula (2):

(wherein all symbols are as defined above) and a compound represented by formula (3):

(wherein W represents a hydroxyl group or a chlorine atom, and other symbols are as defined above) to the amidation reaction, and optionally subjecting to the deprotection reaction of the protective group and/or the cleavage reaction from the resin.

This amidation reaction is known and examples thereof include:
(1) a method using an acyl halide,
(2) a method using a mixed acid anhydride, and
(3) a method using a condensing agent.

These methods are described in detail below.

(1) The method using an acyl halide is carried out, for example, by reacting carboxylic acid with an acid halogenating agent (oxalyl chloride, thionyl chloride, etc.) in an organic solvent (chloroform, dichloromethane, diethylether, tetrahydrofuran, etc.) or in the absence of the solvent at −20° C. to reflux temperature. Then the obtained acyl halide derivative may be with amine in the presence of a base (pyridine, triethylamine, N,N-dimethylaniline, 4-dimethylaminopyridine, diisopropylethylamine, etc.) in an organic solvent (chloroform, dichloromethane, diethylether, tetrahydrofuran, etc.) at 0 to 40° C. Alternatively, the obtained acyl halide can be reacted with amine in an organic solvent (dioxane, tetrahydrofuran, etc.) at 0 to 40° C. using an aqueous alkali solution (sodium bicarbonate water or sodium hydroxide solution, etc.).

(2) The method using a mixed acid anhydride is carried out, for example, by reacting carboxylic acid with an acyl halide (pivaloyl chloride, tosyl chloride, mesyl chloride, etc.) or an acid derivative (ethyl chloroformate, butyl chloroformate, etc.) in the presence of a base (pyridine, triethylamine, N,N-dimethylaniline, 4-dimethylaminopyridine, diisopropylethylamine, etc.) in an organic solvent (chloroform, dichloromethane, diethylether, tetrahydrofuran, etc.) or in the absence of the solvent at 0 to 40° C., and reacting the resulting mixed acid anhydride with amine in an organic solvent (chloroform, dichloromethane, diethylether, tetrahydrofuran, etc.) at 0 to 40° C.

(3) The method using a condensing agent is carried out, for example, by reacting carboxylic acid with amine in an organic solvent (chloroform, dichloromethane, dimethyl formamide, diethylether, tetrahydrofuran, etc.) or in the absence of the solvent at 0 to 40° C. in the presence or absence of a base (pyridine, triethylamine, diisopropylethylamine, N,N-dimethylaniline, N-methylmorpholine, 4-dimethylaminopyridine, etc.), using a condensing agent (1,3-dicyclohexylcarbodiimide (DCC), 1-ethyl-3-[3-(dimethylamino)propyl] carbodiimide (EDC), 1,1'-carbonyldiimidazole (CDI), O-(7-azabenzotriazol-1-yl)N,N,N',N'-tetramethyluronium hexafluorophosphate (HATU), 2-chloro-1-methylpyridiniumiodine, 1-propylphosphonic acid cyclic anhydride (1-propanephosphonic acid cyclic anhydride, PPA), etc.) and using, or not using, 1-hydroxybenztriazole (HOBt) or 1-hydroxy-7-azabenzotriazole (HOAt).

The reactions described in (1), (2) and (3) are preferably carried out under an inert gas (argon, nitrogen, etc.) atmosphere on anhydrous condition.

The deprotection reaction of a protective group can be carried out by a known method, for example, a method described in Protective Groups in Organic Synthesis (written by T. W. Greene, John Wiley & Sons Inc, 1999).

If the compound has a moiety to bind to a resin in the molecule and the resin is a polystyrene resin, the compound of the present invention can be cleaved from the resin by the following method. The reaction for cleavage from the resin is known and can be carried out, for example, by reacting in an organic solvent (dichloromethane, 1,2-dichloroethane, toluene, etc.) at 0 to 100° C. using an acid (acetic acid, trifluoroacetic acid, hydrochloric acid, etc.).

If necessary, the procedure of converting into the objective salt may be carried out by a known method after this reaction.

A compound wherein G represents —SO$_2$— among the compounds of the present invention represented by formula (I), namely, a compound represented by formula (I-B):

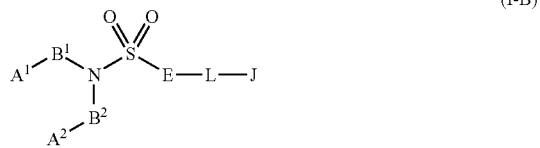

(I-B)

(wherein all symbols are as defined above) can be prepared by subjecting a compound represented by formula (2) and a compound represented by formula (4):

(4)

(wherein X represents a halogen atom, and other symbols are as defined above) to the sulfonamidation reaction, and optionally subjecting to the deprotection reaction of the protective group and/or the cleavage reaction from the resin.

The sulfonamidation reaction is known and can be carried out by the following method. For example, a sulfonyl halide can be synthesized by reacting a sulfonic acid with an acyl halide (oxalyl chloride, thionyl chloride, phosphorous pentachloride, phosphorus trichloride or phosphorus oxychloride, or a mixture thereof, etc.) in an organic solvent (chloroform, dichloromethane, dichloroethane, diethylether, tetrahydrofuran, methyl t-butyl ether, etc.) or in the absence of the solvent at −20° C. to reflux temperature in the presence or absence of dimethyl formamide, or reacting a thiol with a chlorine gas in an aqueous acid solution (for example, hydrochloric acid, sulfuric acid, nitric acid, acetic acid, etc.) at 0° C. to reflux temperature. The sulfonyl halide thus synthesized can be reacted with amine in the presence of a base (diisopropylethylamine, pyridine, triethylamine, N,N-dimethylaniline, 4-dimethylaminopyridine, etc.) in an organic solvent (chloroform, dichloromethane, dichloroethane, diethylether, tetrahydrofuran, etc.) at 0 to 40° C. The deprotection reaction of a protective group or the cleavage reaction from the resin can be carried out by the same method as described above.

A compound wherein G represents -(a carbon atom substituted by an oxo group)-NH— among the compound of the present invention represented by formula (I), namely, a compound represented by formula (I-N):

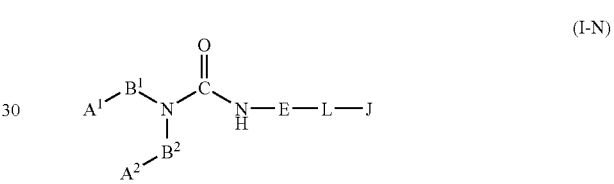

(I-N)

(wherein all symbols are as defined above) can be prepared by subjecting a compound represented by general formula (2), a phosgene equivalent (phosgene, diphosgene, triphosgene, carbonyldiimidazole, etc.) and a compound represented by formula (28):

H$_2$N-E-L-J (28)

(wherein all symbols are as defined above) to the urea reaction, and optionally subjecting to the deprotection reaction of the protective group and/or the cleavage reaction from the resin.

This urea reaction is known and is conducted, for example, by reacting a compound represented by formula (2) with a phosgene derivative (phosgene, diphosgene, triphosgene, carbonyldiimidazole, etc.) at −78° C. to 40° C. in an organic solvent (dichloromethane, chloroform, diethylether, tetrahydrofuran, etc.) or in the absence of the solvent in the presence of a base (pyridine, triethylamine, N,N-diisopropylethylamine, 4-dimethylaminopyridine, N-methylmorpholine, etc.). Furthermore, the reaction is conducted by reacting the resulting compound with a compound represented by formula (28) at −78° C. to 40° C. in an organic solvent (dichloromethane, chloroform, diethylether, tetrahydrofuran, etc.) or in the absence of the solvent in the presence of a base (pyridine, triethylamine, N,N-diisopropylethylamine, 4-dimethylaminopyridine, N-methylmorpholine, etc.).

This reaction is preferably performed in an inert gas (argon, nitrogen, etc.) atmosphere under anhydrous conditions.

The deprotection reaction of a protective group or the cleavage reaction from the resin can be carried out by the same method as described above.

If necessary, this reaction may be followed by an operation of converting into the objective salt by using a known method.

A compound wherein L represents an amide bond among the compounds of the present invention represented by formula (I), namely, a compound represented by formula (I-C-1):

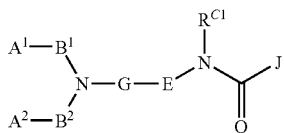

(I-C-1)

(wherein $R^{C1}$ represents a hydrogen atom, or a substituent or a hydrogen atom in a "divalent nitrogen atom which may have a substituent(s)" defined in L. and other symbols are as defined above) or a compound represented by formula (I-C-2):

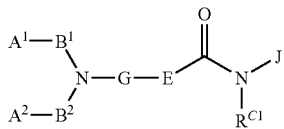

(I-C-2)

(wherein all symbols are as defined above) can be prepared by subjecting a compound represented by formula (5):

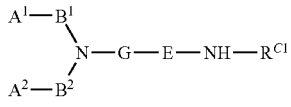

(5)

(wherein all symbols are as defined above) and a compound represented by formula (6):

(6)

(wherein all symbols are as defined above) to the amidation reaction, and optionally subjecting to the deprotection reaction of the protective group and/or the cleavage reaction from the resin, or subjecting a compound represented by formula (7):

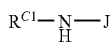

(7)

(wherein all symbols are as defined above) and a compound represented by formula (8):

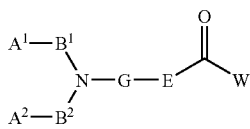

(8)

(wherein all symbols are as defined above) to the amidation reaction, and optionally subjecting to the deprotection reaction of the protective group and/or the cleavage reaction from the resin.

The amidation reaction, the deprotection reaction of a protective group, or the cleavage reaction from the resin can be carried out by the same method as described above.

A compound wherein L represents a sulfonamide bond among the compounds of the present invention represented by formula (I), namely, a compound represented by formula (I-D-1):

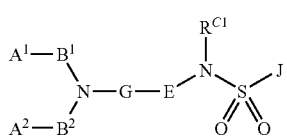

(I-D-1)

(wherein all symbols are as defined above) or a compound represented by formula (I-D-2):

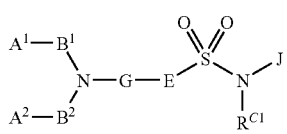

(I-D-2)

(wherein all symbols are as defined above) can be prepared by subjecting a compound represented by formula (5) and a compound represented by formula (9):

(9)

(wherein all symbols are as defined above) to the sulfonamidation reaction, and optionally subjecting to the deprotection reaction of the protective group and/or the cleavage reaction from the resin, or subjecting a compound represented by formula (7) and a compound represented by formula (10):

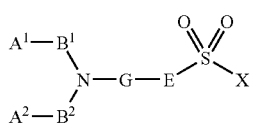

(10)

(wherein all symbols are as defined above) to the sulfonamidation reaction, and optionally subjecting to the deprotection reaction of the protective group and/or the cleavage reaction from the resin.

The sulfonamidation reaction, the deprotection reaction of a protective group, or the cleavage reaction from the resin can be carried out by the same method as described above.

A compound wherein L represents an optionally substituted —CH(—$R^{E1}$)—NH— or —NH—CH(—$R^{E1}$)— (in the group, $R^{E1}$ has the same meaning as the substituent of "a divalent aliphatic hydrocarbon group having 1 to 4 carbon atom(s) which may have a substituent(s)" in a hydrogen atom or L among the compounds of the present invention represented by formula (I), namely, a compound represented by formula (I-E-1):

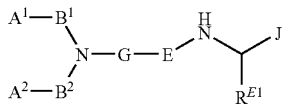
(I-E-1)

(wherein all symbols are as defined above) or a compound represented by formula (I-E-2):

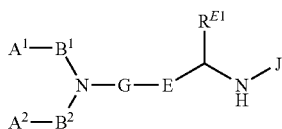
(I-E-2)

(wherein all symbols are as defined above) can be prepared by subjecting a compound represented by formula (11):

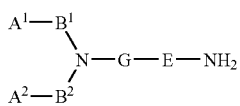
(11)

(wherein all symbols are as defined above) and a compound represented by formula (12):

(12)

(wherein all symbols are as defined above) to the reductive amination reaction, or optionally subjecting to the deprotection reaction of the protective group and/or the cleavage reaction from the resin, or subjecting a compound represented by formula (13):

 (13)

(wherein all symbols are as defined above) and a compound represented by formula (14):

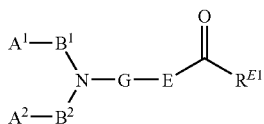
(14)

(wherein all symbols are as defined above) to the reductive amination reaction, and optionally subjecting to the deprotection reaction of the protective group and/or the cleavage reaction from the resin.

This reductive amination reaction is known and is carried out, for example, in an organic solvent (dichloroethane, dichloromethane, dimethyl formamide, acetic acid, a mixture thereof, etc.) at 0 to 40° C. in the presence of a reducing agent (sodium triacetoxyborohydride, sodium cyanoborohydride, sodium borohydride, etc.). The deprotection reaction of a protective group or the cleavage reaction from the resin can be carried out by the same method as described above.

A compound wherein a basic group in a J group is a mono-substituted amino group among the compounds of the present invention represented by formula (I), namely, a compound represented by formula (I-F):

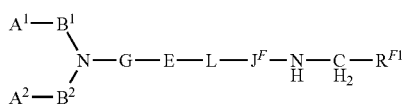
(I-F)

(wherein $J^F$ represents a divalent aliphatic hydrocarbon group which may have a substituent(s), a divalent cyclic group which may have a substituent(s), a divalent aliphatic hydrocarbon group substituted with a cyclic group which may have a substituent(s), a divalent cyclic group substituted with an aliphatic hydrocarbon group which may have a substituent(s), a divalent spirocyclic group which may have a substituent(s), or a divalent bridged cyclic group which may have a substituent(s), $R^{F1}$ represents a substituent in a substituent bonded to an amino group via $CH_2$ among a "mono-substituted amino group" defined in J, and other symbols are as defined above) can be prepared, for example, by subjecting the compound prepared by the above method, namely a compound represented by formula (I-F-1):

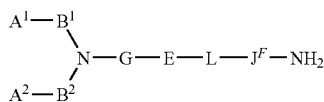
(I-F-1)

(wherein all symbols are as defined above) and a compound represented by formula (15):

$R^{F1}$—CHO (15)

(wherein all symbols are as defined above) to the reductive amination reaction, and optionally subjecting to the deprotection reaction of the protective group and/or the cleavage reaction from the resin.

The reductive amination reaction, the deprotection reaction of a protective group, or the cleavage reaction from the resin can be carried out by the same method as described above.

A compound wherein a basic group in a J group is a di-substituted amino group among the compounds of the present invention represented by formula (I), namely, a compound represented by formula (I-G):

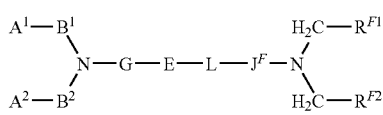
(I-G)

(wherein $R^{F2}$ represents a substituent in a substituent bonded to an amino group via $CH_2$ among substituents in a "di-substituted amino group" defined in J, and other symbols are as defined above) can be prepared by the compound prepared by the above method, namely, a compound represented by formula (I-F) and a compound represented by formula (16):

$$R^{F2}—CHO \qquad (16)$$

(wherein all symbols are as defined above) to the reductive amination reaction, and optionally subjecting to the deprotection reaction of the protective group and/or the cleavage reaction from the resin.

The reductive amination reaction, the deprotection reaction of a protective group, or the cleavage reaction from the resin can be carried out by the same method as described above.

A compound wherein $R^{F1}$ and $R^{F2}$ represent the same substituent among the compounds of the present invention represented by formula (I-G) can be prepared by subjecting a compound represented by formula (I-F-1) and two or more equivalents of a compound represented by formula (15) or formula (16) to the reductive amination reaction, and optionally subjecting to the deprotection reaction of the protective group and/or the cleavage reaction from the resin.

The reductive amination reaction, the deprotection reaction of the protective group, or the cleavage reaction from the resin can be conducted by the same method as described above.

A compound wherein $A^1$ and $A^2$ represent an imidazol-2-yl group among the compound of the present invention represented by formula (I), namely, a compound represented by formula (I-H):

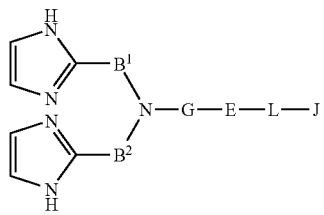

(I-H)

(wherein all symbols are as defined above) can be prepared by subjecting a compound represented by formula (17):

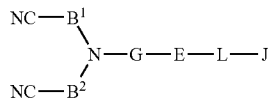

(17)

(wherein all symbols are as defined above) and [2,2-bis(methyloxy)ethyl]amine or [2,2-bis(ethyloxy)ethyl]amine to the cyclization reaction, and optionally subjecting to the deprotection reaction of the protective group and/or the cleavage reaction from the resin.

This cyclization reaction is known and can be performed, for example, by improving the method described in Synthesis, 2001, (10), 1546-1550. For example, it is performed by reacting a nitrile compound in an organic solvent (methanol, ethanol, etc.) in the presence of a base (sodium methoxide, sodium ethoxide, etc.) at 0 to 40° C. and reacting the solution in the presence of acetal and a dehydrating agent (glacial acetic acid) at 40 to 150° C. Also, a deprotection reaction of a protective group or a cleavage reaction from a resin can be performed by the same method as described above.

A compound wherein a divalent group adjacent to a nitrogen atom is a divalent group in $B^1$ among the compounds of the present invention represented by formula (I), namely, a compound represented by formula (I-K):

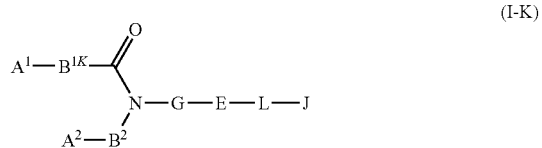

(I-K)

(wherein $B^{1K}$ represents a bond or a spacer having a main chain of 1 to 3 atom(s), and other symbols are as defined above) can be prepared by subjecting a compound represented by formula (20):

$$A^2\text{-}B^2\text{—NH-G-E-L-J} \qquad (20)$$

(wherein all symbols are as defined above) and a compound represented by formula (21):

(21)

(wherein all symbols are as defined above) to the amidation reaction, and optionally subjecting to the deprotection reaction of the protective group and/or the cleavage reaction from the resin.

The amidation reaction, the deprotection reaction of a protective group, or the cleavage reaction from the resin can be carried out by the same method as described above.

A compound wherein a divalent group adjacent to a nitrogen atom is —SO₂— in $B^1$ among the compounds of the present invention of formula (I), namely, a compound represented by formula (I-L):

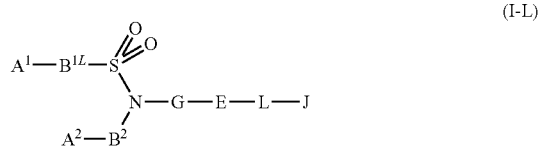

(I-L)

(wherein $B^{1L}$ represents a bond or a spacer having a main chain of 1 to 3 atom(s), and other symbols are as defined above) can be prepared by subjecting a compound represented by formula (20) and a compound represented by formula (22):

(22)

(wherein all symbols are as defined above) to the sulfonamidation reaction, and optionally subjecting to the deprotection reaction of the protective group and/or the cleavage reaction from the resin.

The sulfonamidation reaction, the deprotection reaction of a protective group, or the cleavage reaction from the resin can be carried out by the same method as described above.

A compound wherein G represents one carbon atom which may have a substituent(s) and a divalent group adjacent to a nitrogen atom is —CH$_2$— in B$^1$ and B$^2$ among the compounds represented by formula (I), namely, a compound represented by formula (I-M):

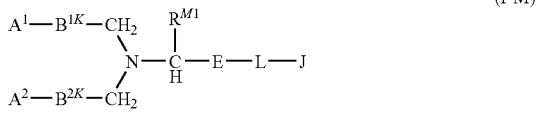
(I-M)

(wherein B$^{1K}$ and B$^{2K}$ each independently represents a bond or a spacer having a main chain of 1 to 3 atom(s), R$^{M1}$ represents a hydrogen atom or a substituent in a "carbon atom which may have a substituent(s)" defined in G, and other symbols are as defined above) can be prepared by subjecting a compound represented by formula (23):

(23)

(wherein all symbols are as defined above) and a compound represented by formula (24):

(24)

(wherein all symbols are as defined above) to the reductive amination reaction, and optionally subjecting to the deprotection reaction of the protective group and/or the cleavage reaction from the resin.

The reductive amination reaction, the deprotection reaction of a protective group, or the cleavage reaction from the resin can be carried out by the same method as described above.

A compound represented by formula (I-M) can be prepared by subjecting a compound represented by formula (25):

(25)

(wherein all symbols are as defined above) and a compound represented by formula (26):

A$^1$-B$^{1K}$—CHO      (26)

(wherein all symbols are as defined above) to the reductive amination reaction, subjecting the resulting compound and a compound represented by formula (27):

A$^2$-B$^{2K}$—CHO      (27)

(wherein all symbols are as defined above) to the reductive amination reaction, and optionally subjecting to the deprotection reaction of the protective group and/or the cleavage reaction from the resin.

The reductive amination reaction, the deprotection reaction of a protective group, or the cleavage reaction from the resin can be carried out by the same method as described above.

A compound wherein an A$^1$-B$^{1K}$—CH$_2$ group and an A$^2$-B$^{2K}$—CH$_2$ group represent the same substituent among the compounds of the present invention represented by formula (I-M) can be prepared by subjecting a compound represented by formula (25) and two or more equivalents of a compound represented by formula (26) or compound represented by formula (27) to the reductive amination reaction, and optionally subjecting to the deprotection reaction of the protective group and/or the cleavage reaction from the resin.

The reductive amination reaction, the deprotection reaction of a protective group, or the cleavage reaction from the resin can be carried out by the same method as described above.

A compound wherein G is bond among the compounds represented by formula (I), namely, a compound represented by formula (I-P):

(I-P)

(wherein all symbols are as defined above) can be prepared by subjecting a compound represented by formula (26) and a compound represented by formula (28) to the reductive amination reaction, subjecting a resulting compound and a compound represented by formula (27) to the reductive amination reaction, and optionally subjecting to the deprotection reaction of the protective group and/or the cleavage reaction from the resin.

The reductive amination reaction, the deprotection reaction of a protective group, or the cleavage reaction from the resin can be carried out by the same method as described above.

A compound wherein an A$^1$-B$^{1K}$—CH$_2$ group and an A$^2$-B$^{2K}$—CH$_2$ group represent the same substituent among the compounds of the present invention represented by formula (I-P) can be prepared by subjecting a compound represented by formula (28) and two or more equivalents of a compound represented by formula (26) or a compound represented by formula (27) to the reductive amination reaction, and optionally subjecting to the deprotection reaction of the protective group and/or the cleavage reaction from the resin.

The compounds represented by formulas (2) to (28) used as other starting materials or reagents can be easily prepared by using per se known methods or known methods, for example, methods described in Comprehensive Organic Transformations: A Guide to Functional Group Preparations, Second edition (written by Richard C. Larch, John Wiley & Sons Inc, 1999) in combination.

In the respective reactions in the present specification, as is apparent to those skilled in the art, the reaction with heating can be carried out using a water bath, an oil bath, a sand bath, or microwave.

In the respective reactions in the present specification, a solid phase supported reagent obtained by supporting on a polymer (for example, polystyrene, polyacrylamide, polypropylene, polyethylene glycol, etc.) may be used.

In the respective reactions in the present specification, the reaction product can be purified by conventional purification means, for example, distillation under normal pressure or reduced pressure, high performance liquid chromatography using a silica gel or magnesium silicate, thin layer chromatography, ion-exchange resin, scavenger resin or chromatography or washing, or recrystallization. The purification may be carried out for every reaction, or may be carried out after the completion of some reactions.

In the reaction using a polystyrene resin in the present specification, the reaction product can be purified by conventional purification methods, for example, washing plural times with a solvent (N,N-dimethyl formamide, dichloromethane, methanol, tetrahydrofuran, toluene, acetic acid/toluene, etc.).

[Toxicity]

The compound of the present invention has very low toxicity and is sufficiently safe for use as pharmaceuticals.

[Application to Pharmaceuticals]

The compound of the present invention has CXCR4 antagonistic activity in an animal including human, particularly human, and is therefore effective, for example, for a preventive and/or therapeutic agent for inflammatory and immune diseases, allergic diseases, infections, particularly HIV infection, and diseases associated with the infection, psychoneurotic diseases, cerebral diseases, cardiovascular diseases, metabolic diseases, and cancerous diseases. Also, the compound is useful as an agent for regeneration therapy for the purpose of in vitro or in vivo amplification of stem cells for gene therapy as well as peripheral blood stem cells mobilization and tissue repair. The compound is particularly useful as an agent for transplantation medical treatment used in organ transplantation including bone marrow transplantation, peripheral blood stem cell transplantation and tissue repair among in the regeneration therapy. Furthermore, the compound is useful as an antiangiogenic agent which is effective for prevention and/or treatment of diseases associated with neoangiogenesis, such as retinopathy (diabetic retinopathy, aged macular degeneration, glaucoma, etc.) and cancer proliferation.

Examples of the inflammatory and immune disease include rheumatoid arthritis, arthritis, retinopathy, systemic erythematosus, gout, rejection of transplanted organ, graft-versus-host disease (GVHD), nephritis, psoriasis, rhinitis, conjunctivitis, multiple sclerosis, ulcerative colitis, Crohn's disease, shock associated with bacterial infection, pulmonary fibrosis, systemic inflammatory response syndrome (SIRS), acute lung injury, diabetes and the like.

Examples of the allergic disease include asthma, atopic dermatitis, rhinitis, conjunctivitis and the like.

Examples of infections include, for example, HIV infection, various infections caused by *streptococcus* (Group A β-hemolytic *streptococcus, Streptococcus pneumoniae*, etc.), *staphylococcus aureus* (MSSA, MRSA), *Staphylococcus epidermidis, enterococcus, Listeria, meningococcus, gonococcus, E. coli* bacteria (O157:H7, etc.), *klebsiella (Klebsiella pneumoniae), Proteus,* tussis convulsiva, *Pseudomonas aeruginosa, Serratia marcescens*, Shiorobactar, Ashinetobactar, Enterobactar, *mycoplasma, chlamydia,* and Crostorigeum, cholera, diphtheria, dysentery, scarlet fever, anthrax, trachoma, syphilis, tetanus, Hansen's disease, *legionella*, Reptospira, Lyme disease, tularaemia, Q fever, meningitis, encephalitis, rhinitis, sinusitis, pharyngitis, laryngitis, orbital cellulitis, thyroiditis, Lemierre syndrome, pneumonia, bronchitis, tuberculosis, infectious endocarditis, pericarditis, myocarditis, infectious aortitis, septicemia, cholecystitis, cholangitis, hepatitis, liver abscess, acute pancreatitis, splenic abscess, enteritis, iliopsoas abscess, pyelonephritis, cystitis, prostatitis, colpitis, Pelvic inflammatory disease, cellulitis, panniculitis, gas gangrene, furuncle, carbuncle, contagious impetigo, staphylococcal scalded skin syndrome, herpes zoster, varicella, measles, rubella, impetigo, scabies, infectious arthritis, osteomyelitis, fasciitis, myositis, and lymphadenitis.

Examples of the disease associated with infection, particularly HIV infection, include acquired immunodeficiency syndrome (AIDS), candidiasis, *Pneumocystis carinii* pneumonia, Cytomegalovirus retinitis, Kaposi's sarcoma, malignant lymphoma, AIDS encephalopathy, bacterial sepsis and the like.

Examples of the psychoneurotic disease and cerebral disease include dementia including Alzheimer's disease, Parkinson's disease, stroke, cerebral infarction, cerebral hemorrhage, epilepsy, schizophrenia, peripheral nerve disorder and the like.

Examples of the cardiovascular disease include arteriosclerosis, ischemia reperfusion, hypertension, myocardial infarction, stenocardia, heart failure, chronic arterial occlusive disease and the like.

Examples of the metabolic diseases include diabetes, osteoporosis, enlarged prostate, frequent micturition and the like.

Macular degeneration is a disease wherein progressive disorder arises in macula lutea that is present in the center of retina and controls visual acuity, and age-related one is referred to as age-related macular degeneration. Macular degeneration includes atrophy type (dry type) macular degeneration wherein macula lutea tissue causes atrophy and exudation type (wet type) macular degeneration wherein new blood vessel are formed in the chorioidea of the macula lutea site.

Examples of the cancerous disease include malignant tumor such as breast cancer or malignant lymphoma, cancer metastasis, myelosuppression or thrombocytopenia after radiation therapy/chemotherapy and the like.

The compound of the present invention may be administered as a concomitant drug by using in combination with other drugs for the purpose of:
1) complementation and/or enhancement of the preventive and/or therapeutic effects of the compound,
2) improvement of pharmacokinetics and absorption of the compound and reduction of the dosage, and/or
3) reduction of side effects of the compound.

Also, the compound of the present invention may be administered as a concomitant drug by using in combination with other drugs the purpose of (1) complementation and/or enhancement of preventive and/or therapeutic effects, (2) improvement of pharmacokinetics and absorption of the compound and reduction of the dosage, and/or (3) reduction of side effects.

The concomitant drug of the compound of the present invention and other drugs may be administered in the form of a compounding agent(s) comprising both these components, or may be in the form of separately. In case of separately administering a preparation, simultaneous administration and administration with time-lag are included. In case of administration with time-lag, other drugs may be administered after the compound of the present invention is administered, or the compound of the present invention may be administered after other drugs may be administered. The administration method may be the same or different.

The disease, on which the preventive and/or therapeutic effects are exerted by the concomitant drug, is not specifically limited, and may be any disease which complements and/or enhances the preventive and/or therapeutic effects of the compound of the present invention.

A mass ratio of the compound of the present invention drug to other drugs is not specifically limited.

A combination of any two or more kinds other drugs may be administered.

The other drugs, which complements and/or enhances the preventive and/or therapeutic effects of the compound of the present invention, includes not only those which have ever been found based on the above described mechanism, but also those which may be found in future.

Examples of the preventive and/or therapeutic agents for HIV infection and acquired immunodeficiency syndrome, which is used in combination of the compound of the present invention, include reverse transcriptase inhibitors, protease inhibitors, chemokine (for example, CCR2, CCR3, CCR4, CCR5, CXCR4, etc.) antagonists, CD4 antagonists, antibody against surface antigen of HIV (for example, HIV-1, HIV-2, etc.), vaccine of HIV (for example, HIV-1, HIV-2, etc.), short-interfering RNAs targeting a HIV-related factor and the like.

Examples of the reverse transcriptase inhibitors include (1) nucleoside reverse transcriptase inhibitors such as zidovudine (trade name: Retrovir), didanosine (trade name: Videx), zalcitabine (trade name: Hivid), stavudine (trade name: Zerit), lamivudine (trade name: Epivir), abacavir (trade name: Ziagen), didanosine (trade name: videx), adefovir, dipivoxil, emtricitabine (trade name: coviracil), tenofovir (trade name: viread), Combivir, Trizivir, truvada, epzicom, and the like, (2) non-nucleoside reverse transcriptase inhibitors such as nevirapine (trade name: viramune), delavirdine (trade name: Rescriptor), efavirenz (trade name: Sustiva, Stocrin), capravirine (AG1549), and the like.

Examples of the protease inhibitors include indinavir (trade name: Kurikisiban), ritonavir (trade name: norvir), nelfinavir (trade name: Viracept), saquinavir (trade name: Invirase, Fortovase), amprenavir (trade name: agenerase), lopinavir (trade name: Kaletra), atazanavir (trade name: Reyataz), fosamprenavir (trade name: lexiva), tipranavir and the like.

Examples of the chemokine antagonists include endogenous ligands of a chemokine receptor, or derivatives and nonpeptidic low molecular compounds thereof, an antibody against a chemokine receptor and the like.

Examples of the endogenous ligands of the chemokine receptor include MIP-1α, MIP-1β, RANTES, SDF-1α, SDF-1β, MCP-1, MCP-2, MCP-4, eotaxin, MDC and the like.

Examples of the derivative of the endogenous ligands include AOP-RANTES, Met-SDF-1α, Met-SDF-1β and the like.

Examples of the antibody of the chemokine receptor include Pro-140 and the like.

Examples of the CCR2 antagonists include compounds described in WO99/07351, WO99/40913, WO0/46195, WO0/46196, WO0/46197, WO0/46198, WO0/46199, WO0/69432, WO0/69815, and Bioorg. Med. Chem. Lett., 10, 1803 (2000), and the like.

Examples of the CCR3 antagonists include compounds described in DE19837386, WO99/55324, WO99/55330, WO0/04003, WO0/27800, WO0/27835, WO0/27843, WO0/29377, WO0/31032, WO0/31033, WO0/34278, WO0/35449, WO0/35451, WO0/35452, WO0/35453, WO0/35454, WO0/35876, WO0/35877, WO0/41685, WO0/51607, WO0/51608, WO0/51609, WO00/51610, WO0/53172, WO0/53600, WO0/58305, WO0/59497, WO0/59498, WO0/59502, WO0/59503, WO0/62814, WO0/73327, and WO01/09088, and the like.

Examples of the CCR4 antagonists include compounds described in WO02/030357 and WO02/030358, and the like.

Examples of the CCR5 antagonists include compounds described in WO99/17773, WO99/32100, WO0/06085, WO00/06146, WO00/10965, WO00/06153, WO00/21916, WO0/37455, EP1013276, WO0/38680, WO00/39125, WO0/40239, WO0/42045, WO00/53175, WO0/42852, WO00/66551, WO0/66558, WO0/66559, WO00/66141, WO0/68203, JP2000-309598, WO0/51607, WO0/51608, WO0/51609, WO00/51610, WO0/56729, WO0/59497, WO0/59498, WO0/59502, WO0/59503, WO0/76933, WO98/25605, WO99/04794, WO99/38514 and Bioorg. Med. Chem. Lett., 10, 1803 (2000), TAK-779, SCH-351125 (SCH-C), SCH-417690 (SCH-D), UK-427857, GW 873140A (ONO-4128), TAK-220, TAK-652, and the like.

Examples of the CXCR4 antagonists include AMD-3100, AMD-070, T-22, KRH-1120, KRH-1636, KRH-2731, CS-3955, and compounds described in WO0/66112, WO2004/024697, WO2004/052862, EP01493438, JP2002-371042, JP2004-196769, US2004/0132642, US2005/0192272, US2005/0215543, US2005/0215544, US2005/0215545, WO99/36091, WO02/094261, WO02/096397, WO03/029218, WO03079020, WO2004/020462, WO2004/024178, WO2004/024697, WO2004/054603, WO2004/059285, WO2004/087068, WO2004/093817, WO2004/096838, WO2004/096839, WO2004/096840, WO2005/002522, WO2005/002551, WO2005/025565, WO2005/085209, WO2005/085219, WO2006/020415, WO2006/022454, WO2006/023400, WO2006/039252, and the like.

Examples of the fusion inhibitors include T-20 (pentafuside) T-1249, and the like.

Examples of the HIV integrase inhibitors include Equisetin, Temacrazine, PL-2500, V-165, NSC-618929, L-870810, L-708906 analog, S-1360, 1838 and the like.

The Short Interfering short-interfering RNAs targeting a HIV-related factor include those which target a gene of a HIV-related factor. Examples of the HIV-related factors include reverse transcriptase, protease, chemokine (CCR2, CCR3, CCR4, CCR5, CXCR4, etc.), CD4, HIV (HIV1, HIV2, etc.) and the like.

The conventional clinical dosage of typical reverse transcriptase inhibitors and protease inhibitors is, for example, as described below, but is not limited thereto in the present invention.

Zidovudine: 100 mg capsule, three times per day in a dosage of 200 mg; 300 mg tablet, twice per day in a dosage of 300 mg;

Didanosine: 25 to 200 mg tablet, twice per day in a dosage of 125 to 200 mg;

Zalcitabine: 0.375 mg to 0.75 mg tablet, three times per day in a dosage of 0.75 mg;

Stavudine: 15 to 40 mg capsule, twice per day in a dosage of 30 to 40 mg;

Lamivudine: 150 mg tablet, twice per day in a dosage of 150 mg;

Abacavir: 300 mg tablet, twice per day in a dosage of 300 mg;

Nevirapine: 200 mg tablet, once per day for 14 days in a dosage of 200 mg, followed by twice per day;

Delavirdine: 100 mg tablet, three times per day in a dosage of 400 mg;

Efavirenz: 50 to 200 mg capsule, once per day in a dosage of 600 mg;

Indinavir: 200 to 400 mg capsule, three times per day in a dosage of 800 mg;

Ritonavir: 100 mg capsule, twice per day in a dosage of 600 mg;

Nelfinavir: 250 mg tablet, three times per day in a dosage of 750 mg;

Saquinavir: 200 mg capsule, three times per day in a dosage of 1,200 mg;

Amprenavir: 50 to 150 mg tablet, twice per day in a dosage of 1,200 mg.

Examples of the other drugs for complementation and/or enhancement of the preventive and/or therapeutic effects of the compound of the present invention against asthma include antihistaminic agents, antiallergic agents (chemical mediator release inhibitors, histamine antagonists, thromboxane synthetase inhibitors, thromboxane antagonists, Th2 cytokine inhibitors), steroids, bronchodilator agents (xanthine derivatives, sympathomimetic agents, parasympathomimetic agents), vaccinotherapeutic agents, gold preparations, Chinese medicines, basic nonsteroidal anti-inflammatory drugs, 5-lipoxygenase inhibitors, 5-lipoxygenase activation protein antagonists, leukotriene synthesis inhibitors, prostaglandins, cannabinoid-2 receptor stimulants, antitussive drugs, expectorants, and the like.

Examples of the antihistaminic agents include diphenhydramine, diphenylpyraline hydrochloride, diphenylpyraline chlorotheophyllinate, clemastine fumarate, dimenhydrinate, dl-chlorpheniramine maleate, d-chlorpheniramine maleate, triprolidine hydrochloride, promethazine hydrochloride, alimemazine tartrate, isothipendyl hydrochloride, homochlorcyclizine hydrochloride, hydroxyzine, cyproheptadine hydrochloride, levocabastine hydrochloride, astemizole, bepotastine, desloratadine, TAK-427, ZCR-2060, NIP-530, mometasone furoate, mizolastine, BP-294, andolast, auranofin, acrivastine and the like.

Examples of the chemical mediator release inhibitors include disodium cromoglycate, tranilast, amlexanox, repirinast, ibudilast, pemirolast potassium, tazanolast, nedocromil, cromoglicate, israpafant and the like.

Examples of the histamine antagonists include ketotifen fumarate, azelastine hydrochloride, oxatomide, mequitazine, terfenadine, emedastine fumarate, epinastine hydrochloride, ebastine, cetirizine hydrochloride, olopatadine hydrochloride, loratadine, fexofenadine and the like.

Examples of the thromboxane synthetase inhibitors include ozagrel hydrochloride imitrodast sodium and the like.

Examples of the thromboxane antagonists include seratrodast, ramatroban, domitroban calcium hydrate, KT-2-962 and the like.

Examples of the Th2 cytokine inhibitors include suplatast tosilate and the like.

Examples of the steroids include, for example, external medicine such as clobetasol propionate, diflorasone diacetate, fluocinonide, mometasone furoate, betamethasone dipropionate, betamethasone butyrate propionate, betamethasone valerate, difluprednate, budesonide, diflucortolone valerate, amcinonide, halcinonide, dexamethasone, dexamethasone propionate, dexamethasone valerate, dexamethasone acetate, hydrocortisone acetate, hydrocortisone butyrate, hydrocortisone butyrate propionate, deprodone propionate, prednisolone valerate acetate, fluocinolone acetonide, beclometasone dipropionate, triamcinolone acetonide, flumetasone pivalate, alclometasone propionate, clobetasone butyrate, prednisolone, beclomethasone propionate, fludroxycortide, and the like.

Examples of the xanthine derivative include aminophylline, theophylline, doxophylline, cipamfylline, diprophylline, proxyphylline, and choline theophylline.

Examples of the sympathomimetic agents include epinephrine, ephedrine hydrochloride, dl-methylephedrine hydrochloride, methoxyphenamine hydrochloride, isoproterenol sulfate, isoproterenol hydrochloride, orciprenaline sulfate, chloroprenaline hydrochloride, trimetoquinol hydrochloride, salbutamol sulfate, terbutaline sulfate, hexoprenaline sulfate, tulobuterol hydrochloride, procaterol hydrochloride, fenoterol hydrobromate, formoterol fumarate, clenbuterol hydrochloride, mabuterol hydrochloride, salmeterol xinafoate, R,R-formoterol, tulobuterol, pirbuterol hydrochloride, ritodrine hydrochloride, bambuterol, dopexamine hydrochloride, meluadrine tartrate, AR-C68397, levosalbutamol, KUR-1246, KUL-7211, AR-C89855, S-1319 and the like.

Examples of the parasympathomimetic agents include ipratropium bromide, flutropium bromide, oxitropium bromide, cimetropium bromide, temiverine, tiotropium bromide, revatropate (UK-112166) and the like.

Examples of the vaccinotherapeutic agents include paspat, asthremedin, Broncasma Berna, CS-560 and the like.

Examples of the gold preparations include gold sodium thiomalate and the like.

Examples of the basic nonsteroidal anti-inflammatory drugs include tiaramide hydrochloride, tinoridine hydrochloride, epirizole, emorfazone and the like.

Examples of the 5-lipoxygenase inhibitors include zyleuton, docebenone, piriprost, SCH-40120, WY-50295, E-6700, ML-3000, TMK-688, ZD-2138, dalbufelone mesilate, R-68151, E-6080, DuP-654, SC-45662, CV-6504, NE-11740, CMI-977, NC-2000, E-3040, PD-136095, CMI-392, TZI-41078, Orf-20485, IDB-18024, BF-389, A-78773, TA-270, FLM-5011, CGS-23885, A-79175, ETH-615 and the like.

Examples of the 5-lipoxygenase activation protein antagonists include MK-591, MK-886 and the like.

Examples of the leukotriene synthesis inhibitors include auranofin, proglumetacin maleate, L-674636, A-81834, UPA-780, A-93178, MK-886, REV-5901A, SCH-40120, MK-591, Bay-x-1005, Bay-y-1015, DTI-0026, Amlexanox, E-6700 and the like.

Examples of the prostaglandins (hereinafter abbreviated to as PG) include PG receptor agonists, PG receptor antagonists and the like.

Examples of the PG receptor include PGE receptor (EP1, EP2, EP3, and EP4), PGD receptor (DP, CRTH2), PGF receptor (FP), PGI receptor (IP), TX receptor (TP) and the like.

Examples of the antitussive drugs include codeine phosphate, dihydrocodeine phosphate, oxymetebanol, dextromethorphan hydrobromate, pentoxyverine citrate, dimemorfan phosphate, oxeladin citrate, cloperastine, benproperine phosphate, clofedanol hydrochloride, fominoben hydrochloride, noscapine, tipepidine hibenzate, eprazinone hydrochloride, *plantago* herb extract and the like.

Examples of the expectorants include foeniculated ammonia spirit, sodium hydrogencarbonate, potassium iodide, bromhexine hydrochloride, cherry bark extract, carbocysteine, fudosteine, ambroxol hydrochloride, ambroxol hydrochloride sustained-release tablet, methylcysteine hydrochloride, acetylcysteine, L-ethylcysteine hydrochloride, tyloxapol and the like.

Examples of the other drugs for complementation and/or enhancement of the preventive and/or therapeutic effects against atopic dermatitis (urticaria, etc.) of the compound of the present invention include steroids, non-steroid anti-inflammatory drug (NSAID), immune inhibitor, prostaglandins, antiallergic agent, mediator release inhibitor, antihistaminic agent, forskolin preparation, phosphodiesterase inhibitor, cannabinoid-2 receptor stimulant and the like.

Examples of the other drugs for complementation and/or enhancement of the preventive and/or therapeutic effects against allergic diseases (allergic bronchopulmonary aspergillosis, allergic eoisinophilic gastroenteritis, etc.) of the compound of the present invention include antiasthmatic drug, inhaled steroid drug, inhaled β2 stimulant, methylxanthine-based stimulant, antiallergic agent, anti-inflammatory agent, anticholinergic agent, thromboxane antagonist, leukotriene antagonist, LTD4 antagonist, PAF antagonist, phosphodiesterase inhibitor, β2 agonist, steroid drug, mediator release inhibitor, eosinophile leukocytechemotaxis inhibitor, macrolide-based antibiotic, immune inhibitor, hyposensitization (allergen) injection and the like.

Examples of the antiasthmatic drug include theophylline, procaterol, ketotifen, azelastine and the like.

Examples of the inhaled steroid drug include beclomethasone, fluticasone, budesonide and the like.

Examples of the inhaled β2 stimulant include fenoterol, salbutamol, formoterol, salmeterol and the like.

Examples of the methylxanthine-based stimulant include theophylline and the like.

Examples of the antiallergic agent include ketotifen, terfenadine, azelastine, epinastine, suplatast, disodium cromoglycate and the like.

Examples of the anti-inflammatory agent include dichlofenac sodium, ibuprofen, indomethacin and the like.

Examples of the anticholinergic agent include ipratropium bromide, flutropium bromide, oxitropium bromide, tiotropium bromide and the like.

Examples of the thromboxane antagonist include ozagrel, seratrodast and the like.

Examples of the macrolide-based antibiotic include erythromycin, roxithromycin and the like.

Examples of the leukotriene antagonist include pranlukast, montelukast, zafirlukast, zyleuton and the like.

Examples of the immune inhibitor include cyclosporine, tacrolimus, FTY720, and the like.

Examples of the other drug for complementation and/or enhancement of the preventive and/or therapeutic effects against hepatitis of the compound of the present invention include liver hydrolysate preparation, polyenephosphatidylcholine, glycyrrhizin preparation, protoporphyrin sodium, ursodeoxycholic acid, steroids, anticholinergic agent, gastric antiacid, propagermanium, lipid peroxidase inhibitor, and mitochondrial benzodiazepine receptor antagonist.

Examples of the other drug for complementation and/or enhancement of the preventive and/or therapeutic effects against arthritis and rheumatoid arthritis of the compound of the present invention include metalloproteinase inhibitor, immune inhibitor, non-steroid anti-inflammatory drug (NSAID), steroid drug, prostaglandins, phosphodiesterase inhibitor, cannabinoid-2 receptor stimulant, disease modifying anti-rheumatic drug (slow-acting anti-rheumatic drug), anti-inflammatory enzyme preparation, cartilage protective agent, T cell inhibitor, TNFα inhibitor, prostaglandin synthetase inhibitor, IL-6 inhibitor, interferon γ agonist, IL-1 inhibitor and the like.

Examples of the other drug for complementation and/or enhancement of the preventive and/or therapeutic effects against psoriasis of the compound of the present invention include steroids, vitamin D derivative and the like.

Examples of the other drug for complementation and/or enhancement of the preventive and/or therapeutic effects against rhinitis of the compound of the present invention include antihistaminic agent, mediator release inhibitor, thromboxane synthetase inhibitor, thromboxane A₂ receptor antagonist, leukotriene receptor antagonist, steroids, a adrenalin receptor stimulant, xanthine derivative, anticholinergic agent, prostaglandins, nitrogen monoxide synthetase inhibitor, β2 adrenalin receptor stimulant, phosphodiesterase inhibitor, cannabinoid-2 receptor stimulant and the like.

Examples of the other drug for complementation and/or enhancement of the preventive and/or therapeutic effects against conjunctivitis of the compound of the present invention include leukotriene receptor antagonist, antihistaminic agent, mediator release inhibitor, non-steroid anti-inflammatory drug, prostaglandins, steroid drug, nitrogen monoxide synthetase inhibitor, cannabinoid-2 receptor stimulant and the like.

Examples of the other drug for complementation and/or enhancement of the preventive and/or therapeutic effects against multiple sclerosis of the compound of the present invention include immune inhibitor, cannabinoid-2 receptor stimulant and the like.

Examples of the other drug for complementation and/or enhancement of the preventive and/or therapeutic effects against ulcerative colitis of the compound of the present invention include mesalazine, salazosulfapyridine, digestive tract ulcer therapeutic substance, anticholinergic agent, steroid drug, 5-lipoxygenase inhibitor, antioxidant, LTB4 antagonist, local anesthetic, immune inhibitor, protection factor enhancer, MMP inhibitor, and mitochondrial benzodiazepine receptor antagonist.

Examples of the other drug for complementation and/or enhancement of the preventive and/or therapeutic effects against diabetic complication of the compound of the present invention include sulfonyl urea-based hypoglycemic agent, biguanide-based drug, α-glucosidase inhibitor, ultrashort-acting insulinotropic agent, insulin drug, PPAR agonist, insulin sensitive enhancer having no PPAR antagonism, β3 adrenalin receptor agonist, aldose reductase inhibitor, dipeptidyl peptidase IV inhibitor and the like.

Examples of the sulfonyl urea-based hypoglycemic agent include acetohexamide, glibenclamide, gliclazide, glyclopyramide, chlorpropamide, tolazamide, tolbutamide, Glimepiride and the like.

Examples of the biguanide-based drug include buformin hydrochloride, metformin hydrochloride and the like.

Examples of the α-glucosidase inhibitor include acarbose, voglibose and the like.

Examples of the ultrashort-acting insulinotropic agent include nateglinide, repaglinide and the like.

Examples of the PPAR agonist include pioglitazone, troglitazone, rosiglitazone, JTT-501, and the like.

Examples of the insulin sensitive enhancer having no PPAR antagonism include ONO-5816, YM-440 and the like.

Examples of the β3 adrenalin receptor agonist include AJ9677, L750355, CP331648 and the like.

Examples of the aldose reductase inhibitor include epalrestat, fidarestat, zenarestat and the like.

Examples of the other drug for complementation and/or enhancement of the preventive and/or therapeutic effects against cancer (malignant tumor) and cancer metastasis of the compound of the present invention include anticancer agent (for example, MMP inhibitor, alkylation agent (for example, cyclophosphamide, melphalan, thiotepa, mytomycin C, busulfan, procarbazine hydrochloride, etc.), antimetabolite (for example, methotrexate, mercaptpurine, azathiopurine, fluorouracil, tegafur, cytarabine, azaserine, etc.), antibiotic (for example, mytomycin C, bleomycin, Peplomycin, doxorubicin hydrochloride, aclarubicin, daunorubicin, actinomycin D, etc.), mitosis inhibitor, platinum complex (for example, Cisplatin), plant-derived antineoplastic agent (for example, vincristine sulfate, vinblastine sulfate, etc.), anti-cancerous hormone (for example, methyltestosterone, testosterone propionate, testosterone enanthate, mepitiostane, fosfestrol, chlormadinone acetate, etc.), immunopotentiator (for example, picibanil, krestin, etc.), and interferon (for example, IFNα, IFNα-2a, IFNα-2b, IFNβ, IFNγ-1a, etc.). Examples thereof include biologics capable of conducting T cell activation (for example, anti-CTLA-4 antibody, anti-PD-1 antibody, etc.), antiangiogenic agent (for example, bevacizumab, pegaptanib, SU-6668, vatalanib, ranibizumab, sorafenib, SU-11248, neovastat), etc.), and the like.

Examples of the other drug for complementation and/or enhancement of the preventive and/or therapeutic effects against immune disease (for example, autoimmune disease, transplanted organ rejection, etc.) of the compound of the present invention include immune inhibitor (for example, cyclosporine, tacrolimus, FTY720, etc.) and the like.

Examples of the other drug for complementation and/or enhancement of the preventive and/or therapeutic effects against dementia such as Senile dementia with Alzheimer's type of the compound of the present invention include acetylcholine esterase inhibitor, nicotinic receptor modifier, cerebral ameliorator, monoamineoxidase inhibitor, vitamin E, aldose reductase inhibitor and the like.

Examples of the other drug for complementation and/or enhancement of the preventive and/or therapeutic effects against epilepsia of the compound of the present invention include phenyloin, trimethadione, ethosuximide, carbamazepine, phenobarbitone, primidone, acetazolamide, sultiame, sodium valproate, clonazepam, diazepam, nitrazepam and the like.

Examples of the other drug for complementation and/or enhancement of the preventive and/or therapeutic effects against arteriosclerosis of the compound of the present invention include HMG-CoA reductase inhibitor, fibrates, probucol preparation, anion-exchange resin, EPA preparation, nicotinic acid preparation, MTP inhibitor, other anti-high cholesterol agent, EDG-2 antagonist and the like.

Examples of the other drug for complementation and/or enhancement of the effects when the compound of the present invention is used in a regeneration therapy include cytokines and various growth factors, for example, various CSFs (for example, G-CSF, GM-CSF, etc.), various interleukins (for example, IL-3, 6, 7, 11, 12, etc.), EPO, TPO, SCF, FLT3 ligand, MIP-1α and the like.

Examples of the other drug for complementation and/or enhancement of the preventive and/or therapeutic effects against retinopathy of the compound of the present invention include antiangiogenic agent (for example, bevacizumab, pegaptanib, SU-6668, vatalanib, ranibizumab, sorafenib, SU-11248, neovastat, etc.) and the like.

Examples of other drugs for complementation and/or enhancement of the preventive and/or therapeutic effect against infections of the compound of the present invention include antibiotics, synthetic antimicrobials, anti-viral drugs, and the like.

Examples of the antibiotic include cefuroxime sodium, meropenem trihydrate, netilmicin sulfate, sisomicin sulfate, ceftibuten, PA-1806, IB-367, tobramycin, PA-1420, doxorubicin, astromicin sulfate, cefetamet pivoxil hydrochloride, and the like. Examples of the antibiotic used in inhalation include PA-1806, IB-367, tobramycin, PA-1420, doxorubicin, astromicin sulfate, cefetamet pivoxil hydrochloride, and the like.

Examples of the anti-viral drug include amantadine, rimantadine, oseltamivir, zanamivir, and the like.

Examples of the synthetic antimicrobial include quinolone-based antibiotic, sulfa drug, ST mixture, and the like.

Of the synthetic antimicrobials, the quinolone-based antibiotic included, for example, norfloxacin, enoxacin, ciprofloxacin hydrochloride, ofloxacin, lomefloxacin hydrochloride, tosufloxacin tosylate, sparfloxacin, fleroxacin, levofloxacin, and the like.

Of synthetic antimicrobials, the sulfa drug includes, for example, dimexine, sulxin, sulfadimethoxine, and the like.

The compound of the present invention is safe and has low toxicity and therefore can be administered to human and mammal other than human (for example, rat, mouse, rabbit, sheep, pig, cow, cat, dog, monkey, etc.).

In order to use a pharmaceutical composition comprising the compound of the present invention or a concomitant drug of the compound of the present invention and other drugs, it is commonly administered, systematically or locally, in an oral or parenteral dosage form.

The dosage of the pharmaceutical preparation varies depending on the age, body weight, symptom, the desired therapeutic effect, the route of administration and duration of treatment. For the human adult, the dosage per person is between 1 ng and 1000 mg, by oral administration, up to several times per day, between 0.1 ng and 100 mg, by parenteral administration, or continuous administration 1 hour to 24 hours per day from vein.

As a matter of course, since the dosage varies under various conditions as is described above, the dosage may be sometimes sufficient which is smaller than the above range, or sometimes the dosage must be more than the above range.

In case of administering a pharmaceutical composition comprising the compound of the present invention, or a concomitant drug of the compound of the present invention and other drugs, it is used as solid preparations for internal use and solutions for internal use for oral administration, and injections, external preparations, suppositories, ophthalmic solutions, nasal drops, inhalants and the like for parenteral administration.

Examples of the solid preparation for internal use for oral administration include tablets, pills, capsules, powders, and granules. Capsules include hard capsules and soft capsules.

In such a solid preparation for internal use, one or more active substances are used as they are, or used after mixing with excipients (lactose, mannitol, glucose, microcrystalline cellulose, starch, etc.), binders (hydroxypropyl cellulose, polyvinyl pyrrolidone, magnesium aluminometasilicate, etc.), disintegrants (calcium carboxymethyl cellulose, etc.), lubricants (magnesium stearate, etc.), stabilizers and solubilizing agents (glutamic acid, aspartic acid, etc.) and forming into a preparation according to a conventional method. If necessary, the preparation may be coated with a coating agent (saccharose, gelatin, hydroxypropyl cellulose, hydroxylpropylmethy cellulosephthalate, etc.) or may be coated with two or more layers. Furthermore, capsules made of an absorbable substance such as gelatin is included.

The solutions for internal use for oral administration include pharmaceutically acceptable water, suspensions, emulsions, syrups, and elixirs. In such a solution, one or more active substances are dissolved, suspended or emulsified in a diluent used commonly (purified water, ethanol, mixed solution thereof, etc.). Furthermore, this solution may contain humectants, suspending agents, emulsifiers, sweeteners, flavors, aromatics, preservatives, buffers, and the like.

The dosage form of the external preparation for parenteral administration includes, for example, ointment, gel, cream, fomentation, patch, liniment, propellant, inhalant, spray, aerosol, ophthalmic solution, and nasal drop. These products contain one or more active substances and are prepared according to the formulation which is known or commonly used.

An ointment is prepared in accordance with a well known formulation or a commonly employed formulation. For example, it is prepared by triturating or dissolving one or more active substances in a base. An ointment base is selected from well known ones or those commonly employed. For example, those selected from higher fatty acids or higher fatty acid esters (adipic acid, myristic acid, palmitic acid, stearic acid, oleic acid, adipate ester, myristate ester, palmitate ester, stearate ester, oleate ester, etc.), waxes (beeswax, whale wax, ceresin, etc.), surfactants (polyoxyethylene alkyl ether phosphate ester, etc.), higher alcohols (cetanol, stearyl alcohol, cetostearyl alcohol, etc.), silicone oils (dimethylpolysiloxane, etc.), hydrocarbons (hydrophilic petrolatum, white petrolatum, purified lanolin, liquid paraffin, etc.), glycols (ethylene glycol, diethylene glycol, propylene glycol, polyethylene glycol, macrogol, etc.), vegetable oils (castor oil, olive oil, sesame oil, turpentine oil, etc.), animal oils (mink oil, egg yolk oil, squalane, squalene, etc.), water, absorption accelerators, agents for preventing contact dermatitis are used alone or in combination. Furthermore, it may contain humectants, preservatives, stabilizers, antioxidizing agents, flavors, and the like.

A gel is prepared according to the formulation which is known or commonly used. For example, it is prepared by dissolving one or more active substances in a base. A gel base is selected from a base which is known or commonly used. For example, those selected from lower alcohols (ethanol, isopropyl alcohol, etc.), gelling agents (carboxymethyl cellulose, hydroxyethyl cellulose, hydroxypropyl cellulose, ethyl cellulose, etc.), neutralizers (triethanolamine, diisopropanolamine, etc.), surfactants (monostearic acid polyethylene glycol, etc.), gums, water, absorption accelerator, and agent for preventing contact dermatitis are used alone or in combination. Furthermore, it may contain preservatives, antioxidizing agents, and flavoring agent.

A cream is prepared according to the formulation which is known or commonly used. For example, it is prepared by dissolving or emulsifying one or more active substances in a base. A cream base is selected from a base which is known or commonly used. For example, those selected from higher fatty acid esters, lower alcohols, hydrocarbons, polyhydric alcohols (propylene glycol, 1,3-butylene glycol, etc.), higher alcohols (2-hexyl decanol, cetanol, etc.), emulsifiers (polyoxyethylene alkyl ethers, fatty acid esters, etc.), water, absorption accelerators, and agents for preventing contact dermatitis are used alone or in combination. Furthermore, it may contain preservatives, antioxidizing agents, and flavoring agents.

A fomentation is prepared according to the formulation which is known or commonly used. For example, it is prepared by dissolving one or more active substances in a base to obtain a kneaded mixture and spreading the kneaded mixture over a substrate. A fomentation base is selected from a base which is known or commonly used. For example, those selected from thickeners (polyacrylic acid, polyvinyl pyrrolidone, gum arabic, starch, gelatin, methyl cellulose, etc.), humectants (urea, glycerin, propylene glycol, etc.), fillers (kaolin, zinc oxide, talc, calcium, magnesium, etc.), water, solubilizing agents, tackifiers, and agents for preventing contact dermatitis are used alone or in combination. Furthermore, it may contain preservatives, antioxidizing agents, and flavoring agent.

A patch is prepared according to the formulation which is known or commonly used. For example, it is prepared by dissolving one or more active substances in a base, and spreading the solution over a substrate. A patch base is selected from a base which is known or commonly used. For example, those selected from polymer bases, fats and oils, higher fatty acids, tackifiers, and agents for preventing contact dermatitis are used alone or in combination. Furthermore, it may contain preservatives, antioxidizing agents, and flavoring agent.

A liniment is prepared according to the formulation which is known or commonly used. For example, it is prepared by dissolving, suspending or emulsifying one or more active substances in one or more kinds selected from water, alcohol (ethanol, polyethylene glycol, etc.), higher fatty acid, glycerin, soap, emulsifier, and suspending agent. Furthermore, it may contain preservatives, antioxidizing agents, and flavoring agent.

A propellant, an inhalant, and a spray may contain, in addition to a diluent used commonly, a stabilizer such as sodium hydrogensulfite and a buffer capable of imparting isotonicity, for example, an isotonicity such as sodium chloride, sodium citrate or citric acid.

An injection for parenteral administration includes all injections and also includes a drop. For example, it includes intramuscular injection, subcutaneous injection, endodermic injection, intraarterial injection, intravenous injection, intraperitoneal injection, intraspinal injection, and intravenous drop.

The injection for parenteral administration includes solutions, suspensions, emulsions, and solid injections used by dissolving or suspending in a solvent before use. The injection is used after dissolving, suspending, or emulsifying one or more active substances in a solvent. As the solvent, for example, distilled water for injection, physiological saline, vegetable oil, and alcohols such as propylene glycol, polyethylene glycol or ethanol are used alone or in combination. Furthermore, the injection may contain stabilizers, solubilizing agents (glutamic acid, aspartic acid, polysolvate 80®, etc.), suspending agents, emulsifiers, soothing agents, buffers, and preservatives. These injections are prepared by sterilizing in the final process, or prepared by an aseptic treatment. Also, a sterile solid, for example, a freeze-dried product is prepared and can be used after dissolving in sterilized distilled water or distilled water for sterile injection, or the other solvent before use.

An ophthalmic solution for parenteral administration includes ophthalmic solution, suspension type ophthalmic solution, emulsion type ophthalmic solution, ophthalmic solution soluble when used, and eye ointment.

These ophthalmic solutions are prepared according to a known method. For example, one or more active substances are dissolved, suspended or emulsified in a solvent before use. As the solvent for ophthalmic solution, for example, sterilized purified water, physiological saline, and other aqueous solvent or non-aqueous agent for injection (for example, vegetable oil, etc.) are used alone or in combination. If necessary, the ophthalmic solution may contain appropriately selected isotonizing agents (sodium chloride, concentrated glycerin, etc.), buffering agents (sodium phosphoate, sodium acetate, etc.), surfactants (polysolvate 80 (trade name), polyoxyl 40 stearate, polyoxyethylene hardened castor oil, etc.), stabilizers (sodium citrate, sodium edetate, etc.), and antiseptics (benzalkonium chloride, paraben, etc.) These ophthalmic solutions are prepared by sterilizing in the final process, or prepared by an aseptic treatment. Also, a sterile solid, for example, a freeze-dried product is prepared and can be used after dissolving in sterilized distilled water or distilled water for sterile injection, or the other solvent before use.

An inhalant for parenteral administration includes aerozol, inhalation powder, and inhalation solution, and the inhalation solution may be such a configuration that it is used after dissolving in water or other suitable medium at the point of use.

These inhalants are prepared according to a known method.

For example, an inhalation solution is prepared by appropriately selecting antiseptics (benzalkonium chloride, paraben, etc.), colorants, buffering agents (sodium phosphate, sodium acetate, etc.), isotonizing agents (sodium chloride, concentrated glycerin, etc.), thickeners (carboxyvinyl polymer, etc.), and absorption accelerator, if necessary.

An inhalation powder is prepared by appropriately selecting lubricants (stearic acid and a salt thereof, etc.), binders (starch, dextrin, etc.), excipients (lactose, cellulose, etc.), colorants, antiseptics (benzalkonium chloride, paraben, etc.), and absorption accelerator if necessary.

In case of administering the inhalation solution, a spraying apparatus (atomizer, nebulizer) is commonly used. In case of administering the inhalation powder, an inhalation administration apparatus for powder is commonly used.

The other composition for parenteral administration includes suppositories for intrarectal injection and pessaries for vaginal administration, which contain one or more active substances and are formulate by a conventional method.

Designation of the compound of the present invention is described below.

The compounds used in the present invention were commonly designated using a computer program ACD/Name Batch® (manufactured by Advanced Chemistry Development Inc.) which designates according to the regulation of IUPAC, or commonly designated according to IUPAC Nomenclature. For example, a compound wherein $A^1$ and $A^2$ represent an imidazol-2-yl group, $B^1$ and $B^2$ represent a methylene group, G represents a carbon atom substituted by a oxo group, E represents a 1,4-phenylene group, L represents —$CH_2$—NH—, and J represents a trans-4-(1-piperidinyl) cyclohexyl group, namely, a compound represented by the following formula:

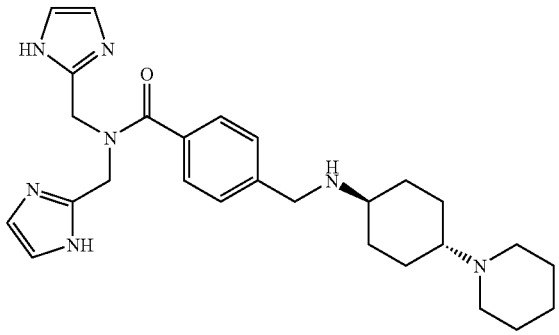

is designated as N,N-bis(1H-imidazol-2-ylmethyl)-4-({[trans-4-(1-piperidinyl)cyclohexyl]amino}methyl)benzamide.

EXAMPLES

The present invention is described in detail based on Examples, but the present invention is not limited thereto.

Crystallinity of the compound, to which properties had been described, was confirmed using a polarizing microscope.

The point of separation by chromatography and the solvent in the parentheses shown in TLC indicate a dissolution medium or an eluent used, and the proportion indicates a volume ratio.

NMR is a measured value of $^1$HNMR at 300 MHz and the solvent shown in the parentheses of NMR indicates a solvent used in the measurement.

Example 1

2-formyl-N,N-dimethyl-1H-imidazole-1-sulfonamide

To an acetonitrile (500 mL) solution of 1H-imidazole-2-carboaldehyde (64 g) and triethylamine (140 mL), dimethylsulfamoyl chloride (100 g) was added at room temperature. The reaction solution was stirred at 50° C. for 16 hours. After the reaction solution was cooled to room temperature, the precipitated crystal was removed by filtration and the filtrate was concentrated under reduced pressure. The residue was washed with ethyl acetate to obtain the crude title compound. The washing was washed with saturated brine and then dried over anhydrous sodium sulfate. After removing the anhydrous sodium sulfate by filtration, the filtrate was concentrated. The residue was purified by silica gel chromatography (ethyl acetate) to obtain the crude title compound. The obtained compound was combined with the crystal obtained previously and then washed with ether to obtain the title compound (88.32 g) having the following physical properties.

TLC: Rf 0.64 (ethyl acetate);
NMR (CDCl$_3$): δ 9.94 (s, 1H), 7.59 (m, 1H), 7.30 (m, 1H), 3.01 (s, 6H).

Example 2

2,2'-[(benzylimino)bis(methylene)]bis(N,N-dimethyl-1H-imidazole-1-sulfonamide)

To a 1% acetate-N,N-dimethylformamide (500 mL) solution of the compound (70 g) obtained in Example 1, benzylamine (17.9 mL) was added at 0° C. To the solution, sodium triacetoxyboron (52 g) was added. The reaction solution was stirred at 0° C. for 30 minutes. To the reaction solution, sodium triacetoxyboron (52 g) was added. The reaction solution was heated to room temperature and then stirred at room temperature for 40 hours. The reaction solution was concentrated under reduced pressure. To the residue, an aqueous 5N sodium hydroxide solution was added, thereby adjusting the pH to 12. The aqueous layer was extracted with ethyl acetate. The combined organic layer was washed with saturated brine and then dried over anhydrous magnesium sulfate. After removing the anhydrous sodium sulfate by filtration, the filtrate was concentrated. Without purifying the residue, the title compound (79 g) having the following physical properties was obtained.

TLC: Rf 0.38 (ethyl acetate:methanol:28% aqueous ammonia=90:10:2);
NMR (CDCl$_3$): δ 7.25 (m, 7H), 6.98 (m, 2H), 4.19 (s, 4H), 4.09 (s, 2H), 2.79 (s, 12H).

Example 3

2,2'-[iminobis(methylene)]bis(N,N-dimethyl-1H-imidazole-1-sulfonamide)

To an ethanol (350 mL) solution of the compound (55.7 g) obtained in Example 2, 20% palladium hydroxide-carbon (13.6 g) was added under an argon atmosphere. The reaction mixture was stirred under a hydrogen atmosphere at 60° C. for 6 hours. The reaction mixture was cooled to room temperature and then filtered through Celite. The filtrate was concentrated under reduced pressure. The residue was purified by silica gel chromatography (ethyl acetate:10%-saturated aqueous ammonia-methanol=1:0→8:2) to obtain the title compound (28.5 g) having the following physical properties.

TLC: Rf 0.66 (dichlorolomethane:methanol:28% aqueous ammonia=80:20:3);

NMR (CDCl$_3$): δ 7.22 (m, 2H), 6.96 (m, 2H), 4.14 (s, 4H), 2.90 (s, 12H).

Example 4

N,N-bis({1-[(dimethylamino)sulfonyl]-1H-imidazol-2-yl}methyl)-4-formylbenzamide

To an N,N-dimethylformamide (100 mL) solution of 4-formylbenzoic acid (9.57 g), 1-ethyl-3-[3-(dimethylamino)propyl]carbodiimide hydrochloride (12.21 g) was added at 0° C. The reaction solution was stirred at 0° C. for one hour. To the solution, the compound (20.78 g) obtained in Example 3 was added. The reaction solution was heated to room temperature and then stirred for 4 hours. The reaction solution was concentrated under reduced pressure. To the residue, an aqueous saturated sodium hydrogen carbonate solution was added. The aqueous layer was extracted with ethyl acetate. The aqueous layer was combined with the organic layer, washed in turn with 1N hydrochloric acid, water and saturated brine, and then dried over anhydrous sodium sulfate. After removing the anhydrous sodium sulfate by filtration, the filtrate was concentrated. The residue was purified by silica gel chromatography (ethyl acetate: 10%-saturated aqueous ammonia-methanol=1:0→8:2) to obtain the title compound (21.27 g) having the following physical properties.

TLC: Rf 0.52 (ethyl acetate:methanol=9:1);

NMR (CDCl$_3$): δ 10.01 (s, 1H), 7.87 (d, J=8.4 Hz, 2H), 7.73 (d, J=8.4 Hz, 2H), 7.26 (m, 1H), 7.22 (m, 1H), 7.09 (m, 1H), 7.00 (m, 1H), 5.06 (s, 2H), 4.94 (s, 2H), 3.03 (s, 6H), 2.65 (s, 6H).

Example 5

4-formyl-N,N-bis(1H-imidazol-2-ylmethyl)benzamide

To the compound (27.28 g) obtained in Example 4, 2N hydrochloric acid (135 mL) was added. The mixture was stirred at 80° C. for 2 hours. After the reaction solution was cooled to room temperature, an aqueous 5N sodium hydroxide solution was added until the pH is adjusted to 12. To the aqueous layer, sodium chloride was added, followed by extraction with ethyl acetate. The combined organic layer was washed with saturated brine and then dried over anhydrous sodium sulfate. After removing the anhydrous sodium sulfate by filtration, the filtrate was concentrated. The residue was purified by silica gel chromatography (ethyl acetate: 10%-saturated aqueous ammonia-methanol=1:0→8:2) to obtain the title compound (10.49 g) having the following physical properties.

TLC: Rf 0.61 (methanol:28% aqueous ammonia=99:1);

NMR (CDCl$_3$): δ 10.03 (s, 1H), 7.93 (d, J=8.4 Hz, 2H), 7.83 (d, J=8.4 Hz, 2H), 7.26 (m, 1H), 7.22 (m, 1H), 7.09 (m, 1H), 7.00 (m, 1H), 4.68 (s, 2H), 4.56 (s, 2H).

Example 6 tert-butyl(trans-4-piperidin-1-ylcyclohexyl)carbamate

Trans-4-tert-butoxycarbonylamino-aminocyclohexane (1 g) and potassium carbonate (1.3 g) were suspended in ethanol (20 mL), and then 1,5-dibromopentane (1.07 g) was added thereto. The reaction solution was stirred at 80° C. for 48 hours. After the reaction solution was cooled to room temperature, the solvent was concentrated under reduced pressure. The residue was dissolved in water (50 mL). The aqueous layer was extracted twice with dichloromethane (50 mL). The combined organic layer was washed with saturated brine and then dried over anhydrous magnesium sulfate. After removing the anhydrous sodium sulfate by filtration, the filtrate was concentrated. The residue was purified by silica gel chromatography (ethyl acetate: 10%-saturated aqueous ammonia-methanol=1:0→10:1) to obtain the title compound (492 mg) having the following physical properties.

TLC: Rf 0.47 (chloroform:methanol:28% aqueous ammonia=80:10:1);

NMR (CDCl$_3$): δ 4.34 (m, 1H), 3.35 (m, 1H), 2.48 (m, 4H), 2.27 (m, 1H), 2.04 (m, 2H), 1.88 (m, 2H), 1.57 (m, 4H), 1.44 (s, 9H), 1.68 (m, 1H), 1.38 (m, 2H), 1.15 (m, 2H).

Example 7 trans-4-piperidin-1-ylcyclohexaneamine

To a methanol (4 mL) solution of the compound (480 mg) obtained in Example 6, 4N hydrogen chloride-ethyl acetate solution (4 mL) was added at 0° C. The reaction solution was stirred at 0° C. for one hour. The reaction solution was concentrated under reduced pressure, and then an aqueous 2N sodium hydroxide solution (20 mL) was added to the residue until the pH is adjusted to 12. The aqueous layer was extracted twice with dichloromethane (50 mL). The combined organic layer was washed with saturated brine and then dried over anhydrous magnesium sulfate. After removing the anhydrous sodium sulfate by filtration, the filtrate was concentrated. The residue was used in the subsequent reaction without being purified.

TLC: Rf 0.23 (chloroform:methanol:28% aqueous ammonia=80:10:1);

NMR (CDCl$_3$): δ 2.61 (m, 1H), 2.54 (m, 4H), 2.29 (m, 1H), 1.90 (m, 4H), 1.62 (m, 6H), 1.46 (m, 2H), 1.31 (m, 2H), 1.13 (m, 2H).

Example 8

N,N-bis(1H-imidazol-2-ylmethyl)-4-({[trans-4-(1-piperidinyl)cyclohexyl]amino}methyl)benzamide The same operation as in Example 2 was performed, except for using the compound (250 mg) obtained in Example 7 and the compound (212 mg) obtained in Example 5, and then the obtained crude product was purified by silica gel chromatography (dichrolomethane:methanol: 28% aqueous ammonia=10:1:0→80:10:1) to obtain the title compound (161 mg) having the following physical properties.

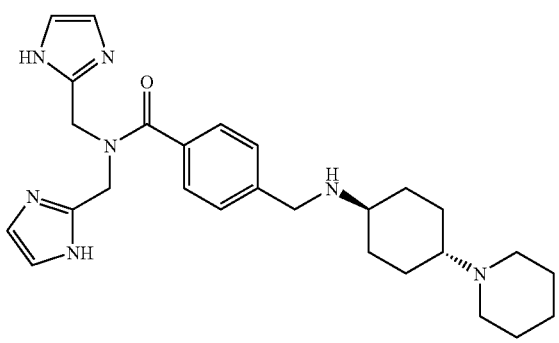

Description: amorphous;
TLC: Rf 0.36 (chloroform:methanol:28% aqueous ammonia=80:10:1);
NMR (DMSO-$d_6$): δ 0.86-1.07 (m, 2H), 1.08-1.26 (m, 2H), 1.26-1.37 (m, 2H), 1.37-1.53 (m, 4H), 1.59-1.76 (m, 2H), 1.82-2.01 (m, 2H), 2.07-2.32 (m, 2H), 2.33-2.46 (m, 4H), 3.69 (s, 2H), 4.45-4.69 (m, 4H), 6.75-7.20 (m, 4H), 7.31 (d, J=8.10 Hz, 2H), 7.41 (d, J=8.10 Hz, 2H), 11.76-12.84 (m, 2H).

Example 8(1) to Example 8(128)

The same operation as in Example 8 was performed, except for using corresponding amine in place of trans-4-piperidin-1-ylcyclohexaneamine and corresponding aldehyde in place of 4-formyl-N,N-bis(1H-imidazol-2-ylmethyl)benzamide in Example 8, to obtain the following compound.

Example 8(1)

4-({[4-(dipropylamino)-2-butyn-1-yl]amino}methyl)-N,N-bis(1H-imidazol-2-ylmethyl)benzamide TLC: Rf 0.44 (methanol:28% aqueous ammonia=98:2);
NMR (CDCl$_3$): δ 0.89 (t, J=7.20 Hz, 6H), 1.36-1.64 (m, 4H), 2.31-2.56 (m, 4H), 3.33-3.51 (m, 4H), 3.88 (s, 2H), 4.53-4.78 (m, 4H), 6.88-7.12 (m, 4H), 7.35 (d, J=8.10 Hz, 2H), 7.52 (d, J=8.10 Hz, 2H).

Example 8(2)

4-({[[(2-cycloheptyl-1,2,3,4-tetrahydro-7-isoquinolinyl)methyl]amino}methyl)-N,N-bis(1H-imidazol-2-ylmethyl)benzamide Description: amorphous;
TLC: Rf 0.38 (methanol:28% aqueous ammonia=98:2);
NMR (CDCl$_3$): δ 1.32-1.65 (m, 8H), 1.65-1.81 (m, 2H), 1.84-2.01 (m, 2H), 2.68-2.93 (m, 5H), 3.71 (s, 2H), 3.74 (s, 2H), 3.77 (s, 2H), 4.47-4.75 (m, 4H), 6.89-7.13 (m, 7H), 7.36 (d, J=8.40 Hz, 2H), 7.60 (d, J=8.40 Hz, 2H).

Example 8(3)

4-({[4-(1,3-dihydro-2H-isoindol-2-yl)cyclohexyl]amino}methyl)-N,N-bis(1H-imidazol-2-ylmethyl)benzamide (Low Polar Compound)

Description: amorphous;
TLC: Rf 0.60 (ethyl acetate:methanol:28% aqueous ammonia=80:20:2);
NMR (CDCl$_3$): δ 1.55-1.94 (m, 8H), 2.55 (m, 1H), 2.73 (m, 1H), 3.82 (s, 2H), 3.95 (s, 4H), 4.50-4.72 (m, 4H), 6.90-7.12 (m, 4H), 7.16-7.24 (m, 4H), 7.37 (d, J=8.1 Hz, 2H), 7.55 (d, J=8.1 Hz, 2H).

Example 8(4)

4-({[4-(1,3-dihydro-2H-isoindol-2-yl)cyclohexyl]amino}methyl)-N,N-bis(1H-imidazol-2-ylmethyl)benzamide (High Polar Compound)

Description: amorphous;
TLC: Rf 0.35 (ethyl acetate:methanol:28% aqueous ammonia=80:20:2);
NMR (CDCl$_3$): δ 1.18-1.43 (m, 4H), 1.98-2.16 (m, 4H), 2.41 (m, 1H), 2.55 (m, 1H), 3.85 (s, 2H), 3.98 (s, 4H), 4.52-4.75 (m, 4H), 6.95-7.10 (m, 4H), 7.18-7.22 (m, 4H), 7.38 (d, J=8.1 Hz, 2H), 7.59 (d, J=8.1 Hz, 2H).

Example 8(5)

4-{[({trans-4-[(dipropylamino)methyl]cyclohexyl}methyl)(methyl)amino]methyl}-N,N-bis(1H-imidazol-2-ylmethyl)benzamide Description: amorphous;
TLC: Rf 0.39 (28% aqueous ammonia:methanol=2:98);
NMR (CDCl$_3$): δ 0.77-0.89 (m, 10H), 1.32-1.48 (m, 6H), 1.77-1.91 (m, 4H), 2.08-2.19 (m, 7H), 2.24-2.36 (m, 4H), 3.44 (s, 2H), 4.60-4.72 (m, 4H), 6.95-7.10 (m, 4H), 7.32-7.40 (m, 2H), 7.54-7.62 (m, 2H).

Example 8(6)

4-[({4-[cycloheptyl(propyl)amino]cyclohexyl}amino)methyl]-N,N-bis(1H-imidazol-2-ylmethyl)benzamide (Low Polar Compound)

Description: amorphous;
TLC: Rf 0.47 (ethyl acetate:methanol:28% aqueous ammonia=90:10:2);
NMR (CDCl$_3$): δ 0.83 (t, J=7.5 Hz, 3H), 1.30-1.90 (m, 22H), 2.44 (m, 2H), 2.56 (m, 1H), 2.76 (m, 1H), 2.86 (m, 1H), 3.77 (s, 2H), 4.55-4.78 (m, 4H), 6.98-7.08 (m, 4H), 7.40 (d, J=8.1 Hz, 2H), 7.61 (d, J=8.1 Hz, 2H).

Example 8(7)

4-[({4-[cycloheptyl(propyl)amino]cyclohexyl}amino)methyl]-N,N-bis(1H-imidazol-2-ylmethyl)benzamide (High Polar Compound)

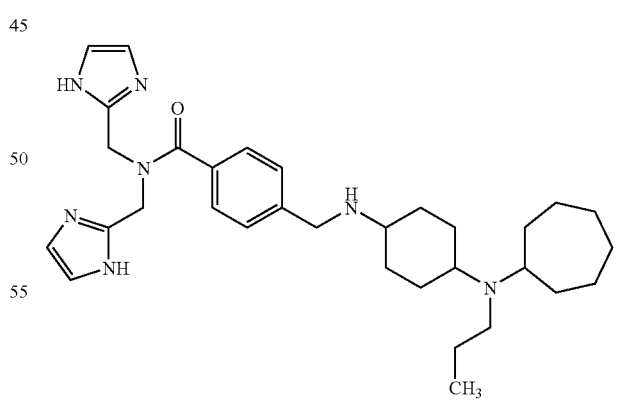

Description: amorphous;
TLC: Rf 0.40 (ethyl acetate:methanol:28% aqueous ammonia=90:10:2);
NMR (CDCl$_3$): δ 0.83 (t, J=7.5 Hz, 3H), 1.05-1.82 (m, 20H), 1.92-2.02 (m, 2H), 2.32-2.46 (m, 3H), 2.52 (m, 1H), 2.76 (m, 1H), 3.81 (s, 2H), 4.55-4.75 (m, 4H), 6.98-7.10 (m, 4H), 7.36 (d, J=8.1 Hz, 2H), 7.62 (d, J=8.1 Hz, 2H).

Example 8(8)

4-[(8-cyclohexyl-2,8-diazaspiro[4.5]dec-2-yl)methyl]-N,N-bis(1H-imidazol-2-ylmethyl)-2,6-dimethylbenzamide Description: amorphous;
TLC: Rf 0.51 (dichrolomethane:methanol:28% aqueous ammonia=50:10:1);
NMR (CDCl$_3$): δ 1.10-1.30 (m, 6H), 1.58-1.65 (m, 8H), 1.80-1.93 (m, 4H), 2.01 (s, 6H), 2.30 (m, 1H), 2.50-2.60 (m, 6H), 3.50 (s, 2H), 4.49 (s, 2H), 4.89 (s, 2H), 6.96 (s, 2H), 6.98 (s, 2H), 7.04 (s, 2H).

Example 8(9)

3-[(8-cyclohexyl-2,8-diazaspiro[4.5]dec-2-yl)methyl]-N,N-bis(1H-imidazol-2-ylmethyl)benzamide Description: amorphous;
TLC: Rf 0.53 (dichrolomethane:methanol:28% aqueous ammonia=50:10:1);
NMR (CDCl$_3$): δ 1.15-1.30 (m, 6H), 1.58-1.90 (m, 12H), 2.26 (m, 1H), 2.44-2.58 (m, 4H), 2.58 (t, J=6.90 Hz, 2H), 3.59 (s, 2H), 4.53 (br-s, 2H), 4.70 (br-s, 2H), 7.03 (br-s, 2H), 7.07 (br-s, 2H), 7.38-7.40 (m, 2H), 7.57-7.61 (m, 2H).

Example 8(10)

4-{[8-(2,2-dimethylpropyl)-2,8-diazaspiro[4.5]dec-2-yl]methyl}-N,N-bis(1H-imidazol-2-ylmethyl)benzamide

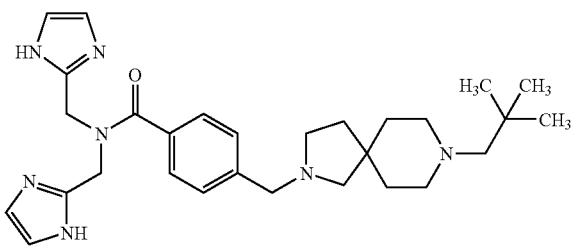

Description: amorphous;
TLC: Rf 0.50 (methanol:28% aqueous ammonia=98:2);
NMR (CDCl$_3$): δ 0.83 (s, 9H), 1.43-1.68 (m, 6H), 1.99 (s, 2H), 2.27-2.48 (m, 6H), 2.55 (t, J=6.90 Hz, 2H), 3.58 (s, 2H), 4.50-4.75 (m, 4H), 6.86-7.13 (m, 4H), 7.36 (d, J=8.10 Hz, 2H), 7.59 (d, J=8.10 Hz, 2H).

Example 8(11)

4-{[[trans-4-(dipropylamino)-4-methylcyclohexyl](methyl)amino]methyl}-N,N-bis(1H-imidazol-2-ylmethyl)benzamide Description: amorphous;
TLC: Rf 0.17 (28% aqueous ammonia:methanol=2:98);
NMR (CDCl$_3$): δ 0.72-0.86 (m, 6H), 0.98 (s, 3H), 1.33-1.49 (m, 8H), 1.65-1.79 (m, 4H), 2.10 (s, 3H), 2.31-2.47 (m, 5H), 3.50 (s, 2H), 4.56-4.70 (m, 4H), 6.83-6.98 (m, 4H), 7.25-7.34 (m, 2H), 7.43-7.55 (m, 2H).

Example 8(12)

N,N-bis(1H-imidazol-2-ylmethyl)-4-({8-[(4-methyl-2-thienyl)methyl]-2,8-diazaspiro[4.5]dec-2-yl}methyl)benzamide Description: amorphous;
TLC: Rf 0.24 (28% aqueous ammonia:methanol=2:98);
NMR (CDCl$_3$): δ 1.53-1.65 (m, 6H), 2.20 (s, 3H), 2.30-2.44 (m, 6H), 2.48-2.58 (m, 2H), 3.56 (s, 2H), 3.60 (s, 2H), 4.60-4.72 (m, 4H), 6.68-6.71 (m, 1H), 6.74-6.79 (m, 1H), 6.95-7.09 (m, 4H), 7.32-7.39 (m, 2H), 7.52-7.62 (m, 2H).

Example 8(13)

N,N-bis(1H-imidazol-2-ylmethyl)-4-({2-[(4-methyl-2-thienyl)methyl]-2,7-diazaspiro[3.5]non-7-yl}methyl)benzamide Description: amorphous;
TLC: Rf 0.24 (28% aqueous ammonia:methanol=2:98);
NMR (CDCl$_3$): δ 1.67-1.79 (m, 4H), 2.20 (s, 3H), 2.24-2.37 (m, 4H), 3.01 (s, 4H), 3.42 (s, 2H), 3.73 (s, 2H), 4.58-4.71 (m, 4H), 6.66-6.71 (m, 1H), 6.72-6.77 (m, 1H), 6.94-7.08 (m, 4H), 7.29-7.37 (m, 2H), 7.53-7.61 (m, 2H).

Example 8(14)

4-{[8-(3-hydroxypropyl)-2,8-diazaspiro[4.5]dec-2-yl]methyl}-N,N-bis(1H-imidazol-2-ylmethyl)benzamide Description: amorphous;
TLC: Rf 0.20 (methanol:28% aqueous ammonia=98:2);
NMR (CDCl$_3$): δ 1.47-1.84 (m, 8H), 2.34 (s, 2H), 2.36-2.72 (m, 8H), 3.59 (s, 2H), 3.71-3.85 (m, 2H), 4.49-4.74 (m, 4H), 6.89-7.14 (m, 4H), 7.37 (d, J=8.10 Hz, 2H), 7.65 (d, J=8.10 Hz, 2H).

Example 8(15)

4-{[[2-(1-cycloheptyl-4-piperidinyl)ethyl]amino}methyl)-N,N-bis(1H-imidazol-2-ylmethyl)benzamide Description: amorphous;
TLC: Rf 0.15 (methanol:28% aqueous ammonia=98:2);
NMR (CDCl$_3$): δ 1.13-1.92 (m, 19H), 2.14-2.33 (m, 2H), 2.48-2.69 (m, 3H), 2.69-2.87 (m, 2H), 3.79 (s, 2H), 4.47-4.74 (m, 4H), 6.88-7.16 (m, 4H), 7.35 (d, J=8.10 Hz, 2H), 7.63 (d, J=8.10 Hz, 2H).

Example 8(16)

4-{[(1-cycloheptyl-4-piperidinyl)amino]methyl}-N,N-bis(1H-imidazol-2-ylmethyl)benzamide

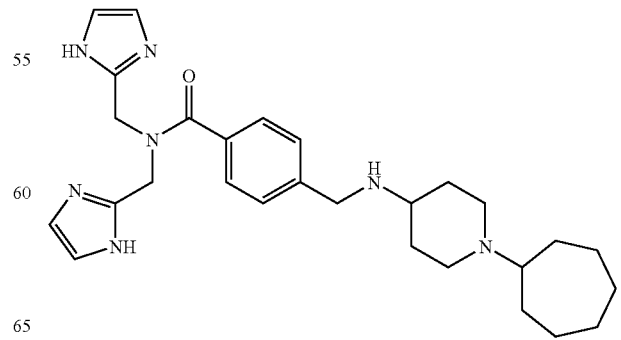

Description: amorphous;
TLC: Rf 0.25 (methanol:28% aqueous ammonia=98:2);
NMR (CDCl$_3$): δ 1.27-1.73 (m, 12H), 1.74-1.97 (m, 4H), 2.20-2.39 (m, 2H), 2.40-2.54 (m, 1H), 2.54-2.71 (m, 1H), 2.73-2.92 (m, 2H), 3.81 (s, 2H), 4.45-4.75 (m, 4H), 6.87-7.14 (m, 4H), 7.35 (d, J=8.10 Hz, 2H), 7.60 (d, J=8.10 Hz, 2H).

Example 8(17)

N,N-bis({1-[(dimethylamino)sulfonyl]-1H-imidazol-2-yl}methyl)-4-({[trans-4-(dipropylamino)cyclohexyl]amino}methyl)benzamide Description: amorphous;
TLC: Rf 0.41 (chloroform:methanol:28% aqueous ammonia=80:10:1);
NMR (DMSO-d$_6$): δ 0.79 (t, J=7.50 Hz, 6H), 0.89-1.05 (m, 2H), 1.06-1.21 (m, 2H), 1.21-1.38 (m, 4H), 1.55-1.68 (m, 2H), 1.82-1.95 (m, 2H), 2.14-2.41 (m, 6H), 2.56 (s, 6H), 2.90 (s, 6H), 3.68 (s, 2H), 4.82 (s, 2H), 4.96 (s, 2H), 7.05 (d, J=1.50 Hz, 1H), 7.12 (d, J=1.50 Hz, 1H), 7.25 (d, J=8.10 Hz, 2H), 7.32 (d, J=8.10 Hz, 2H), 7.51-7.61 (m, 2H).

Example 8(18)

4-[(8-cyclohexyl-2,8-diazaspiro[4.5]dec-2-yl)methyl]-N,N-bis(1H-imidazol-2-ylmethyl)-3-methoxybenzamide

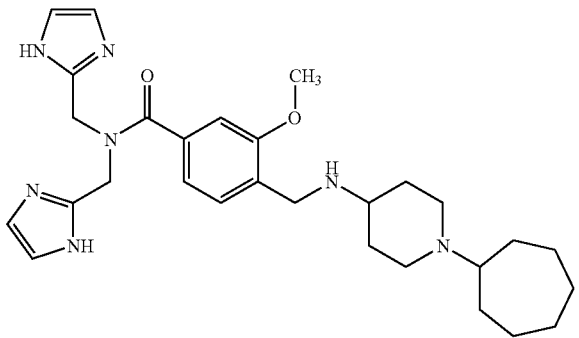

Description: amorphous;
TLC: Rf 0.76 (chloroform:methanol:28% aqueous ammonia=40:10:2);
NMR (CD$_3$OD): δ 1.04-1.35 (m, 6H), 1.56-1.69 (m, 6H), 1.76-1.98 (m, 4H), 2.28-2.37 (m, 1H), 2.44 (s, 2H), 2.49-2.68 (m, 6H), 3.63 (s, 2H), 3.68 (s, 3H), 4.49-4.88 (m, 4H), 6.91-7.21 (m, 6H), 7.33 (d, J=7.8 Hz, 1H).

Example 8(19)

4-({[trans-4-(dipropylamino)-1-methylcyclohexyl]amino}methyl)-N,N-bis(1H-imidazol-2-ylmethyl)benzamide Description: amorphous;
TLC: Rf 0.10 (28% aqueous ammonia:methanol:ethyl acetate=2:8:90);
NMR (CDCl$_3$): δ 0.81-0.93 (m, 6H), 1.18 (s, 3H), 1.37-1.51 (m, 8H), 1.67-1.81 (m, 4H), 2.41-2.56 (m, 5H), 3.77 (s, 2H), 4.53-4.68 (m, 4H), 6.95-7.09 (m, 4H), 7.33-7.42 (m, 2H), 7.50-7.60 (m, 2H).

Example 8(20)

4-{[[trans-4-(dipropylamino)-1-methylcyclohexyl](methyl)amino]methyl}-N,N-bis(1H-imidazol-2-ylmethyl)benzamide Description: amorphous;
TLC: Rf 0.26 (28% aqueous ammonia:methanol:ethyl acetate=2:8:90);
NMR (CDCl$_3$): δ 0.82-0.94 (m, 6H), 1.04 (s, 3H), 1.39-1.54 (m, 8H), 1.73-1.88 (m, 4H), 2.05 (s, 3H), 2.44-2.58 (m, 5H), 3.53 (s, 2H), 4.60-4.73 (m, 4H), 6.94-7.08 (m, 4H), 7.33-7.44 (m, 2H), 7.49-7.59 (m, 2H).

Example 8(21)

N,N-bis(1H-imidazol-2-ylmethyl)-4-[(8-{[3-(methoxymethyl)-2-thienyl]methyl}-2,8-diazaspiro[4.5]dec-2-yl)methyl]benzamide Description: amorphous;
TLC: Rf 0.23 (28% aqueous ammonia:methanol:ethyl acetate=2:8:90);
NMR (CDCl$_3$): δ 1.52-1.65 (m, 6H), 2.31-2.45 (m, 6H), 2.50-2.60 (m, 2H), 3.32 (s, 3H), 3.57 (s, 2H), 3.63 (s, 2H), 4.40 (s, 2H), 4.58-4.71 (m, 4H), 6.92-7.07 (m, 5H), 7.11-7.18 (m, 1H), 7.31-7.40 (m, 2H), 7.57-7.64 (m, 2H).

Example 8(22)

4-({8-[(3-chloro-2-thienyl)methyl]-2,8-diazaspiro[4.5]dec-2-yl}methyl)-N,N-bis(1H-imidazol-2-ylmethyl)benzamide Description: amorphous;
TLC: Rf 0.21 (28% aqueous ammonia:methanol:ethyl acetate=2:8:90);
NMR (CDCl$_3$): δ 1.52-1.66 (m, 6H), 2.35-2.49 (m, 6H), 2.52-2.63 (m, 2H), 3.61 (s, 2H), 3.67 (s, 2H), 4.58-4.71 (m, 4H), 6.82-6.88 (m, 1H), 6.94-7.08 (m, 4H), 7.17-7.23 (m, 1H), 7.33-7.41 (m, 2H), 7.59-7.66 (m, 2H).

Example 8(23)

4-({[2-(1-cycloheptyl-4-piperidinylidene)ethyl]amino}methyl)-N,N-bis(1H-imidazol-2-ylmethyl)benzamide

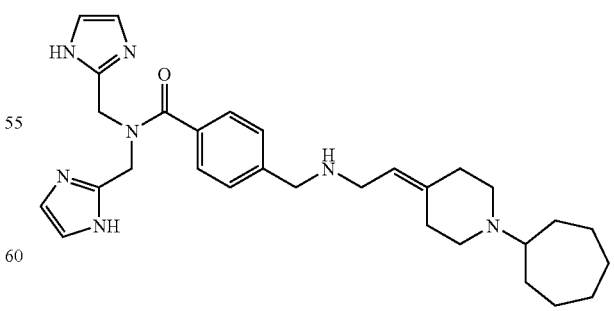

Description: amorphous;
TLC: Rf 0.28 (methanol:28% aqueous ammonia=98:2);
NMR (CDCl$_3$): δ 1.27-1.91 (m, 12H), 2.11-2.33 (m, 4H), 2.40-2.73 (m, 5H), 3.21 (d, J=6.9 Hz, 2H), 3.78 (s, 2H), 4.43-4.77 (m, 4H), 5.23 (t, J=6.9 Hz, 1H), 6.85-7.12 (m, 4H), 7.34 (d, J=8.1 Hz, 2H), 7.59 (d, J=8.1 Hz, 2H).

Example 8(24)

N,N-bis(1H-imidazol-2-ylmethyl)-4-({[trans-4-(2,3,6,7-tetrahydro-1H-azepin-1-yl)cyclohexyl]amino}methyl)benzamide

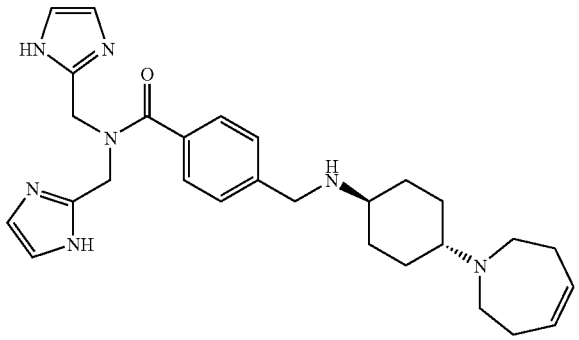

Description: amorphous;

TLC: Rf 0.28 (chloroform:methanol:28% aqueous ammonia=80:10:1);

NMR (DMSO-d$_6$): δ 0.90-1.09 (m, 2H), 1.09-1.28 (m, 2H), 1.60-1.76 (m, 2H), 1.82-1.98 (m, 2H), 2.03-2.15 (m, 4H), 2.16-2.31 (m, 2H), 2.33-2.46 (m, 2H), 2.51-2.58 (m, 2H), 3.68 (s, 2H), 4.42-4.71 (m, 4H), 5.62-5.75 (m, 2H), 6.75-7.16 (m, 4H), 7.30 (d, J=8.10 Hz, 2H), 7.39 (d, J=8.10 Hz, 2H), 11.69-12.81 (m, 2H).

Example 8(25)

N,N-bis(1H-imidazol-2-ylmethyl)-4-{8-[(3-methyl-2-thienyl)methyl]-2,8-diazaspiro[4.5]dec-2-yl}cyclohexanecarboxamide (Low Polar Compound)

Description: amorphous;

TLC: Rf 0.57 (ethyl acetate:methanol:28% aqueous ammonia=50:10:1);

NMR (CDCl$_3$): δ 1.22-2.60 (m, 19H), 2.18 (s, 3H), 2.86 (br-s, 2H), 3.00-3.20 (m, 3H), 3.60 (s, 2H), 4.66 (br-s, 4H), 6.77 (d, J=5.4 Hz, 1H), 7.00 (br-s, 2H), 7.03 (br-s, 2H), 7.12 (d, J=5.4 Hz, 1H).

Example 8(26)

N,N-bis(1H-imidazol-2-ylmethyl)-4-{8-[(3-methyl-2-thienyl)methyl]-2,8-diazaspiro[4.5]dec-2-yl}cyclohexanecarboxamide (High Polar Compound)

Description: amorphous;

TLC: Rf 0.53 (ethyl acetate:methanol:28% aqueous ammonia=50:10:1);

NMR (CDCl$_3$): δ 1.22-2.18 (m, 15H), 2.18 (s, 3H), 2.30-2.45 (m, 4H), 2.50 (s, 2H), 2.65-2.75 (m, 3H), 3.57 (s, 2H), 4.61 (br-s, 2H), 4.73 (br-s, 2H), 6.77 (d, J=5.1 Hz, 1H), 6.98 (br-s, 4H), 7.11 (d, J=5.1 Hz, 1H).

Example 8(27)

N,N-bis(1H-imidazol-2-ylmethyl)-4-{[8-(2-methylbenzyl)-2,8-diazaspiro[4.5]dec-2-yl]methyl}benzamide Description: amorphous;

TLC: Rf 0.57 (ethyl acetate:methanol:28% aqueous ammonia=50:10:1);

NMR (CDCl$_3$): δ 1.50-1.63 (m, 6H), 2.33 (s, 3H), 2.33-2.40 (m, 6H), 2.56 (t, J=6.9 Hz, 2H), 3.39 (s, 2H), 3.59 (s, 2H), 4.62 (br-s, 2H), 4.65 (br-s, 2H), 6.99 (br-s, 2H), 7.06 (br-s, 2H), 7.13-7.26 (m, 4H), 7.38 (d, J=8.1 Hz, 2H), 7.64 (d, J=8.1 Hz, 2H).

Example 8(28)

N,N-bis(1H-imidazol-2-ylmethyl)-4-{[8-(3-methylbenzyl)-2,8-diazaspiro[4.5]dec-2-yl]methyl}benzamide Description: amorphous;

TLC: Rf 0.52 (ethyl acetate:methanol:28% aqueous ammonia=50:10:1);

NMR (CDCl$_3$): δ 1.54-1.62 (m, 6H), 2.33 (m, 9H), 2.54 (t, J=6.9 Hz, 2H), 3.41 (s, 2H), 3.57 (s, 2H), 4.63 (br-s, 4H), 6.99-7.21 (m, 8H), 7.37 (d, J=8.4 Hz, 2H), 7.65 (d, J=8.4 Hz, 2H).

Example 8(29)

N,N-bis(1H-imidazol-2-ylmethyl)-4-{[8-(4-methylbenzyl)-2,8-diazaspiro[4.5]dec-2-yl]methyl}benzamide Description: amorphous;

TLC: Rf 0.50 (ethyl acetate:methanol:28% aqueous ammonia=50:10:1);

NMR (CDCl$_3$): δ 1.54-1.61 (m, 6H), 2.32 (m, 9H), 2.54 (t, J=6.9 Hz, 2H), 3.41 (s, 2H), 3.57 (s, 2H), 4.63 (br-s, 4H), 7.00 (br-s, 2H), 7.07 (br-s, 2H), 7.10 (d, J=7.8 Hz, 2H), 7.18 (d, J=7.8 Hz, 2H), 7.37 (d, J=8.1 Hz, 2H), 7.66 (d, J=8.1 Hz, 2H).

Example 8(30)

N,N-bis(1H-imidazol-2-ylmethyl)-4-{[8-(2-methoxybenzyl)-2,8-diazaspiro[4.5]dec-2-yl]methyl}benzamide Description: amorphous;

TLC: Rf 0.26 (dichrolomethane:methanol:28% aqueous ammonia=50:10:1);

NMR (CDCl$_3$): δ 1.50-1.64 (m, 6H), 2.35-2.45 (m, 6H), 2.53 (t, J=7.8 Hz, 2H), 3.51 (s, 2H), 3.57 (s, 2H), 3.80 (s, 3H), 4.62 (br-s, 4H), 6.85 (d, J=7.5 Hz, 1H), 6.91 (dt, J=7.5, 1.5 Hz, 1H), 7.00 (br-s, 2H), 7.07 (br-s, 2H), 7.21 (dt, J=7.5, 1.5 Hz, 1H), 7.34 (dd, J=7.5, 1.5 Hz, 1H), 7.38 (d, J=8.4 Hz, 2H), 7.66 (d, J=8.4 Hz, 2H).

Example 8(31)

N,N-bis(1H-imidazol-2-ylmethyl)-4-{[8-(3-methoxybenzyl)-2,8-diazaspiro[4.5]dec-2-yl]methyl}benzamide Description: amorphous;

TLC: Rf 0.26 (dichrolomethane:methanol:28% aqueous ammonia=50:10:1);

NMR (CDCl$_3$): δ 1.54-1.64 (m, 6H), 2.30-2.40 (m, 6H), 2.55 (t, J=6.9 Hz, 2H), 3.43 (s, 2H), 3.58 (s, 2H), 3.79 (s, 3H), 4.62 (br-s, 2H), 4.64 (br-s, 2H), 6.77 (dd, J=8.1, 2.1 Hz, 1H), 6.87-6.89 (m, 2H), 6.98 (br-s, 2H), 7.06 (br-s, 2H), 7.20 (t, J=8.1 Hz, 1H), 7.37 (d, J=8.1 Hz, 2H), 7.64 (d, J=8.1 Hz, 2H).

Example 8(32)

N,N-bis(1H-imidazol-2-ylmethyl)-4-{[8-(4-methoxybenzyl)-2,8-diazaspiro[4.5]dec-2-yl]methyl}benzamide Description: amorphous;
TLC: Rf 0.28 (dichrolomethane:methanol:28% aqueous ammonia=50:10:1);
NMR (CDCl$_3$): δ 1.54-1.64 (m, 6H), 2.28-2.38 (m, 6H), 2.54 (t, J=6.9 Hz, 2H), 3.39 (s, 2H), 3.57 (s, 2H), 3.79 (s, 3H), 4.63 (br-s, 4H), 6.83 (d, J=8.4 Hz, 2H), 7.00 (br-s, 2H), 7.07 (br-s, 2H), 7.20 (d, J=8.4 Hz, 2H), 7.37 (d, J=8.1 Hz, 2H), 7.66 (d, J=8.1 Hz, 2H).

Example 8(33)

N,N-bis(1H-imidazol-2-ylmethyl)-4-({8-[2-(trifluoromethyl)benzyl]-2,8-diazaspiro[4.5]dec-2-yl}methyl)benzamide Description: amorphous;
TLC: Rf 0.52 (ethyl acetate:methanol:28% aqueous ammonia=50:10:1);
NMR (CDCl$_3$): δ 1.56-1.65 (m, 6H), 2.38 (m, 6H), 2.57 (t, J=6.9 Hz, 2H), 3.60 (s, 4H), 4.64 (br-s, 4H), 7.00 (br-s, 2H), 7.07 (br-s, 2H), 7.30 (m, 1H), 7.39 (d, J=8.1 Hz, 2H), 7.49 (t, J=7.5 Hz, 1H), 7.59 (d, J=7.5 Hz, 1H), 7.66 (d, J=8.1 Hz, 2H), 7.80 (d, J=7.5 Hz, 1H).

Example 8(34)

N,N-bis(1H-imidazol-2-ylmethyl)-4-({8-[3-(trifluoromethyl)benzyl]-2,8-diazaspiro[4.5]dec-2-yl}methyl)benzamide Description: amorphous;
TLC: Rf 0.46 (ethyl acetate:methanol:28% aqueous ammonia=50:10:1);
NMR (CDCl$_3$): δ 1.50-1.63 (m, 6H), 2.34 (m, 6H), 2.55 (t, J=6.9 Hz, 2H), 3.48 (s, 2H), 3.58 (s, 2H), 4.63 (br-s, 4H), 7.00 (br-s, 2H), 7.08 (br-s, 2H), 7.38 (d, J=8.1 Hz, 2H), 7.43 (m, 1H), 7.48-7.51 (m, 2H), 7.56 (m, 1H), 7.67 (d, J=8.1 Hz, 2H).

Example 8(35)

N,N-bis(1H-imidazol-2-ylmethyl)-4-({8-[4-(trifluoromethyl)benzyl]-2,8-diazaspiro[4.5]dec-2-yl}methyl)benzamide Description: amorphous;
TLC: Rf 0.41 (ethyl acetate:methanol:28% aqueous ammonia=50:10:1);
NMR (CDCl$_3$): δ 1.56-1.67 (m, 6H), 2.35-2.42 (m, 6H), 2.62 (t, J=6.6 Hz, 2H), 3.55 (s, 2H), 3.63 (s, 2H), 4.60 (br-s, 4H), 7.02 (br-s, 4H), 7.37 (d, J=8.1 Hz, 2H), 7.48 (d, J=7.8 Hz, 2H), 7.50 (d, J=7.8 Hz, 2H), 7.60 (d, J=8.1 Hz, 2H).

Example 8(36)

2,6-dichloro-N,N-bis(1H-imidazol-2-ylmethyl)-4-({8-[(3-methyl-2-thienyl)methyl]-2,8-diazaspiro[4.5]dec-2-yl}methyl)benzamide Description: amorphous;
TLC: Rf 0.42 (ethyl acetate:methanol:28% aqueous ammonia=90:10:2);
NMR (CDCl$_3$): δ 1.48-1.68 (m, 6H), 2.17 (s, 3H), 2.25-2.50 (m, 6H), 2.53 (t, J=6.9 Hz, 2H), 3.50 (s, 2H), 3.58 (s, 2H), 4.50 (s, 2H), 4.79 (s, 2H), 6.75 (d, J=4.8 Hz, 1H), 6.95 (s, 2H), 7.03 (s, 2H), 7.09 (d, J=4.8 Hz, 1H), 7.25 (s, 2H).

Example 8(37)

4-{[[trans-4-(dipropylamino)cyclohexyl](methyl)amino]methyl}-N,N-bis(1H-imidazol-2-ylmethyl)benzamide

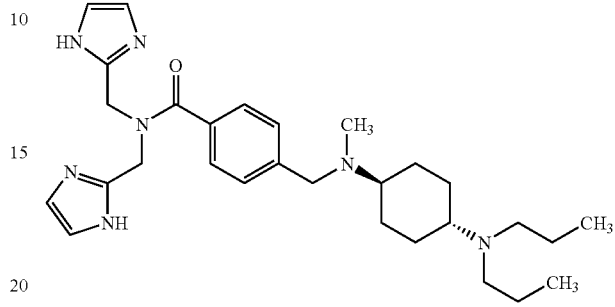

Description: amorphous;
TLC: Rf 0.21 (chloroform:methanol:28% aqueous ammonia=80:10:1);
NMR (DMSO-d$_6$): δ 0.80 (t, J=7.50 Hz, 6H), 1.06-1.42 (m, 8H), 1.63-1.75 (m, 2H), 1.75-1.88 (m, 2H), 2.05 (s, 3H), 2.21-2.44 (m, 6H), 3.50 (s, 2H), 4.45-4.70 (m, 4H), 6.68-7.19 (m, 4H), 7.27 (d, J=8.10 Hz, 2H), 7.41 (d, J=8.10 Hz, 2H), 11.81-12.73 (m, 2H).

Example 8(38)

4-{[[trans-4-(dipropylamino)cyclohexyl](ethyl)amino]methyl}-N,N-bis(1H-imidazol-2-ylmethyl)benzamide Description: amorphous;
TLC: Rf 0.35 (chloroform:methanol:28% aqueous ammonia=80:10:1);
NMR (DMSO-d$_6$): δ 0.81 (t, J=7.20 Hz, 6H), 0.90 (t, J=6.90 Hz, 3H), 1.13-1.50 (m, 8H), 1.63-1.90 (m, 4H), 2.22-2.48 (m, 8H), 3.52-3.63 (m, 2H), 4.44-4.70 (m, 4H), 6.86-7.09 (m, 4H), 7.31 (d, J=8.10 Hz, 2H), 7.42 (d, J=8.10 Hz, 2H), 11.83-12.80 (m, 2H).

Example 8(39)

N,N-bis(1H-imidazol-2-ylmethyl)-4-[(8-{[3-(trifluoromethyl)-2-thienyl]methyl}-2,8-diazaspiro[4.5]dec-2-yl)methyl]benzamide Description: amorphous;
TLC: Rf 0.37 (28% aqueous ammonia:methanol:ethyl acetate=2:8:90);
NMR (CDCl$_3$): δ 1.56-1.67 (m, 6H), 2.35-2.49 (m, 6H), 2.52-2.63 (m, 2H), 3.60 (s, 2H), 3.72 (s, 2H), 4.61-4.74 (m, 4H), 6.94-7.10 (m, 5H), 7.15-7.24 (m, 1H), 7.31-7.40 (m, 2H), 7.50-7.59 (m, 2H).

Example 8(40)

4-[(8-{[3-(hydroxymethyl)-2-thienyl]methyl}-2,8-diazaspiro[4.5]dec-2-yl)methyl]-N,N-bis(1H-imidazol-2-ylmethyl)benzamide Description: amorphous;
TLC: Rf 0.53 (28% aqueous ammonia:methanol:chloroform=2:13:90);
NMR (CDCl$_3$): δ 1.52-1.66 (m, 6H), 2.34-2.50 (m, 6H), 2.53-2.64 (m, 2H), 3.61 (s, 4H), 4.57 (s, 2H), 4.60-4.71 (m, 4H), 6.94-7.09 (m, 6H), 7.32-7.44 (m, 2H), 7.59-7.70 (m, 2H).

Example 8(41)

2-{[2-(4-{[bis(1H-imidazol-2-ylmethyl)amino]carbonyl}benzyl)-2,8-diazaspiro[4.5]dec-8-yl]methyl}-3-thiophenecarboxylic Acid Description: amorphous;
TLC: Rf 0.70 (28% aqueous ammonia:methanol:chloroform=5:15:35);
NMR (CD$_3$OD): δ 1.74-1.87 (m, 6H), 2.58 (s, 2H), 2.70-2.80 (m, 2H), 3.03-3.17 (m, 4H), 3.74 (s, 2H), 4.38 (s, 2H), 4.61-4.78 (m, 4H), 7.03 (s, 4H), 7.34-7.43 (m, 3H), 7.43-7.51 (m, 3H).

Example 8(42)

2-{[2-(4-{[bis(1H-imidazol-2-ylmethyl)amino]carbonyl}benzyl)-2,8-diazaspiro[4.5]dec-8-yl]methyl}-3-thiophenecarboxamide Description: amorphous;
TLC: Rf 0.45 (28% aqueous ammonia:methanol:chloroform=2:13:90);
NMR (CD$_3$OD): δ 1.54-1.68 (m, 6H), 2.34-2.50 (m, 6H), 2.52-2.65 (m, 2H), 3.60 (s, 2H), 3.73 (s, 2H), 4.61-4.80 (m, 4H), 7.00 (s, 4H), 7.23-7.30 (m, 1H), 7.33-7.41 (m, 3H), 7.43-7.51 (m, 2H).

Example 8(43)

N,N-bis(1H-imidazol-2-ylmethyl)-4-({8-[(3-methoxy-2-thienyl)methyl]-2,8-diazaspiro[4.5]dec-2-yl}methyl)benzamide

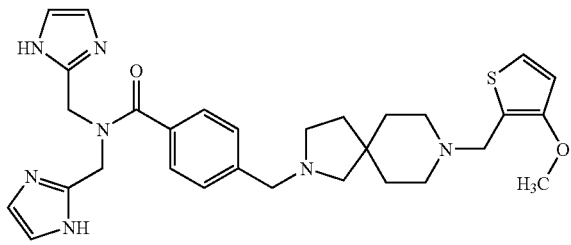

Description: amorphous;
TLC: Rf 0.23 (28% aqueous ammonia:methanol:ethyl acetate=2:8:90);
NMR (CDCl$_3$): δ 1.51-1.65 (m, 6H), 2.31-2.46 (m, 6H), 2.49-2.58 (m, 2H), 3.55 (s, 2H), 3.62 (s, 2H), 3.79 (s, 3H), 4.58-4.72 (m, 4H), 6.77-6.83 (m, 1H), 6.89-7.04 (m, 4H), 7.07-7.14 (m, 1H), 7.29-7.38 (m, 2H), 7.54-7.66 (m, 2H).

Example 8(44)

4-({benzyl[trans-4-(dipropylamino)cyclohexyl]amino}methyl)-N,N-bis(1H-imidazol-2-ylmethyl)benzamide Description: amorphous;
TLC: Rf 0.57 (chloroform:methanol:28% aqueous ammonia=80:10:1);
NMR (DMSO-d$_6$): δ 0.81 (t, J=7.50 Hz, 6H), 1.31 (m, 8H), 1.87 (m, 4H), 2.37 (m, 6H), 3.57 (m, 4H), 4.54 (m, 4H), 6.97 (m, 4H), 7.22 (m, 7H), 7.41 (d, J=8.10 Hz, 2H), 12.23 (m, 2H).

Example 8(45)

4-[({trans-4-[(2-hydroxyethyl)(2-thienylmethyl)amino]cyclohexyl}amino)methyl]-N,N-bis(1H-imidazol-2-ylmethyl)benzamide Description: amorphous;
TLC: Rf 0.63 (methanol:28% aqueous ammonia=98:2);
NMR (CDCl$_3$): δ 0.98-1.20 (m, 2H), 1.20-1.45 (m, 2H), 1.73-1.91 (m, 2H), 1.92-2.12 (m, 2H), 2.30-2.47 (m, 1H), 2.50-2.66 (m, 1H), 2.69 (t, J=5.40 Hz, 2H), 3.41-3.57 (m, 2H), 3.80 (s, 2H), 3.84 (s, 2H), 4.49-4.75 (m, 4H), 6.87 (dd, J=3.60, 1.20 Hz, 1H), 6.92 (dd, J=5.10, 3.60 Hz, 1H), 6.94-7.11 (m, 4H), 7.20 (dd, J=5.10, 1.20 Hz, 1H), 7.34 (d, J=8.40 Hz, 2H), 7.58 (d, J=8.40 Hz, 2H).

Example 8(46)

4-[({trans-4-[(3-hydroxypropyl)(2-thienylmethyl)amino]cyclohexyl}amino)methyl]-N,N-bis(1H-imidazol-2-ylmethyl)benzamide Description: amorphous;
TLC: Rf 0.63 (methanol:28% aqueous ammonia=98:2);
NMR (CDCl$_3$): δ 0.96-1.22 (m, 2H), 1.22-1.47 (m, 2H), 1.60-1.77 (m, 2H), 1.76-1.92 (m, 2H), 1.91-2.11 (m, 2H), 2.28-2.48 (m, 1H), 2.56-2.80 (m, 3H), 3.66-3.90 (m, 6H), 4.50-4.75 (m, 4H), 6.87-6.96 (m, 2H), 6.96-7.11 (m, 4H), 7.21 (dd, J=4.8, 1.5 Hz, 1H), 7.34 (d, J=8.1 Hz, 2H), 7.60 (d, J=8.1 Hz, 2H).

Example 8(47)

4-{[(trans-4-{(2-hydroxyethyl)[(3-methyl-2-thienyl)methyl]amino}cyclohexyl)amino]methyl}-N,N-bis(1H-imidazol-2-ylmethyl)benzamide Description: amorphous;
TLC: Rf 0.64 (methanol:28% aqueous ammonia=98:2);
NMR (CDCl$_3$): δ 0.97-1.21 (m, 2H), 1.21-1.47 (m, 2H), 1.72-1.91 (m, 2H), 1.92-2.10 (m, 2H), 2.16 (s, 3H), 2.30-2.50 (m, 1H), 2.48-2.76 (m, 3H), 3.39-3.56 (m, 2H), 3.73 (s, 2H), 3.80 (s, 2H), 4.48-4.76 (m, 4H), 6.77 (d, J=5.1 Hz, 1H), 6.87-7.07 (m, 4H), 7.09 (d, J=5.1 Hz, 1H), 7.34 (d, J=8.1 Hz, 2H), 7.59 (d, J=8.1 Hz, 2H).

Example 8(48)

4-{[(trans-4-{(3-hydroxypropyl)[(3-methyl-2-thienyl)methyl]amino}cyclohexyl)amino]methyl}-N,N-bis(1H-imidazol-2-ylmethyl)benzamide Description: amorphous;
TLC: Rf 0.69 (methanol:28% aqueous ammonia=98:2);
NMR (CDCl$_3$): δ 0.97-1.22 (m, 2H), 1.22-1.49 (m, 2H), 1.58-1.75 (m, 2H), 1.75-1.92 (m, 2H), 1.92-2.10 (m, 2H), 2.18 (s, 3H), 2.29-2.48 (m, 1H), 2.55-2.79 (m, 3H), 3.60-3.77 (m, 4H), 3.81 (s, 2H), 4.49-4.73 (m, 4H), 6.77 (d, J=5.10 Hz, 1H), 6.92-7.10 (m, 4H), 7.12 (d, J=5.10 Hz, 1H), 7.36 (d, J=8.10 Hz, 2H), 7.65 (d, J=8.10 Hz, 2H).

Example 8(49)

N,N-bis(1H-imidazol-2-ylmethyl)-4-[({trans-4-[propyl(2-thienylmethyl)amino]cyclohexyl}amino)methyl]benzamide Description: amorphous;
TLC: Rf 0.64 (methanol:28% aqueous ammonia=98:2);
NMR (CDCl$_3$): δ 0.85 (t, J=7.20 Hz, 3H), 0.97-1.55 (m, 6H), 1.72-1.91 (m, 2H), 1.91-2.09 (m, 2H), 2.29-2.64 (m, 4H), 3.69-3.90 (m, 4H), 4.48-4.77 (m, 4H), 6.85 (dd, J=3.30, 1.20 Hz, 1H), 6.91 (dd, J=5.10, 3.30 Hz, 1H), 6.93-7.10 (m, 4H), 7.16 (dd, J=5.10, 1.20 Hz, 1H), 7.33 (d, J=8.10 Hz, 2H), 7.55 (d, J=8.10 Hz, 2H).

Example 8(50)

N,N-bis(1H-imidazol-2-ylmethyl)-4-[({trans-4-[[(3-methyl-2-thienyl)methyl](propyl)amino]cyclohexyl}amino)methyl]benzamide Description: amorphous;
TLC: Rf 0.67 (methanol:28% aqueous ammonia=98:2);
NMR (CDCl$_3$): δ 0.85 (t, J=7.20 Hz, 3H), 0.98-1.19 (m, 2H), 1.20-1.53 (m, 4H), 1.72-1.91 (m, 2H), 1.91-2.08 (m, 2H), 2.15 (s, 3H), 2.29-2.65 (m, 4H), 3.66 (s, 2H), 3.80 (s, 2H), 4.48-4.78 (m, 4H), 6.75 (d, J=5.10 Hz, 1H), 6.91-7.12 (m, 5H), 7.34 (d, J=8.10 Hz, 2H), 7.56 (d, J=8.10 Hz, 2H).

Example 8(51)

N,N-bis(1H-imidazol-2-ylmethyl)-4-{[(trans-4-{[(3-methyl-2-thienyl)methyl]amino}cyclohexyl)amino]methyl}benzamide Description: amorphous;
TLC: Rf 0.53 (methanol:28% aqueous ammonia=98:2);
NMR (CDCl$_3$): δ 1.01-1.30 (m, 4H), 1.84-2.08 (m, 4H), 2.18 (s, 3H), 2.36-2.64 (m, 2H), 3.82 (s, 2H), 3.90 (s, 2H), 4.46-4.78 (m, 4H), 6.79 (d, J=5.10 Hz, 1H), 6.92-7.07 (m, 4H), 7.08 (d, J=5.10 Hz, 1H), 7.35 (d, J=8.10 Hz, 2H), 7.58 (d, J=8.10 Hz, 2H).

Example 8(52)

4-(2-{[4-(dipropylamino)cyclohexyl]amino}ethyl)-N,N-bis(1H-imidazol-2-ylmethyl)benzamide Description: amorphous;
TLC: Rf 0.63 (ethyl acetate:methanol:28% aqueous ammonia=50:10:1);
NMR (CDCl$_3$): δ 0.82 (t, J=7.2 Hz, 6H), 1.25-1.46 (m, 10H), 1.65-1.74 (m, 2H), 2.34-2.45 (m, 5H), 2.72 (m, 1H), 2.79-2.83 (m, 4H), 4.58 (br-s, 2H), 4.64 (br-s, 2H), 7.01 (br-s, 2H), 7.08 (br-s, 2H), 7.27 (d, J=8.4 Hz, 2H), 7.66 (d, J=8.4 Hz, 2H).

Example 8(53)

N,N-bis(1H-imidazol-2-ylmethyl)-4-{[8-(2-nitrobenzyl)-2,8-diazaspiro[4.5]dec-2-yl]methyl}benzamide Description: amorphous;
TLC: Rf 0.60 (dichrolomethane:methanol:28% aqueous ammonia=50:10:1);
NMR (CDCl$_3$): δ 1.52-1.61 (m, 6H), 2.26-2.36 (m, 6H), 2.54 (t, J=6.9 Hz, 2H), 3.58 (s, 2H), 3.72 (s, 2H), 4.61 (br-s, 4H), 6.99 (br-s, 2H), 7.07 (br-s, 2H), 7.35 (m, 1H), 7.37 (d, J=8.3 Hz, 2H), 7.50 (m, 1H), 7.59 (d, J=8.1 Hz, 1H), 7.68 (d, J=8.3 Hz, 2H), 7.78 (d, J=8.1 Hz, 1H).

Example 8(54)

4-{[8-(2-cyanobenzyl)-2,8-diazaspiro[4.5]dec-2-yl]methyl}-N,N-bis(1H-imidazol-2-ylmethyl)benzamide Description: amorphous;
TLC: Rf 0.53 (dichrolomethane:methanol:28% aqueous ammonia=50:10:1);
NMR (CDCl$_3$): δ 1.55-1.63 (m, 6H), 2.35-2.44 (m, 6H), 2.55 (t, J=6.9 Hz, 2H), 3.59 (s, 2H), 3.64 (s, 2H), 4.63 (br-s, 4H), 7.02 (br-s, 2H), 7.09 (br-s, 2H), 7.32 (m, 1H), 7.38 (d, J=8.1 Hz, 2H), 7.53-7.55 (m, 2H), 7.62 (d, J=7.2 Hz, 1H), 7.67 (d, J=8.1 Hz, 2H).

Example 8(55)

N,N-bis(1H-imidazol-2-ylmethyl)-4-({8-[2-(trifluoromethoxy)benzyl]-2,8-diazaspiro[4.5]dec-2-yl}methyl)benzamide Description: amorphous;
TLC: Rf 0.50 (dichrolomethane:methanol:28% aqueous ammonia=50:10:1);
NMR (CDCl$_3$): δ 1.55-1.66 (m, 6H), 2.33-2.40 (m, 6H), 2.55 (t, J=6.9 Hz, 2H), 3.52 (s, 2H), 3.58 (s, 2H), 4.67 (br-s, 2H), 4.71 (br-s, 2H), 7.01 (br-s, 2H), 7.04 (br-s, 2H), 7.20-7.26 (m, 3H), 7.35 (d, J=8.1 Hz, 2H), 7.50 (d, J=8.0 Hz, 2H), 7.56 (m, 1H).

Example 8(56)

N,N-bis(1H-imidazol-2-ylmethyl)-4-({8-[2-(methylthio)benzyl]-2,8-diazaspiro[4.5]dec-2-yl}methyl)benzamide Description: amorphous;
TLC: Rf 0.51 (dichrolomethane:methanol:28% aqueous ammonia=50:10:1);
NMR (CDCl$_3$): δ 1.54-1.63 (m, 6H), 2.35-2.42 (m, 6H), 2.43 (s, 3H), 2.54 (t, J=6.9 Hz, 2H), 3.50 (s, 2H), 3.57 (s, 2H), 4.67 (br-s, 2H), 4.72 (br-s, 2H), 6.99 (br-s, 2H), 7.04 (br-s, 2H), 7.09 (m, 1H), 7.21-7.23 (m, 2H), 7.31 (m, 1H), 7.34 (d, J=8.1 Hz, 2H), 7.49 (d, J=8.1 Hz, 2H).

Example 8(57)

4-{[8-(2-hydroxybenzyl)-2,8-diazaspiro[4.5]dec-2-yl]methyl}-N,N-bis(1H-imidazol-2-ylmethyl)benzamide Description: amorphous;
TLC: Rf 0.55 (dichloromethane:methanol:28% aqueous ammonia=50:10:1);
NMR (CDCl$_3$): δ 1.58-1.66 (m, 6H), 2.33-2.37 (m, 6H), 2.56 (t, J=6.9 Hz, 2H), 3.57 (s, 2H), 3.66 (s, 2H), 4.67 (br-s, 2H), 4.71 (br-s, 2H), 6.73-6.81 (m, 2H), 6.93 (d, J=7.8 Hz, 1H), 7.00 (br-s, 2H), 7.05 (br-s, 2H), 7.15 (m, 1H), 7.34 (d, J=8.1 Hz, 2H), 7.51 (d, J=8.1 Hz, 2H).

Example 8(58)

4-({[2-(4-cyclohexyl-1-piperazinyl)-2-oxoethyl]amino}methyl)-N,N-bis(1H-imidazol-2-ylmethyl)benzamide Description: amorphous;
TLC: Rf 0.83 (chloroform:methanol:28% aqueous ammonia=40:10:2);
NMR (CD$_3$OD): δ 1.05-1.35 (m, 5H), 1.57-1.68 (m, 1H), 1.73-1.91 (m, 4H), 2.22-2.38 (m, 1H), 2.52-2.61 (m, 4H), 3.39-3.44 (m, 2H), 3.45 (s, 2H), 3.52-3.60 (m, 2H), 3.78 (s, 2H), 4.50-4.81 (m, 4H), 7.02 (s, 4H), 7.39 (d, J=8.4 Hz, 2H), 7.49 (d, J=8.4 Hz, 2H).

Example 8(59)

4-({8-[(3-fluoro-2-thienyl)methyl]-2,8-diazaspiro[4.5]dec-2-yl}methyl)-N,N-bis(1H-imidazol-2-ylmethyl)benzamide Description: amorphous;
TLC: Rf 0.20 (28% aqueous ammonia:methanol:ethyl acetate=2:8:90);
NMR (CDCl$_3$): δ 1.51-1.65 (m, 6H), 2.31-2.45 (m, 6H), 2.51-2.62 (m, 2H), 3.54-3.65 (m, 4H), 4.61-4.72 (m, 4H), 6.71-6.75 (m, 1H), 6.93-7.04 (m, 4H), 7.06-7.10 (m, 1H), 7.30-7.38 (m, 2H), 7.55-7.60 (m, 2H).

Example 8(60)

N,N-bis(1H-imidazol-2-ylmethyl)-4-({8-[(5-nitro-2-thienyl)methyl]-2,8-diazaspiro[4.5]dec-2-yl}methyl)benzamide Description: amorphous;
TLC: Rf 0.11 (28% aqueous ammonia:methanol:ethyl acetate=2:8:90);
NMR (CDCl$_3$): δ 1.55-1.68 (m, 6H), 2.35-2.49 (m, 6H), 2.51-2.65 (m, 2H), 3.55-3.67 (m, 4H), 4.62-4.76 (m, 4H), 6.76-6.86 (m, 1H), 6.90-7.04 (m, 4H), 7.29-7.39 (m, 2H), 7.48-7.60 (m, 2H), 7.71-7.84 (m, 1H).

Example 8(61)

4-{[[trans-4-(dipropylamino)cyclohexyl](1H-imidazol-2-ylmethyl)amino]methyl}-N,N-bis(1H-imidazol-2-ylmethyl)benzamide Description: amorphous;
TLC: Rf 0.67 (chloroform:methanol:28% aqueous ammonia=80:20:4);
NMR (DMSO-d$_6$): δ 0.78 (t, J=7.20 Hz, 6H), 1.07 (m, 2H), 1.29 (m, 6H), 1.66 (m, 2H), 1.80 (m, 2H), 2.29 (m, 6H), 3.59 (m, 4H), 4.56 (m, 4H), 6.72 (m, 4H), 6.97 (m, 5H), 7.38 (m, 4H), 11.59 (m, 1H), 12.27 (m, 2H).

Example 8(62)

N,N-bis(1H-imidazol-2-ylmethyl)-4-{[9-(2-thienylmethyl)-3,9-diazaspiro[5.5]undec-3-yl]methyl}benzamide Description: amorphous;
TLC: Rf 0.58 (chloroform:methanol:28% aqueous ammonia=40:9:1);
NMR (CDCl$_3$): δ 1.41-1.55 (m, 8H), 2.28-2.46 (m, 8H), 3.47 (s, 2H), 3.71 (s, 2H), 4.62 (s, 2H), 4.66 (s, 2H), 6.88 (dd, J=3.6, 0.9 Hz, 1H), 6.93 (dd, J=5.1, 3.6 Hz, 1H), 6.95 (s, 2H), 7.02 (s, 2H), 7.20 (dd, J=5.1, 0.9 Hz, 1H), 7.34 (d, J=8.1 Hz, 2H), 7.57 (d, J=8.1 Hz, 2H).

Example 8(63)

N-(1H-imidazol-2-ylmethyl)-N-[4-({8-[(3-methyl-2-thienyl)methyl]-2,8-diazaspiro[4.5]dec-2-yl}methyl)benzyl]-1H-imidazole-2-carboxamide Description: amorphous;
TLC: Rf 0.52 (chloroform:methanol:28% aqueous ammonia=80:10:1);
NMR (CDCl$_3$): δ 1.46-1.81 (m, 6H), 2.17 (s, 3H), 2.31-2.48 (m, 6H), 2.56 (t, J=6.6 Hz, 2H), 3.57 (s, 4H), 4.75 (s, 2H), 4.95 (s, 2H), 6.76 (d, J=5.1 Hz, 1H), 7.07 (s, 2H), 7.10 (d, J=5.1 Hz, 1H), 7.18-7.32 (m, 4H), 7.37 (d, J=8.1 Hz, 2H), 11.04 (s, 1H), 12.10 (s, 1H).

Example 8(64)

N,N-bis(1H-imidazol-2-ylmethyl)-4-({2-[(3-methyl-2-thienyl)methyl]-2,8-diazaspiro[4.5]dec-8-yl}methyl)benzamide Description: amorphous;
TLC: Rf 0.13 (28% aqueous ammonia:methanol:ethyl acetate=2:8:90);
NMR (CDCl$_3$): δ 1.51-1.65 (m, 6H), 2.20 (s, 3H), 2.27-2.43 (m, 6H), 2.57-2.67 (m, 2H), 3.46 (s, 2H), 3.70 (s, 2H), 4.60-4.74 (m, 4H), 6.73-6.81 (m, 1H), 6.96-7.10 (m, 5H), 7.28-7.38 (m, 2H), 7.49-7.58 (m, 2H).

Example 8(65)

N,N-bis(1H-imidazol-2-ylmethyl)-4-{[2-(2-thienylmethyl)-2,9-diazaspiro[5.5]undec-9-yl]methyl}benzamide Description: amorphous;
TLC: Rf 0.18 (28% aqueous ammonia:methanol:ethyl acetate=2:8:90);
NMR (CDCl$_3$): δ 1.23-1.36 (m, 2H), 1.46-1.61 (m, 6H), 2.12-2.18 (m, 2H), 2.22-2.29 (m, 2H), 2.31-2.43 (m, 4H), 3.43 (s, 2H), 3.61 (s, 2H), 4.60-4.74 (m, 4H), 6.82-6.87 (m, 1H), 6.88-6.95 (m, 1H), 6.95-7.07 (m, 4H), 7.15-7.21 (m, 1H), 7.28-7.36 (m, 2H), 7.47-7.56 (m, 2H).

Example 8(66)

N,N-bis(1H-imidazol-2-ylmethyl)-4-({2-[(3-methyl-2-thienyl)methyl]-2,9-diazaspiro[5.5]undec-9-yl}methyl)benzamide Description: amorphous;
TLC: Rf 0.18 (28% aqueous ammonia:methanol:ethyl acetate=2:8:90);
NMR (CDCl$_3$): δ 1.23-1.36 (m, 2H), 1.45-1.60 (m, 6H), 2.14-2.28 (m, 7H), 2.31-2.42 (m, 4H), 3.44 (s, 2H), 3.50 (s, 2H), 4.60-4.74 (m, 4H), 6.72-6.80 (m, 1H), 6.95-7.09 (m, 5H), 7.27-7.36 (m, 2H), 7.46-7.56 (m, 2H).

Example 8(67)

N,N-bis(1H-imidazol-2-ylmethyl)-4-{[9-(2-thienyl-methyl)-2,9-diazaspiro[5.5]undec-2-yl]methyl}benzamide Description: amorphous;
TLC: Rf 0.28 (28% aqueous ammonia:methanol:ethyl acetate=2:8:90);
NMR (CDCl$_3$): δ 1.22-1.36 (m, 2H), 1.46-1.61 (m, 6H), 2.00-2.15 (m, 2H), 2.27-2.43 (m, 6H), 3.39 (s, 2H), 3.66 (s, 2H), 4.60-4.75 (m, 4H), 6.81-6.86 (m, 1H), 6.87-6.93 (m, 1H), 6.95-7.08 (m, 4H), 7.13-7.21 (m, 1H), 7.28-7.38 (m, 2H), 7.46-7.60 (m, 2H).

Example 8(68)

N,N-bis(1H-imidazol-2-ylmethyl)-4-({9-[(3-methyl-2-thienyl)methyl]-2,9-diazaspiro[5.5]undec-2-yl}methyl)benzamide Description: amorphous;
TLC: Rf 0.30 (28% aqueous ammonia:methanol:ethyl acetate=2:8:90);
NMR (CDCl$_3$): δ 1.24-1.38 (m, 2H), 1.46-1.61 (m, 6H), 2.05-2.20 (m, 5H), 2.27-2.43 (m, 6H), 3.41 (s, 2H), 3.57 (s, 2H), 4.60-4.75 (m, 4H), 6.71-6.78 (m, 1H), 6.95-7.10 (m, 5H), 7.29-7.39 (m, 2H), 7.47-7.60 (m, 2H).

Example 8(69)

N,N-bis(1H-imidazol-2-ylmethyl)-4-({4-[(3-methyl-2-thienyl)methyl]-1-oxa-4,9-diazaspiro[5.5]undec-9-yl}methyl)benzamide Description: amorphous;
TLC: Rf 0.20 (28% aqueous ammonia:methanol:ethyl acetate=2:8:90);
NMR (CDCl$_3$): δ 1.49-1.62 (m, 2H), 1.88-2.02 (m, 2H), 2.17 (s, 3H), 2.21-2.27 (m, 2H), 2.30-2.39 (m, 2H), 2.42-2.50 (m, 4H), 3.46-3.57 (m, 4H), 3.66-3.77 (m, 2H), 4.60-4.74 (m, 4H), 6.73-6.80 (m, 1H), 6.96-7.11 (m, 5H), 7.29-7.39 (m, 2H), 7.49-7.58 (m, 2H).

Example 8(70)

4-[(8-{[3-(1-hydroxyethyl)-2-thienyl]methyl}-2,8-diazaspiro[4.5]dec-2-yl)methyl]-N,N-bis(1H-imidazol-2-ylmethyl)benzamide Description: amorphous;
TLC: Rf 0.57 (28% aqueous ammonia:methanol:chloroform=2:13:90);
NMR (CDCl$_3$): δ 1.49-1.63 (m, 9H), 2.33-2.56 (m, 8H), 3.39-3.48 (m, 1H), 3.56 (s, 2H), 3.70-3.80 (m, 1H), 4.57-4.70 (m, 4H), 4.85-4.93 (m, 1H), 6.95-7.09 (m, 6H), 7.31-7.39 (m, 2H), 7.57-7.65 (m, 2H).

Example 8(71)

N,N-bis(1H-imidazol-2-ylmethyl)-4-({8-[(3-methyl-2-thienyl)carbonyl]-2,8-diazaspiro[4.5]dec-2-yl}methyl)benzamide Description: amorphous;
TLC: Rf 0.67 (ethyl acetate:methanol:28% aqueous ammonia=80:20:2);
NMR (CDCl$_3$): δ d 1.55-1.65 (m, 4H), 1.68 (t, J=7.2 Hz, 2H), 2.24 (s, 3H), 2.40 (s, 2H), 2.60 (t, J=7.2 Hz, 2H), 3.42-3.60 (m, 4H), 3.60 (s, 2H), 4.60-4.78 (m, 4H), 6.81 (d, J=4.8 Hz, 1H), 6.98-7.14 (m, 4H), 7.24 (d, J=4.8 Hz, 1H), 7.37 (d, J=8.4 Hz, 2H), 7.60 (d, J=8.4 Hz, 2H).

Example 8(72)

ethyl{(4-{[bis(1H-imidazol-2-ylmethyl)amino]carbonyl}benzyl)[trans-4-(dipropylamino)cyclo-hexyl]amino}acetate Description: amorphous;
TLC: Rf 0.28 (chloroform:methanol:28% aqueous ammonia=80:10:1);
NMR (DMSO-d$_6$): δ 0.83 (t, J=7.50 Hz, 6H), 1.12 (t, J=7.20 Hz, 3H), 1.18-1.62 (m, 8H), 1.71-1.96 (m, 4H), 2.23-2.75 (m, 6H), 3.28 (s, 2H), 3.73 (s, 2H), 4.00 (q, J=6.90 Hz, 2H), 4.46-4.68 (m, 4H), 6.86-7.10 (m, 4H), 7.34 (d, J=8.10 Hz, 2H), 7.42 (d, J=8.10 Hz, 2H), 11.41-13.06 (m, 2H).

Example 8(73)

N,N-bis(1H-imidazol-2-ylmethyl)-4-{[7-(2-thienyl-methyl)-2,7-diazaspiro[4.4]non-2-yl]methyl}benzamide Description: amorphous;
TLC: Rf 0.45 (chloroform:methanol:28% aqueous ammonia=40:9:1);
NMR (CDCl$_3$): δ 1.73-1.92 (m, 4H), 2.32-2.67 (m, 8H), 3.58 (s, 2H), 3.79 (s, 2H), 4.60-4.73 (m, 4H), 6.86-6.89 (m, 1H), 6.91 (dd, J=5.00, 3.50 Hz, 1H), 6.95-7.10 (m, 4H), 7.19 (dd, J=5.00, 1.50 Hz, 1H), 7.34 (d, J=8.00 Hz, 2H), 7.55 (d, J=8.00 Hz, 2H).

Example 8(74)

N,N-bis(1H-imidazol-2-ylmethyl)-4-{[9-(2-thienyl-methyl)-1-oxa-4,9-diazaspiro[5.5]undec-4-yl]methyl}benzamide Description: amorphous;
TLC: Rf 0.60 (chloroform:methanol:28% aqueous ammonia=40:9:1);
NMR (CDCl$_3$): δ 1.48-1.60 (m, 2H), 1.90-2.01 (m, 2H), 2.19 (s, 2H), 2.32-2.41 (m, 4H), 2.49-2.58 (m, 2H), 3.43 (s, 2H), 3.67-3.72 (m, 4H), 4.59-4.71 (m, 4H), 6.87-6.90 (m, 1H), 6.92 (dd, J=5.1, 3.6 Hz, 1H), 6.97-7.10 (m, 4H), 7.20 (dd, J=5.1, 1.50 Hz, 1H), 7.36 (d, J=8.4 Hz, 2H), 7.60 (d, J=8.4 Hz, 2H).

Example 8(75)

N,N-bis(1H-imidazol-2-ylmethyl)-4-({9-[(3-methyl-2-thienyl)methyl]-1-oxa-4,9-diazaspiro[5.5]undec-4-yl}methyl)benzamide Description: amorphous;
TLC: Rf 0.61 (chloroform:methanol:28% aqueous ammonia=40:9:1);
NMR (CDCl$_3$): δ 1.46-1.59 (m, 2H), 1.90-2.01 (m, 2H), 2.17 (s, 3H), 2.17-2.21 (m, 2H), 2.31-2.42 (m, 4H), 2.50-2.60 (m, 2H), 3.43 (s, 2H), 3.59 (s, 2H), 3.67-3.74 (m, 2H), 4.59-4.71 (m, 4H), 6.76 (d, J=5.1 Hz, 1H), 6.97-7.09 (m, 4H), 7.10 (d, J=5.1 Hz, 1H), 7.36 (d, J=8.1 Hz, 2H), 7.60 (d, J=8.1 Hz, 2H).

Example 8(76)

N,N-bis(1H-imidazol-2-ylmethyl)-4-{[2-(2-thienylmethyl)-2,7-diazaspiro[3.5]non-7-yl]methyl}benzamide Description: amorphous;
TLC: Rf 0.59 (chloroform:methanol:28% aqueous ammonia=40:9:1);
NMR (CDCl$_3$): δ 1.70-1.76 (m, 4H), 2.22-2.36 (m, 4H), 3.03 (s, 4H), 3.43 (s, 2H), 3.79 (s, 2H), 4.59-4.69 (m, 4H), 6.87-6.90 (m, 1H), 6.93 (dd, J=5.1, 3.6 Hz, 1H), 6.96-7.10 (m, 4H), 7.19 (dd, J=5.1, 1.5 Hz, 1H), 7.35 (d, J=8.1 Hz, 2H), 7.61 (d, J=8.1 Hz, 2H).

Example 8(77)

N,N-bis(1H-imidazol-2-ylmethyl)-4-({2-[(3-methyl-2-thienyl)methyl]-2,7-diazaspiro[3.5]non-7-yl}methyl)benzamide Description: amorphous;
TLC: Rf 0.61 (chloroform:methanol:28% aqueous ammonia=40:9:1);
NMR (CDCl$_3$): δ 1.70-1.76 (m, 4H), 2.17 (s, 3H), 2.22-2.36 (m, 4H), 3.03 (s, 4H), 3.43 (s, 2H), 3.70 (s, 2H), 4.59-4.68 (m, 4H), 6.78 (d, J=5.1 Hz, 1H), 6.98-7.10 (m, 4H), 7.09 (d, J=5.1 Hz, 1H), 7.35 (d, J=8.4 Hz, 2H), 7.62 (d, J=8.4 Hz, 2H).

Example 8(78)

N,N-bis(1H-imidazol-2-ylmethyl)-4-({7-[(3-methyl-2-thienyl)methyl]-2,7-diazaspiro[4.4]non-2-yl}methyl)benzamide Description: amorphous;
TLC: Rf 0.65 (chloroform:methanol:28% aqueous ammonia=40:9:1);
NMR (CDCl$_3$): δ 1.73-1.92 (m, 4H), 2.17 (s, 3H), 2.55 (d, 8H), 3.56 (d, J=14.1 Hz, 1H), 3.61 (d, J=14.1 Hz, 1H), 3.70 (s, 2H), 4.60-4.71 (m, 4H), 6.76 (d, J=5.1 Hz, 1H), 6.96-7.07 (m, 4H), 7.08 (d, J=5.1 Hz, 1H), 7.35 (d, J=8.4 Hz, 2H), 7.58 (d, J=8.4 Hz, 2H).

Example 8(79)

N,N-bis(1H-imidazol-2-ylmethyl)-4-({9-[(3-methyl-2-thienyl)methyl]-3,9-diazaspiro[5.5]undec-3-yl}methyl)benzamide Description: amorphous;
TLC: Rf 0.64 (chloroform:methanol:28% aqueous ammonia=40:9:1);
NMR (CDCl$_3$): δ 1.43-1.53 (m, 8H), 2.18 (s, 3H), 2.31-2.38 (m, 4H), 2.38-2.45 (m, 4H), 3.49 (s, 2H), 3.60 (s, 2H), 4.59-4.70 (m, 4H), 6.77 (d, J=5.1 Hz, 1H), 6.97-7.09 (m, 4H), 7.11 (d, J=5.1 Hz, 1H), 7.36 (d, J=8.4 Hz, 2H), 7.60 (d, J=8.4 Hz, 2H).

Example 8(80)

N,N-bis(1H-imidazol-2-ylmethyl)-4-{[7-(2-thienylmethyl)-2,7-diazaspiro[3.5]non-2-yl]methyl}benzamide Description: amorphous;
TLC: Rf 0.59 (chloroform:methanol:28% aqueous ammonia=40:9:1);
NMR (CDCl$_3$): δ 1.76 (t, J=5.4 Hz, 4H), 2.29-2.42 (m, 4H), 2.99 (s, 4H), 3.63 (s, 2H), 3.65 (s, 2H), 4.57-4.69 (m, 4H), 6.86-6.89 (m, 1H), 6.92 (dd, J=5.1, 3.6 Hz, 1H), 6.96-7.10 (m, 4H), 7.21 (dd, J=5.1, 0.9 Hz, 1H), 7.31 (d, J=8.4 Hz, 2H), 7.59 (d, J=8.4 Hz, 2H).

Example 8(81)

N,N-bis(1H-imidazol-2-ylmethyl)-4-({7-[(3-methyl-2-thienyl)methyl]-2,7-diazaspiro[3.5]non-2-yl}methyl)benzamide Description: amorphous;
TLC: Rf 0.60 (chloroform:methanol:28% aqueous ammonia=40:9:1);
NMR (CDCl$_3$): δ 1.75 (t, J=5.4 Hz, 4H), 2.16 (s, 3H), 2.30-2.41 (m, 4H), 3.00 (s, 4H), 3.54 (s, 2H), 3.63 (s, 2H), 4.58-4.69 (m, 4H), 6.76 (d, J=5.1 Hz, 1H), 6.96-7.10 (m, 4H), 7.10 (d, J=5.1 Hz, 1H), 7.31 (d, J=8.4 Hz, 2H), 7.59 (d, J=8.4 Hz, 2H).

Example 8(82)

4-{[8-(2-hydroxy-2-methylpropyl)-2,8-diazaspiro[4.5]dec-2-yl]methyl}-N,N-bis(1H-imidazol-2-ylmethyl)benzamide Description: amorphous;
TLC: Rf 0.30 (dichrolomethane:methanol:28% aqueous ammonia=90:10:1);
NMR (CDCl$_3$): δ 1.14 (s, 6H), 1.52-1.65 (m, 6H), 2.26 (s, 2H), 2.33 (s, 2H), 2.44-2.60 (m, 6H), 3.57 (s, 2H), 4.60-4.73 (m, 4H), 6.95-7.10 (m, 4H), 7.36 (d, J=8.4 Hz, 2H), 7.57 (d, J=8.4 Hz, 2H).

Example 8(83)

4-{[8-(3-hydroxy-3-methylbutyl)-2,8-diazaspiro[4.5]dec-2-yl]methyl}-N,N-bis(1H-imidazol-2-ylmethyl)benzamide Description: amorphous;
TLC: Rf 0.31 (dichrolomethane:methanol:28% aqueous ammonia=90:10:1);
NMR (CDCl$_3$): δ 1.20 (s, 6H), 1.50-1.65 (m, 8H), 2.20-2.61 (m, 10H), 3.56 (s, 2H), 4.60-4.73 (m, 4H), 6.95-7.09 (m, 4H), 7.35 (d, J=8.1 Hz, 2H), 7.56 (d, J=8.1 Hz, 2H).

Example 8(84)

4-{[8-(4-hydroxy-4-methylpentyl)-2,8-diazaspiro[4.5]dec-2-yl]methyl}-N,N-bis(1H-imidazol-2-ylmethyl)benzamide Description: amorphous;
TLC: Rf 0.32 (dichrolomethane:methanol:28% aqueous ammonia=90:10:1);
NMR (CDCl$_3$): δ 1.19 (s, 6H), 1.54-1.70 (m, 10H), 2.20-2.58 (m, 10H), 3.56 (s, 2H), 4.60-4.75 (m, 4H), 6.94-7.10 (m, 4H), 7.35 (d, J=8.1 Hz, 2H), 7.56 (d, J=8.1 Hz, 2H).

Example 8(85)

N,N-bis(1H-imidazol-2-ylmethyl)-4-[({(3S)-1-[(3-methyl-2-thienyl)methyl]-3-piperidinyl}amino)methyl]benzamide Description: amorphous;
TLC: Rf 0.33 (chloroform:methanol:28% aqueous ammonia=80:10:1);
NMR (CDCl$_3$): δ 1.18-1.37 (m, 1H), 1.42-1.61 (m, 1H), 1.61-1.88 (m, 2H), 1.95-2.36 (m, 5H), 2.50-2.66 (m, 1H), 2.66-2.86 (m, 2H), 3.60 (s, 2H), 3.77 (s, 2H), 4.56-4.75 (m, 4H), 6.77 (d, J=5.1 Hz, 1H), 6.97-7.09 (m, 4H), 7.11 (d, J=5.1 Hz, 1H), 7.34 (d, J=8.1 Hz, 2H), 7.56 (d, J=8.1 Hz, 2H).

Example 8(86)

4-{[8-(2-ethyl-2-hydroxybutyl)-2,8-diazaspiro[4.5]dec-2-yl]methyl}-N,N-bis(1H-imidazol-2-ylmethyl)benzamide Description: amorphous;
TLC: Rf 0.36 (dichrolomethane:methanol:28% aqueous ammonia=90:10:1);
NMR (CDCl$_3$): δ 0.83 (t, J=7.2 Hz, 6H), 1.33-1.48 (m, 4H), 1.52-1.65 (m, 6H), 2.25 (s, 2H), 2.32 (s, 2H), 2.42-2.60 (m, 6H), 3.57 (s, 2H), 4.63-4.75 (m, 4H), 6.94-7.10 (m, 4H), 7.35 (d, J=8.1 Hz, 2H), 7.51 (d, J=8.1 Hz, 2H).

Example 8(87)

4-({8-[(1-hydroxycyclohexyl)methyl]-2,8-diazaspiro[4.5]dec-2-yl}methyl)-N,N-bis(1H-imidazol-2-ylmethyl)benzamide Description: amorphous;
TLC: Rf 0.33 (dichrolomethane:methanol:28% aqueous ammonia=90:10:1);
NMR (CDCl$_3$): δ 1.20-1.71 (m, 16H), 2.25 (s, 2H), 2.31 (s, 2H), 2.41-2.60 (m, 6H), 3.56 (s, 2H), 4.62-4.78 (m, 4H), 6.92-7.10 (m, 4H), 7.34 (d, J=8.1 Hz, 2H), 7.51 (d, J=8.1 Hz, 2H).

Example 8(88)

N,N-bis(1H-imidazol-2-ylmethyl)-4-{[8-(1-propylbutyl)-2,8-diazaspiro[4.5]dec-2-yl]methyl}benzamide

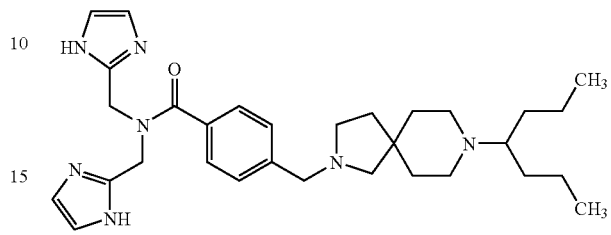

Description: amorphous;
TLC: Rf 0.32 (ethyl acetate:methanol: 28% aqueous ammonia=90:8:2);
NMR (CDCl$_3$): δ 0.82-0.94 (m, 6H), 1.13-1.22 (m, 2H), 1.26-1.34 (m, 4H), 1.36-1.45 (m, 2H), 1.48-1.62 (m, 6H), 2.27-2.43 (m, 7H), 2.48-2.60 (m, 2H), 3.58 (s, 2H), 4.59-4.73 (m, 4H), 6.95-7.10 (m, 4H), 7.32-7.42 (m, 2H), 7.53-7.65 (m, 2H).

Example 8(89)

4-({8-[2-hydroxy-1-(hydroxymethyl)ethyl]-2,8-diazaspiro[4.5]dec-2-yl}methyl)-N,N-bis(1H-imidazol-2-ylmethyl)benzamide Description: amorphous;
TLC: Rf 0.13 (chloroform:methanol:28% aqueous ammonia=90:13:2);
NMR (CDCl$_3$): δ 1.51-1.65 (m, 6H), 2.25 (s, 2H), 2.55-2.69 (m, 6H), 2.74-2.85 (m, 1H), 3.51-3.62 (m, 6H), 4.56-4.69 (m, 4H), 6.95-7.08 (m, 4H), 7.30-7.38 (m, 2H), 7.45-7.54 (m, 2H).

Example 8(90)

4-{[8-(2-hydroxy-2-propylpentyl)-2,8-diazaspiro[4.5]dec-2-yl]methyl}-N,N-bis(1H-imidazol-2-ylmethyl)benzamide Description: amorphous;
TLC: Rf 0.36 (dichrolomethane:methanol:28% aqueous ammonia=90:10:1);
NMR (CDCl$_3$): δ 0.89 (t, J=7.2 Hz, 6H), 1.19-1.43 (m, 8H), 1.48-1.65 (m, 6H), 2.25 (s, 2H), 2.32 (s, 2H), 2.40-2.60 (m, 6H), 3.57 (s, 2H), 4.62-4.75 (m, 4H), 6.95-7.10 (m, 4H), 7.35 (d, J=8.1 Hz, 2H), 7.52 (d, J=8.1 Hz, 2H).

Example 8(91)

N,N-bis(1H-imidazol-2-ylmethyl)-4-({[(3S)-1-(1-propylbutyl)-3-piperidinyl]amino}methyl)benzamide Description: amorphous;
TLC: Rf 0.35 (chloroform:methanol:28% aqueous ammonia=80:10:1);
NMR (CDCl$_3$): δ 0.87 (t, J=7.2 Hz, 6H), 1.08-1.53 (m, 10H), 1.54-1.79 (m, 2H), 2.18-2.40 (m, 3H), 2.42-2.54 (m, 1H), 2.55-2.78 (m, 2H), 3.80 (s, 2H), 4.56-4.75 (m, 4H), 6.93-7.10 (m, 4H), 7.36 (d, J=8.1 Hz, 2H), 7.51 (d, J=8.1 Hz, 2H).

Example 8(92)

4-{[(3S)-3-(dipropylamino)-1-piperidinyl]methyl}-N,N-bis(1H-imidazol-2-ylmethyl)benzamide Description: amorphous;
TLC: Rf 0.34 (chloroform:methanol:28% aqueous ammonia=80:10:1);
NMR (CDCl$_3$): δ 0.83 (t, J=7.2 Hz, 6H), 1.08-1.28 (m, 1H), 1.29-1.58 (m, 5H), 1.59-1.93 (m, 4H), 2.32-2.48 (m, 4H), 2.62-2.79 (m, 2H), 2.86-2.96 (m, 1H), 3.44 (d, J=13.5 Hz, 1H), 3.55 (d, J=13.5 Hz, 1H), 4.58-4.78 (m, 4H), 6.92-7.10 (m, 4H), 7.34 (d, J=8.1 Hz, 2H), 7.53 (d, J=8.1 Hz, 2H).

Example 8(93)

4-{[[trans-4-(dipropylamino)cyclohexyl](2-hydroxyethyl)amino]methyl}-N,N-bis(1H-imidazol-2-ylmethyl)benzamide Description: amorphous;
TLC: Rf 0.25 (chloroform:methanol:28% aqueous ammonia=80:10:1);
NMR (DMSO-d$_6$): δ 0.80 (t, J=7.2 Hz, 6H), 1.04-1.46 (m, 8H), 1.59-1.85 (m, 4H), 2.17-2.45 (m, 8H), 3.22-3.30 (m, 2H), 3.60 (s, 2H), 4.23 (t, J=5.1 Hz, 1H), 4.49-4.65 (m, 4H), 6.76-7.18 (m, 4H), 7.32 (d, J=8.1 Hz, 2H), 7.42 (d, J=8.1 Hz, 2H), 11.86-12.65 (m, 2H).

Example 8(94)

4-{[[trans-4-(dipropylamino)cyclohexyl](3-hydroxypropyl)amino]methyl}-N,N-bis(1H-imidazol-2-ylmethyl)benzamide

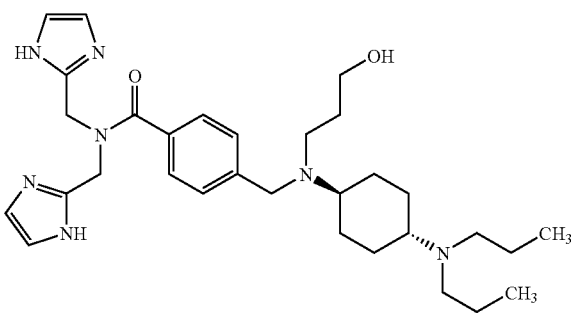

Description: amorphous;
TLC: Rf 0.29 (chloroform:methanol:28% aqueous ammonia=80:10:1);
NMR (DMSO-d$_6$): δ 0.79 (t, J=7.2 Hz, 6H), 1.03-1.39 (m, 8H), 1.39-1.53 (m, 2H), 1.58-1.84 (m, 4H), 2.17-2.45 (m, 8H), 3.23-3.31 (m, 2H), 3.55 (s, 2H), 4.27-4.42 (m, 1H), 4.48-4.66 (m, 4H), 6.75-7.19 (m, 4H), 7.29 (d, J=8.1 Hz, 2H), 7.41 (d, J=8.1 Hz, 2H), 11.85-12.62 (m, 2H).

Example 8(95)

4-[(8-cyclohexyl-2,8-diazaspiro[4.5]dec-2-yl)methyl]-N,N-bis(1H-imidazol-2-ylmethyl)cyclohexanecarboxamide

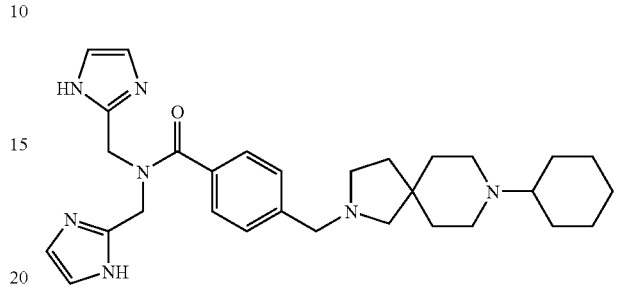

Description: amorphous;
TLC: Rf 0.20 (chloroform:methanol:28% aqueous ammonia=80:10:1);
NMR (DMSO-d$_6$): δ 0.59-1.85 (m, 27H), 2.01-2.64 (m, 10H), 4.51-4.62 (m, 2H), 4.64-4.74 (m, 2H), 6.62-7.41 (m, 4H), 11.78-13.36 (m, 2H).

Example 8(96)

N,N-bis(1H-imidazol-2-ylmethyl)-4-({8-[2-methoxy-1-(methoxymethyl)ethyl]-2,8-diazaspiro[4.5]dec-2-yl}methyl)benzamide Description: amorphous;
TLC: Rf 0.49 (chloroform:methanol:28% aqueous ammonia=90:13:2);
NMR (CDCl$_3$): δ 1.51-1.65 (m, 6H), 2.39 (s, 2H), 2.50-2.64 (m, 6H), 2.72-2.80 (m, 1H), 3.32 (s, 6H), 3.41-3.55 (m, 4H), 3.61 (s, 2H), 4.61-4.76 (m, 4H), 6.97-7.08 (m, 4H), 7.32-7.41 (m, 2H), 7.53-7.61 (m, 2H).

Example 8(97)

4-{[9-(2-ethylbutyl)-3,9-diazaspiro[5.5]undec-3-yl]methyl}-N,N-bis(1H-imidazol-2-ylmethyl)benzamide

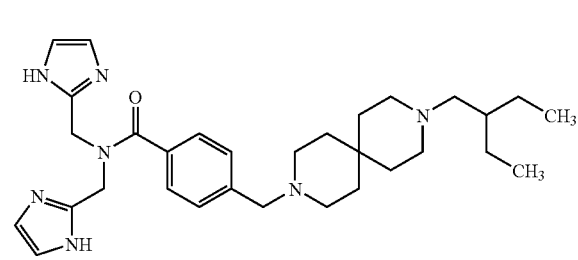

Description: amorphous;
TLC: Rf 0.27 (dichrolomethane:methanol:28% aqueous ammonia=90:10:1);
NMR (CDCl$_3$): δ 0.84 (t, J=7.2 Hz, 6H), 1.19-1.52 (m, 13H), 2.10 (d, J=6.6 Hz, 2H), 2.24-2.39 (m, 8H), 3.48 (s, 2H), 4.60-4.74 (m, 4H), 6.94-7.10 (m, 4H), 7.35 (d, J=8.4 Hz, 2H), 7.54 (d, J=8.4 Hz, 2H).

Example 8(98)

N,N-bis(1H-imidazol-2-ylmethyl)-4-[(9-isobutyl-3,9-diazaspiro[5.5]undec-3-yl)methyl]benzamide Description: amorphous;
TLC: Rf 0.24 (dichrolomethane:methanol:28% aqueous ammonia=90:10:1);
NMR (CDCl$_3$): δ 0.87 (d, J=6.6 Hz, 6H), 1.42-1.53 (m, 8H), 1.76 (m, 1H), 2.05 (d, J=7.5 Hz, 2H), 2.24-2.42 (m, 8H), 3.48 (s, 2H), 4.60-4.75 (m, 4H), 6.94-7.10 (m, 4H), 7.35 (d, J=8.4 Hz, 2H), 7.53 (d, J=8.4 Hz, 2H).

Example 8(99)

N,N-bis(1H-imidazol-2-ylmethyl)-4-{[9-(tetrahydro-2H-pyran-4-yl)-3,9-diazaspiro[5.5]undec-3-yl]methyl}benzamide Description: amorphous;
TLC: Rf 0.16 (dichrolomethane:methanol:28% aqueous ammonia=90:10:1);
NMR (CDCl$_3$): δ 1.42-1.67 (m, 10H), 1.71-1.81 (m, 2H), 2.30-2.51 (m, 9H), 3.30-3.42 (m, 2H), 3.48 (s, 2H), 3.96-4.08 (m, 2H), 4.60-4.74 (m, 4H), 6.95-7.10 (m, 4H), 7.35 (d, J=8.1 Hz, 2H), 7.55 (d, J=8.1 Hz, 2H).

Example 8(100)

4-[(9-cyclobutyl-3,9-diazaspiro[5.5]undec-3-yl)methyl]-N,N-bis(1H-imidazol-2-ylmethyl)benzamide Description: amorphous;
TLC: Rf 0.22 (dichrolomethane:methanol:28% aqueous ammonia=90:10:1);
NMR (CDCl$_3$): δ 1.40-1.53 (m, 8H), 1.58-1.74 (m, 2H), 1.78-2.17 (m, 4H), 2.19-2.40 (m, 8H), 2.67 (m, 1H), 3.48 (s, 2H), 4.60-4.72 (m, 4H), 6.95-7.10 (m, 4H), 7.35 (d, J=7.8 Hz, 2H), 7.53 (d, J=7.8 Hz, 2H).

Example 8(101)

N,N-bis(1H-imidazol-2-ylmethyl)-4-[(9-isobutyl-2,9-diazaspiro[5.5]undec-2-yl)methyl]benzamide
TLC: Rf 0.39 (dichrolomethane:methanol:28% aqueous ammonia=9:1:0.1);

NMR (CDCl$_3$): δ 0.84 (d, J=6.59 Hz, 6H), 1.21-1.63 (m, 8H), 1.64-1.80 (m, 1H), 1.99 (d, J=7.32 Hz, 2H), 2.04-2.41 (m, 8H), 3.42 (s, 2H), 4.56-4.71 (m, 4H), 6.95-7.15 (m, 4H), 7.37 (d, J=8.42 Hz, 2H), 7.62 (d, J=8.42 Hz, 2H), 9.83-11.12 (m, 1H), 11.78-12.90 (m, 1H).

Example 8(102)

4-{[9-(cyclobutylmethyl)-3,9-diazaspiro[5.5]undec-3-yl]methyl}-N,N-bis(1H-imidazol-2-ylmethyl)benzamide

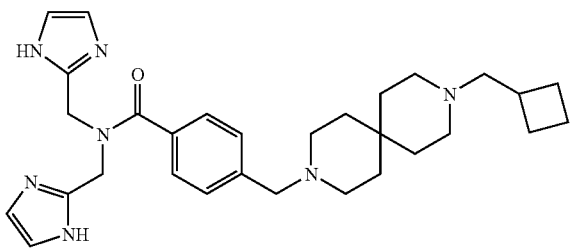

Description: amorphous;
TLC: Rf 0.19 (dichrolomethane:methanol:28% aqueous ammonia=90:10:1);
NMR (CDCl$_3$): δ 1.37-1.59 (m, 8H), 1.60-2.45 (m, 16H), 2.53 (m, 1H), 3.48 (s, 2H), 4.61-4.75 (m, 4H), 6.97-7.12 (m, 4H), 7.35 (d, J=8.1 Hz, 2H), 7.56 (d, J=8.1 Hz, 2H).

Example 8(103)

4-({9-[(3-chloro-2-thienyl)methyl]-3,9-diazaspiro[5.5]undec-3-yl}methyl)-N,N-bis(1H-imidazol-2-ylmethyl)benzamide Description: amorphous;
TLC: Rf 0.33 (dichrolomethane:methanol:28% aqueous ammonia=90:10:1);
NMR (CDCl$_3$): δ 1.42-1.54 (m, 8H), 2.30-2.40 (m, 4H), 2.41-2.50 (m, 4H), 3.48 (s, 2H), 3.70 (s, 2H), 4.60-4.72 (m, 4H), 6.85 (d, J=5.1 Hz, 1H), 6.94-7.10 (m, 4H), 7.20 (d, J=5.1 Hz, 1H), 7.35 (d, J=8.1 Hz, 2H), 7.55 (d, J=8.1 Hz, 2H).

Example 8(104)

3-[2-(8-cyclohexyl-2,8-diazaspiro[4.5]dec-2-yl)ethyl]-N,N-bis(1H-imidazol-2-ylmethyl)benzamide Description: amorphous;
TLC: Rf 0.30 (dichrolomethane:methanol:28% aqueous ammonia=40:10:1);
NMR (CDCl$_3$): δ 1.01-1.32 (m, 6H), 1.48-2.00 (m, 10H), 2.16-2.32 (m, 1H), 2.38-2.55 (m, 4H), 2.42 (s, 2H), 2.55-2.70 (m, 4H), 2.72-2.83 (m, 2H), 4.55-4.86 (m, 4H), 6.90-7.10 (m, 4H), 7.22-7.37 (m, 4H), 10.49-12.72 (m, 2H).

Example 8(105)

4-[(9-isobutyl-1-oxa-4,9-diazaspiro[5.5]undec-4-yl)methyl]-N,N-bis[(1-methyl-1H-imidazol-2-yl)methyl]benzamide Description: amorphous;
TLC: Rf 0.65 (ethyl acetate:methanol:28% aqueous ammonia=40:10:2);
NMR (CDCl$_3$): δ 0.87 (d, J=6.6 Hz, 6H), 1.43-1.61 (m, 2H), 1.65-1.84 (m, 1H), 1.85-1.98 (m, 2H), 2.00-2.49 (m, 10H), 3.42 (s, 2H), 3.49 (s, 3H), 3.66-3.75 (m, 2H), 3.79 (s, 3H), 4.66 (s, 2H), 4.83 (s, 2H), 6.80 (s, 2H), 6.87-7.06 (m, 2H), 7.32 (d, J=8.1 Hz, 2H), 7.61 (d, J=8.1 Hz, 2H).

Example 8(106)

4-[(8-isobutyl-2,8-diazaspiro[4.5]dec-2-yl)methyl]-N,N-bis[(1-methyl-1H-imidazol-2-yl)methyl]benzamide TLC: Rf 0.58 (ethyl acetate:methanol:28% aqueous ammonia=40:10:2);

NMR (CDCl$_3$): δ 0.87 (d, J=6.6 Hz, 6H), 1.50-1.64 (m, 6H), 1.67-1.85 (m, 1H), 2.02 (d, J=7.2 Hz, 2H), 2.20-2.31 (m, 4H), 2.32 (s, 2H), 2.54 (t, J=6.9 Hz, 2H), 3.45 (s, 3H), 3.56 (s, 2H), 3.79 (s, 3H), 4.66 (s, 2H), 4.85 (s, 2H), 6.79 (s, 2H), 6.88-7.07 (m, 2H), 7.31 (d, J=8.1 Hz, 2H), 7.57 (d, J=8.1 Hz, 2H).

Example 8(107)

4-[(9-isobutyl-3,9-diazaspiro[5.5]undec-3-yl)methyl]-N,N-bis[(1-methyl-1H-imidazol-2-yl)methyl]benzamide Description: amorphous;
TLC: Rf 0.58 (ethyl acetate:methanol:28% aqueous ammonia=40:10:2);
NMR (CDCl$_3$): δ 0.87 (d, J=6.6 Hz, 6H), 1.33-1.60 (m, 8H), 1.68-1.87 (m, 1H), 2.05 (d, J=7.2 Hz, 2H), 2.21-2.46 (m, 8H), 3.33-3.59 (m, 5H), 3.79 (s, 3H), 4.65 (s, 2H), 4.85 (s, 2H), 6.79 (s, 2H), 6.87-7.06 (m, 2H), 7.30 (d, J=8.1 Hz, 2H), 7.58 (d, J=8.1 Hz, 2H).

Example 8(108)

N-(1H-imidazol-2-ylmethyl)-4-[(9-isobutyl-1-oxa-4,9-diazaspiro[5.5]undec-4-yl)methyl]-N-[(1-methyl-1H-imidazol-2-yl)methyl]benzamide Description: amorphous;
TLC: Rf 0.58 (ethyl acetate:methanol:28% aqueous ammonia=40:10:2);
NMR (CDCl$_3$): δ 0.88 (d, J=6.6 Hz, 6H), 1.48-1.63 (m, 2H), 1.64-1.83 (m, 1H), 1.85-1.99 (m, 2H), 2.02-2.10 (m, 2H), 2.15-2.52 (m, 8H), 3.34-3.94 (m, 7H), 4.50-4.83 (m, 4H), 6.89 (s, 1H), 6.98-7.19 (m, 3H), 7.30-7.65 (m, 4H), 13.73-14.01 (m, 1H).

Example 8(109)

N-(1H-imidazol-2-ylmethyl)-4-[(8-isobutyl-2,8-diazaspiro[4.5]dec-2-yl)methyl]-N-[(1-methyl-1H-imidazol-2-yl)methyl]benzamide

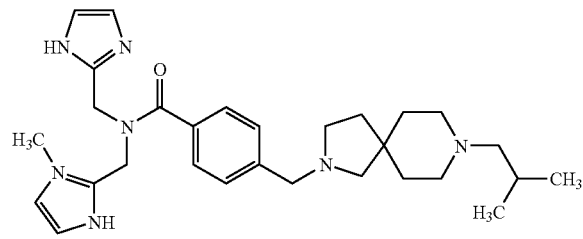

Description: amorphous;
TLC: Rf 0.62 (ethyl acetate:methanol:28% aqueous ammonia=40:10:2);
NMR (CDCl$_3$): δ 0.87 (d, J=6.6 Hz, 6H), 1.49-1.64 (m, 6H), 1.69-1.85 (m, 1H), 2.02 (d, J=7.2 Hz, 2H), 2.21-2.31 (m, 4H), 2.32 (s, 2H), 2.53 (t, J=6.9 Hz, 2H), 3.33-3.62 (m, 3H), 3.86 (s, 2H), 4.50-4.82 (m, 4H), 6.88 (s, 1H), 7.05 (s, 1H), 7.07-7.13 (m, 2H), 7.29-7.61 (m, 4H), 13.69-14.02 (m, 1H).

Example 8(110)

N-(1H-imidazol-2-ylmethyl)-4-[(9-isobutyl-3,9-diazaspiro[5.5]undec-3-yl)methyl]-N-[(1-methyl-1H-imidazol-2-yl)methyl]benzamide Description: amorphous;
TLC: Rf 0.62 (ethyl acetate:methanol:28% aqueous ammonia=40:10:2);
NMR (CDCl$_3$): δ 0.87 (d, J=6.6 Hz, 6H), 1.39-1.52 (m, 8H), 1.68-1.87 (m, 1H), 2.05 (d, J=7.1 Hz, 2H), 2.21-2.40 (m, 8H), 3.34-3.51 (m, 3H), 3.86 (s, 2H), 4.48-4.82 (m, 4H), 6.88 (s, 1H), 6.97-7.16 (m, 3H), 7.28-7.65 (m, 4H), 13.67-14.03 (m, 1H).

Example 8(111)

N,N-bis(1H-imidazol-2-ylmethyl)-4-[(7-isobutyl-2,7-diazaspiro[3.5]non-2-yl)methyl]benzamide TLC: Rf 0.29 (dichrolomethane:methanol:28% aqueous ammonia=9:1:0.1);
NMR (CDCl$_3$): δ 0.86 (d, J=6.59 Hz, 6H), 1.69-1.82 (m, 5H), 1.99 (d, J=7.32 Hz, 2H), 2.17-2.31 (m, 4H), 2.99 (s, 4H), 3.63 (s, 2H), 4.58-4.73 (m, 4H), 6.95-7.13 (m, 4H), 7.31 (d, J=8.42 Hz, 2H), 7.54 (d, J=8.42 Hz, 2H), 9.92-11.03 (m, 1H), 12.02-12.86 (m, 1H).

Example 8(112)

N,N-bis(1H-imidazol-2-ylmethyl)-4-[(2-isobutyl-2,7-diazaspiro[3.5]non-7-yl)methyl]benzamide TLC: Rf 0.27 (dichrolomethane:methanol:28% aqueous ammonia=9:1:0.1);
NMR (CDCl$_3$): δ 0.86 (d, J=6.59 Hz, 6H), 1.50-1.66 (m, 1H), 1.67-1.75 (m, 4H), 2.19-2.36 (m, 4H), 2.23 (d, J=6.96 Hz, 2H), 2.94 (s, 4H), 3.43 (s, 2H), 4.58-4.74 (m, 4H), 6.90-7.15 (m, 4H), 7.34 (d, J=8.24 Hz, 2H), 7.55 (d, J=8.24 Hz, 2H), 10.09-10.82 (m, 1H), 12.21-12.87 (m, 1H).

Example 8(113)

N,N-bis(1H-imidazol-2-ylmethyl)-4-[(2-isobutyl-2,8-diazaspiro[4.5]dec-8-yl)methyl]benzamide TLC: Rf 0.35 (dichrolomethane:methanol:28% aqueous ammonia=9:1:0.1);
NMR (CDCl$_3$): δ 0.88 (d, J=6.59 Hz, 6H), 1.46-1.78 (m, 7H), 2.13 (d, J=7.32 Hz, 2H), 2.24-2.40 (m, 4H), 2.28 (s, 2H), 2.49 (t, J=6.87 Hz, 2H), 3.46 (s, 2H), 4.58-4.77 (m, 4H), 6.95-7.16 (m, 4H), 7.35 (d, J=8.42 Hz, 2H), 7.54 (d, J=8.42 Hz, 2H), 10.09-10.79 (m, 1H), 12.12-12.88 (m, 1H).

Example 8(114)

4-{[2-(2,2-dimethylpropyl)-2,8-diazaspiro[4.5]dec-8-yl]methyl}-N,N-bis(1H-imidazol-2-ylmethyl)benzamide TLC: Rf 0.40 (dichrolomethane:methanol:28% aqueous ammonia=9:1:0.1);
NMR (CDCl$_3$): δ 0.86 (s, 9H), 1.44-1.65 (m, 6H), 2.16 (s, 2H), 2.22-2.40 (m, 4H), 2.43 (s, 2H), 2.63 (t, J=6.96 Hz, 2H), 3.46 (s, 2H), 4.57-4.76 (m, 4H), 6.94-7.16 (m, 4H), 7.35 (d, J=8.24 Hz, 2H), 7.49-7.60 (m, J=8.24 Hz, 2H), 9.91-10.99 (m, 1H), 11.99-13.03 (m, 1H).

Example 8(115)

4-{[2-(1-ethylpropyl)-2,8-diazaspiro[4.5]dec-8-yl]methyl}-N,N-bis(1H-imidazol-2-ylmethyl)benzamide

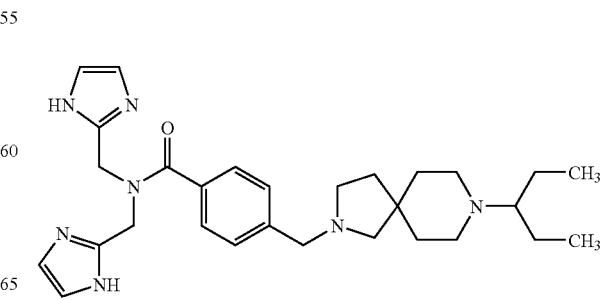

TLC: Rf 0.41 (dichrolomethane:methanol:28% aqueous ammonia=9:1:0.1);
NMR (CDCl$_3$): δ 0.85 (t, J=7.4 Hz, 6H), 1.31-1.65 (m, 10H), 1.92-2.05 (m, 1H), 2.24-2.43 (m, 4H), 2.38 (s, 2H), 2.58 (t, J=6.9 Hz, 2H), 3.46 (s, 2H), 4.55-4.74 (m, 4H), 6.93-7.14 (m, 4H), 7.36 (d, J=8.2 Hz, 2H), 7.59 (d, J=8.2 Hz, 2H).

Example 8(116)

4-{[9-(1-ethylpropyl)-2,9-diazaspiro[5.5]undec-2-yl]methyl}-N,N-bis(1H-imidazol-2-ylmethyl)benzamide TLC: Rf 0.46 (dichrolomethane:methanol:28% aqueous ammonia=9:1:0.1);
NMR (CDCl$_3$): δ 0.83 (t, J=7.3 Hz, 6H), 1.12-1.63 (m, 12H), 2.00-2.15 (m, 3H), 2.22-2.49 (m, 6H), 3.42 (s, 2H), 4.55-4.74 (m, 4H), 6.95-7.14 (m, 4H), 7.37 (d, J=8.2 Hz, 2H), 7.60 (d, J=8.2 Hz, 2H).

Example 8(117)

4-{[9-(2,2-dimethylpropyl)-2,9-diazaspiro[5.5]undec-2-yl]methyl}-N,N-bis(1H-imidazol-2-ylmethyl)benzamide TLC: Rf 0.59 (dichrolomethane:methanol:28% aqueous ammonia=9:1:0.1);
NMR (CDCl$_3$): δ 0.81 (s, 9H), 1.20-1.63 (m, 8H), 1.95 (s, 2H), 2.03-2.14 (m, 2H), 2.21-2.47 (m, 6H), 3.42 (s, 2H), 4.56-4.73 (m, 4H), 6.93-7.15 (m, 4H), 7.36 (d, J=8.2 Hz, 2H), 7.59 (d, J=8.2 Hz, 2H), 9.98-11.02 (m, 1H), 11.88-12.89 (m, 1H).

Example 8(118)

N,N-bis(1H-imidazol-2-ylmethyl)-4-[(4-isobutyl-1-oxa-4,9-diazaspiro[5.5]undec-9-yl)methyl]benzamide TLC: Rf 0.46 (dichrolomethane:methanol:28% aqueous ammonia=9:1:0.1);
NMR (CDCl$_3$): δ 0.86 (d, J=6.4 Hz, 6H), 1.47-2.03 (m, 5H), 1.98 (d, J=7.3 Hz, 2H), 2.16 (s, 2H), 2.26-2.54 (m, 6H), 3.50 (s, 2H), 3.62-3.76 (m, 2H), 4.50-4.76 (m, 4H), 6.91-7.19 (m, 4H), 7.37 (d, J=8.2 Hz, 2H), 7.61 (d, J=8.2 Hz, 2H), 9.88-11.07 (m, 1H), 11.98-12.96 (m, 1H).

Example 8(119)

4-{[4-(1-ethylpropyl)-1-oxa-4,9-diazaspiro[5.5]undec-9-yl]methyl}-N,N-bis(1H-imidazol-2-ylmethyl)benzamide TLC: Rf 0.50 (dichrolomethane:methanol:28% aqueous ammonia=9:1:0.1);
NMR (CDCl$_3$): δ 0.87 (t, J=7.3 Hz, 6H), 1.15-1.63 (m, 6H), 1.74-2.12 (m, 3H), 2.27-2.52 (m, 8H), 3.50 (s, 2H), 3.62-3.70 (m, 2H), 4.57-4.72 (m, 4H), 6.95-7.12 (m, 4H), 7.37 (d, J=8.2 Hz, 2H), 7.57-7.65 (m, J=8.2 Hz, 2H), 9.78-10.92 (m, 1H), 11.82-13.17 (m, 1H).

Example 8(120)

4-{[2-(2,2-dimethylpropyl)-2,7-diazaspiro[3.5]non-7-yl]methyl}-N,N-bis(1H-imidazol-2-ylmethyl)benzamide TLC: Rf 0.42 (dichrolomethane:methanol:28% aqueous ammonia=9:1:0.1);
NMR (CDCl$_3$): δ 0.83 (s, 9H), 1.65-1.76 (m, 4H), 2.18 (s, 2H), 2.20-2.37 (m, 4H), 2.98 (s, 4H), 3.42 (s, 2H), 4.57-4.77 (m, 4H), 6.93-7.13 (m, 4H), 7.33 (d, J=8.2 Hz, 2H), 7.43-7.55 (m, J=8.2 Hz, 2H), 9.97-10.84 (m, 1H), 12.01-12.97 (m, 1H).

Example 8(121)

4-{[2-(1-ethylpropyl)-2,7-diazaspiro[3.5]non-7-yl]methyl}-N,N-bis(1H-imidazol-2-ylmethyl)benzamide TLC: Rf 0.41 (dichrolomethane:methanol:28% aqueous ammonia=9:1:0.1);
NMR (CDCl$_3$): δ 0.81 (t, J=7.4 Hz, 6H), 1.21-1.44 (m, 4H), 1.67-1.75 (m, 4H), 1.92-2.03 (m, 1H), 2.23-2.37 (m, 4H), 2.93 (s, 4H), 3.43 (s, 2H), 4.59-4.74 (m, 4H), 6.95-7.11 (m, 4H), 7.34 (d, J=8.2 Hz, 2H), 7.55 (d, J=8.2 Hz, 2H), 10.04-10.97 (m, 1H), 12.04-12.94 (m, 1H).

Example 8(122)

4-{[7-(2,2-dimethylpropyl)-2,7-diazaspiro[3.5]non-2-yl]methyl}-N,N-bis(1H-imidazol-2-ylmethyl)benzamide TLC: Rf 0.39 (dichrolomethane:methanol:28% aqueous ammonia=9:1:0.1);
NMR (CDCl$_3$): δ 0.83 (s, 9H), 1.65-1.75 (m, 4H), 1.96 (s, 2H), 2.30-2.42 (m, 4H), 2.98 (s, 4H), 3.63 (s, 2H), 4.53-4.76 (m, 4H), 6.91-7.15 (m, 4H), 7.31 (d, J=8.4 Hz, 2H), 7.50-7.62 (m, J=8.4 Hz, 2H), 10.11-11.11 (m, 1H), 11.97-13.06 (m, 1H).

Example 8(123)

4-{[7-(1-ethylpropyl)-2,7-diazaspiro[3.5]non-2-yl]methyl}-N,N-bis(1H-imidazol-2-ylmethyl)benzamide TLC: Rf 0.36 (dichrolomethane:methanol:28% aqueous ammonia=9:1:0.1);
NMR (CDCl$_3$): δ 0.86 (t, J=7.4 Hz, 6H), 1.15-1.54 (m, 4H), 1.65-1.74 (m, 4H), 2.01-2.17 (m, 1H), 2.31-2.42 (m, 4H), 2.99 (s, 4H), 3.64 (s, 2H), 4.52-4.71 (m, 4H), 6.95-7.15 (m, 4H), 7.33 (d, J=7.9 Hz, 2H), 7.66 (d, J=7.9 Hz, 2H).

Example 8(124)

N,N-bis(1H-imidazol-2-ylmethyl)-4-[(2-isobutyl-2,9-diazaspiro[5.5]undec-9-yl)methyl]benzamide TLC: Rf 0.36 (dichrolomethane:methanol:28% aqueous ammonia=9:1:0.1);

NMR (CDCl$_3$): δ 0.85 (d, J=6.6 Hz, 6H), 1.17-1.64 (m, 8H), 1.64-1.82 (m, 1H), 1.95 (d, J=7.3 Hz, 2H), 1.99-2.49 (m, 8H), 3.48 (s, 2H), 4.47-4.77 (m, 4H), 6.89-7.18 (m, 4H), 7.38 (d, J=8.2 Hz, 2H), 7.65 (d, J=8.2 Hz, 2H).

Example 8(125)

4-{[2-(2,2-dimethylpropyl)-2,9-diazaspiro[5.5]undec-9-yl]methyl}-N,N-bis(1H-imidazol-2-ylmethyl)benzamide TLC: Rf 0.38 (dichrolomethane:methanol:28% aqueous ammonia=9:1:0.1);

NMR (CDCl$_3$): δ 0.83 (s, 9H), 1.13-1.67 (m, 8H), 1.94 (s, 2H), 2.16-2.47 (m, 8H), 3.48 (s, 2H), 4.54-4.70 (m, 4H), 6.95-7.15 (m, 4H), 7.38 (d, J=8.1 Hz, 2H), 7.66 (d, J=8.1 Hz, 2H).

Example 8(126)

4-{[2-(1-ethylpropyl)-2,9-diazaspiro[5.5]undec-9-yl]methyl}-N,N-bis(1H-imidazol-2-ylmethyl)benzamide TLC: Rf 0.45 (dichrolomethane:methanol:28% aqueous ammonia=9:1:0.1);

NMR (CDCl$_3$): δ 0.86 (t, J=7.3 Hz, 6H), 1.08-1.64 (m, 12H), 1.98-2.12 (m, 1H), 2.18-2.50 (m, 8H), 3.49 (s, 2H), 4.51-4.71 (m, 4H), 6.92-7.18 (m, 4H), 7.38 (d, J=8.1 Hz, 2H), 7.66 (d, J=8.1 Hz, 2H).

Example 8(127)

4-{[9-(2,2-dimethylpropyl)-3,9-diazaspiro[5.5]undec-3-yl]methyl}-N,N-bis(1H-imidazol-2-ylmethyl)benzamide TLC: Rf 0.49 (dichrolomethane:methanol:28% aqueous ammonia=9:1:0.1);

NMR (CDCl$_3$): δ 0.83 (s, 9H), 1.34-1.55 (m, 8H), 2.00 (s, 2H), 2.25-2.50 (m, 8H), 3.47 (s, 2H), 4.54-4.81 (m, 4H), 6.88-7.17 (m, 4H), 7.34 (d, J=8.1 Hz, 2H), 7.51 (d, J=8.1 Hz, 2H).

Example 8(128)

4-[2-(8-cyclohexyl-2,8-diazaspiro[4.5]dec-2-yl)ethyl]-N,N-bis(1H-imidazol-2-ylmethyl)benzamide TLC: Rf 0.24 (dichrolomethane:methanol:28% aqueous ammonia=9:1:0.1);

NMR (CDCl$_3$): δ 0.98-1.34 (m, 6H), 1.49-2.10 (m, 10H), 2.16-2.32 (m, 1H), 2.40 (s, 2H), 2.44-2.55 (m, 4H), 2.54-2.67 (m, 4H), 2.74-2.86 (m, 2H), 4.53-4.78 (m, 4H), 6.94-7.15 (m, 4H), 7.24 (d, J=8.1 Hz, 2H), 7.51 (d, J=8.1 Hz, 2H), 10.26-10.83 (m, 1H), 12.29-12.85 (m, 1H).

Example 9 tert-butyl 4-[({[bis({1-[(dimethylamino)sulfonyl]-1H-imidazol-2-yl}methyl]amino}carbonyl)amino]methyl}piperidine-1-carboxylate Under an argon atmosphere, to an anhydrous tetrahydrofuran (25 mL) solution of trichloromethyl 3,3,3-trichloro-2-oxopropanoic acid (519 mg), triethylamine (4.9 mL) and an anhydrous tetrahydrofuran (5 mL) solution of the compound (1.53 g) obtained in Example 3 were sequentially added at −40° C. After the reaction solution was stirred at 0° C. for one hour, an anhydrous tetrahydrofuran (5 mL) solution of tert-butyl 4-(aminomethyl)piperidine-1-carboxylate (750 mg) was added at 0° C. The reaction solution was stirred at room temperature for 6 hours. To the reaction solution, an aqueous saturated sodium hydrogen carbonate solution (50 mL) was added, followed by stirring for 5 minutes. The aqueous layer was extracted twice with ethyl acetate (50 mL). The combined organic layer was washed with saturated brine and then dried over anhydrous magnesium sulfate. After removing the anhydrous sodium sulfate by filtration, the filtrate was concentrated. Without purifying the residue, the title compound (3.03 g) having the following physical properties was obtained.

TLC: Rf 0.37 (chloroform:methanol=9:1).

Example 10

N,N-bis(1H-imidazol-2-ylmethyl)-N'-(piperidin-4-ylmethyl)urea

To the compound (3.00 g) obtained in Example 9, 4N hydrogen chloride/dioxane (15 mL) was added. The reaction solution was stirred at 60° C. for 15 hours. The reaction solution was concentrated under reduced pressure. The residue was dissolved in methanol (20 mL) and a carbonate resin (trade name: MP-Carbonate, manufactured by Argonaut Co., product number: 800267, 10 g) was added, followed by stirring at room temperature for 3 hours. After the resin was removed by filtration, the filtrate was concentrated under reduced pressure. The title compound was obtained without purifying the residue.

Example 11

N'-({1-[4-(dipropylamino)butyl]-4-piperidinyl}methyl)-N,N-bis(1H-imidazol-2-ylmethyl)urea

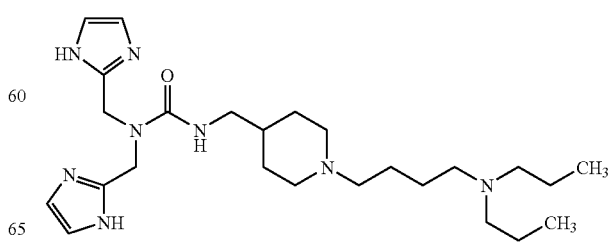

Under an argon atmosphere, to a methanol (2.3 mL) solution of the compound (73 mg) obtained in Example 10, 4-(dipropylamino)butanal (39 mg) and trimethyl orthoformate (49 mg) were added at 0° C. The reaction solution was stirred at room temperature for 2 hours. To the reaction solution, sodium borohydride (17 mg) was added at 0° C., followed by stirring for one hour. The reaction solution was concentrated under reduced pressure, and then an aqueous 5N sodium hydroxide solution (10 mL) was added to the residue. The aqueous layer was extracted twice with chloroform (30 mL). The combined organic layer was dried over anhydrous magnesium sulfate. After removing the anhydrous sodium sulfate by filtration, the filtrate was concentrated. The residue was purified by silica gel chromatography (dichrolomethane:methanol:28% aqueous ammonia=10:1:0→80:10:1) to obtain the title compound (37 mg) having the following physical properties.

TLC: Rf 0.39 (chloroform:methanol:28% aqueous ammonia=90:10:1);

NMR (CD$_3$OD): δ 0.92 (t, J=7.50 Hz, 6H), 1.04-1.35 (m, 2H), 1.38-1.74 (m, 11H), 1.95-2.12 (m, 2H), 2.30-2.48 (m, 2H), 2.49-2.69 (m, 6H), 2.89-3.11 (m, 4H), 4.55 (s, 4H), 6.95-7.03 (m, 4H).

Example 11(1) to Example 11(11)

The same operation as in Example 9→Example 10→Example 11 was performed, except for using corresponding amine in place of tert-butyl 4-(aminomethyl)piperidine-1-carboxylate in Example 9 and corresponding aldehyde in place of 4-(dipropylamino)butanal in Example 11, to obtain the following compound.

Example 11 (1)

N'-({1-[(1-cycloheptyl-4-piperidinyl)methyl]-4-piperidinyl}methyl)-N,N-bis(H-imidazol-2-ylmethyl)urea

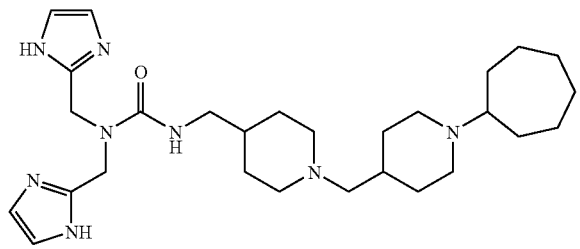

Description: amorphous;
TLC: Rf 0.78 (chloroform:methanol:28% aqueous ammonia=40:10:2);

NMR (CD$_3$OD): δ 1.09-1.32 (m, 4H), 1.38-1.61 (m, 12H), 1.63-1.81 (m, 4H), 1.81-1.93 (m, 4H), 2.16 (d, J=6.9 Hz, 2H), 2.27-2.42 (m, 2H), 2.53-2.68 (m, 1H), 2.73-2.91 (m, 4H), 3.03 (d, J=6.6 Hz, 2H), 4.55 (s, 4H), 6.98 (s, 4H).

Example 11 (2)

N'-{trans-4-[(8-cyclohexyl-2,8-diazaspiro[4.5]dec-2-yl)methyl]cyclohexyl}-N,N-bis(1H-imidazol-2-ylmethyl)urea

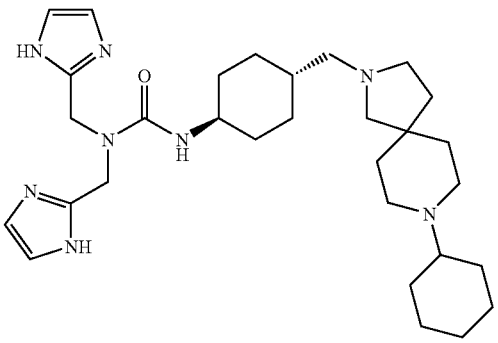

Description: amorphous;
TLC: Rf 0.62 (ethyl acetate:methanol:28% aqueous ammonia=50:10:1);

NMR (CDCl$_3$): δ 0.85-0.96 (m, 2H), 1.08-1.36 (m, 8H), 1.56-2.00 (m, 14H), 2.17 (d, J=6.9 Hz, 2H), 2.30 (s, 2H), 2.48-2.52 (m, 4H), 2.60-2.71 (m, 4H), 3.41 (m, 1H), 4.58 (br-s, 4H), 6.11 (m, 1H), 6.95 (br-s, 4H).

Example 11 (3)

N'-[4-(8-cyclohexyl-2,8-diazaspiro[4.5]dec-2-yl)cyclohexyl]-N,N-bis(1H-imidazol-2-ylmethyl)urea

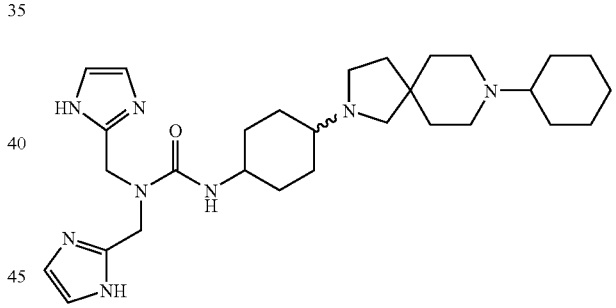

Description: amorphous;
TLC: Rf 0.20 (ethyl acetate:methanol:28% aqueous ammonia=50:10:1);

NMR (CDCl$_3$): δ 1.12-1.51 (m, 8H), 1.69-1.99 (m, 16H), 2.25 (br-s, 2H), 2.52-2.81 (m, 8H), 3.79 (m, 1H), 4.61 (br-s, 4H), 6.12 (d, J=6.6 Hz, 1H), 6.96 (br-s, 4H).

Example 11 (4)

N,N-bis(1H-imidazol-2-ylmethyl)-N'-{4-[(8-isobutyl-2,8-diazaspiro[4.5]dec-2-yl)methyl]phenyl}urea Description: amorphous;
TLC: Rf 0.38 (ethyl acetate:methanol:28% aqueous ammonia=80:10:2);

NMR (CDCl$_3$): δ 0.87 (d, J=6.6 Hz, 6H), 1.49-1.65 (m, 6H), 1.68-1.83 (m, 1H), 2.01 (d, J=7.2 Hz, 2H), 2.21-2.30 (m, 4H), 2.31 (s, 2H), 2.53 (t, J=6.9 Hz, 2H), 3.51 (s, 2H), 4.72 (s, 4H), 6.91 (s, 4H), 7.21 (d, J=8.4 Hz, 2H), 7.28 (d, J=8.4 Hz, 2H), 8.73 (s, 1H).

Example 11 (5)

N,N-bis(1H-imidazol-2-ylmethyl)-N'-(4-{[8-(2-thienylmethyl)-2,8-diazaspiro[4.5]dec-2-yl]methyl}phenyl)urea Description: amorphous;
TLC: Rf 0.38 (ethyl acetate:methanol:28% aqueous ammonia=80:10:2);
NMR (CDCl$_3$): δ 1.51-1.64 (m, 6H), 2.32 (s, 2H), 2.33-2.43 (m, 4H), 2.53 (t, J=6.9 Hz, 2H), 3.51 (s, 2H), 3.67 (s, 2H), 4.73 (s, 4H), 6.84-6.98 (m, 6H), 7.17-7.34 (m, 5H), 8.69 (s, 1H).

Example 11 (6)

N,N-bis(1H-imidazol-2-ylmethyl)-N'-[4-({8-[(3-methyl-2-thienyl)methyl]-2,8-diazaspiro[4.5]dec-2-yl}methyl)phenyl]urea Description: amorphous;
TLC: Rf 0.39 (ethyl acetate:methanol:28% aqueous ammonia=80:10:2);
NMR (CDCl$_3$): δ 1.48-1.66 (m, 6H), 2.17 (s, 3H), 2.32 (s, 2H), 2.34-2.45 (m, 4H), 2.53 (t, J=6.9 Hz, 2H), 3.51 (s, 2H), 3.56 (s, 2H), 4.73 (s, 4H), 6.77 (d, J=4.8 Hz, 1H), 6.82-7.00 (m, 4H), 7.11 (d, J=4.8 Hz, 1H), 7.21 (d, J=9.0 Hz, 2H), 7.29 (d, J=9.0 Hz, 2H), 8.72 (s, 1H).

Example 11 (7)

N'-[4-({[trans-4-(dipropylamino)cyclohexyl]amino}methyl)phenyl]-N,N-bis(1H-imidazol-2-ylmethyl)urea Description: amorphous;
TLC: Rf 0.56 (ethyl acetate:methanol:28% aqueous ammonia=40:10:2);
NMR (CDCl$_3$): δ 0.84 (t, J=7.2 Hz, 6H), 1.05-1.47 (m, 8H), 1.72-1.84 (m, 2H), 1.96-2.03 (m, 2H), 2.33-2.54 (m, 6H), 3.74 (s, 2H), 4.71 (s, 4H), 6.92 (s, 4H), 7.19 (d, J=8.7 Hz, 2H), 7.29 (d, J=8.7 Hz, 2H), 8.73 (s, 1H).

Example 11 (8)

N'-[4-({[4-(dipropylamino)butyl]amino}methyl)phenyl]-N,N-bis(1H-imidazol-2-ylmethyl)urea Description: amorphous;
TLC: Rf 0.58 (ethyl acetate:methanol:28% aqueous ammonia=40:10:2);
NMR (CDCl$_3$): δ 0.86 (t, J=7.2 Hz, 6H), 1.33-1.54 (m, 8H), 2.26-2.46 (m, 6H), 2.61 (t, J=6.6 Hz, 2H), 3.72 (s, 2H), 4.72 (s, 4H), 6.91 (s, 4H), 7.20 (d, =8.7 Hz, 2H), 7.29 (d, =8.7 Hz, 2H), 8.75 (s, 1H).

Example 11 (9)

N-{4-[(8-cyclohexyl-2,8-diazaspiro[4.5]dec-2-yl)methyl]benzyl}-N,N'-bis(1H-imidazol-2-ylmethyl)urea Description: amorphous;
TLC: Rf 0.24 (dichlorolomethane:methanol:28% aqueous ammonia=90:10:1);
NMR (CDCl$_3$): δ 1.00-1.32 (m, 6H), 1.50-1.70 (m, 6H), 1.70-1.90 (m, 4H), 2.24 (m, 1H), 2.34 (s, 2H), 2.40-2.60 (m, 6H), 3.53 (s, 2H), 4.28-4.30 (m, 2H), 4.40-4.52 (m, 4H), 6.71 (m, 1H), 6.86 (s, 2H), 6.91 (s, 2H), 7.06 (d, J=7.8 Hz, 2H), 7.22 (d, J=7.8 Hz, 2H).

Example 11(10)

N'-{4-[(8-cyclohexyl-2,8-diazaspiro[4.5]dec-2-yl)methyl]phenyl}-N,N-bis(1H-imidazol-2-ylmethyl)urea Description: amorphous;
TLC: Rf 0.36 (ethyl acetate:methanol:28% aqueous ammonia=80:10:2);
NMR (CDCl$_3$): δ 0.95-1.92 (m, 16H), 2.11-2.28 (m, 1H), 2.31 (s, 2H), 2.40-2.50 (m, 4H), 2.53 (t, J=6.9 Hz, 2H), 3.51 (s, 2H), 4.74 (s, 4H), 6.89 (s, 4H), 7.21 (d, J=8.4 Hz, 2H), 7.27 (d, J=8.4 Hz, 2H), 8.65 (s, 1H), 10.53-12.50 (m, 2H).

Example 11(11)

4-({8-[(2,4-dimethyl-1,3-thiazol-5-yl)methyl]-2,8-diazaspiro[4.5]dec-2-yl}methyl)-N,N-bis(1H-imidazol-2-ylmethyl)benzamide Description: amorphous;
TLC: Rf 0.14 (dichrolomethane:methanol:28% aqueous ammonia=90:10:1);
NMR (CDCl$_3$): δ 1.48-1.65 (m, 6H), 2.23-2.46 (m, 9H), 2.48-2.58 (m, 2H), 2.61 (s, 3H), 3.51 (s, 2H), 3.57 (s, 2H), 4.60-4.78 (m, 4H), 6.96-7.12 (m, 4H), 7.35 (d, J=8.4 Hz, 2H), 7.49 (d, J=8.4 Hz, 2H).

Example 12

1-[4-(diethoxymethyl)phenyl]-N-[(1-{[2-(trimethylsilyl)ethoxy]methyl}-1H-imidazol-2-yl)methyl]methanamine With 4-(diethoxymethy)benzaldehyde (957 mg) and 1-(1-{[2-(trimethylsilyl)ethoxy]methyl}-1H-imidazol-2-yl)methanamine (1.05 g), the same operation as in Example 2 was performed to obtain the title compound (2.05 g) having the following physical properties.
TLC: Rf 0.63 (chloroform:methanol:28% aqueous ammonia=80:10:1);
NMR (CDCl$_3$): δ 7.43 (d, J=7.8 Hz, 2H), 7.33 (d, J=7.8 Hz, 2H), 6.97 (m, 2H), 5.49 (s, 1H), 5.32 (s, 2H), 3.94 (s, 2H), 3.84 (s, 2H), 3.52 (m, 6H), 1.24 (m, 6H), 0.88 (m, 2H), −0.03 (s, 9H).

Example 13

Benzyl[4-(diethoxymethyl)benzyl][(1-{[2-(trimethylsilyl)ethoxy]methyl}-1H-imidazol-2-yl)methyl]carbamate To a dichloromethane (30 mL) solution of compound (3.65 g) obtained in Example 12 and triethylamine (2.64 g), benzyl chloroformate (2.97 g) was added at 0° C. The reaction solution was stirred at 0° C. for 4 hours. To the reaction solution, an aqueous 1N sodium hydroxide solution (100 mL) was added. The aqueous layer was extracted twice with dichloromethane (100 mL). The combined organic layer was washed with saturated brine and then dried over anhydrous magnesium sulfate. After removing the anhydrous sodium sulfate by filtration, the filtrate was concentrated. The residue was purified by silica gel chromatography (n-hexane:ethyl acetate=1:0→0:1) to obtain the title compound (1.80 g) having the following physical properties.

TLC: Rf 0.16 (n-hexane:ethyl acetate=3:1);
NMR (CDCl$_3$): δ 7.32 (m, 9H), 7.09 (m, 1H), 7.01 (m, 1H), 5.45 (s, 2H), 5.41 (s, 1H), 5.20 (s, 2H), 4.74 (m, 4H), 3.58 (m, 6H), 1.27 (m, 6H), 0.90 (m, 2H), −0.02 (s, 9H).

Example 14 benzyl(4-formylbenzyl)(1H-imidazol-2-ylmethyl)carbamate

A 50% trifluoroacetic acid/dichloromethane (12 mL) solution of the compound (1.79 g) obtained in Example 13 was stirred at room temperature for 8 hours. The reaction solution was concentrated under reduced pressure. To the residue, an aqueous 2N sodium hydroxide solution (75 mL) was added. The aqueous layer was extracted twice with dichloromethane (100 mL). The combined organic layer was washed with saturated brine and then dried over anhydrous magnesium sulfate. After removing the anhydrous sodium sulfate by filtration, the filtrate was concentrated. The residue was purified by silica gel chromatography (n-hexane:ethyl acetate=3:1→0:1) to obtain the title compound (875 mg) having the following physical properties.
TLC: Rf 0.38 (ethyl acetate);
NMR (CDCl$_3$): δ 9.99 (s, 1H), 7.80 (m, 2H), 7.28 (m, 7H), 6.99 (m, 2H), 5.20 (s, 2H), 4.62 (s, 2H), 4.46 (s, 2H).

Example 15 benzyl{4-[(8-cyclohexyl-2,8-diazaspiro[4.5]dec-2-yl)methyl]benzyl}(1H-imidazol-2-ylmethyl)carbamate The same operation as in Example 2 was performed, except for using the compound (643 mg) obtained in Example 14 and 8-cyclohexyl-2,8-diazaspiro[4.5]decane (500 mg), the obtained crude product was purified by silica gel chromatography (ethyl acetate:10%-saturated aqueous ammonia-methanol=1:0→7:3) to obtain the title compound (806 mg) having the following physical properties.
Description: amorphous;
TLC: Rf 0.50 (chloroform:methanol:28% aqueous ammonia=80:10:1);
NMR (CDCl$_3$): δ 0.97-1.35 (m, 5H), 1.51-1.67 (m, 6H), 1.67-1.90 (m, 7H), 2.14-2.30 (m, 1H), 2.34 (s, 2H), 2.39-2.61 (m, 4H), 3.55 (s, 2H), 4.41 (s, 2H), 4.51 (s, 2H), 5.21 (s, 2H), 6.96 (s, 2H), 7.09-7.19 (m, 2H), 7.20-7.26 (m, 2H), 7.28-7.48 (m, 5H), 9.63-10.14 (m, 1H).

Example 16

N,N-bis({1-[(dimethylamino)sulfonyl]-1H-imidazol-2-yl}methyl)-4-({[trans-4-(dipropylaminoamino)cyclohexyl]amino}methyl)benzamide The same operation as in Example 2 was performed, except for using the compound (1.5 g) obtained in Example 4 and trans-N,N-dipropylcyclohexane-1,4-diamine (682 mg), and then the obtained crude product was purified by silica gel chromatography (ethyl acetate:10%-saturated aqueous ammonia-methanol=1:0→8:2) to obtain the title compound (1.78 g) having the following physical properties.
Description: amorphous;
TLC: Rf 0.41 (chloroform:methanol:28% aqueous ammonia=80:10:1);
NMR (DMSO-d$_6$): δ 0.79 (t, J=7.5 Hz, 6H), 0.89-1.05 (m, 2H), 1.06-1.21 (m, 2H), 1.21-1.38 (m, 4H), 1.55-1.68 (m, 2H), 1.82-1.95 (m, 2H), 2.14-2.41 (m, 6H), 2.56 (s, 6H), 2.90 (s, 6H), 3.68 (s, 2H), 4.82 (s, 2H), 4.96 (s, 2H), 7.05 (d, J=1.5 Hz, 1H), 7.12 (d, J=1.5 Hz, 1H), 7.25 (d, J=8.1 Hz, 2H), 7.32 (d, J=8.1 Hz, 2H), 7.51-7.61 (m, 2H).

Example 17 methyl (4-{[bis({1-[(dimethylamino)sulfonyl]-1H-imidazol-2-yl}methyl)amino]carbonyl}benzyl)[trans-4-(dipropylaminoamino)cyclohexyl]carbamate The same operation as in Example 13 was performed, except for using the compound (200 mg) obtained in Example 16 and methyl chloroformate (54 mg), and then the obtained crude product was purified by silica gel chromatography (ethyl acetate:10%-saturated aqueous ammonia-methanol=1:0→85:15) to obtain the title compound (210 mg) having the following physical properties.
TLC: Rf 0.74 (chloroform:methanol:28% aqueous ammonia=80:10:1);
NMR (CDCl$_3$): δ 7.50 (d, J=8.1 Hz, 2H), 7.25 (m, 2H), 7.20 (m, 2H), 7.08 (m, 1H), 6.98 (m, 1H), 5.03 (m, 4H), 4.39 (s, 2H), 3.80 (m, 1H), 3.68 (m, 4H), 3.01 (s, 6H), 2.66 (m, 6H), 2.33 (m, 5H), 1.73 (m, 5H), 1.36 (m, 6H), 0.83 (t, J=7.5 Hz, 6H).

Example 18 methyl (4-{[bis(1H-imidazol-2-ylmethyl)amino]carbonyl}benzyl)[trans-4-(dipropylamino)cyclohexyl]carbamate The same operation as in Example 5 was performed, except for using the compound (205 mg) obtained in Example 18, and then the obtained crude product was purified by silica gel chromatography (dichlorolomethane:methanol:28% aqueous ammonia=10:1:0→80:10:1) to obtain the title compound (58 mg) having the following physical properties.

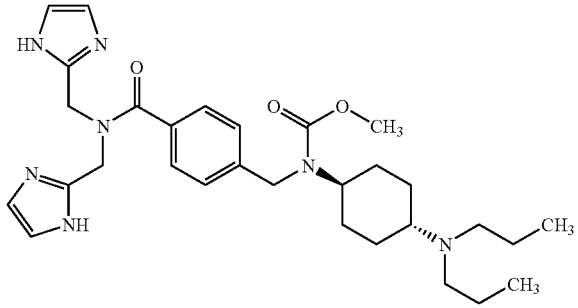

Description: amorphous;
TLC: Rf 0.33 (chloroform:methanol:28% aqueous ammonia=80:10:1);
NMR (DMSO-d$_6$): δ 0.79 (t, J=7.50 Hz, 6H), 1.07-1.80 (m, 12H), 2.11-2.42 (m, 5H), 3.44-3.69 (m, 3H), 3.69-3.91 (m, 1H), 4.38 (s, 2H), 4.46-4.70 (m, 4H), 6.67-7.09 (m, 4H), 7.19 (d, J=8.10 Hz, 2H), 7.42 (d, J=8.10 Hz, 2H), 11.78-12.69 (m, 2H).

Example 18(1) to Example 18(3)

The same operation as in Example 17→Example 18 was performed, except for using a corresponding chloride in place of methyl chloroformate in Example 17, to obtain the following compound.

Example 18(1)

ethyl (4-{[bis(1H-imidazol-2-ylmethyl)amino]carbonyl}benzyl)[trans-4-(dipropylamino)cyclohexyl]carbamate Description: amorphous;
TLC: Rf 0.46 (chloroform:methanol:28% aqueous ammonia=80:10:1);
NMR (DMSO-$d_6$): δ 0.80 (t, J=7.2 Hz, 6H), 0.94-1.81 (m, 15H), 2.12-2.47 (m, 5H), 3.61-3.89 (m, 1H), 3.90-4.16 (m, 2H), 4.37 (s, 2H), 4.46-4.72 (m, 4H), 6.76-7.11 (m, 4H), 7.19 (d, J=8.1 Hz, 2H), 7.42 (d, J=8.1 Hz, 2H), 11.91-12.59 (m, 2H).

Example 18(2)

phenyl (4-{[bis(1H-imidazol-2-ylmethyl)amino]carbonyl}benzyl)[trans-4-(dipropylamino)cyclohexyl]carbamate Description: amorphous;
TLC: Rf 0.49 (chloroform:methanol:28% aqueous ammonia=80:10:1);
NMR (DMSO-$d_6$): δ 0.81 (t, J=7.2 Hz, 6H), 1.11-1.97 (m, 12H), 2.15-2.67 (m, 5H), 3.75-4.09 (m, 1H), 4.30-4.80 (m, 6H), 6.75-7.07 (m, 5H), 7.09-7.25 (m, 2H), 7.26-7.44 (m, 4H), 7.44-7.62 (m, 2H), 11.91-12.63 (m, 2H).

Example 18(3)

benzyl(4-{[bis(1H-imidazol-2-ylmethyl)amino]carbonyl}benzyl)[trans-4-(dipropylamino)cyclohexyl]carbamate Description: amorphous;
TLC: Rf 0.32 (chloroform:methanol:28% aqueous ammonia=80:10:1);
NMR (DMSO-$d_6$): δ 0.80 (t, J=7.2 Hz, 6H), 1.14-1.84 (m, 12H), 2.12-2.46 (m, 5H), 3.72-3.99 (m, 1H), 4.42 (s, 2H), 4.47-4.68 (m, 4H), 4.95-5.21 (m, 2H), 6.84-7.04 (m, 4H), 7.05-7.14 (m, 1H), 7.14-7.27 (m, 4H), 7.27-7.40 (m, 2H), 7.43 (d, J=8.4 Hz, 2H), 11.76-12.78 (m, 2H).

Example 19

2,2'-[{[(4-formylphenyl)sulfonyl]imino}bis(methylene)]bis(N,N-dimethyl-1H-imidazole-1-sulfonamide)

To a dichloromethane (5 mL) solution of the compound (500 mg) obtained in Example 3 and triethylamine (0.27 mL), 4-formylbenzenesulfonyl chloride (340 mg) was added at 0° C. The reaction solution was stirred at 0° C. for 16 hours. To the reaction solution, water (30 mL) was added, followed by extraction of the aqueous layer twice with dichloromethane (50 mL). The combined organic layer was washed with saturated brine and then dried over anhydrous magnesium sulfate. After removing the anhydrous sodium sulfate by filtration, the filtrate was concentrated. The residue was washed with ethyl acetate and then purified to obtain the title compound (606 mg) having the following physical properties.
TLC: Rf 0.67 (ethyl acetate);
NMR (DMSO-$d_6$): δ 2.83 (s, 12H), 5.01 (s, 4H), 6.86 (d, J=1.8 Hz, 2H), 7.48 (d, J=1.8 Hz, 2H), 7.90 (d, J=8.1 Hz, 2H), 8.00 (d, J=8.1 Hz, 2H), 10.06 (s, 1H).

Example 20

4-formyl-N,N-bis(1H-imidazol-2-ylmethyl)benzenesulfonamide

The same operation as in Example 5 was performed, except for using the compound (600 mg) obtained in Example 19, to obtain the title compound (373 mg) having the following physical properties.
TLC: Rf 0.49 (chloroform:methanol:28% aqueous ammonia=80:10:1);
NMR (CD$_3$OD): δ 4.59 (s, 4H), 6.91 (s, 4H), 7.72 (d, J=8.0 Hz, 2H), 7.92 (d, J=8.0 Hz, 2H), 10.02 (s, 1H).

Example 21

4-[(8-cyclohexyl-2,8-diazaspiro[4.5]dec-2-yl)methyl]-N,N-bis(1H-imidazol-2-ylmethyl)benzenesulfonamide

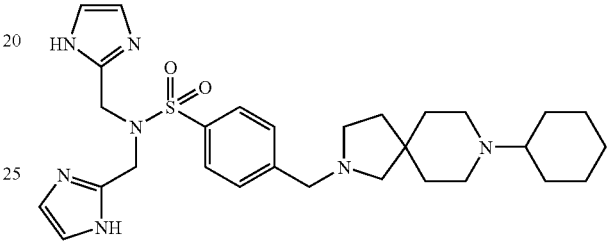

With the compound produced in Example 20 and 8-cyclohexyl-2,8-diazaspiro[4.5]decane dihydrochloride, the same operation as in Example 2 was performed to obtain the title compound having the following physical properties.
Description: amorphous;
TLC: Rf 0.49 (dichlolomethane:methanol:28% aqueous ammonia=50:10:1);
NMR (CDCl$_3$): δ 1.10-1.30 (m, 6H), 1.60-1.68 (m, 8H), 1.79-1.92 (m, 4H), 2.29 (m, 1H), 2.50-2.62 (m, 6H), 3.62 (s, 2H), 4.52 (s, 4H), 6.91 (s, 4H), 7.41 (d, J=8.1 Hz, 2H), 7.57 (d, J=8.1 Hz, 2H).

Example 21 (1) to Example 21(21)

Except for using the corresponding aldehyde in Example 21 in place of the compound produced in Example 20 and using the corresponding amine salt or amine in place of 8-cyclohexyl-2,8-diazaspiro[4.5]decane dihydrochloride, the same operation as in Example 21 was performed to obtain the following compound.

Example 21 (1)

4-({[trans-4-(dipropylamino)cyclohexyl]amino}methyl)-N,N-bis(1H-imidazol-2-ylmethyl)benzenesulfonamide

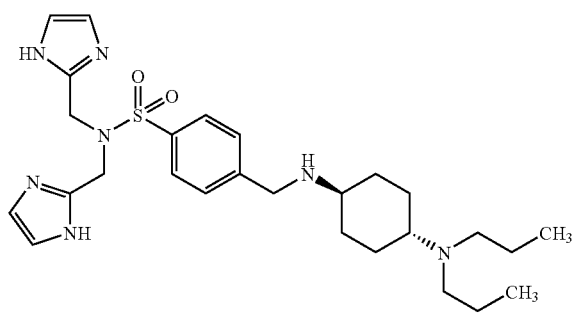

Description: amorphous;
TLC: Rf 0.33 (chloroform:methanol:28% aqueous ammonia=80:10:1);
NMR (DMSO-d$_6$): δ 0.80 (t, J=6.90 Hz, 6H), 0.90-1.07 (m, 2H), 1.07-1.24 (m, 2H), 1.23-1.43 (m, 4H), 1.56-1.73 (m, 2H), 1.82-1.98 (m, 2H), 2.14-2.45 (m, 6H), 3.73 (s, 2H), 4.49 (s, 4H), 6.75-7.09 (m, 4H), 7.41 (d, J=8.10 Hz, 2H), 7.54 (d, J=8.10 Hz, 2H), 11.86-12.93 (m, 2H).

Example 21(2)

N,N-bis(1H-imidazol-2-ylmethyl)-4-({[trans-4-(2,3,6,7-tetrahydro-1H-azepin-1-yl)cyclohexyl]amino}methyl)benzenesulfonamide Description: amorphous;
TLC: Rf 0.68 (chloroform:methanol:28% aqueous ammonia=80:20:4);
NMR (DMSO-d$_6$): δ 0.90-1.10 (m, 2H), 1.10-1.30 (m, 2H), 1.62-1.78 (m, 2H), 1.82-1.97 (m, 2H), 2.00-2.16 (m, 4H), 2.16-2.30 (m, 1H), 2.34-2.46 (m, 1H), 2.51-2.60 (m, 4H), 3.73 (s, 2H), 4.48 (s, 4H), 5.71 (t, J=3.00 Hz, 2H), 6.78-7.04 (m, 4H), 7.41 (d, J=8.40 Hz, 2H), 7.54 (d, J=8.40 Hz, 2H), 11.60-13.13 (m, 2H).

Example 21(3)

N,N-bis(1H-imidazol-2-ylmethyl)-4-({[trans-4-(1-piperidinyl)cyclohexyl]amino}methyl)benzenesulfonamide Description: amorphous;
TLC: Rf 0.66 (chloroform:methanol:28% aqueous ammonia=80:20:4);
NMR (DMSO-d$_6$): δ 0.89-1.09 (m, 2H), 1.09-1.27 (m, 2H), 1.28-1.38 (m, 2H), 1.38-1.52 (m, 4H), 1.63-1.78 (m, 2H), 1.83-1.99 (m, 2H), 2.10-2.29 (m, 2H), 2.34-2.46 (m, 4H), 3.73 (s, 2H), 4.48 (s, 4H), 6.66-7.19 (m, 4H), 7.41 (d, J=8.40 Hz, 2H), 7.54 (d, J=8.40 Hz, 2H), 12.10-12.77 (m, 2H).

Example 21(4)

4-({[trans-4-(1-azepanyl)cyclohexyl]amino}methyl)-N,N-bis(1H-imidazol-2-ylmethyl)benzenesulfonamide Description: amorphous;
TLC: Rf 0.58 (chloroform:methanol:28% aqueous ammonia=80:20:4);
NMR (DMSO-d$_6$): δ 0.89-1.08 (m, 2H), 1.08-1.29 (m, 2H), 1.43-1.56 (m, 8H), 1.61-1.76 (m, 2H), 1.80-1.98 (m, 2H), 2.13-2.28 (m, 1H), 2.29-2.44 (m, 1H), 2.52-2.62 (m, 4H), 3.73 (s, 2H), 4.48 (s, 4H), 6.69-7.13 (m, 4H), 7.41 (d, J=8.20 Hz, 2H), 7.54 (d, J=8.10 Hz, 2H), 12.15-12.71 (m, 2H).

Example 21(5)

N,N-bis(1H-imidazol-2-ylmethyl)-4-({2-[(3-methyl-2-thienyl)methyl]-2,8-diazaspiro[4.5]dec-8-yl}methyl)benzenesulfonamide Description: amorphous;
TLC: Rf 0.47 (chloroform:methanol:28% aqueous ammonia=80:10:1);
NMR (DMSO-d$_6$): δ 1.37-1.65 (m, 6H), 2.12 (s, 3H), 2.17-2.31 (m, 4H), 2.34 (s, 2H), 2.52-2.61 (m, 2H), 3.43 (s, 2H), 3.62 (s, 2H), 4.51 (s, 4H), 6.67-7.10 (m, 5H), 7.25 (d, J=5.10 Hz, 1H), 7.33 (d, J=8.10 Hz, 2H), 7.51 (d, J=8.10 Hz, 2H), 12.03-12.82 (m, 2H).

Example 21(6)

N,N-bis(1H-imidazol-2-ylmethyl)-4-{[2-(2-thienylmethyl)-2,9-diazaspiro[5.5]undec-9-yl]methyl}benzenesulfonamide Description: amorphous;
TLC: Rf 0.33 (chloroform:methanol:28% aqueous ammonia=80:10:1);
NMR (DMSO-d$_6$): δ 1.19-1.33 (m, 2H), 1.33-1.62 (m, 6H), 2.03-2.21 (m, 4H), 2.21-2.42 (m, 4H), 3.40 (s, 2H), 3.60

(s, 2H), 4.51 (s, 4H), 6.62-7.16 (m, 6H), 7.23-7.34 (m, J=8.10 Hz, 2H), 7.38 (dd, J=5.10, 1.50 Hz, 1H), 7.49 (d, J=8.10 Hz, 2H), 12.04-12.65 (m, 2H).

Example 21(7)

N,N-bis(1H-imidazol-2-ylmethyl)-4-({2-[(3-methyl-2-thienyl)methyl]-2,9-diazaspiro[5.5]undec-9-yl}methyl)benzenesulfonamide Description: amorphous;
TLC: Rf 0.31 (chloroform:methanol:28% aqueous ammonia=80:10:1);
NMR (DMSO-$d_6$): δ 1.17-1.32 (m, 2H), 1.32-1.59 (m, 6H), 2.02-2.20 (m, 7H), 2.21-2.40 (m, 4H), 3.40 (s, 2H), 3.48 (s, 2H), 4.50 (s, 4H), 6.70-7.06 (m, 5H), 7.26 (d, J=4.80 Hz, 1H), 7.30 (d, J=8.70 Hz, 2H), 7.49 (d, J=8.70 Hz, 2H), 12.01-12.73 (m, 2H).

Example 21(8)

N,N-bis(1H-imidazol-2-ylmethyl)-4-{[9-(2-thienyl-methyl)-2,9-diazaspiro[5.5]undec-2-yl]methyl}benzenesulfonamide Description: amorphous;
TLC: Rf 0.36 (chloroform:methanol:28% aqueous ammonia=80:10:1);
NMR (DMSO-$d_6$): δ 1.13-1.34 (m, 2H), 1.36-1.63 (m, 6H), 1.92-2.12 (m, 2H), 2.17-2.39 (m, 6H), 3.42 (s, 2H), 3.59 (s, 2H), 4.52 (s, 4H), 6.71-6.85 (m, 2H), 6.85-6.94 (m, 2H), 6.94-7.11 (m, 2H), 7.28-7.40 (m, 3H), 7.53 (d, J=7.80 Hz, 2H), 12.14-12.58 (m, 2H).

Example 21(9)

N,N-bis(1H-imidazol-2-ylmethyl)-4-({9-[(3-methyl-2-thienyl)methyl]-2,9-diazaspiro[5.5]undec-2-yl}methyl)benzenesulfonamide Description: amorphous;
TLC: Rf 0.36 (chloroform:methanol:28% aqueous ammonia=80:10:1);
NMR (DMSO-$d_6$): δ 1.19-1.35 (m, 2H), 1.36-1.60 (m, 6H), 2.00-2.07 (m, 2H), 2.09 (s, 3H), 2.19-2.40 (m, 6H), 3.42 (s, 2H), 3.50 (s, 2H), 4.52 (s, 4H), 6.78 (d, J=5.10 Hz, 1H), 6.82-6.99 (m, 4H), 7.25 (d, J=5.10 Hz, 1H), 7.34 (d, J=8.40 Hz, 2H), 7.52 (d, J=8.40 Hz, 2H), 11.80-13.16 (m, 2H).

Example 21 (10)

N,N-bis(1H-imidazol-2-ylmethyl)-4-({4-[(3-methyl-2-thienyl)methyl]-1-oxa-4,9-diazaspiro[5.5]undec-9-yl}methyl)benzenesulfonamide Description: amorphous;
TLC: Rf 0.35 (chloroform:methanol:28% aqueous ammonia=80:10:1);
NMR (DMSO-$d_6$): δ 1.39-1.59 (m, 2H), 1.70-1.90 (m, 2H), 2.13 (s, 3H), 2.17-2.44 (m, 6H), 3.16 (s, 2H), 3.45 (s, 2H), 3.51 (s, 2H), 3.56-3.65 (m, 2H), 4.51 (s, 4H), 6.66-7.13 (m, 5H), 7.29 (d, J=5.10 Hz, 1H), 7.33 (d, J=8.40 Hz, 2H), 7.50 (d, J=8.40 Hz, 2H), 12.08-12.65 (m, 2H).

Example 21 (11)

N,N-bis(1H-imidazol-2-ylmethyl)-4-{[9-(2-thienyl-methyl)-3,9-diazaspiro[5.5]undec-3-yl]methyl}benzenesulfonamide Description: amorphous;
TLC: Rf 0.65 (chloroform:methanol:28% aqueous ammonia=40:9:1);
NMR (CDCl$_3$): δ 1.45-1.55 (m, 8H), 2.31-2.37 (m, 4H), 2.40-2.47 (m, 4H), 3.50 (s, 2H), 3.73 (s, 2H), 4.44 (s, 4H), 6.89-6.91 (m, 1H), 6.94 (dd, J=5.1, 3.6 Hz, 1H), 7.00 (s, 4H), 7.22 (dd, J=5.1, 0.9 Hz, 1H), 7.39 (d, J=8.4 Hz, 2H), 7.69 (d, J=8.4 Hz, 2H).

Example 21(12)

N,N-bis(1H-imidazol-2-ylmethyl)-4-({9-[(3-methyl-2-thienyl)methyl]-3,9-diazaspiro[5.5]undec-3-yl}methyl)benzenesulfonamide Description: amorphous;
TLC: Rf 0.65 (chloroform:methanol:28% aqueous ammonia=40:9:1);
NMR (CDCl$_3$): δ 1.45-1.55 (m, 8H), 2.19 (s, 3H), 2.31-2.38 (m, 4H), 2.40-2.48 (m, 4H), 3.50 (s, 2H), 3.63 (s, 2H), 4.44 (s, 4H), 6.78 (d, J=5.1 Hz, 1H), 7.00 (s, 4H), 7.12 (d, J=5.1 Hz, 1H), 7.40 (d, J=8.4 Hz, 2H), 7.69 (d, J=8.4 Hz, 2H).

Example 21(13)

ethyl{(4-{[bis(1H-imidazol-2-ylmethyl)amino]sulfonyl}benzyl)[trans-4-(dipropylamino)cyclohexyl]amino}acetate Description: amorphous;
TLC: Rf 0.26 (chloroform:methanol:28% aqueous ammonia=80:10:1);
NMR (DMSO-$d_6$): δ 0.82 (t, J=7.50 Hz, 6H), 1.16 (t, J=7.20 Hz, 3H), 1.20-1.51 (m, 8H), 1.66-1.91 (m, 4H), 2.22-2.65 (m, 6H), 3.29 (s, 2H), 3.76 (s, 2H), 4.04 (q, J=7.20 Hz, 2H), 4.51 (s, 4H), 6.75-7.01 (m, 4H), 7.42 (d, J=8.70 Hz, 2H), 7.51 (d, J=8.70 Hz, 2H), 11.86-12.89 (m, 2H).

Example 21(14)

{(4-{[bis(1H-imidazol-2-ylmethyl)amino]sulfonyl}benzyl)[trans-4-(dipropylamino)cyclohexyl]amino}acetic acid dihydrochloride Description: amorphous;
TLC: Rf 0.16 (chloroform:methanol:28% aqueous ammonia=80:20:4);
NMR (DMSO-$d_6$): δ 0.90 (t, J=7.20 Hz, 6H), 1.54-1.86 (m, 8H), 2.10-2.34 (m, 4H), 2.79-3.16 (m, 4H), 3.17-3.52 (m, 2H), 4.01 (s, 2H), 4.51 (s, 2H), 4.93 (s, 4H), 7.64 (s, 4H), 7.88-8.08 (m, 4H), 10.33-10.61 (m, 2H).

Example 21(15)

ethyl{(4-{[bis(1H-imidazol-2-ylmethyl)amino]sulfonyl}benzyl)[trans-4-(dipropylamino)cyclohexyl]amino}acetate Description: amorphous;
TLC: Rf 0.26 (chloroform:methanol:28% aqueous ammonia=80:10:1);
NMR (DMSO-$d_6$): δ 0.82 (t, J=7.50 Hz, 6H), 1.16 (t, J=7.20 Hz, 3H), 1.20-1.51 (m, 8H), 1.66-1.91 (m, 4H), 2.22-

2.65 (m, 6H), 3.29 (s, 2H), 3.76 (s, 2H), 4.04 (q, J=7.20 Hz, 2H), 4.51 (s, 4H), 6.75-7.01 (m, 4H), 7.42 (d, J=8.70 Hz, 2H), 7.51 (d, J=8.70 Hz, 2H), 11.86-12.89 (m, 2H).

Example 21(16)

{(4-{[bis(1H-imidazol-2-ylmethyl)amino]sulfonyl}benzyl)[trans-4-(dipropylamino)cyclohexyl]amino}acetic acid dihydrochloride Description: amorphous;
TLC: Rf 0.16 (chloroform:methanol:28% aqueous ammonia=80:20:4);
NMR (DMSO-$d_6$): δ 0.90 (t, J=7.20 Hz, 6H), 1.54-1.86 (m, 8H), 2.10-2.34 (m, 4H), 2.79-3.16 (m, 4H), 3.17-3.52 (m, 2H), 4.01 (s, 2H), 4.51 (s, 2H), 4.93 (s, 4H), 7.64 (s, 4H), 7.88-8.08 (m, 4H), 10.33-10.61 (m, 2H).

Example 21(17)

N,N-bis(1H-imidazol-2-ylmethyl)-4-({7-[(3-methyl-2-thienyl)methyl]-2,7-diazaspiro[4.4]non-2-yl}methyl)benzenesulfonamide Description: amorphous;
TLC: Rf 0.38 (dichrolomethane:methanol:28% aqueous ammonia=90:10:1);
NMR (CDCl$_3$): δ 1.62-1.98 (m, 4H), 2.18 (s, 3H), 2.34-2.76 (m, 8H), 3.61 (s, 2H), 3.71 (s, 2H), 4.43 (s, 4H), 6.78 (d, J=5.1 Hz, 1H), 7.02 (s, 4H), 7.11 (d, J=5.1 Hz, 1H), 7.41 (d, J=8.4 Hz, 2H), 7.71 (d, J=8.4 Hz, 2H), 10.58-11.24 (m, 2H).

Example 21(18)

N,N-bis(1H-imidazol-2-ylmethyl)-4-({[(3S)-1-(1-propylbutyl)-3-piperidinyl]amino}methyl)benzenesulfonamide Description: amorphous;
TLC: Rf 0.28 (ethyl acetate:methanol:28% aqueous ammonia=90:10:1);
NMR (CD$_3$OD): δ 0.86-0.94 (m, 6H), 1.12-1.59 (m, 10H), 1.61-1.74 (m, 1H), 1.85 (s, 1H), 2.13-2.25 (m, 1H), 2.27-2.44 (m, 2H), 2.52-2.66 (m, 2H), 2.82 (dd, J=10.8, 3.3 Hz, 1H), 3.82 (s, 2H), 4.51 (s, 4H), 6.92 (s, 4H), 7.44 (d, J=8.4 Hz, 2H), 7.59 (d, J=8.4 Hz, 2H).

Example 21(19)

N,N-bis(1H-imidazol-2-ylmethyl)-4-[({(3S)-1-[(3-methyl-2-thienyl)methyl]-3-piperidinyl}amino)methyl]benzenesulfonamide Description: amorphous;
TLC: Rf 0.17 (ethyl acetate:methanol:28% aqueous ammonia=90:10:1);
NMR (CD$_3$OD): δ 1.14-1.30 (m, 1H), 1.47-1.63 (m, 1H), 1.65-1.79 (m, 1H), 1.82-2.07 (m, 2H), 2.08-2.22 (m, 4H), 2.55-2.67 (m, 1H), 2.74 (d, J=11.1 Hz, 1H), 2.91 (d, J=9.9 Hz, 1H), 3.59-3.67 (m, 2H), 3.77 (s, 2H), 4.50 (s, 4H), 6.80 (d, J=5.1 Hz, 1H), 6.92 (s, 4H), 7.20 (d, J=5.1 Hz, 1H), 7.39 (d, J=8.7 Hz, 2H), 7.56 (d, J=8.7 Hz, 2H).

Example 21(20)

4-{[(3S)-3-(dipropylamino)-1-piperidinyl]methyl}-N,N-bis(1H-imidazol-2-ylmethyl)benzenesulfonamide Description: amorphous;
TLC: Rf 0.30 (ethyl acetate:methanol:28% aqueous ammonia=90:10:1);
NMR (CD$_3$OD): δ 0.86 (t, J=7.5 Hz, 6H), 1.17-1.64 (m, 6H), 1.68-1.97 (m, 4H), 2.38-2.49 (m, 4H), 2.68-2.81 (m, 2H), 2.92 (dd, J=10.5, 1.5 Hz, 1H), 3.52-3.60 (m, 2H), 4.52 (s, 4H), 6.91 (s, 4H), 7.42 (d, J=8.7 Hz, 2H), 7.54-7.61 (m, 2H).

Example 21(21)

N,N-bis(1H-imidazol-2-ylmethyl)-4-{[7-(2-thienylmethyl)-2,7-diazaspiro[4.4]non-2-yl]methyl}benzenesulfonamide Description: amorphous;
TLC: Rf 0.33 (dichrolomethane:methanol:28% aqueous ammonia=90:10:1);
NMR (CDCl$_3$): δ 1.66-1.95 (m, 4H), 2.34-2.74 (m, 8H), 3.61 (s, 2H), 3.80 (s, 2H), 4.43 (s, 4H), 6.87-6.91 (m, 1H), 6.93 (dd, J=5.1, 3.6 Hz, 1H), 7.02 (s, 4H), 7.21 (dd, J=5.1, 1.2 Hz, 1H), 7.40 (d, J=8.4 Hz, 2H), 7.70 (d, J=8.4 Hz, 2H), 10.59-11.36 (m, 2H).

Example 22 tert-butyl[trans-4-(hydroxymethyl)cyclohexyl]carbamate

To anhydrous tetrahydrofuran (30 mL) solution of trans-4-[(tert-butoxycarbonyl)amino]cyclohexanecalboxylic acid (2.17 g), 1N-boran-tetrahydrofuran complex/tetrahydrofuran solution (17.8 mL) was slowly added at 0° C. The reaction solution was stirred at 0° C. for 2 hours. To the reaction solution, an aqueous saturated sodium hydrogen carbonate solution (100 mL) was added, and then aqueous layer was extracted twice with 100 mL of ethyl acetate. The combined organic layer was washed with saturated brine and then dried over anhydrous magnesium sulfate. After removing the anhydrous sodium sulfate by filtration, the filtrate was concentrated. Without purifying the residue, the title compound (1.6 g) having the following physical properties was obtained.
TLC: Rf 0.60 (ethyl acetate);
NMR (CDCl$_3$): δ 0.97-1.16 (m, 4H), 1.44 (s, 9H), 1.80-1.84 (m, 2H), 2.03-2.06 (m, 2H), 3.31 (m, 1H), 3.45 (d, J=6.6 Hz, 2H), 4.37 (m, 1H).

Example 23 tert-butyl(trans-4-formyl cyclohexyl)carbamate

To a dichloromethane (30 mL) solution of the compound (1.6 g) obtained in Example 22, a Dess-Martin reagent (3.97 g) was added at 0° C. The reaction solution was stirred at room temperature for 16 hours. To the reaction solution, an aqueous saturated sodium hydrogen carbonate solution (50 mL) was added, and then aqueous layer was extracted with dichloromethane. The combined organic layer was washed with saturated brine and then dried over anhydrous magnesium sulfate. After removing the anhydrous sodium sulfate by filtration, the filtrate was concentrated. The residue was purified by silica gel chromatography (n-hexane:ethyl acetate=1: 0→8:2) to obtain the title compound (1.60 g) having the following physical properties.

TLC: Rf 0.80 (ethyl acetate);

NMR (DMSO-$d_6$): δ 1.09-1.24 (m, 4H), 1.45 (s, 9H), 2.00-2.20 (m, 4H), 3.39 (m, 1H), 4.40 (m, 1H), 9.60 (d, J=1.2 Hz, 1H).

Example 24 tert-butyl {trans-4-[(8-cyclohexyl-2,8-diazaspiro[4.5]dec-2-yl)methyl]cyclohexyl}carbamate The same operation as in Example 2 was performed, except for using the compound (402 mg) obtained in Example 23 and 8-cyclohexyl-2,8-diazaspiro[4.5]decane (500 mg), to obtain the title compound (806 mg) having the following physical properties.

TLC: Rf 0.55 (dichrolomethane:methanol:28% aqueous ammonia=50:10:1);

NMR (CDCl$_3$): δ 0.91-1.86 (m, 24H), 1.45 (s, 9H), 1.99-2.05 (m, 2H), 2.18 (d, J=7.2 Hz, 2H), 2.28 (s, 2H), 2.46-2.51 (m, 5H), 3.35 (m, 1H), 4.35 (m, 1H).

Example 25 trans-4-[(8-cyclohexyl-2,8-diazaspiro[4.5]dec-2-yl)methyl]cyclohexaneamine trihydrochloride To a methanol (3 mL) solution of the compound (806 mg) obtained in Example 24, a 4N-hydrogen chloride/1,4-dioxane solution (6 mL) was added. The reaction solution was stirred at room temperature for 2 hours. The reaction solution was concentrated under reduced pressure. The title compound (749 mg) having the following physical properties were obtained without purifying the residue.

TLC: Rf 0.17 (dichrolomethane:methanol:28% aqueous ammonia=50:10:1);

NMR (CD$_3$OD): δ 1.19-2.24 (m, 24H), 3.00-4.00 (m, 12H).

Example 26 trans-4-[(8-cyclohexyl-2,8-diazaspiro[4.5]dec-2-yl)methyl]-N,N-bis(1H-imidazol-2-ylmethyl)cyclohexanamine

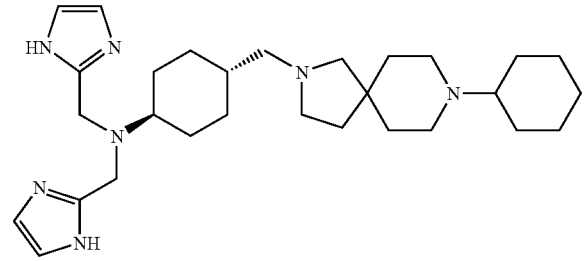

With the compound produced in Example 25 and 1H-imidazole-2-carbaldehyde, the same operation as in Example 2 was performed to obtain the title compound having the following physical properties.

Description: amorphous;

TLC: Rf 0.55 (ethyl acetate:methanol:28% aqueous ammonia=50:10:1);

NMR (CDCl$_3$): δ 0.79-0.90 (m, 2H), 1.10-1.31 (m, 8H), 1.54-1.65 (m, 7H), 1.81-1.90 (m, 8H), 2.15 (d, J=6.9 Hz, 2H), 2.27 (s, 2H), 2.30 (m, 1H), 2.46-2.56 (m, 7H), 3.77 (br-s, 4H), 6.98 (br-s, 4H).

Example 26(1) to Example 26(16)

The same operation as in Example 26 was performed, except for using the corresponding amine in place of the compound obtained in Example 25 in Example 26, to obtain the following compound.

Example 26(1)

cis-4-[(8-cyclohexyl-2,8-diazaspiro[4.5]dec-2-yl)methyl]-N,N-bis(1H-imidazol-2-ylmethyl)cyclohexanamine

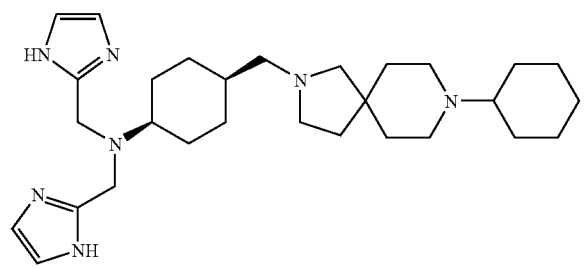

Description: amorphous;

TLC: Rf 0.70 (chloroform:methanol:28% aqueous ammonia=40:10:2);

NMR (CDCl$_3$): δ 1.00-1.94 (m, 25H), 2.18-2.63 (m, 12H), 3.71 (s, 4H), 7.02 (s, 4H).

Example 26(2)

trans-4-[(8-cyclopentyl-2,8-diazaspiro[4.5]dec-2-yl)methyl]-N,N-bis(1H-imidazol-2-ylmethyl)cyclohexanamine

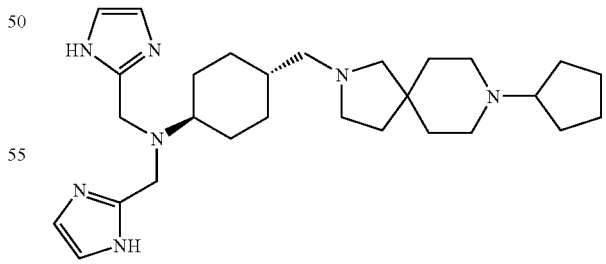

Description: amorphous;

TLC: Rf 0.69 (chloroform:methanol:28% aqueous ammonia=40:10:2);

NMR (CDCl$_3$): δ 0.75-0.98 (m, 4H), 1.14-1.96 (m, 19H), 2.15 (d, J=7.2 Hz, 2H), 2.27 (s, 2H), 2.29-2.59 (m, 8H), 3.77 (s, 4H), 6.98 (s, 4H).

Example 26(3)

trans-N,N-bis(1H-imidazol-2-ylmethyl)-4-[(8-isobutyl-2,8-diazaspiro[4.5]dec-2-yl)methyl]cyclohexanamine Description: amorphous;
TLC: Rf 0.69 (chloroform:methanol:28% aqueous ammonia=40:10:2);
NMR (CDCl$_3$): δ 0.75-1.96 (m, 16H), 0.88 (d, J=6.6 Hz, 6H), 2.04 (d, J=7.2 Hz, 2H), 2.16 (d, J=6.9 Hz, 2H), 2.20-2.58 (m, 9H), 3.78 (s, 4H), 6.99 (s, 4H).

Example 26(4)

trans-N,N-bis(1H-imidazol-2-ylmethyl)-4-({8-[(3-methyl-2-thienyl)methyl]-2,8-diazaspiro[4.5]dec-2-yl}methyl)cyclohexanamine

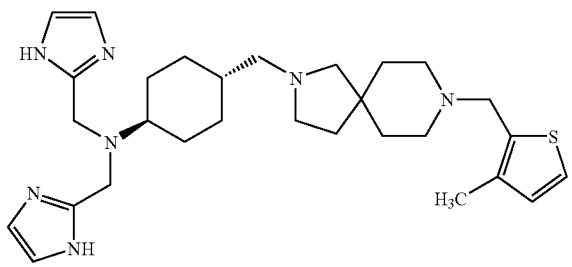

Description: amorphous;
TLC: Rf 0.69 (chloroform:methanol:28% aqueous ammonia=40:10:2);
NMR (CDCl$_3$): δ 0.77-1.98 (m, 15H), 2.05-2.63 (m, 14H), 3.58 (s, 2H), 3.68-3.79 (m, 4H), 6.77 (d, J=5.1 Hz, 1H), 6.98-7.02 (m, 4H), 7.10 (d, J=5.1 Hz, 1H).

Example 26(5)

4-(8-cyclohexyl-2,8-diazaspiro[4.5]dec-2-yl)-N,N-bis(1H-imidazol-2-ylmethyl)cyclohexanamine

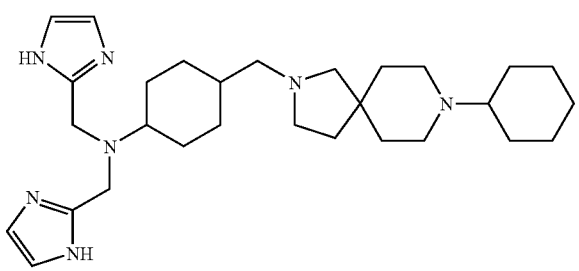

Description: amorphous;
TLC: Rf 0.60 (chloroform:methanol:28% aqueous ammonia=40:10:2);
NMR (CDCl$_3$): δ 1.00-2.02 (m, 24H), 2.04-2.68 (m, 9H), 2.41 (s, 2H), 3.68 (s, 4H), 7.02 (s, 4H).

Example 26(6)

1-{trans-4-[(8-cyclohexyl-2,8-diazaspiro[4.5]dec-2-yl)methyl]cyclohexyl}-N,N-bis(1H-imidazol-2-ylmethyl)methanamine

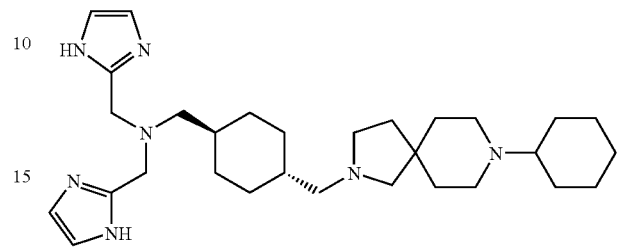

Description: amorphous;
TLC: Rf 0.60 (chloroform:methanol:28% aqueous ammonia=40:10:2);
NMR (CDCl$_3$): δ 0.76-1.94 (m, 26H), 2.14-2.38 (m, 2H), 2.19 (d, J=6.9 Hz, 2H), 2.29 (s, 2H), 2.32 (d, J=6.9 Hz, 2H), 2.42-2.56 (m, 5H), 3.58 (s, 4H), 7.05 (s, 4H).

Example 26(7)

4-[(8-cyclohexyl-2,8-diazaspiro[4.5]dec-2-yl)methyl]-N-(1H-imidazol-2-ylmethyl)-N-(2-pyridinylmethyl)cyclohexanamine Description: amorphous;
TLC: Rf 0.38 (dichrolomethane:methanol:28% aqueous ammonia=90:10:1);
NMR (CDCl$_3$): δ 0.85 (m, 1H), 1.00-1.98 (m, 24H), 2.12-2.38 (m, 5H), 2.42-2.60 (m, 7H), 3.80-3.94 (m, 4H), 6.97-7.02 (m, 2H), 7.18-7.32 (m, 2H), 7.65 (m, 1H), 8.62 (m, 1H).

Example 26(8)

4-[(8-cyclohexyl-2,8-diazaspiro[4.5]dec-2-yl)methyl]-N-(1H-imidazol-2-ylmethyl)-N-[(6-methyl-2-pyridinyl)methyl]cyclohexanamine Description: amorphous;
TLC: Rf 0.32 (dichrolomethane:methanol:28% aqueous ammonia=90:10:1);
NMR (CDCl$_3$): δ 0.85 (m, 1H), 1.00-2.00 (m, 24H), 2.10-2.34 (m, 5H), 2.40-2.57 (m, 7H), 2.62 (s, 3H), 3.78-3.94 (m, 4H), 6.97-7.11 (m, 4H), 7.55 (m, 1H), 12.55 (m, 1H).

Example 26(9)

4-[(8-cyclohexyl-2,8-diazaspiro[4.5]dec-2-yl)methyl]-N-(1H-imidazol-2-ylmethyl)-N-[(3-methyl-2-pyridinyl)methyl]cyclohexanamine Description: amorphous;
TLC: Rf 0.24 (dichrolomethane:methanol:28% aqueous ammonia=90:10:1);
NMR (CDCl$_3$): δ 0.88 (m, 1H), 1.00-1.97 (m, 24H), 2.12-2.34 (m, 5H), 2.38-2.60 (m, 10H), 3.70-3.90, (m, 4H), 6.98-7.05 (m, 2H), 7.16 (m, 1H), 7.49 (m, 1H), 8.45 (m, 1H), 12.28 (m, 1H).

Example 26(10)

4-[(8-cyclohexyl-2,8-diazaspiro[4.5]dec-2-yl)methyl]-N-(1H-imidazol-2-ylmethyl)-N-(1,3-oxazol-2-ylmethyl)cyclohexanamine Description: amorphous;
TLC: Rf 0.28 (dichrolomethane:methanol:28% aqueous ammonia=90:10:1);
NMR (CDCl$_3$): δ 0.88 (m, 1H), 1.00-1.97 (m, 24H), 2.12-2.35 (m, 5H), 2.42-2.61 (m, 7H), 3.87-3.92, (m, 4H), 6.98-7.02 (m, 2H), 7.10 (m, 1H), 7.63 (m, 1H), 10.89 (m, 1H).

Example 26(11)

trans-4-[(9-cyclohexyl-2,9-diazaspiro[5.5]undec-2-yl)methyl]-N,N-bis(1H-imidazol-2-ylmethyl)cyclohexanamine

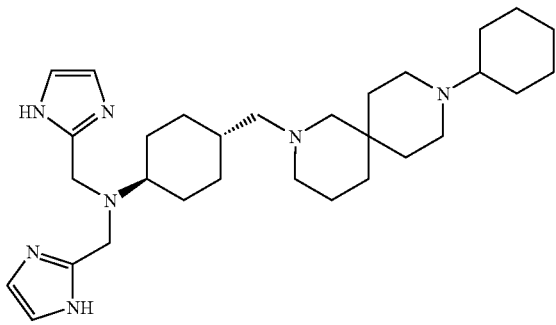

Description: amorphous;
TLC: Rf 0.61 (ethyl acetate:methanol:28% aqueous ammonia=40:10:2);
NMR (CDCl$_3$): δ 0.65-2.10 (m, 29H), 2.16-2.33 (m, 4H), 2.39-2.59 (m, 6H), 3.80 (s, 4H), 7.01 (s, 4H).

Example 26(12)

trans-4-[(7-cyclohexyl-2,7-diazaspiro[4.4]non-2-yl)methyl]-N,N-bis(1H-imidazol-2-ylmethyl)cyclohexanamine Description: amorphous;
TLC: Rf 0.43 (ethyl acetate:methanol:28% aqueous ammonia=40:10:2);
NMR (CDCl$_3$): δ 0.72-2.07 (m, 23H), 2.18 (d, J=7.2 Hz, 2H), 2.27-2.79 (m, 10H), 3.79 (s, 4H), 7.01 (s, 4H).

Example 26(13)

4-[(8-cyclohexyl-2,8-diazaspiro[4.5]dec-2-yl)methyl]-N-(1H-imidazol-2-ylmethyl)-N-(1,3-thiazol-2-ylmethyl)cyclohexanamine Description: amorphous;
TLC: Rf 0.28 (dichrolomethane:methanol:28% aqueous ammonia=90:10:1);
NMR (CDCl$_3$): δ 0.85 (m, 1H), 1.00-1.96 (m, 24H), 2.10-2.34 (m, 5H), 2.38-2.60 (m, 7H), 3.85-3.93, (m, 2H), 4.00-4.06 (m, 2H), 6.98-7.02 (m, 2H), 7.28 (m, 1H), 7.73 (m, 1H), 10.07-10.21 (m, 1H).

Example 26(14)

trans-4-[(7-cyclohexyl-2,7-diazaspiro[3.5]non-2-yl)methyl]-N,N-bis(1H-imidazol-2-ylmethyl)cyclohexanamine

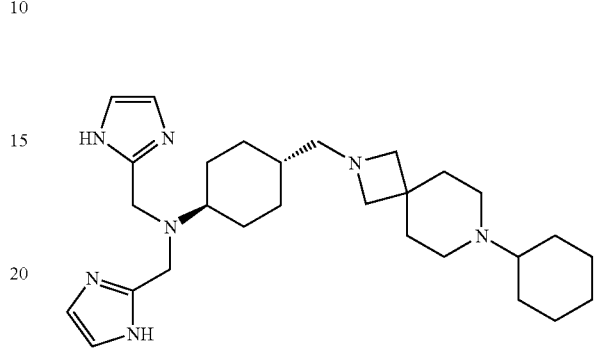

Description: amorphous;
TLC: Rf 0.60 (dichrolomethane:methanol:28% aqueous ammonia=40:10:2);
NMR (CDCl$_3$): δ 0.74-1.95 (m, 23H), 2.16-2.29 (m, 3H), 2.36-2.55 (m, 5H), 2.93 (s, 4H), 3.76 (s, 4H), 7.00 (s, 4H).

Example 26(15)

trans-4-[(9-cyclohexyl-3,9-diazaspiro[5.5]undec-3-yl)methyl]-N,N-bis(1H-imidazol-2-ylmethyl)cyclohexanamine

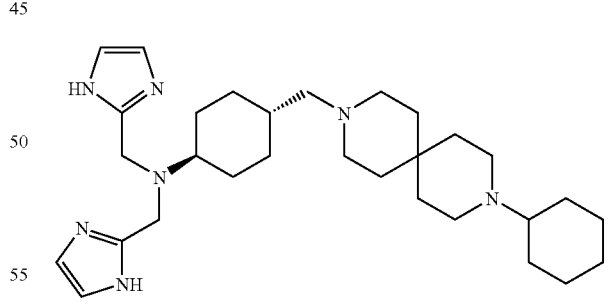

Description: amorphous;
TLC: Rf 0.50 (ethyl acetate:methanol:28% aqueous ammonia=40:10:2);
NMR (CDCl$_3$): δ 0.72-1.96 (m, 27H), 2.00-2.11 (m, 2H), 2.16-2.33 (m, 5H), 2.40-2.60 (m, 5H), 3.78 (s, 4H), 7.01 (s, 4H).

Example 26(16)

trans-4-[(9-cyclohexyl-1-oxa-4,9-diazaspiro[5.5]undec-4-yl)methyl]-N,N-bis(1H-imidazol-2-ylmethyl)cyclohexanamine

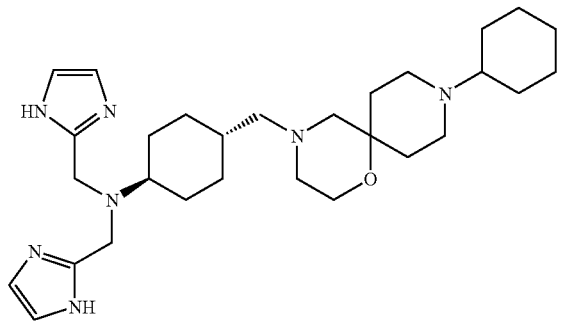

Description: amorphous;

TLC: Rf 0.58 (ethyl acetate:methanol:28% aqueous ammonia=40:10:2);

NMR (CDCl$_3$): δ 0.64-2.03 (m, 25H), 2.11 (s, 2H), 2.22-2.35 (m, 3H), 2.43-2.65 (m, 5H), 3.68 (t, J=4.8 Hz, 2H), 3.79 (s, 4H), 7.01 (s, 4H).

Example 27

2,2'-[{[4-(diethoxymethyl)benzyl]imino}bis(methylene)]bis(N,N-dimethyl-1H-imidazole-1-sulfonamide)

With 4-(diethoxymethyl)benzaldehyde (250 mg) and the compound produced in Example 3 (470 mg), the same operation as in Example 2 was performed. The obtained crude product was purified by silica gel chromatography (ethyl acetate:10%-saturated aqueous ammonia-methanol=1:0→10:1) to obtain the title compound (580 mg) having the following physical properties.

TLC: Rf 0.56 (chloroform:methanol:28% aqueous ammonia=80:10:1);

NMR (CDCl$_3$): δ 7.79 (m, 1H), 7.54 (m, 1H), 7.35 (m, 2H), 7.23 (m, 2H), 6.99 (m, 2H), 5.45 (s, 1H), 4.18 (m, 4H), 4.11 (s, 2H), 3.56 (m, 4H), 2.80 (s, 12H), 1.23 (m, 6H).

Example 28

4-{[bis(1H-imidazol-2-ylmethyl)amino]methyl}benzaldehyde

Except for using the compound (575 mg) produced in Example 27, the same operation as in Example 5 was performed to obtain the title compound (290 mg) having the following physical properties.

Description: amorphous;

TLC: Rf 0.53 (chloroform:methanol:28% aqueous ammonia=80:20:4);

NMR (CDCl$_3$): δ 9.92 (s, 1H), 7.82 (d, J=8.4 Hz, 2H), 7.54 (d, J=8.4 Hz, 2H), 6.99 (s, 4H), 3.70 (s, 4H), 3.62 (s, 2H).

Example 29

1-(1H-imidazol-2-yl)-N-(1H-imidazol-2-ylmethyl)-N-(4-{[8-(2-thienylmethyl)-2,8-diazaspiro[4.5]dec-2-yl]methyl}benzyl)methanamine

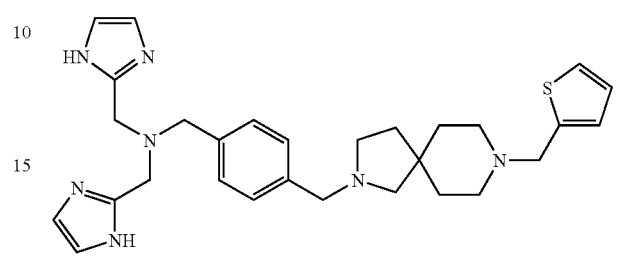

With the compound produced in Example 28 (80 mg) and 8-(2-thienyl)-2,8-diazaspiro[4.5]decane (160 mg), the same operation as in Example 2 was performed. The obtained crude product was purified by silica gel chromatography (ethyl acetate:10%-saturated aqueous ammonia-methanol=1:0→7:3) to obtain the title compound (122 mg) having the following physical properties.

Description: amorphous;

TLC: Rf 0.29 (28% aqueous ammonia:methanol=2:98);

NMR (CDCl$_3$): δ 1.55-1.67 (m, 6H), 2.32-2.46 (m, 6H), 2.54-2.65 (m, 2H), 3.55-3.65 (m, 8H), 3.67 (s, 2H), 6.86-6.97 (m, 2H), 7.03 (s, 4H), 7.18-7.31 (m, 5H).

Example 29(1) to Example 29(61)

The same operation as in Example 27→Example 28→Example 29 was performed, except for using a corresponding aldehyde and a corresponding amine in place of 4-(diethoxymethyl)benzaldehyde and the compound obtained in Example 3 in Example 27, and a corresponding amine in place of 8-(2-thienyl)-2,8-diazaspiro[4.5]decane in Example 29, to obtain the title compound having the following physical properties.

Example 29(1)

N—(H-benzimidazol-2-ylmethyl)-N-[4-(2,8-diazaspiro[4.5]dec-2-ylmethyl)benzyl]-5,6,7,8-tetrahydroquinolin-8-amine Description: amorphous;

TLC: Rf 0.24 (chloroform:methanol:28% aqueous ammonia=80:10:1);

NMR (DMSO-d$_6$): δ 1.29-1.43 (m, 4H), 1.49 (t, J=7.2 Hz, 2H), 1.53-1.68 (m, 1H), 1.82-2.05 (m, 2H), 2.08-2.21 (m, 1H), 2.23 (s, 2H), 2.39 (t, J=7.2 Hz, 2H), 2.53-2.70 (m, 5H), 2.70-2.87 (m, 1H), 3.43 (s, 2H), 3.64-3.78 (m, 1H), 3.83-4.01 (m, 3H), 4.01-4.11 (m, 1H), 7.03-7.13 (m, 2H), 7.15 (d, J=7.8 Hz, 2H), 7.21 (dd, J=7.8, 4.8 Hz, 1H), 7.35 (d, J=7.8 Hz, 2H), 7.44-7.57 (m, 3H), 8.59 (dd, J=4.8, 1.2 Hz, 1H), 12.20-12.92 (m, 1H).

Example 29(2)

1-(1H-imidazol-2-yl)-N-(1H-imidazol-2-ylmethyl)-N-[4-({8-[(3-methyl-2-thienyl)methyl]-2,8-diazaspiro[4.5]dec-2-yl}methyl)benzyl]methanamine

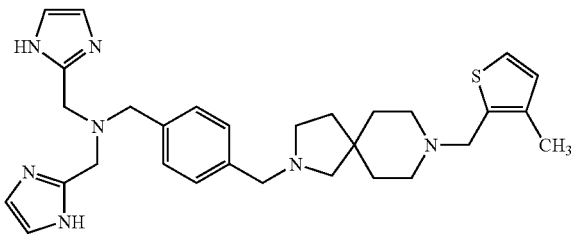

Description: amorphous;
TLC: Rf 0.23 (28% aqueous ammonia:methanol=2:98);
NMR (CDCl₃): δ 1.54-1.67 (m, 6H), 2.17 (s, 3H), 2.32-2.47 (m, 6H), 2.54-2.67 (m, 2H), 3.54-3.68 (m, 10H), 6.73-6.80 (m, 1H), 7.00-7.08 (m, 4H), 7.08-7.13 (m, 1H), 7.20-7.32 (m, 4H).

Example 29(3)

4-(8-cyclohexyl-2,8-diazaspiro[4.5]dec-2-yl)-N,N-bis(1H-imidazol-2-ylmethyl)butan-1-amine

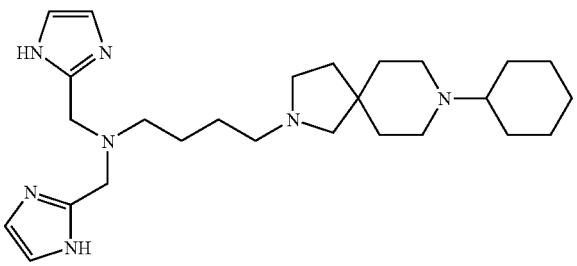

TLC: Rf 0.91 (chloroform:methanol:28% aqueous ammonia=40:10:2);
NMR (CD₃OD): δ 1.14-1.33 (m, 5H), 1.36-1.52 (m, 4H), 1.55-1.68 (m, 6H), 1.79-2.03 (m, 5H), 2.23-2.46 (m, 8H), 2.49-2.63 (m, 5H), 3.68 (s, 4H), 6.99 (s, 4H).

Example 29(4)

N,N-bis(1H-imidazol-2-ylmethyl)-4-{8-[(3-methyl-2-thienyl)methyl]-2,8-diazaspiro[4.5]dec-2-yl}butan-1-amine

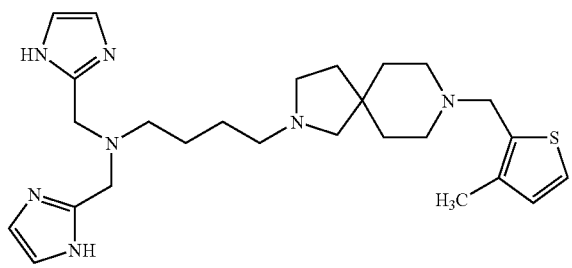

TLC: Rf 0.91 (chloroform:methanol:28% aqueous ammonia=40:10:2);
NMR (CD₃OD): δ 1.34-1.52 (m, 5H), 1.52-1.72 (m, 5H), 2.19 (s, 3H), 2.25-2.61 (m, 12H), 3.62 (s, 2H), 3.68 (s, 4H), 6.78 (d, J=5.1 Hz, 1H), 6.98 (s, 4H), 7.18 (d, J=5.1 Hz, 1H).

Example 29(5)

N-(1H-benzimidazol-2-ylmethyl)-N-{4-[(8-cyclohexyl-2,8-diazaspiro[4.5]dec-2-yl)methyl]benzyl}-5,6,7,8-tetrahydroquinolin-8-amine Description: amorphous;
TLC: Rf 0.43 (chloroform:methanol:28% aqueous ammonia=80:10:1);
NMR (DMSO-d₆): δ 0.96-1.29 (m, 5H), 1.33-1.55 (m, 8H), 1.59-1.74 (m, 4H), 1.83-2.03 (m, 2H), 2.06-2.25 (m, 4H), 2.26-2.46 (m, 5H), 2.56-2.89 (m, 3H), 3.42 (s, 2H), 3.70 (d, J=13.50 Hz, 1H), 3.82-4.13 (m, 4H), 7.00-7.16 (m, 4H), 7.20 (dd, J=7.80, 4.80 Hz, 1H), 7.33 (d, J=7.80 Hz, 2H), 7.42-7.56 (m, 3H), 8.50-8.65 (m, 1H), 12.48 (s, 1H).

Example 29(6)

N,N-bis(1H-imidazol-2-ylmethyl)-3-{8-[(3-methyl-2-thienyl)methyl]-2,8-diazaspiro[4.5]dec-2-yl}propan-1-amine Description: amorphous;
TLC: Rf 0.70 (chloroform:methanol:28% aqueous ammonia=40:10:2);
NMR (CD₃OD): δ 1.48-1.69 (m, 8H), 2.19 (s, 3H), 2.26-2.61 (m, 12H), 3.62 (s, 2H), 3.69 (s, 4H), 6.79 (d, J=5.1 Hz, 1H), 6.98 (s, 4H), 7.19 (d, J=5.1 Hz, 1H).

Example 29(7)

N,N-bis(1H-imidazol-2-ylmethyl)-5-{8-[(3-methyl-2-thienyl)methyl]-2,8-diazaspiro[4.5]dec-2-yl}-1-pentanamine

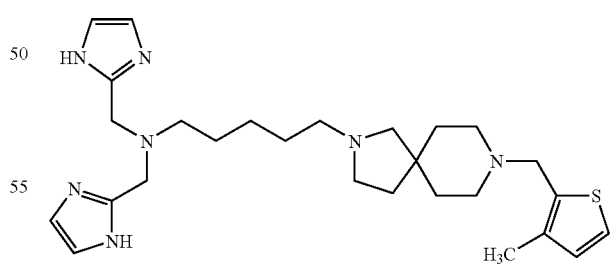

Description: amorphous;
TLC: Rf 0.70 (chloroform:methanol:28% aqueous ammonia=40:10:2);
NMR (CD₃OD): δ 1.16-1.30 (m, 2H), 1.33-1.51 (m, 4H), 1.55-1.69 (m, 6H), 2.19 (s, 3H), 2.29-2.51 (m, 10H), 2.53-2.66 (m, 2H), 3.62 (s, 2H), 3.68 (s, 4H), 6.78 (d, J=5.1 Hz, 1H), 6.97 (s, 4H), 7.18 (d, J=5.1 Hz, 1H).

Example 29(8)

N,N-bis(1H-imidazol-2-ylmethyl)-6-{8-[(3-methyl-2-thienyl)methyl]-2,8-diazaspiro[4.5]dec-2-yl}hexane-1-amine

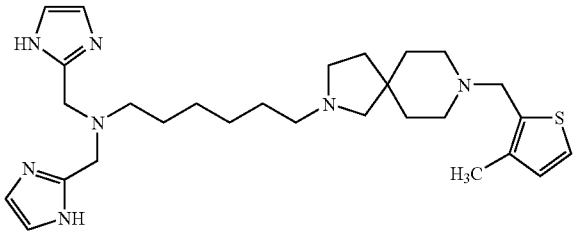

TLC: Rf 0.75 (chloroform:methanol:28% aqueous ammonia=40:10:2);
NMR (CD$_3$OD): δ 1.11-1.32 (m, 4H), 1.34-1.50 (m, 4H), 1.54-1.72 (m, 6H), 2.19 (s, 3H), 2.26-2.53 (m, 10H), 2.53-2.63 (m, 2H), 3.62 (s, 2H), 3.68 (s, 4H), 6.78 (d, J=5.1 Hz, 1H), 6.97 (s, 4H), 7.18 (d, J=5.1 Hz, 1H).

Example 29(9)

1-{4-[(8-cyclohexyl-2,8-diazaspiro[4.5]dec-2-yl)methyl]phenyl}-N-(1H-imidazol-2-ylmethyl)-N-(2-pyridinylmethyl)methanamine

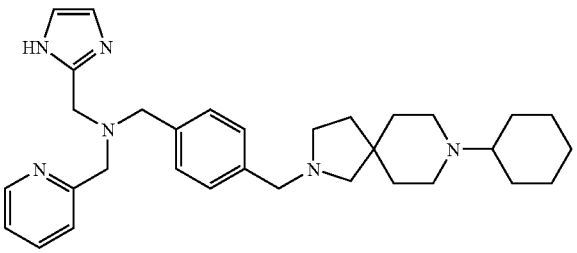

TLC: Rf 0.80 (chloroform:methanol:28% aqueous ammonia=40:10:2);
NMR (CD$_3$OD): δ 1.04-1.31 (m, 6H), 1.55-1.67 (m, 6H), 1.74-1.92 (m, 4H), 2.21-2.33 (m, 1H), 2.38 (s, 2H), 2.46-2.63 (m, 6H), 3.55 (s, 2H), 3.57 (s, 2H), 3.69 (s, 2H), 3.70 (s, 2H), 6.96 (s, 2H), 7.16-7.39 (m, 5H), 7.54-7.66 (m, 1H), 7.78 (dt, J=7.8, 1.8 Hz, 1H), 8.41-8.50 (m, 1H).

Example 29(10)

1-{4-[(8-cyclohexyl-2,8-diazaspiro[4.5]dec-2-yl)methyl]phenyl}-N-(1H-imidazol-2-ylmethyl)-N-(3-pyridinylmethyl)methanamine Description: amorphous;
TLC: Rf 0.78 (chloroform:methanol:28% aqueous ammonia=40:10:2);
NMR (CD$_3$OD): δ 1.11-1.33 (m, 6H), 1.54-1.68 (m, 6H), 1.74-1.92 (m, 4H), 2.21-2.33 (m, 1H), 2.39 (s, 2H), 2.48-2.63 (m, 6H), 3.57 (s, 2H), 3.58 (s, 2H), 3.59 (s, 2H), 3.67 (s, 2H), 6.93 (s, 2H), 7.28 (d, J=8.1 Hz, 2H), 7.31-7.37 (m, 3H), 7.79-7.87 (m, 1H), 8.36 (dd, J=4.8, 1.5 Hz, 1H), 8.47 (d, J=1.5 Hz, 1H).

Example 29(11)

1-{4-[(8-cyclohexyl-2,8-diazaspiro[4.5]dec-2-yl)methyl]phenyl}-N-(1H-imidazol-2-ylmethyl)-N-(4-pyridinylmethyl)methanamine Description: amorphous;
TLC: Rf 0.78 (chloroform:methanol:28% aqueous ammonia=40:10:2);
NMR (CD$_3$OD): δ 1.01-1.32 (m, 6H), 1.52-1.68 (m, 6H), 1.72-1.91 (m, 4H), 2.21-2.32 (m, 1H), 2.38 (s, 2H), 2.46-2.64 (m, 6H), 3.57 (s, 2H), 3.59 (s, 4H), 3.68 (s, 2H), 6.94 (s, 2H), 7.28 (d, J=8.1 Hz, 2H), 7.36 (d, J=8.1 Hz, 2H), 7.45 (d, J=6.0 Hz, 2H), 8.40 (d, J=6.0 Hz, 2H).

Example 29(12)

1-{4-[(8-cyclohexyl-2,8-diazaspiro[4.5]dec-2-yl)methyl]phenyl}-N-(1H-imidazol-2-ylmethyl)-N-[(3-methyl-2-pyridinyl)methyl]methanamine

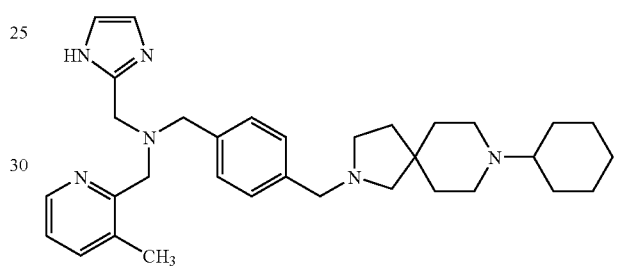

TLC: Rf 0.63 (chloroform:methanol:28% aqueous ammonia=40:10:2);
NMR (CD$_3$OD): δ 1.06-1.42 (m, 6H), 1.55-1.69 (m, 6H), 1.74-1.92 (m, 4H), 2.20 (s, 3H), 2.23-2.33 (m, 1H), 2.37 (s, 2H), 2.48-2.62 (m, 6H), 3.53 (s, 2H), 3.55 (s, 2H), 3.68 (s, 2H), 3.70 (s, 2H), 6.97 (s, 2H), 7.11-7.29 (m, 5H), 7.46-7.60 (m, 1H), 8.30 (dd, J=5.1, 1.2 Hz, 1H).

Example 29(13)

N-{4-[(8-cyclohexyl-2,8-diazaspiro[4.5]dec-2-yl)methyl]benzyl}-N-(1H-imidazol-2-ylmethyl)-2-(1-piperidinyl)ethanamine TLC: Rf 0.85 (chloroform:methanol:28% aqueous ammonia=40:10:2);
NMR (CD$_3$OD): δ 1.14-1.31 (m, 6H), 1.50-1.70 (m, 12H), 1.77-1.96 (m, 4H), 2.21-2.67 (m, 17H), 3.56 (s, 2H), 3.60 (s, 2H), 3.70 (s, 2H), 6.96 (s, 2H), 7.19-7.35 (m, 4H).

Example 29(14)

N-{4-[(8-cyclohexyl-2,8-diazaspiro[4.5]dec-2-yl)methyl]benzyl}-N-(1H-imidazol-2-ylmethyl)-2-(4-morpholinyl)ethanamine TLC: Rf 0.83 (chloroform:methanol:28% aqueous ammonia=40:10:2);
NMR (CD$_3$OD): δ 1.15-1.32 (m, 6H), 1.53-1.68 (m, 6H), 1.73-1.96 (m, 4H), 2.19-2.64 (m, 17H), 3.56 (s, 2H), 3.59-3.65 (m, 6H), 3.72 (s, 2H), 6.96 (s, 2H), 7.16-7.39 (m, 4H).

Example 29(15)

N-{4-[(8-cyclohexyl-2,8-diazaspiro[4.5]dec-2-yl)methyl]benzyl}-2-(1H-imidazol-1-yl)-N-(1H-imidazol-2-ylmethyl)ethanamine TLC: Rf 0.74 (chloroform:methanol:28% aqueous ammonia=40:10:2);
NMR (CD$_3$OD): δ 1.03-1.39 (m, 6H), 1.59-1.74 (m, 6H), 1.79-2.04 (m, 4H), 2.42 (s, 2H), 2.48-2.68 (m, 3H), 2.68-2.85 (m, 6H), 3.58 (s, 2H), 3.62 (s, 2H), 3.74 (s, 2H), 3.96 (t, J=6.3 Hz, 2H), 6.82-6.89 (m, 1H), 6.91-7.06 (m, 3H), 7.10-7.37 (m, 4H), 7.50 (t, J=1.2 Hz, 1H).

Example 29(16)

N-{4-[(8-cyclohexyl-2,8-diazaspiro[4.5]dec-2-yl)methyl]benzyl}-2-(1H-imidazol-4-yl)-N-(1H-imidazol-2-ylmethyl)ethanamine TLC: Rf 0.72 (chloroform:methanol:28% aqueous ammonia=40:10:2);
NMR (CD$_3$OD): δ 1.08-1.36 (m, 6H), 1.51-1.69 (m, 6H), 1.74-1.99 (m, 4H), 2.19-2.43 (m, 3H), 2.49-2.79 (m, 10H), 3.56 (s, 2H), 3.63 (s, 2H), 3.73 (s, 2H), 6.68 (s, 1H), 6.95 (s, 2H), 7.18-7.32 (m, 4H), 7.51 (d, J=1.1 Hz, 1H).

Example 29(17)

1-(1H-imidazol-2-yl)-N-(1H-imidazol-2-ylmethyl)-N-(4-{[7-(2-thienylmethyl)-2,7-diazaspiro[3.5]non-2-yl]methyl}benzyl)methanamine

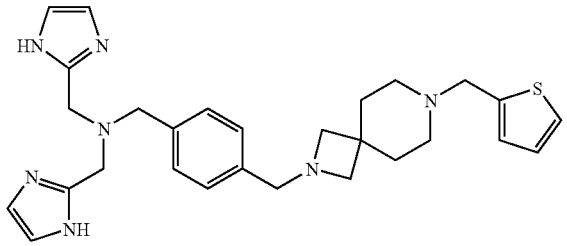

Description: amorphous;
TLC: Rf 0.24 (dichrolomethane:methanol:28% aqueous ammonia=90:10:1);
NMR (CDCl$_3$): δ 1.73-1.80 (m, 4H), 2.29-2.42 (m, 4H), 3.04 (s, 4H), 3.59 (s, 4H), 3.61 (s, 2H), 3.62 (s, 2H), 3.65 (s, 2H), 6.85-6.89 (m, 1H), 6.93 (dd, J=5.1, 3.3 Hz, 1H), 7.05 (s, 4H), 7.18-7.23 (m, 3H), 7.29 (d, J=8.1 Hz, 2H).

Example 29(18)

1-(1H-imidazol-2-yl)-N-(1H-imidazol-2-ylmethyl)-N-[4-({7-[(3-methyl-2-thienyl)methyl]-2,7-diazaspiro[3.5]non-2-yl}methyl)benzyl]methanamine

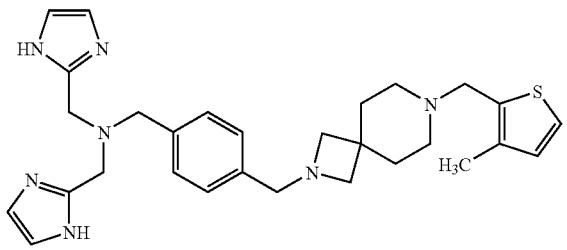

Description: amorphous;
TLC: Rf 0.39 (dichrolomethane:methanol:28% aqueous ammonia=90:10:1);
NMR (CDCl$_3$): δ 1.72-1.80 (m, 4H), 2.16 (s, 3H), 2.27-2.43 (m, 4H), 3.04 (s, 4H), 3.54 (s, 2H), 3.59 (s, 4H), 3.60 (s, 2H), 3.61-3.63 (m, 2H), 6.77 (d, J=4.8 Hz, 1H), 7.05 (s, 4H), 7.11 (d, J=4.8 Hz, 1H), 7.20 (d, J=8.1 Hz, 2H), 7.29 (d, J=8.1 Hz, 2H).

Example 29(19)

1-(1H-imidazol-2-yl)-N-(1H-imidazol-2-ylmethyl)-N-(4-{[2-(2-thienylmethyl)-2,7-diazaspiro[3.5]non-7-yl]methyl}benzyl)methanamine

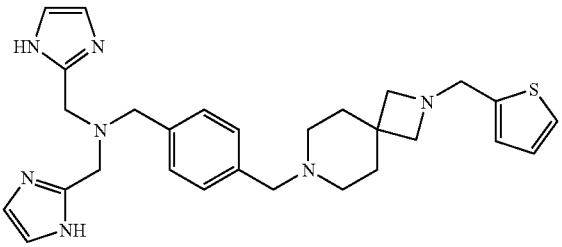

Description: amorphous;
TLC: Rf 0.30 (dichrolomethane:methanol:28% aqueous ammonia=90:10:1);
NMR (CDCl$_3$): δ 1.70-1.78 (m, 4H), 2.24-2.38 (m, 4H), 3.04 (s, 4H), 3.40 (s, 2H), 3.60 (s, 4H), 3.62 (s, 2H), 3.78-3.81 (m, 2H), 6.87-6.90 (m, 1H), 6.93 (dd, J=5.1, 3.6 Hz, 1H), 7.05 (s, 4H), 7.21 (dd, J=5.1, 1.2 Hz, 1H), 7.22 (d, J=8.1 Hz, 2H), 7.30 (d, J=8.1 Hz, 2H).

Example 29(20)

1-(1H-imidazol-2-yl)-N-(1H-imidazol-2-ylmethyl)-N-[4-({2-[(3-methyl-2-thienyl)methyl]-2,7-diazaspiro[3.5]non-7-yl}methyl)benzyl]methanamine

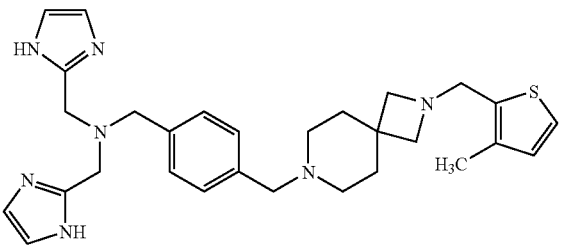

Description: amorphous;
TLC: Rf 0.34 (dichrolomethane:methanol:28% aqueous ammonia=90:10:1);
NMR (CDCl$_3$): δ 1.70-1.79 (m, 4H), 2.17 (s, 3H), 2.23-2.41 (m, 4H), 3.04 (s, 4H), 3.40 (s, 2H), 3.60 (s, 4H), 3.62 (s, 2H), 3.71 (s, 2H), 6.78 (d, J=5.1 Hz, 1H), 7.05 (s, 4H), 7.09 (d, J=5.1 Hz, 1H), 7.23 (d, J=8.1 Hz, 2H), 7.30 (d, J=8.1 Hz, 2H).

Example 29(21)

N-benzyl-1-{4-[(8-cyclohexyl-2,8-diazaspiro[4.5]
dec-2-yl)methyl]phenyl}-N-(1H-imidazol-2-ylm-
ethyl)methanamine Description: amorphous;
TLC: Rf 0.59 (chloroform:methanol:28% aqueous ammonia=90:10:1);
NMR (CD$_3$OD): δ 1.13-1.36 (m, 6H), 1.53-1.72 (m, 6H), 1.74-1.99 (m, 4H), 2.24-2.35 (m, 1H), 2.40 (s, 2H), 2.49-2.66 (m, 6H), 3.52 (s, 4H), 3.57 (s, 2H), 3.62 (s, 2H), 6.94 (s, 2H), 7.15-7.46 (m, 9H).

Example 29(22)

1-(1H-imidazol-2-yl)-N-(1H-imidazol-2-ylmethyl)-
N-[4-({2-[(3-methyl-2-thienyl)methyl]-2,8-diaza-
spiro[4.5]dec-8-yl}methyl)benzyl]methanamine

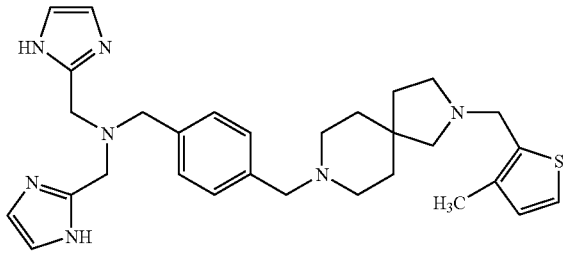

Description: amorphous;
TLC: Rf 0.28 (dichrolomethane:methanol:28% aqueous ammonia=90:10:1);
NMR (CDCl$_3$): δ 1.52-1.66 (m, 6H), 2.18 (s, 3H), 2.28-2.40 (m, 4H), 2.41 (s, 2H), 2.58-2.66 (m, 2H), 3.42 (s, 2H), 3.60 (s, 4H), 3.63 (s, 2H), 3.68 (s, 2H), 6.77 (d, J=5.1 Hz, 1H), 7.05 (s, 4H), 7.10 (d, J=5.1 Hz, 1H), 7.24 (d, J=8.1 Hz, 2H), 7.30 (d, J=8.1 Hz, 2H).

Example 29(23)

1-(1H-imidazol-2-yl)-N-(1H-imidazol-2-ylmethyl)-
N-(4-{[2-(2-thienylmethyl)-2,9-diazaspiro[5.5]un-
dec-9-yl]methyl}benzyl)methanamine

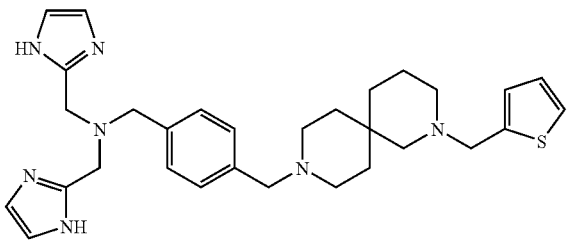

Description: amorphous;
TLC: Rf 0.29 (dichrolomethane:methanol:28% aqueous ammonia=90:10:1);
NMR (CDCl$_3$): δ 1.22-1.37 (m, 2H), 1.41-1.64 (m, 6H), 2.08-2.47 (m, 8H), 3.41 (s, 2H), 3.59 (s, 4H), 3.61 (s, 2H), 3.62 (s, 2H), 6.84-6.88 (m, 1H), 6.92 (dd, J=5.1, 3.6 Hz, 1H), 7.05 (s, 4H), 7.16-7.32 (m, 5H).

Example 29(24)

1-(1H-imidazol-2-yl)-N-(1H-imidazol-2-ylmethyl)-
N-[4-({2-[(3-methyl-2-thienyl)methyl]-2,9-diaza-
spiro[5.5]undec-9-yl}methyl)benzyl]methanamine Description: amorphous;
TLC: Rf 0.27 (dichrolomethane:methanol:28% aqueous ammonia=90:10:1);
NMR (CDCl$_3$): δ 1.22-1.37 (m, 2H), 1.40-1.67 (m, 6H), 2.12-2.45 (m, 8H), 2.16 (s, 3H), 3.42 (s, 2H), 3.50 (s, 2H), 3.60 (s, 4H), 3.63 (s, 2H), 6.77 (d, J=5.1 Hz, 1H), 7.05 (s, 4H), 7.08 (d, J=5.1 Hz, 1H), 7.23 (d, J=8.1 Hz, 2H), 7.30 (d, J=8.1 Hz, 2H).

Example 29(25)

1-(1H-imidazol-2-yl)-N-(1H-imidazol-2-ylmethyl)-
N-(4-{[9-(2-thienylmethyl)-2,9-diazaspiro[5.5]un-
dec-2-yl]methyl}benzyl)methanamine

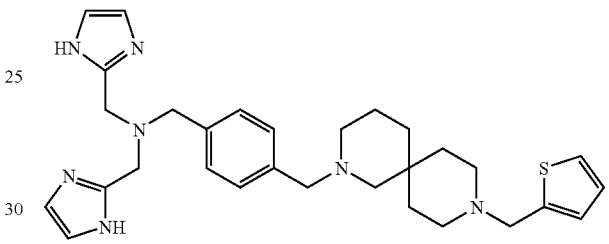

Description: amorphous;
TLC: Rf 0.33 (dichrolomethane:methanol:28% aqueous ammonia=90:10:1);
NMR (CDCl$_3$): δ 1.22-1.38 (m, 2H), 1.45-1.64 (m, 6H), 2.01-2.16 (m, 2H), 2.25-2.45 (m, 6H), 3.39 (s, 2H), 3.62 (s, 4H), 3.65 (s, 4H), 6.83-6.86 (m, 1H), 6.91 (dd, J=5.1, 3.3 Hz, 1H), 7.06 (s, 4H), 7.19 (dd, J=5.1, 1.2 Hz, 1H), 7.24 (d, J=8.1 Hz, 2H), 7.30 (d, J=8.1 Hz, 2H).

Example 29(26)

N-{4-[(8-cyclohexyl-2,8-diazaspiro[4.5]dec-2-yl)
methyl]benzyl}-N-(1H-imidazol-2-ylmethyl)-2-(tet-
rahydro-2H-pyran-4-yl)ethanamine Description: amorphous;
TLC: Rf 0.53 (chloroform:methanol:28% aqueous ammonia=90:10:2);
NMR (CD$_3$OD): δ 1.00-1.44 (m, 12H), 1.56-1.70 (m, 7H), 1.75-1.93 (m, 4H), 2.21-2.34 (m, 1H), 2.34-2.66 (m, 10H), 3.23-3.40 (m, 2H), 3.57 (s, 4H), 3.65 (s, 2H), 3.76-3.86 (m, 2H), 6.95 (s, 2H), 7.27 (d, J=9.00 Hz, 2H), 7.33 (d, J=9.00 Hz, 2H).

Example 29(27)

1-{4-[(8-cyclohexyl-2,8-diazaspiro[4.5]dec-2-yl)
methyl]phenyl}-N-(1H-imidazol-2-ylmethyl)-N-(1,
3-oxazol-2-ylmethyl)methanamine Description: amorphous;
TLC: Rf 0.49 (chloroform:methanol:28% aqueous ammonia=90:10:2);
NMR (CD$_3$OD): δ 1.08-1.32 (m, 6H), 1.53-1.67 (m, 6H), 1.74-1.95 (m, 4H), 2.16-2.31 (m, 1H), 2.38 (s, 2H), 2.43-2.63

(m, 6H), 3.56 (s, 2H), 3.61 (s, 2H), 3.77 (s, 2H), 3.80 (s, 2H), 6.97 (s, 2H), 7.13 (d, J=0.9 Hz, 1H), 7.26 (d, J=9.00 Hz, 2H), 7.32 (d, J=9.00 Hz, 2H), 7.87 (d, J=0.9 Hz, 1H).

Example 29(28)

1-{4-[(8-cyclohexyl-2,8-diazaspiro[4.5]dec-2-yl)methyl]phenyl}-N-(1H-imidazol-2-ylmethyl)-N-(1,3-thiazol-2-ylmethyl)methanamine Description: amorphous;

TLC: Rf 0.51 (chloroform:methanol:28% aqueous ammonia=90:10:2);

NMR (CD$_3$OD): δ 0.94-1.35 (m, 6H), 1.42-1.68 (m, 6H), 1.70-1.93 (m, 4H), 2.17-2.32 (m, 1H), 2.38 (s, 2H), 2.45-2.65 (m, 6H), 3.57 (s, 2H), 3.66 (s, 2H), 3.78 (s, 2H), 3.92 (s, 2H), 6.98 (s, 2H), 7.29 (d, J=8.10 Hz, 2H), 7.39 (d, J=8.10 Hz, 2H), 7.52 (d, J=3.3 Hz, 1H), 7.69 (d, J=3.3 Hz, 1H).

Example 29(29)

1-{4-[(8-cyclohexyl-2,8-diazaspiro[4.5]dec-2-yl)methyl]phenyl}-N-(1H-imidazol-2-ylmethyl)-N-[(6-methyl-2-pyridinyl)methyl]methanamine

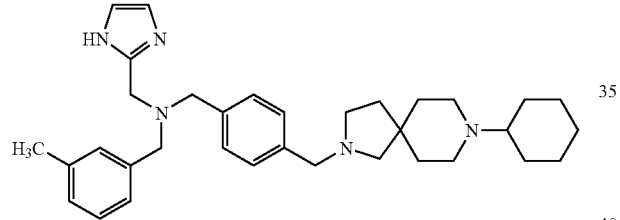

Description: amorphous;

TLC: Rf 0.60 (chloroform:methanol:28% aqueous ammonia=90:10:2);

NMR (CD$_3$OD): δ 1.12-1.32 (m, 6H), 1.52-1.69 (m, 6H), 1.71-1.98 (m, 4H), 2.19-2.33 (m, 1H), 2.38 (s, 2H), 2.48-2.66 (m, 6H), 2.50 (s, 3H), 3.55 (s, 2H), 3.57 (s, 2H), 3.66 (s, 2H), 3.70 (s, 2H), 6.96 (s, 2H), 7.13 (d, J=7.8 Hz, 1H), 7.25 (d, J=7.80 Hz, 2H), 7.32 (d, J=7.80 Hz, 2H), 7.43 (d, J=7.8 Hz, 1H), 7.66 (t, J=7.8 Hz, 1H).

Example 29(30)

1-{4-[(8-cyclohexyl-2,8-diazaspiro[4.5]dec-2-yl)methyl]phenyl}-N,N-bis(2-pyridinyl methyl)methanamine TLC: Rf 0.53 (chloroform:methanol:28% aqueous ammonia=90:10:1);

NMR (CD$_3$OD): δ 1.03-1.35 (m, 6H), 1.46-1.70 (m, 6H), 1.73-1.99 (m, 4H), 2.26 (s, 1H), 2.38 (s, 2H), 2.46-2.68 (m, 6H), 3.56 (s, 2H), 3.65 (s, 2H), 3.75 (s, 4H), 7.09-7.48 (m, 6H), 7.52-7.73 (m, 2H), 7.74-7.87 (m, 2H), 8.26-8.53 (m, 2H).

Example 29(31)

1-(1H-imidazol-2-yl)-N-(1H-imidazol-2-ylmethyl)-N-[4-({9-[(3-methyl-2-thienyl)methyl]-2,9-diazaspiro[5.5]undec-2-yl}methyl)benzyl]methanamine

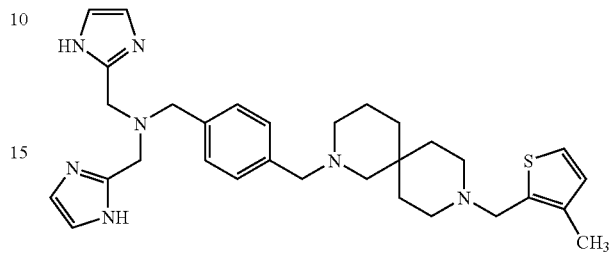

Description: amorphous;

TLC: Rf 0.23 (dichrolomethane:methanol:28% aqueous ammonia=90:10:1);

NMR (CDCl$_3$): δ 1.22-1.38 (m, 2H), 1.44-1.64 (m, 6H), 2.03-2.16 (m, 2H), 2.14 (s, 3H), 2.24-2.47 (m, 6H), 3.40 (s, 2H), 3.54 (s, 2H), 3.62 (s, 4H), 3.66 (s, 2H), 6.76 (d, J=4.8 Hz, 1H), 7.06 (s, 4H), 7.09 (d, J=4.8 Hz, 1H), 7.21-7.33 (m, 4H).

Example 29(32)

1-(1H-imidazol-2-yl)-N-(1H-imidazol-2-ylmethyl)-N-[4-({4-[(3-methyl-2-thienyl)methyl]-1-oxa-4,9-diazaspiro[5.5]undec-9-yl}methyl)benzyl]methanamine Description: amorphous;

TLC: Rf 0.19 (dichrolomethane:methanol:28% aqueous ammonia=90:10:1);

NMR (CDCl$_3$): δ 1.47-1.63 (m, 2H), 1.86-2.02 (m, 2H), 2.16 (s, 3H), 2.21-2.27 (m, 2H), 2.28-2.55 (m, 6H), 3.45 (s, 2H), 3.51 (s, 2H), 3.59 (s, 4H), 3.63 (s, 2H), 3.67-3.75 (m, 2H), 6.76 (d, J=5.1 Hz, 1H), 7.05 (s, 4H), 7.08 (d, J=5.1 Hz, 1H), 7.23 (d, J=8.1 Hz, 2H), 7.28 (d, J=8.1 Hz, 2H).

Example 29(33)

1-(1H-imidazol-2-yl)-N-(1H-imidazol-2-ylmethyl)-N-(4-{[9-(2-thienylmethyl)-3,9-diazaspiro[5.5]undec-3-yl]methyl}benzyl)methanamine Description: amorphous;

TLC: Rf 0.21 (dichrolomethane:methanol:28% aqueous ammonia=90:10:1);

NMR (CDCl$_3$): δ 1.41-1.54 (m, 8H), 2.31-2.45 (m, 8H), 3.45 (s, 2H), 3.60 (s, 4H), 3.64 (s, 2H), 3.71 (s, 2H), 6.87-6.90 (m, 1H), 6.93 (dd, J=5.1, 3.6 Hz, 1H), 7.06 (s, 4H), 7.21 (dd, J=5.1, 1.2 Hz, 1H), 7.25 (d, J=8.4 Hz, 2H), 7.30 (d, J=8.4 Hz, 2H).

Example 29(34)

1-(1H-imidazol-2-yl)-N-(1H-imidazol-2-ylmethyl)-N-[4-({9-[(3-methyl-2-thienyl)methyl]-3,9-diazaspiro[5.5]undec-3-yl}methyl)benzyl]methanamine

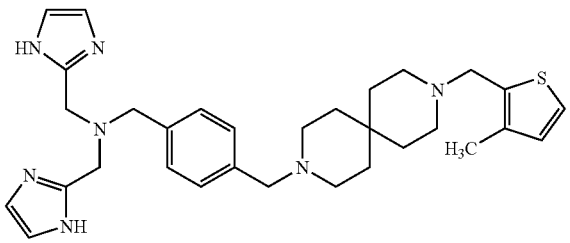

Description: amorphous;
TLC: Rf 0.16 (dichrolomethane:methanol:28% aqueous ammonia=90:10:1);
NMR (CDCl$_3$): δ 1.41-1.53 (m, 8H), 2.18 (s, 3H), 2.31-2.46 (m, 8H), 3.45 (s, 2H), 3.57-3.61 (m, 6H), 3.63 (s, 2H), 6.77 (d, J=5.1 Hz, 1H), 7.06 (s, 4H), 7.11 (d, J=5.1 Hz, 1H), 7.23 (d, J=8.1 Hz, 2H), 7.29 (d, J=8.1 Hz, 2H).

Example 29(35)

1-(1H-imidazol-2-yl)-N-(1H-imidazol-2-ylmethyl)-N-(4-{[9-(2-thienylmethyl)-1-oxa-4,9-diazaspiro[5.5]undec-4-yl]methyl}benzyl)methanamine Description: amorphous;
TLC: Rf 0.20 (dichrolomethane:methanol:28% aqueous ammonia=90:10:1);
NMR (CDCl$_3$): δ 1.45-1.60 (m, 2H), 1.91-2.04 (m, 2H), 2.15-2.21 (m, 2H), 2.28-2.43 (m, 4H), 2.49-2.61 (m, 2H), 3.39 (s, 2H), 3.60 (s, 4H), 3.64 (s, 2H), 3.66-3.74 (m, 2H), 3.68 (s, 2H), 6.85-6.89 (m, 1H), 6.91 (dd, J=4.8, 3.6 Hz, 1H), 7.05 (s, 4H), 7.19 (dd, J=4.8, 1.2 Hz, 1H), 7.23 (d, J=8.1 Hz, 2H), 7.29 (d, J=8.1 Hz, 2H).

Example 29(36)

1-(1H-imidazol-2-yl)-N-(1H-imidazol-2-ylmethyl)-N-[4-({9-[(3-methyl-2-thienyl)methyl]-1-oxa-4,9-diazaspiro[5.5]undec-4-yl}methyl)benzyl]methanamine Description: amorphous;
TLC: Rf 0.23 (dichrolomethane:methanol:28% aqueous ammonia=90:10:1);
NMR (CDCl$_3$): δ 1.42-1.60 (m, 2H), 1.90-2.05 (m, 2H), 2.16 (s, 3H), 2.18 (s, 2H), 2.29-2.45 (m, 4H), 2.50-2.62 (m, 2H), 3.40 (s, 2H), 3.58 (s, 2H), 3.60 (s, 4H), 3.64 (s, 2H), 3.67-3.76 (m, 2H), 6.75 (d, J=5.1 Hz, 1H), 7.05 (s, 4H), 7.09 (d, J=5.1 Hz, 1H), 7.19-7.34 (m, 4H).

Example 29(37)

1-(1H-imidazol-2-yl)-N-(1H-imidazol-2-ylmethyl)-N-(4-{[7-(2-thienylmethyl)-2,7-diazaspiro[4.4]non-2-yl]methyl}benzyl)methanamine Description: amorphous;
TLC: Rf 0.29 (dichrolomethane:methanol:28% aqueous ammonia=90:10:1);
NMR (CDCl$_3$): δ 1.71-1.93 (m, 4H), 2.39 (d, J=15.3 Hz, 1H), 2.42 (d, J=15.3 Hz, 1H), 2.49-2.71 (m, 6H), 3.52-3.56 (m, 2H), 3.59 (s, 4H), 3.61 (s, 2H), 3.75 (d, J=13.8 Hz, 1H), 3.80 (d, J=13.8 Hz, 1H), 6.84-6.87 (m, 1H), 6.90 (dd, J=5.1, 3.6 Hz, 1H), 7.03 (s, 4H), 7.17 (dd, J=5.1, 1.2 Hz, 1H), 7.19-7.28 (m, 4H).

Example 29(38)

1-(1H-imidazol-2-yl)-N-(1H-imidazol-2-ylmethyl)-N-[4-({7-[(3-methyl-2-thienyl)methyl]-2,7-diazaspiro[4.4]non-2-yl}methyl)benzyl]methanamine Description: amorphous;
TLC: Rf 0.31 (dichrolomethane:methanol:28% aqueous ammonia=90:10:1);
NMR (CDCl$_3$): δ 1.71-1.94 (m, 4H), 2.16 (s, 3H), 2.39 (d, J=14.4 Hz, 1H), 2.42 (d, J=14.4 Hz, 1H), 2.49-2.73 (m, 6H), 3.55 (s, 2H), 3.59 (s, 4H), 3.62 (s, 2H), 3.69 (s, 2H), 6.75 (d, J=5.1 Hz, 1H), 7.04 (s, 4H), 7.07 (d, J=5.1 Hz, 1H), 7.22 (d, J=8.1 Hz, 2H), 7.27 (d, J=8.1 Hz, 2H).

Example 29(39)

1-(1H-imidazol-2-yl)-N-(1H-imidazol-2-ylmethyl)-N-(4-{[7-(2-thienylmethyl)-2,7-diazaspiro[4.4]non-2-yl]methyl}benzyl)methanamine Description: amorphous;
TLC: Rf 0.29 (dichrolomethane:methanol:28% aqueous ammonia=90:10:1);
NMR (CDCl$_3$): δ 1.71-1.93 (m, 4H), 2.39 (d, J=15.3 Hz, 1H), 2.42 (d, J=15.3 Hz, 1H), 2.49-2.71 (m, 6H), 3.52-3.56 (m, 2H), 3.59 (s, 4H), 3.61 (s, 2H), 3.75 (d, J=13.9 Hz, 1H), 3.80 (d, J=13.9 Hz, 1H), 6.84-6.87 (m, 1H), 6.90 (dd, J=5.1, 3.6 Hz, 1H), 7.03 (s, 4H), 7.17 (dd, J=5.1, 1.2 Hz, 1H), 7.19-7.28 (m, 4H).

Example 29(40)

1-(1H-imidazol-2-yl)-N-(1H-imidazol-2-ylmethyl)-N-[4-({7-[(3-methyl-2-thienyl)methyl]-2,7-diazaspiro[4.4]non-2-yl}methyl)benzyl]methanamine

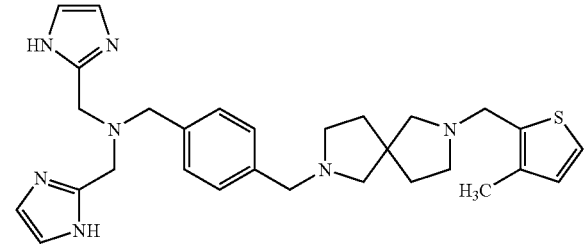

Description: amorphous;
TLC: Rf 0.31 (dichrolomethane:methanol:28% aqueous ammonia=90:10:1);
NMR (CDCl₃): δ 1.71-1.94 (m, 4H), 2.16 (s, 3H), 2.39 (d, J=14.4 Hz, 1H), 2.42 (d, J=14.4 Hz, 1H), 2.49-2.73 (m, 6H), 3.55 (s, 2H), 3.59 (s, 4H), 3.62 (s, 2H), 3.69 (s, 2H), 6.75 (d, J=5.1 Hz, 1H), 7.04 (s, 4H), 7.07 (d, J=5.1 Hz, 1H), 7.22 (d, J=8.1 Hz, 2H), 7.27 (d, J=8.1 Hz, 2H).

Example 29(41)

1-{4-[(8-cyclohexyl-2,8-diazaspiro[4.5]dec-2-yl)methyl]phenyl}-N-(1H-imidazol-2-ylmethyl)-N-[(1-methyl-1H-pyrrol-2-yl)methyl]methanamine Description: amorphous;
TLC: Rf 0.54 (chloroform:methanol:28% aqueous ammonia=90:10:1);
NMR (CD₃OD): δ 1.10-1.38 (m, 6H), 1.54-1.71 (m, 6H), 1.74-1.95 (m, 4H), 2.27-2.36 (m, 1H), 2.39 (s, 2H), 2.49-2.68 (m, 6H), 3.42 (s, 3H), 3.45 (s, 2H), 3.49 (s, 2H), 3.57 (s, 2H), 3.60 (s, 2H), 5.87-5.94 (m, 1H), 5.95-6.01 (m, 1H), 6.45-6.59 (m, 1H), 6.95 (s, 2H), 7.25 (s, 4H).

Example 29(42)

1-{4-[(1'-cyclohexylspiro[indole-3,4'-piperidin]-1(2H)-yl)methyl]phenyl}-N,N-bis(1H-imidazol-2-ylmethyl)methanamine Description: amorphous;
TLC: Rf 0.36 (dichrolomethane:methanol:28% aqueous ammonia=90:10:1);
NMR (CDCl₃): δ 0.96-1.35 (m, 6H), 1.51-2.09 (m, 8H), 2.20-2.40 (m, 3H), 2.81-2.97 (m, 2H), 3.22 (s, 2H), 3.61 (s, 4H), 3.67 (s, 2H), 4.27 (s, 2H), 6.45 (d, J=7.8 Hz, 1H), 6.63-6.72 (m, 1H), 6.97-7.16 (m, 6H), 7.22-7.42 (m, 4H).

Example 29(43)

1-(1H-imidazol-2-yl)-N-(1H-imidazol-2-ylmethyl)-N-{4-[(8-phenyl-2,8-diazaspiro[4.5]dec-2-yl)methyl]benzyl}methanamine Description: amorphous;
TLC: Rf 0.30 (dichrolomethane:methanol:28% aqueous ammonia=90:10:1);
NMR (CDCl₃): δ 1.62-1.77 (m, 6H), 2.42 (s, 2H), 2.56-2.65 (m, 2H), 3.07-3.17 (m, 4H), 3.58 (s, 2H), 3.61 (s, 4H), 3.66 (s, 2H), 6.77-6.85 (m, 1H), 6.89-6.97 (m, 2H), 7.07 (s, 4H), 7.19-7.37 (m, 6H).

Example 29(44)

1-(1H-imidazol-2-yl)-N-(1H-imidazol-2-ylmethyl)-N-(4-{[2-(2-thienylmethyl)-2,8-diazaspiro[4.5]dec-8-yl]methyl}benzyl)methanamine Description: amorphous;
TLC: Rf 0.30 (ethyl acetate:methanol:28% aqueous ammonia=90:8:2);
NMR (CDCl₃): δ 1.52-1.66 (m, 6H), 2.30-2.45 (m, 6H), 2.58-2.67 (m, 2H), 3.45 (s, 2H), 3.60 (s, 4H), 3.65 (s, 2H), 3.77 (s, 2H), 6.87-6.97 (m, 2H), 7.03 (s, 4H), 7.19-7.34 (m, 5H).

Example 29(45)

2-{[{4-[(8-cyclohexyl-2,8-diazaspiro[4.5]dec-2-yl)methyl]benzyl}(1H-imidazol-2-ylmethyl)amino]methyl}-3-pyridinol

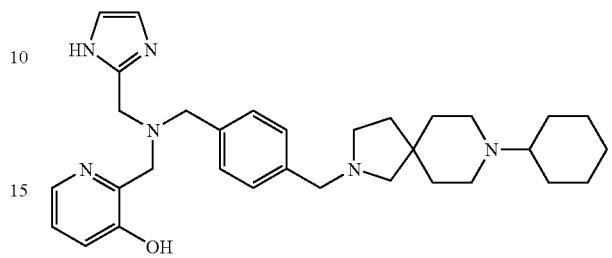

Description: amorphous;
TLC: Rf 0.28 (chloroform:methanol:28% aqueous ammonia=90:10:1);
NMR (CD₃OD): δ 1.02-1.37 (m, 6H), 1.58-1.72 (m, 6H), 1.72-2.01 (m, 4H), 2.24-2.44 (m, 3H), 2.52-2.65 (m, 6H), 3.55 (s, 2H), 3.64 (s, 2H), 3.73 (s, 2H), 3.87 (s, 2H), 6.99 (s, 2H), 7.10-7.22 (m, 1H), 7.21-7.40 (m, 5H), 7.83-7.96 (m, 1H).

Example 29(46)

1-{4-[(8-cyclohexyl-2,8-diazaspiro[4.5]dec-2-yl)methyl]phenyl}-N-(1H-imidazol-2-ylmethyl)-N-[(1-methyl-1H-imidazol-2-yl)methyl]methanamine

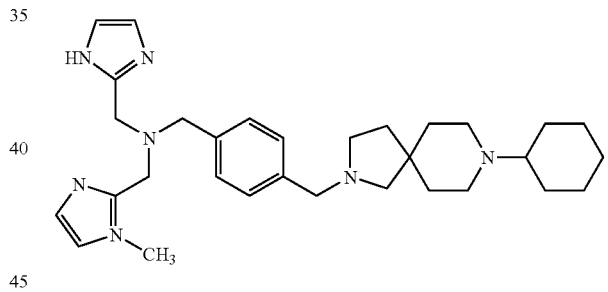

Description: amorphous;
TLC: Rf 0.41 (chloroform:methanol:28% aqueous ammonia=90:10:1);
NMR (CD₃OD): δ 1.02-1.33 (m, 6H), 1.53-1.68 (m, 6H), 1.73-1.94 (m, 4H), 2.20-2.32 (m, 1H), 2.37 (s, 2H), 2.43-2.61 (m, 6H), 3.49 (s, 3H), 3.52 (s, 2H), 3.56 (s, 2H), 3.61 (s, 2H), 3.65 (s, 2H), 6.83 (d, J=1.2 Hz, 1H), 6.95 (d, J=1.2 Hz, 1H), 6.99 (s, 2H), 7.25 (s, 4H).

Example 29(47)

4-{[8-(2-hydroxy-2-methylpropyl)-2,8-diazaspiro[4.5]dec-2-yl]methyl}-N,N-bis(1H-imidazol-2-ylmethyl)benzamide Description: amorphous;
TLC: Rf 0.30 (dichrolomethane:methanol:28% aqueous ammonia=90:10:1);
NMR (CDCl₃): δ 1.14 (s, 6H), 1.52-1.65 (m, 6H), 2.26 (s, 2H), 2.33 (s, 2H), 2.44-2.60 (m, 6H), 3.57 (s, 2H), 4.60-4.73 (m, 4H), 6.95-7.10 (m, 4H), 7.36 (d, J=8.4 Hz, 2H), 7.57 (d, J=8.4 Hz, 2H).

Example 29(48)

4-{[8-(3-hydroxy-3-methylbutyl)-2,8-diazaspiro[4.5]dec-2-yl]methyl}-N,N-bis(1H-imidazol-2-ylmethyl)benzamide Description: amorphous;
TLC: Rf 0.31 (dichrolomethane:methanol:28% aqueous ammonia=90:10:1);
NMR (CDCl$_3$): δ 1.20 (s, 6H), 1.50-1.65 (m, 8H), 2.20-2.61 (m, 10H), 3.56 (s, 2H), 4.60-4.73 (m, 4H), 6.95-7.09 (m, 4H), 7.35 (d, J=8.1 Hz, 2H), 7.56 (d, J=8.1 Hz, 2H).

Example 29(49)

methyl 5-{[bis(1H-imidazol-2-ylmethyl)amino]methyl}-2-({8-[(3-methyl-2-thienyl)methyl]-2,8-diazaspiro[4.5]dec-2-yl}methyl)benzoate

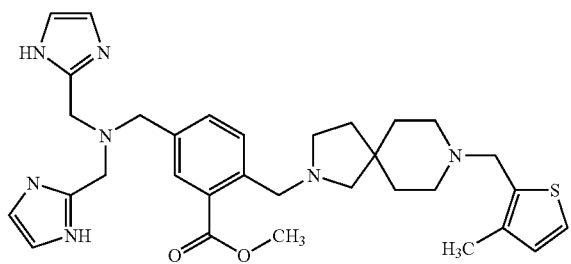

Description: amorphous;
TLC: Rf 0.50 (chloroform:methanol:28% aqueous ammonia=80:10:1);
NMR (DMSO-d$_6$): δ 1.37-1.54 (m, 6H), 2.10 (s, 3H), 2.18-2.35 (m, 6H), 2.40 (t, J=6.6 Hz, 2H), 3.48 (s, 2H), 3.51 (s, 2H), 3.55 (s, 4H), 3.70 (s, 2H), 3.76 (s, 3H), 6.78 (d, J=5.1 Hz, 1H), 6.81-7.20 (m, 4H), 7.25 (d, J=5.1 Hz, 1H), 7.36 (d, J=7.8 Hz, 1H), 7.49 (dd, J=7.8, 1.5 Hz, 1H), 7.57 (d, J=1.5 Hz, 1H), 11.81-12.28 (m, 2H).

Example 29(50)

2,2'-[({4-[(8-cyclohexyl-2,8-diazaspiro[4.5]dec-2-yl)methyl]benzyl}imino)bis(methylene)]di(3-pyridinol)

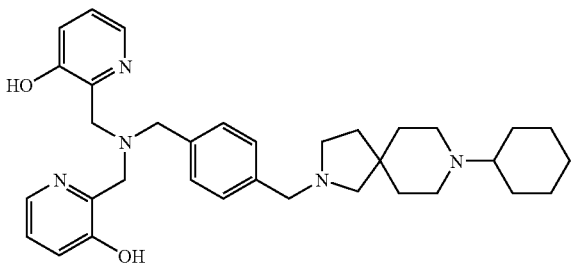

Description: amorphous;
TLC: Rf 0.34 (chloroform:methanol:28% aqueous ammonia=90:10:1);
NMR (CD$_3$OD): δ 0.95-1.36 (m, 6H), 1.48-1.68 (m, 6H), 1.71-1.96 (m, 4H), 2.20-2.46 (m, 3H), 2.48-2.63 (m, 6H), 3.52 (s, 2H), 3.66 (s, 2H), 3.86 (s, 4H), 6.86-7.44 (m, 8H), 7.81-8.09 (m, 2H).

Example 29(51)

1-{4-[(8-cyclohexyl-2,8-diazaspiro[4.5]dec-2-yl)methyl]phenyl}-N-[(1-ethyl-1H-imidazol-2-yl)methyl]-N-(1H-imidazol-2-ylmethyl)methanamine

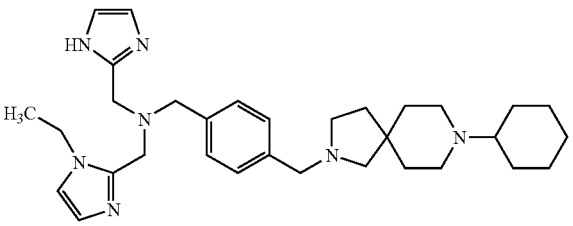

Description: amorphous;
TLC: Rf 0.46 (chloroform:methanol:28% aqueous ammonia=90:10:1);
NMR (CD$_3$OD): δ 1.17 (t, J=7.20 Hz, 3H), 1.19-1.34 (m, 6H), 1.62-1.70 (m, 6H), 1.78-2.02 (m, 4H), 2.41 (s, 2H), 2.48-2.56 (m, 1H), 2.58-2.67 (m, 2H), 2.67-2.82 (m, 4H), 3.53 (s, 2H), 3.59 (s, 2H), 3.60 (s, 2H), 3.64 (s, 2H), 3.88 (q, J=7.20 Hz, 2H), 6.86 (m, 1H), 6.99-7.02 (m, 2H), 7.03 (m, 1H), 7.22-7.36 (m, 4H).

Example 29(52)

1-[4-({8-[(2,4-dimethyl-1,3-thiazol-5-yl)methyl]-2,8-diazaspiro[4.5]dec-2-yl}methyl)phenyl]-N,N-bis(1H-imidazol-2-ylmethyl)methanamine Description: amorphous;
TLC: Rf 0.67 (dichrolomethane:methanol:28% aqueous ammonia=40:10:1);
NMR (CDCl$_3$): δ 1.53-1.65 (m, 6H), 2.30 (s, 3H), 2.31-2.43 (m, 6H), 2.50-2.59 (m, 2H), 2.61 (s, 3H), 3.52 (s, 2H), 3.55 (s, 2H), 3.60 (s, 4H), 3.64 (s, 2H), 7.07 (s, 4H), 7.21-7.35 (m, 4H).

Example 29(53)

1-{4-[(8-cyclohexyl-2,8-diazaspiro[4.5]dec-2-yl)methyl]phenyl}-N-(1H-imidazol-2-ylmethyl)-N-[(1-isopropyl-1H-imidazol-2-yl)methyl]methanamine

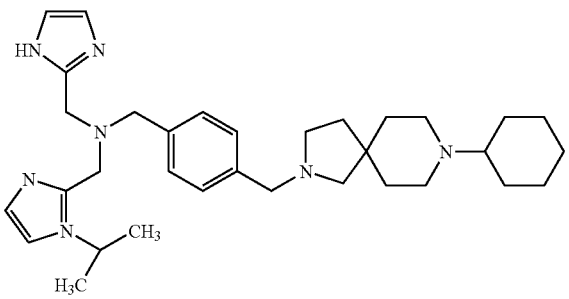

TLC: Rf 0.80 (chloroform:methanol:28% aqueous ammonia=40:10:2);
NMR (CDCl$_3$): δ 1.02-1.28 (m, 6H), 1.37 (d, J=6.6 Hz, 6H), 1.52-1.68 (m, 6H), 1.69-1.96 (m, 4H), 2.19-2.30 (m, 1H), 2.36 (s, 2H), 2.43-2.51 (m, 4H), 2.55 (t, J=6.9 Hz, 2H), 3.47 (s, 2H), 3.57 (s, 2H), 3.60 (s, 2H), 3.67 (s, 2H), 4.35 (m, 1H), 6.99 (d, J=1.2 Hz, 1H), 7.03 (d, J=1.2 Hz, 1H), 7.05-7.17 (m, 2H), 7.25-7.62 (m, 4H), 12.43 (m, 1H).

Example 29(54)

1-{4-[(8-cyclohexyl-2,8-diazaspiro[4.5]dec-2-yl)methyl]phenyl}-N-(1H-imidazol-2-ylmethyl)-N-[(1-isobutyl-1H-imidazol-2-yl)methyl]methanamine

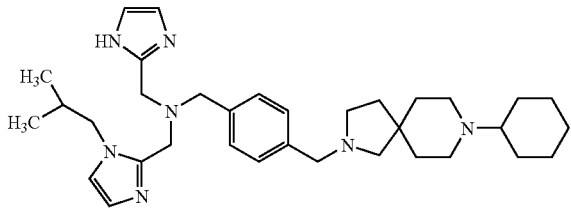

TLC: Rf 0.78 (chloroform:methanol:28% aqueous ammonia=40:10:2);

NMR (CDCl$_3$): δ 0.78 (d, J=6.6 Hz, 6H), 1.07-1.29 (m, 6H), 1.52-1.68 (m, 6H), 1.73-2.01 (m, 5H), 2.19-2.29 (m, 1H), 2.35 (s, 2H), 2.40-2.51 (m, 4H), 2.55 (t, J=6.6 Hz, 2H), 3.40 (s, 2H), 3.49 (s, 2H), 3.56 (s, 2H), 3.61 (d, J=7.5 Hz, 2H), 3.66 (s, 2H), 6.87 (d, J=1.2 Hz, 1H), 7.01 (d, J=1.2 Hz, 1H), 7.02-7.16 (m, 2H), 7.22-7.36 (m, 4H), 12.47 (m, 1H).

Example 29(55)

1-{4-[(8-cyclohexyl-2,8-diazaspiro[4.5]dec-2-yl)methyl]phenyl}-N,N-bis[(1-methyl-1H-imidazol-2-yl)methyl]methanamine

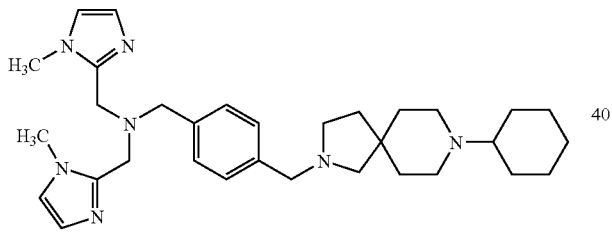

TLC: Rf 0.76 (chloroform:methanol:28% aqueous ammonia=40:10:2);

NMR (CDCl$_3$): δ 1.04-1.25 (m, 6H), 1.52-1.65 (m, 6H), 1.70-1.88 (m, 4H), 2.16-2.26 (m, 1H), 2.30 (s, 2H), 2.40-2.50 (m, 4H), 2.53 (t, J=6.6 Hz, 2H), 3.25-3.26 (m, 6H), 3.54 (s, 2H), 3.60 (s, 2H), 3.68 (s, 4H), 6.77-6.79 (m, 2H), 6.89-6.95 (m, 2H), 7.09-7.19 (m, 2H), 7.20-7.26 (m, 2H).

Example 29(56)

1-{3-[2-(8-cyclohexyl-2,8-diazaspiro[4.5]dec-2-yl)ethyl]phenyl}-N,N-bis(1H-imidazol-2-ylmethyl)methanamine Description: amorphous;

TLC: Rf 0.21 (dichrolomethane:methanol:28% aqueous ammonia=80:20:1);

NMR (CDCl$_3$): δ 0.99-1.30 (m, 6H), 1.41-2.01 (m, 10H), 2.13-2.82 (m, 13H), 3.66 (s, 6H), 6.94-7.13 (m, 5H), 7.13-7.24 (m, 3H), 11.33-11.91 (m, 2H).

Example 29(57)

2-(2-{[{4-[(8-cyclohexyl-2,8-diazaspiro[4.5]dec-2-yl)methyl]benzyl}(1H-imidazol-2-ylmethyl)amino]methyl}-1H-imidazol-1-yl)ethanol Description: amorphous;

TLC: Rf 0.72 (chloroform:methanol:28% aqueous ammonia=40:10:2);

NMR (CDCl$_3$): δ 0.94-1.38 (m, 6H), 1.53-1.66 (m, 6H), 1.70-1.93 (m, 4H), 2.19-2.33 (m, 1H), 2.35 (s, 2H), 2.42-2.52 (m, 4H), 2.56 (t, J=7.2 Hz, 2H), 3.46 (s, 2H), 3.57 (s, 2H), 3.68 (s, 2H), 3.70 (s, 2H), 3.72-3.86 (m, 4H), 6.94 (d, J=1.2 Hz, 1H), 7.05 (d, J=1.2 Hz, 1H), 7.07-7.16 (m, 2H), 7.28-7.42 (m, 4H), 12.19 (m, 1H).

Example 29(58)

6-{[bis(1H-imidazol-2-ylmethyl)amino]methyl}-2-[trans-4-(dipropylamino)cyclohexyl]-1-isoindolinone Description: amorphous;

TLC: Rf 0.23 (chloroform:methanol:28% aqueous ammonia=80:10:1);

NMR (DMSO-d$_6$): δ 0.85 (t, J=7.2 Hz, 6H), 1.01-1.95 (m, 14H), 2.27-2.67 (m, 4H), 2.80-3.03 (m, 1H), 3.56 (s, 4H), 3.92-4.10 (m, 1H), 4.38 (s, 2H), 6.90-7.08 (m, 4H), 7.51 (d, J=7.8 Hz, 1H), 7.58 (dd, J=7.8, 1.5 Hz, 1H), 7.74 (d, J=1.5 Hz, 1H).

Example 29(59)

[2-(4-{[bis(1H-imidazol-2-ylmethyl)amino]methyl}benzyl)-8-cyclohexyl-2,8-diazaspiro[4.5]dec-3-yl]methanol TLC: Rf 0.33 (28% aqueous ammonia:methanol:chloroform=2:13:90);

NMR (CDCl$_3$): δ 1.10-1.24 (m, 5H), 1.48-1.64 (m, 5H), 1.69-1.85 (m, 6H), 2.12-2.27 (m, 2H), 2.37-2.51 (m, 4H), 2.68-2.81 (m, 1H), 2.90 (d, J=9.5 Hz, 1H), 3.29-3.42 (m, 2H), 3.54-3.66 (m, 7H), 3.84 (d, J=13.5 Hz, 1H), 7.05 (s, 4H), 7.18-7.24 (m, 2H), 7.27-7.32 (m, 2H).

Example 29(60)

1-{4-[2-(8-cyclohexyl-2,8-diazaspiro[4.5]dec-2-yl)ethyl]phenyl}-N,N-bis(1H-imidazol-2-ylmethyl)methanamine TLC: Rf 0.53 (dichrolomethane:methanol:28% aqueous ammonia=8:2:0.2);

NMR (CDCl$_3$): δ 1.01-1.33 (m, 6H), 1.49-2.00 (m, 10H), 2.18-2.33 (m, 1H), 2.41 (s, 2H), 2.44-2.56 (m, 4H), 2.56-2.68 (m, 4H), 2.72-2.83 (m, 2H), 3.60 (s, 4H), 3.63 (s, 2H), 7.05 (s, 4H), 7.15 (d, J=8.1 Hz, 2H), 7.28 (d, J=8.1 Hz, 2H).

Example 29(61)

2-(2-{[{4-[(8-cyclohexyl-2,8-diazaspiro[4.5]dec-2-yl)methyl]benzyl}(1H-imidazol-2-ylmethyl)amino]methyl}-1H-imidazol-1-yl)-N,N-dimethylacetamide

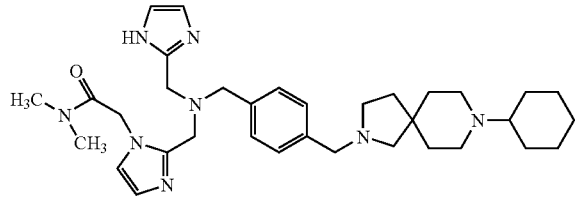

TLC: Rf 0.74 (chloroform:methanol:28% aqueous ammonia=4:1:0.2);

NMR (CD$_3$OD): δ 0.84-1.40 (m, 6H), 1.37-1.71 (m, 6H), 1.72-1.99 (m, 4H), 2.18-2.33 (m, 1H), 2.38 (s, 2H), 2.44-2.73 (m, 6H), 2.93 (s, 3H), 3.01 (s, 3H), 3.40-3.72 (m, 8H), 4.61-4.94 (m, 2H), 6.76-7.05 (m, 4H), 7.11-7.40 (m, 4H).

Example 30 benzyl 6-{[bis({1-[(dimethylamino)sulfonyl]-1H-imidazol-2-yl}methyl)amino]carbonyl}-3,4-dihydroisoquinoline-2(1H)-carboxylate To a dichloromethane (3 mL) solution of 2-[(benzyloxy)carbonyl]-1,2,3,4-tetrahydroisoquinoline-6-carboxylic acid (188 mg), diisopropylethylamine (0.21 mL) and O-(7-azabenzotriazol-1-yl)N,N,N',N'-tetramethyluronium hexafluorophosphate (345 mg) were added. The reaction solution was stirred for 30 minutes. To this solution, the compound (284 mg) obtained in Example 3 was added. The reaction solution was stirred at room temperature for 16 hours. To the reaction solution, an aqueous 1N sodium hydroxide solution (20 mL) was added. The aqueous layer was extracted twice with dichloromethane (50 mL). The combined organic layer was washed with saturated brine (20 mL) and then dried over anhydrous magnesium sulfate. After removing the anhydrous sodium sulfate by filtration, the filtrate was concentrated. The residue was purified by silica gel chromatography (ethyl acetate: 10%-saturated aqueous ammonia-methanol=1:0→10:1) to obtain the title compound (219 mg) having the following physical properties.

TLC: Rf 0.70 (chloroform:methanol:28% aqueous ammonia=80:10:1);

NMR (CDCl$_3$): δ 2.65 (s, 6H), 2.80 (m, 2H), 3.01 (s, 6H), 3.69 (t, J=6.0 Hz, 2H), 4.62 (s, 2H), 5.02 (s, 2H), 5.04 (s, 2H), 5.18 (s, 2H), 6.99 (m, 1H), 7.08 (m, 2H), 7.26 (m, 1H), 7.27 (m, 8H).

Example 31

N,N-bis({1-[(dimethylamino)sulfonyl]-1H-imidazol-2-yl}methyl)-1,2,3,4-tetrahydroisoquinoline-6-carboxamide To an ethanol (3 mL) solution of the compound (210 mg) obtained in Example 30, 10% palladium-carbon (21 mg) was added under an argon atmosphere. This solution was stirred under a hydrogen atmosphere for one hour. The reaction solution was filtrated through Celite (trade name), the filtrate was concentrated. Without purifying the residue, the title compound (158 mg) having the following physical properties was obtained.

TLC: Rf 0.35 (chloroform:methanol:28% aqueous ammonia=80:10:1);

NMR (CDCl$_3$): δ 2.68 (s, 6H), 2.77 (t, J=5.7 Hz, 2H), 3.01 (s, 6H), 3.11 (t, J=5.7 Hz, 2H), 3.94 (s, 2H), 5.04 (m, 4H), 6.97 (m, 2H), 6.99 (m, 1H), 7.09 (m, 1H), 7.25 (m, 3H).

Example 32

N,N-bis({1-[(dimethylamino)sulfonyl]-1H-imidazol-2-yl}methyl)-2-[4-(dipropylamino)cyclohexyl]-1,2,3,4-tetrahydroisoquinoline-6-carboxamide The same operation as in Example 2 was performed, except for using the compound (150 mg) obtained in Example 31 and 4-(dipropylamino)cyclohexanone (269 mg), and then the obtained crude product was purified by silica gel chromatography (dichrolomethane:methanol:28% aqueous ammonia=1:0:0→80:10:1) to obtain the title compound (150 mg) having the following physical properties.

TLC: Rf 0.45 (chloroform:methanol:28% aqueous ammonia=80:10:1).

Example 33

2-[4-(dipropylamino)cyclohexyl]-N,N-bis(1H-imidazol-2-ylmethyl)-1,2,3,4-tetrahydro-6-isoquinolinecarboxamide

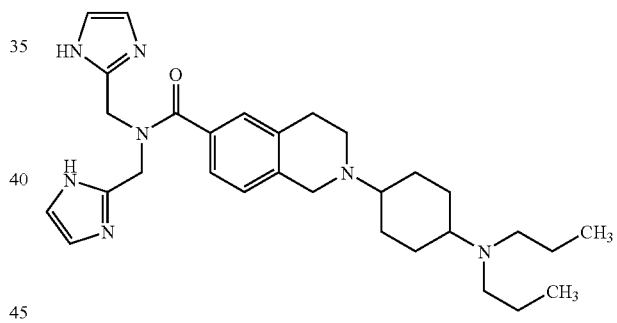

The same operation as in Example 5, except for using the compound (190 mg) obtained in Example 32, and then the obtained product was purified by silica gel chromatography (dichrolomethane:methanol:28% aqueous ammonia=80:10:1→80:20:4) to obtain the following compound (91 mg).

Description: amorphous;

TLC: Rf 0.60 (chloroform:methanol:28% aqueous ammonia=80:20:4);

NMR (DMSO-d$_6$): δ 0.81 (t, J=7.5 Hz, 6H), 1.10-1.45 (m, 8H), 1.62-1.78 (m, 2H), 1.78-1.93 (m, 2H), 2.18-2.44 (m, 6H), 2.69 (s, 4H), 3.65 (s, 2H), 4.38-4.75 (m, 4H), 6.68-7.14 (m, 6H), 7.18 (dd, J=7.8, 1.5 Hz, 1H), 11.87-12.72 (m, 2H).

Example 33(1)

3-{1-[(1-cycloheptyl-4-piperidinyl)methyl]-4-piperidinyl}-N,N-bis(1H-imidazol-2-ylmethyl)propanamide Diacetate Except for using the corresponding carboxylic acid in place of 2-[(benzyloxy)carbonyl]-1,2,3,4-tetrahydroisoquinoline-6-carboxylic acid in Example 30 and using the corresponding ketone in place of 4-(dipropylamino) cyclohexanone in Example 32, the same operation as in Example 30 Example 31→Example 32→Example 33 was performed to obtain the title compound having the following physical properties.

TLC: Rf 0.78 (chloroform:methanol:28% aqueous ammonia=40:10:2);

NMR (CD$_3$OD): δ 1.12-1.90 (m, 20H), 1.91 (s, 6H), 2.10-2.17 (m, 2H), 2.23-2.37 (m, 2H), 2.38-2.52 (m, 2H), 2.51-2.61 (m, 1H), 2.72-2.89 (m, 4H), 4.67 (s, 2H), 4.68 (s, 2H), 6.96 (s, 2H), 7.01 (s, 2H).

Example 34

4-({acetyl[trans-4-(dipropylamino)cyclohexyl]amino}methyl)-N,N-bis({1-[(dimethylamino)sulfonyl]-1H-imidazol-2-yl}methyl)benzamide To a dichloromethane (3 mL) solution of the compound (150 mg) obtained in Example 16 and triethylamine (59 μL), acetyl chloride (20 μL) was added at 0° C. The reaction solution was stirred at 0° C. for one hour. The reaction solution was diluted with dichloromethane (75 mL) and the organic layer was washed in turn with an aqueous saturated sodium hydrogen carbonate solution (20 mL) and saturated brine (20 mL), and then dried over anhydrous magnesium sulfate. After removing the anhydrous sodium sulfate by filtration, the filtrate was concentrated. Without purifying the residue, the title compound (106 mg) having the following physical properties was obtained.

TLC: Rf 0.43 (chloroform:methanol:28% aqueous ammonia=80:10:1);

NMR (CDCl$_3$): δ 0.86 (m, 6H), 1.38 (m, 6H), 1.68 (m, 4H), 2.23 (s, 3H), 2.39 (m, 6H), 2.62 (s, 3H), 2.74 (s, 3H), 3.00 (m, 6H), 3.60 (m, 1H), 4.47 (m, 3H), 5.03 (m, 4H), 6.98-7.61 (m, 8H).

Example 35

4-({acetyl[trans-4-(dipropylamino)cyclohexyl]amino}methyl)-N,N-bis(1H-imidazol-2-ylmethyl)benzamide

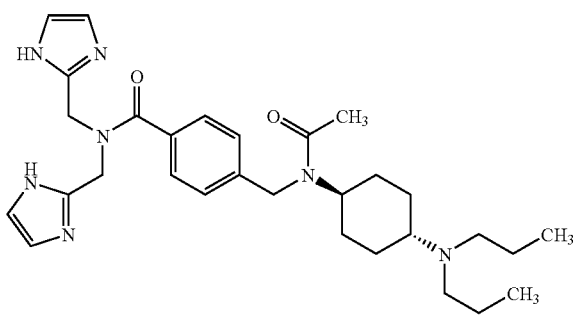

The same operation as in Example 5 was performed, except for using the compound obtained in Example 34 in Example 5, and then the obtained crude product was purified by silica gel chromatography (dichrolomethane:methanol:28% aqueous ammonia=10:1:0→80:10:1) to obtain the title compound having the following physical properties.

Description: amorphous;
TLC: Rf 0.37 (chloroform:methanol:28% aqueous ammonia=80:10:1);

NMR (DMSO-d$_6$): δ 0.68-0.88 (m, 6H), 1.12-1.71 (m, 12H), 1.82-2.19 (m, 3H), 2.19-2.44 (m, 5H), 3.55-4.35 (m, 1H), 4.36-4.67 (m, 6H), 6.75-7.11 (m, 4H), 7.12-7.28 (m, 2H), 7.33-7.55 (m, 2H), 11.97-12.61 (m, 2H).

Example 35(1) to Example 35(2)

Except for using the corresponding chloride in place of acetyl chloride, the same operation as in Example 34→Example 35 was performed to obtain the following compound.

Example 35(1)

4-({benzoyl[trans-4-(dipropylamino)cyclohexyl]amino}methyl)-N,N-bis(1H-imidazol-2-ylmethyl)benzamide Description: amorphous;
TLC: Rf 0.36 (chloroform:methanol:28% aqueous ammonia=80:10:1);

NMR (DMSO-d$_6$): δ 0.62-0.80 (m, 6H), 0.81-1.02 (m, 2H), 1.09-1.40 (m, 4H), 1.44-1.78 (m, 6H), 2.04-2.43 (m, 5H), 3.37-3.60 (m, 1H), 4.38-4.77 (m, 6H), 6.74-7.17 (m, 4H), 7.20-7.65 (m, 9H), 11.91-12.58 (m, 2H).

Example 35(2)

4-{[[trans-4-(dipropylamino)cyclohexyl](phenylacetyl)amino]methyl}-N,N-bis(1H-imidazol-2-ylmethyl)benzamide Description: amorphous;
TLC: Rf 0.41 (chloroform:methanol:28% aqueous ammonia=80:10:1);

NMR (DMSO-d$_6$): δ 0.79 (t, J=7.50 Hz, 6H), 1.06-1.84 (m, 12H), 2.02-2.46 (m, 5H), 3.42-4.36 (m, 3H), 4.36-4.75 (m, 6H), 6.70-7.64 (m, 13H), 11.84-12.74 (m, 2H).

Example 36

1-[4-(diethoxymethyl)phenyl]-N-[(1-{[2-(trimethylsilyl)ethoxy]methyl}-1H-imidazol-2-yl)methyl]methanamine The same operation as in Example 2 was performed, except for using 4-(diethoxymethyl)benzaldehyde in place of 2-formyl-N,N-dimethyl-1H-imidazole-1-sulfonamide and 1-(1-{[2-(trimethylsilyl)ethoxy]methyl}-1H-imidazol-2-yl) methanamine in place of benzylamine, to obtain the title compound having the following physical properties.

TLC: Rf 0.63 (chloroform:methanol:28% aqueous ammonia=80:10:1);

NMR (CDCl$_3$): δ 7.43 (d, J=7.8 Hz, 2H), 7.33 (J=7.8 Hz, 2H), 6.97 (m, 2H), 5.49 (s, 1H), 5.32 (s, 2H), 3.94 (s, 2H), 3.84 (s, 2H), 3.52 (m, 6H), 1.24 (m, 6H), 0.88 (m, 2H), −0.03 (s, 9H).

Example 37

N-[4-(diethoxymethyl)benzyl]-N-[(1-{[2-(trimethylsilyl)ethoxy]methyl}-1H-imidazol-2-yl)methyl]-1H-imidazole-2-carboxamide The same operation as in Example 30 was performed, except for using the compound (1.93 g) obtained in Example 36 and 1H-imidazole-2-carboxylic acid (773 mg), and then the obtained crude product was purified by silica gel chromatography (ethyl acetate:methanol=1:0→10:1) to obtain the title compound (977 mg) having the following physical properties.

TLC: Rf 0.44 (chloroform:methanol:28% aqueous ammonia=80:10:1);

NMR (CDCl$_3$): δ 7.41 (m, 4H), 7.15 (s, 2H), 7.04 (s, 1H), 6.96 (m, 1H), 5.82 (s, 1H), 5.77 (s, 1H), 5.46 (s, 1H), 5.37 (s, 1H), 5.23 (s, 1H), 4.83 (s, 1H), 4.76 (s, 1H), 3.51 (m, 6H), 1.25 (m, 6H), 0.82 (t, J=8.1 Hz, 2H), −0.06 (s, 9H).

Example 38

N-(4-formylbenzyl)-N-(1H-imidazol-2-ylmethyl)-1H-imidazole-2-carboxamide

To the compound (970 mg) obtained in Example 37, a 50% trifluoroacetic acid-dichloromethane solution (10 mL) was added under ice cooling. The reaction mixture was stirred at room temperature for 3 hours. The reaction mixture was concentrated and an aqueous 2N sodium hydroxide solution (20 mL) was added to the residue. The aqueous layer was extracted twice with dichloromethane (50 mL). The combined organic layer was washed with saturated brine and then dried over anhydrous magnesium sulfate to concentrate. Without purifying the residue, the obtained residue was used in the following reaction.

TLC: Rf 0.50 (chloroform:methanol:28% aqueous ammonia=80:10:1);

NMR (CDCl$_3$): δ 9.98 (s, 1H), 7.81 (d, J=8.1 Hz, 2H), 7.49 (d, J=8.1 Hz, 2H), 7.23 (s, 2H), 7.08 (s, 2H), 5.04 (s, 2H), 4.87 (s, 2H).

Example 39

N-(1H-imidazol-2-ylmethyl)-N-(4-{[7-(2-thienylmethyl)-2,7-diazaspiro[4.4]non-2-yl]methyl}benzyl)-1H-imidazole-2-carboxamide

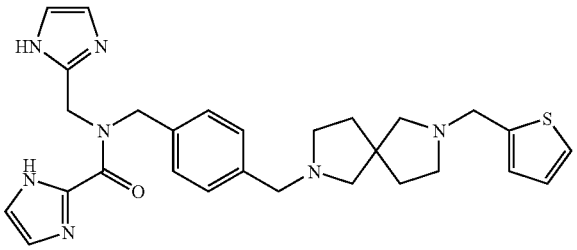

The same operation as in Example 2 was performed, except for using the compound (107 mg) obtained in Example 38 in place of 2-formyl-N,N-dimethyl-1H-imidazole-1-sulfonamide, and 2-(2-thienylmethyl)-2,7-diazaspiro[4.4]nonane (86 mg) in place of benzylamine, to obtain the title compound (97 mg) having the following physical properties.

Description: amorphous;

TLC: Rf 0.65 (chloroform:methanol:28% aqueous ammonia=40:9:1);

NMR (CDCl$_3$): δ 1.69-1.92 (m, 4H), 2.38-2.67 (m, 8H), 3.57 (s, 2H), 3.77-3.81 (m, 2H), 4.75 (s, 2H), 4.95 (s, 2H), 6.86-6.89 (m, 1H), 6.91 (dd, J=5.1, 3.6 Hz, 1H), 7.07 (s, 2H), 7.18 (s, 2H), 7.19 (dd, J=5.1, 1.50 Hz, 1H), 7.26 (d, J=8.1 Hz, 2H), 7.36 (d, J=8.1 Hz, 2H), 11.39 (s, 1H), 12.17 (s, 1H).

Example 39(1) to Example 39(18)

The same operation as in Example 39 was carried out, except for using a corresponding amine in place of 2-(2-thienylmethyl)-2,7-diazaspiro[4.4]nonane in Example 39, to obtain the following compound.

Example 39(1)

N-(1H-imidazol-2-ylmethyl)-N-[4-({2-[(3-methyl-2-thienyl)methyl]-2,8-diazaspiro[4.5]dec-8-yl}methyl)benzyl]-1H-imidazole-2-carboxamide Description: amorphous;

TLC: Rf 0.56 (ethyl acetate:methanol:28% aqueous ammonia=50:10:1);

NMR (CDCl$_3$): δ 1.53-1.75 (m, 6H), 2.18 (s, 3H), 2.28-2.40 (m, 4H), 2.41 (s, 2H), 2.61 (t, J=6.6 Hz, 2H), 3.43 (s, 2H), 3.69 (s, 2H), 4.75 (s, 2H), 4.95 (s, 2H), 6.77 (d, J=5.1 Hz, 1H), 7.07 (s, 2H), 7.10 (d, J=5.1 Hz, 1H), 7.14-7.30 (m, 4H), 7.36 (d, J=8.1 Hz, 2H).

Example 39(2)

N-(1H-imidazol-2-ylmethyl)-N-(4-{[2-(2-thienylmethyl)-2,9-diazaspiro[5.5]undec-9-yl]methyl}benzyl)-1H-imidazole-2-carboxamide Description: amorphous;

TLC: Rf 0.61 (ethyl acetate:methanol:28% aqueous ammonia=50:10:1);

NMR (CDCl$_3$): δ 1.26-1.36 (m, 2H), 1.42-1.65 (m, 6H), 2.10-2.46 (m, 8H), 3.43 (s, 2H), 3.62 (s, 2H), 4.74 (s, 2H), 4.95 (s, 2H), 6.86 (m, 1H), 6.91 (dd, J=3.6, 5.1 Hz, 1H), 7.07, (s, 2H), 7.15-7.30 (m, 5H), 7.35 (d, J=8.4 Hz, 2H).

Example 39(3)

N-(1H-imidazol-2-ylmethyl)-N-[4-({2-[(3-methyl-2-thienyl)methyl]-2,9-diazaspiro[5.5]undec-9-yl}methyl)benzyl]-1H-imidazole-2-carboxamide Description: amorphous;

TLC: Rf 0.61 (ethyl acetate:methanol:28% aqueous ammonia=50:10:1);

NMR (CDCl$_3$): δ 1.25-1.36 (m, 2H), 1.43-1.65 (m, 6H), 2.16 (s, 3H), 2.20-2.47 (m, 8H), 3.43 (s, 2H), 3.50 (s, 2H), 4.74 (s, 2H), 4.95 (s, 2H), 6.77 (d, J=5.1 Hz, 1H), 7.07 (s, 2H), 7.08 (d, J=5.1 Hz, 1H), 7.15-7.30 (m, 4H), 7.35 (d, J=8.1 Hz, 2H).

Example 39(4)

N-(1H-imidazol-2-ylmethyl)-N-(4-{[9-(2-thienylmethyl)-2,9-diazaspiro[5.5]undec-2-yl]methyl}benzyl)-1H-imidazole-2-carboxamide Description: amorphous;

TLC: Rf 0.63 (ethyl acetate:methanol:28% aqueous ammonia=50:10:1);

NMR (CDCl$_3$): δ 1.26-1.38 (m, 2H), 1.46-1.62 (m, 6H), 2.03-2.16 (m, 2H), 2.26-2.45 (m, 6H), 3.40 (s, 2H), 3.65 (s, 2H), 4.76 (s, 2H), 4.97 (s, 2H), 6.85 (dd, J=1.2, 3.6 Hz, 1H), 6.91 (dd, J=3.6, 5.1 Hz, 1H), 7.08 (s, 2H), 7.15-7.22 (m, 2H), 7.23-7.30 (m, 3H), 7.36 (d, J=8.1 Hz, 2H).

Example 39(5)

N-(1H-imidazol-2-ylmethyl)-N-[4-({9-[(3-methyl-2-thienyl)methyl]-2,9-diazaspiro[5.5]undec-2-yl}methyl)benzyl]-1H-imidazole-2-carboxamide Description: amorphous;

TLC: Rf 0.67 (ethyl acetate:methanol:28% aqueous ammonia=50:10:1);

NMR (CDCl$_3$): δ 1.25-1.37 (m, 2H), 1.45-1.62 (m, 6H), 2.05-2.25 (m, 2H), 2.14 (s, 3H), 2.26-2.44 (m, 6H), 3.40 (s, 2H), 3.54 (s, 2H), 4.75 (s, 2H), 4.97 (s, 2H), 6.75 (d, J=5.1 Hz, 1H), 7.07 (s, 2H), 7.09 (d, J=5.1 Hz, 1H), 7.18 (m, 1H), 7.24-7.30 (m, 3H), 7.37 (d, J=8.1 Hz, 2H).

Example 39(6)

N-(1H-imidazol-2-ylmethyl)-N-[4-({4-[(3-methyl-2-thienyl)methyl]-1-oxa-4,9-diazaspiro[5.5]undec-9-yl}methyl)benzyl]-1H-imidazole-2-carboxamide Description: amorphous;

TLC: Rf 0.62 (ethyl acetate:methanol:28% aqueous ammonia=50:10:1);

NMR (CDCl$_3$): δ 1.50-1.65 (m, 2H), 1.89-2.00 (m, 2H), 2.17 (s, 3H), 2.22-2.40 (m, 4H), 2.40-2.52 (m, 4H), 3.46 (s, 2H), 3.52 (s, 2H), 3.72 (t, J=4.5 Hz, 2H), 4.75 (s, 2H), 4.95 (s, 2H), 6.77 (d, J=5.1 Hz, 1H), 7.07 (s, 2H), 7.10 (d, J=5.1 Hz, 1H), 7.14-7.30 (m, 4H), 7.35 (d, J=8.1 Hz, 2H).

Example 39(7)

N-[4-({[trans-4-(1-azepanyl)cyclohexyl]amino}methyl)benzyl]-N-(1H-imidazol-2-ylmethyl)-1H-imidazole-2-carboxamide Description: amorphous;

TLC: Rf 0.48 (chloroform:methanol:28% aqueous ammonia=80:20:4);

NMR (CDCl$_3$): δ 1.05-1.41 (m, 4H), 1.51-1.70 (m, 8H), 1.81-2.09 (m, 4H), 2.35-2.66 (m, 3H), 2.67-2.77 (m, 4H), 3.78 (s, 2H), 4.73 (s, 2H), 4.92 (s, 2H), 7.07 (s, 2H), 7.18-7.30 (m, 4H), 7.34 (d, J=8.1 Hz, 2H), 12.28 (s, 2H).

Example 39(8)

N-[4-({[trans-4-(dipropylamino)cyclohexyl]amino}methyl)benzyl]-N-(1H-imidazol-2-ylmethyl)-1H-imidazole-2-carboxamide Description: amorphous;

TLC: Rf 0.50 (chloroform:methanol:28% aqueous ammonia=80:20:1);

NMR (CDCl$_3$): δ 0.85 (t, J=7.5 Hz, 6H), 1.03-1.33 (m, 5H), 1.33-1.48 (m, 4H), 1.72-1.86 (m, 2H), 1.94-2.07 (m, 2H), 2.30-2.56 (m, 6H), 3.79 (s, 2H), 4.73 (s, 2H), 4.92 (s, 2H), 7.07 (s, 2H), 7.16-7.29 (m, 4H), 7.35 (d, J=7.8 Hz, 2H), 12.21 (s, 2H).

Example 39(9)

N-(1H-imidazol-2-ylmethyl)-N-[4-({[trans-4-(2,3,6,7-tetrahydro-1H-azepin-1-yl)cyclohexyl]amino}methyl)benzyl]-1H-imidazole-2-carboxamide

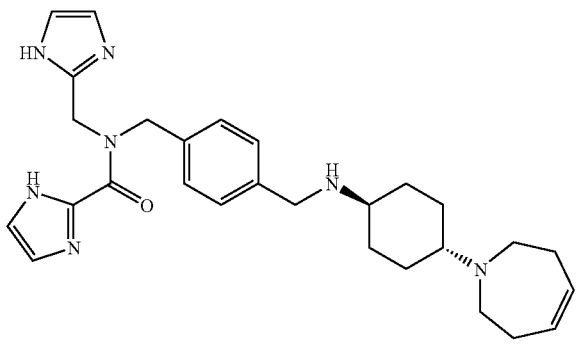

Description: amorphous;

TLC: Rf 0.32 (chloroform:methanol:28% aqueous ammonia=80:20:1);

NMR (CDCl$_3$): δ 1.07-1.42 (m, 4H), 1.86-1.97 (m, 2H), 1.97-2.08 (m, 2H), 2.10-2.18 (m, 1H), 2.21-2.30 (m, 4H), 2.38-2.50 (m, 1H), 2.53-2.65 (m, 1H), 2.70-2.77 (m, 4H), 3.79 (s, 2H), 4.73 (s, 2H), 4.92 (s, 2H), 5.76 (t, J=3.3 Hz, 2H), 7.07 (s, 2H), 7.20-7.29 (m, 4H), 7.35 (d, J=7.8 Hz, 2H), 12.27 (s, 2H).

Example 39(10)

N-{4-[(8-cyclohexyl-2,8-diazaspiro[4.5]dec-2-yl)methyl]benzyl}-N-(1H-imidazol-2-ylmethyl)-1H-imidazole-2-carboxamide Description: amorphous;

TLC: Rf 0.46 (chloroform:methanol:28% aqueous ammonia=80:20:1);

NMR (CDCl$_3$): δ 1.03-1.58 (m, 7H), 1.61-1.75 (m, 1H), 1.80-1.95 (m, 6H), 1.98-2.61 (m, 7H), 2.69-2.89 (m, 2H), 2.93-3.07 (m, 4H), 3.95 (s, 2H), 4.70 (s, 2H), 4.95 (s, 2H), 7.09 (s, 2H), 7.25 (s, 2H), 7.31 (d, J=8.1 Hz, 2H), 7.39 (d, J=8.1 Hz, 2H).

Example 39(11)

N-(1H-imidazol-2-ylmethyl)-N-[4-({[trans-4-(1-piperidinyl)cyclohexyl]amino}methyl)benzyl]-1H-imidazole-2-carboxamide Description: amorphous;

TLC: Rf 0.27 (chloroform:methanol:28% aqueous ammonia=80:20:1);

NMR (CDCl$_3$): δ 1.05-1.51 (m, 6H), 1.54-1.69 (m, 4H), 1.84-2.10 (m, 4H), 2.31-2.50 (m, 3H), 2.51-2.62 (m, 4H), 3.78 (s, 2H), 4.72 (s, 2H), 4.91 (s, 2H), 7.07 (s, 2H), 7.21 (s, 2H), 7.24 (d, J=7.8 Hz, 2H), 7.34 (d, J=7.8 Hz, 2H), 12.52 (s, 2H).

Example 39(12)

N-[4-({[trans-4-(1-azepanyl)cyclohexyl]amino}methyl)benzyl]-N-(1H-imidazol-2-ylmethyl)-1H-imidazole-2-carboxamide

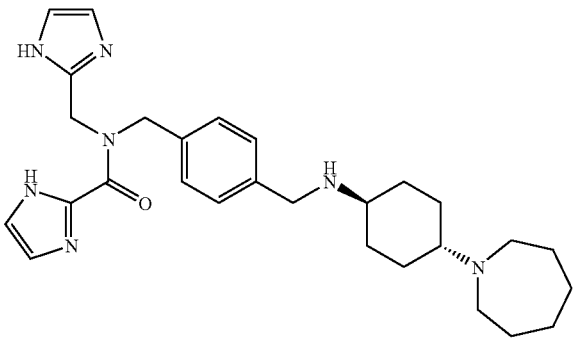

Description: amorphous;
TLC: Rf 0.48 (chloroform:methanol:28% aqueous ammonia=80:20:4);
NMR (CDCl$_3$): δ 1.05-1.41 (m, 4H), 1.51-1.70 (m, 8H), 1.81-2.09 (m, 4H), 2.35-2.66 (m, 3H), 2.67-2.77 (m, 4H), 3.78 (s, 2H), 4.73 (s, 2H), 4.92 (s, 2H), 7.07 (s, 2H), 7.18-7.30 (m, 4H), 7.34 (d, J=8.1 Hz, 2H), 12.28 (s, 2H).

Example 39(13)

N-{4-[(8-cyclohexyl-2,8-diazaspiro[4.5]dec-2-yl)methyl]cyclohexyl}-N—(H-imidazol-2-ylmethyl)-1H-imidazole-2-carboxamide (low polar compound)

Description: amorphous;
TLC: Rf 0.75 (ethyl acetate:methanol:28% aqueous ammonia=40:10:2);
NMR (CDCl$_3$): δ 0.82-2.08 (m, 25H), 2.03-2.69 (m, 11H), 4.00-4.33 (m, 1H), 4.44-5.13 (m, 2H), 5.48-7.31 (m, 4H), 9.96-10.60 (m, 1H), 12.13-12.66 (m, 1H).

Example 39(14)

N-{4-[(8-cyclohexyl-2,8-diazaspiro[4.5]dec-2-yl)methyl]cyclohexyl}-N—(H-imidazol-2-ylmethyl)-1H-imidazole-2-carboxamide (high polar compound)

Description: amorphous;
TLC: Rf 0.75 (ethyl acetate:methanol:28% aqueous ammonia=40:10:2);
NMR (CDCl$_3$): δ 0.80-2.04 (m, 25H), 2.09-2.68 (m, 11H), 4.14-4.45 (m, 1H), 4.54-5.14 (m, 2H), 5.47-7.28 (m, 4H), 9.93-10.50 (m, 1H), 12.31-12.71 (m, 1H).

Example 39(15)

N-[trans-4-({[trans-4-(dipropylamino)cyclohexyl]amino}methyl)cyclohexyl]-N-(1H-imidazol-2-ylmethyl)-1H-imidazole-2-carboxamide Description: amorphous;
TLC: Rf 0.18 (dichrolomethane:methanol:28% aqueous ammonia=90:10:1);
NMR (CDCl$_3$): δ 0.86 (t, J=7.2 Hz, 6H), 0.96-1.19 (m, 4H), 1.20-1.50 (m, 7H), 1.58-1.68 (m, 2H), 1.70-2.00 (m, 8H), 2.23-2.53 (m, 8H), 4.24 (m, 1H), 4.64-5.02 (m, 2H), 6.94 (brs, 1H), 7.02 (s, 2H), 7.21 (s, 2H), 12.35-12.44 (m, 2H).

Example 39(16)

N-[trans-4-({[4-(dipropylamino)butyl]amino}methyl)cyclohexyl]-N-(1H-imidazol-2-ylmethyl)-1H-imidazole-2-carboxamide Description: amorphous;
TLC: Rf 0.20 (dichrolomethane:methanol:28% aqueous ammonia=90:10:1);
NMR (CDCl$_3$): δ 0.87 (t, J=7.2 Hz, 6H), 0.98-1.20 (m, 2H), 1.40-1.98 (m, 15H), 2.34-2.51 (m, 8H), 2.56-2.64 (m, 2H), 4.25 (m, 1H), 4.64-5.06 (m, 2H), 5.74 (m, 1H), 6.93-7.05 (m, 2H), 7.16-7.24 (m, 2H), 12.11-12.75 (m, 2H).

Example 39(17)

N-[trans-4-({[(4-hydroxy-1-methyl-4-piperidinyl)methyl]amino}methyl)cyclohexyl]-N-(1H-imidazol-2-ylmethyl)-1H-imidazole-2-carboxamide Description: amorphous;
TLC: Rf 0.23 (dichrolomethane:methanol:28% aqueous ammonia=90:10:1);
NMR (CDCl$_3$): δ 1.08 (m, 1H), 1.48-1.98 (m, 12H), 2.38-2.70 (m, 7H), 2.70-2.84 (m, 2H), 2.98-3.10 (m, 2H), 4.22 (m, 1H), 4.60-5.00 (m, 2H), 6.93-7.05 (m, 2H), 7.17-7.25 (m, 2H).

Example 39(18)

N-({trans-4-[(8-cyclohexyl-2,8-diazaspiro[4.5]dec-2-yl)methyl]cyclohexyl}methyl)-N-(1H-imidazol-2-ylmethyl)-1H-imidazole-2-carboxamide

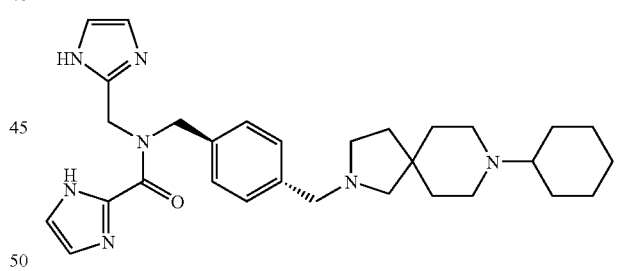

Description: amorphous;
TLC: Rf 0.50 (ethyl acetate:methanol:28% aqueous ammonia=40:10:2);
NMR (CDCl$_3$): δ 0.63-1.98 (m, 26H), 2.09-2.32 (m, 5H), 2.37-2.57 (m, 6H), 3.37-4.40 (m, 2H), 4.61-5.09 (m, 2H), 6.89-7.07 (m, 2H), 7.14-7.35 (m, 2H), 11.95-12.26 (m, 2H).

Example 40(1) to Example 40(79)

The same operation as in Example 4→Example 2→Example 5 was performed, except for using a corresponding carboxylic acid in place of 4-formylbenzoic acid and a corresponding amine in place of 2,2'-[iminobis(methylene)]bis(N,N-dimethyl-1H-imidazole-1-sulfonamide in Example 4, and a corresponding amine was used in place of benzylamine in Example 2, to obtain the following compound.

Example 40(1)

1-(1H-imidazol-2-yl)-N-(1H-imidazol-2-ylmethyl)-N-{4-[(8-isobutyl-2,8-diazaspiro[4.5]dec-2-yl)carbonyl]benzyl}methanamine

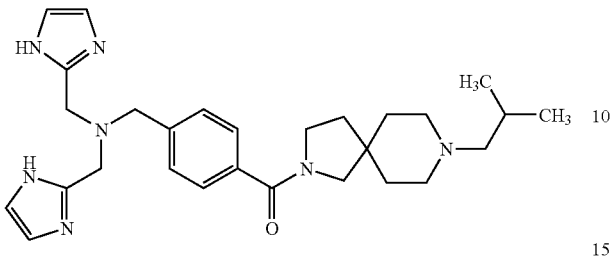

Description: amorphous;
TLC: Rf 0.27 (dichrolomethane:methanol:28% aqueous ammonia=90:10:1);
NMR (DMSO-$d_6$): δ 0.78 (d, J=6.6 Hz, 3H), 0.83 (d, J=6.6 Hz, 3H), 1.33-1.83 (m, 7H), 1.86-2.45 (m, 6H), 3.15-3.63 (m, 10H), 6.80-6.90 (m, 2H), 7.04-7.19 (m, 2H), 7.36-7.51 (m, 4H), 11.95-12.09 (m, 2H).

Example 40(2)

1-(1H-imidazol-2-yl)-N-(1H-imidazol-2-ylmethyl)-N-[4-({8-[(3-methyl-2-thienyl)methyl]-2,8-diazaspiro[4.5]dec-2-yl}carbonyl)benzyl]methanamine

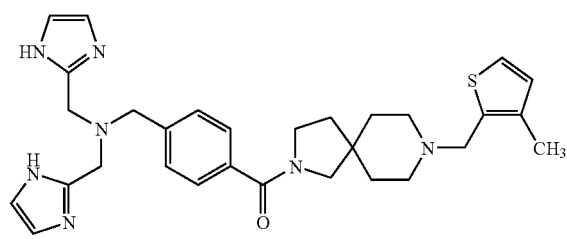

Description: amorphous;
TLC: Rf 0.35 (dichrolomethane:methanol:28% aqueous ammonia=90:10:1);
NMR (DMSO-$d_6$): δ 1.35-1.81 (m, 6H), 2.04-2.57 (m, 7H), 3.17-3.65 (m, 12H), 6.73-6.83 (m, 1H), 6.83-6.89 (m, 2H), 7.08-7.17 (m, 2H), 7.21-7.32 (m, 1H), 7.37-7.50 (m, 4H), 12.03 (s, 2H).

Example 40(3)

1-(4-{[8-(2-ethylbutyl)-2,8-diazaspiro[4.5]dec-2-yl]carbonyl}phenyl)-N,N-bis(1H-imidazol-2-ylmethyl)methanamine

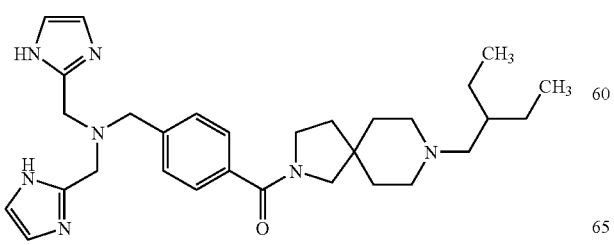

Description: amorphous;
TLC: Rf 0.29 (dichrolomethane:methanol:28% aqueous ammonia=90:10:1);
NMR (DMSO-$d_6$): δ 0.72-0.86 (m, 6H), 1.13-1.80 (m, 11H), 1.95-2.46 (m, 6H), 3.16-3.66 (m, 10H), 6.77-6.94 (m, 2H), 7.06-7.18 (m, 2H), 7.39-7.49 (m, 4H), 11.97-12.12 (m, 2H).

Example 40(4)

1-{4-[(8-cyclopentyl-2,8-diazaspiro[4.5]dec-2-yl)carbonyl]phenyl}-N,N-bis(H-imidazol-2-ylmethyl)methanamine

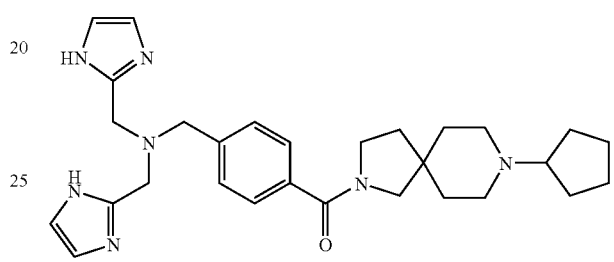

Description: amorphous;
TLC: Rf 0.18 (dichrolomethane:methanol:28% aqueous ammonia=90:10:1);
NMR (DMSO-$d_6$): δ 1.09-1.85 (m, 14H), 2.06-2.58 (m, 5H), 3.14-3.62 (m, 10H), 6.77-6.92 (m, 2H), 7.04-7.18 (m, 2H), 7.38-7.48 (m, 4H), 12.00-12.18 (m, 2H).

Example 40(5)

1-(4-{[8-(cyclohexylmethyl)-2,8-diazaspiro[4.5]dec-2-yl]carbonyl}phenyl)-N,N-bis(1H-imidazol-2-ylmethyl)methanamine

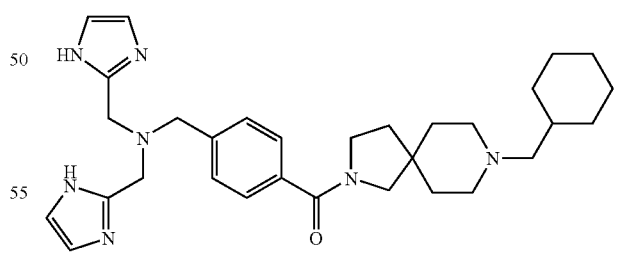

Description: amorphous;
TLC: Rf 0.42 (dichrolomethane:methanol:28% aqueous ammonia=90:10:1);
NMR (DMSO-$d_6$): δ 0.62-1.79 (m, 17H), 1.92-2.44 (m, 6H), 3.14-3.71 (m, 10H), 6.78-6.94 (m, 2H), 7.04-7.19 (m, 2H), 7.36-7.52 (m, 4H), 11.94-12.12 (m, 2H).

Example 40(6)

1-(1H-imidazol-2-yl)-N-(1H-imidazol-2-ylmethyl)-N-(4-{[8-(2-methylbenzyl)-2,8-diazaspiro[4.5]dec-2-yl]carbonyl}benzyl)methanamine Description: amorphous;
TLC: Rf 0.44 (dichrolomethane:methanol:28% aqueous ammonia=90:10:1);
NMR (DMSO-$d_6$): δ 1.34-1.82 (m, 6H), 2.07-2.66 (m, 7H), 3.18-3.66 (m, 12H), 6.77-7.28 (m, 8H), 7.38-7.51 (m, 4H), 11.96-12.08 (m, 2H).

Example 40(7)

4-[(8-cyclohexyl-2,8-diazaspiro[4.5]dec-2-yl)carbonyl]-N,N-bis(1H-imidazol-2-ylmethyl)cyclohexanamine

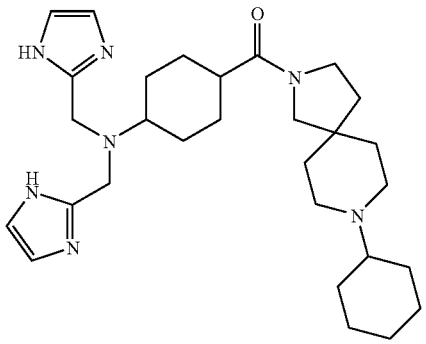

Description: amorphous;
TLC: Rf 0.37 (chloroform:methanol:28% aqueous ammonia=90:13:2);
NMR (CDCl$_3$): δ 1.14-1.92 (m, 24H), 2.24-2.67 (m, 7H), 3.21-3.56 (m, 4H), 3.79-4.41 (m, 4H), 6.83-7.05 (m, 4H).

Example 40(8)

1-(4-{[8-(2,2-dimethylpropyl)-2,8-diazaspiro[4.5]dec-2-yl]carbonyl}phenyl)-N,N-bis(1H-imidazol-2-ylmethyl)methanamine

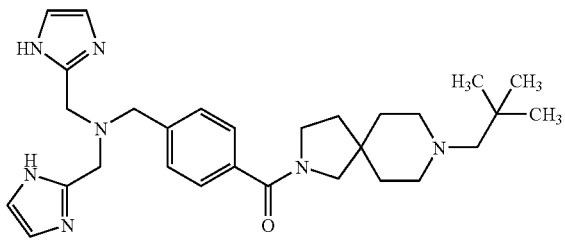

Description: amorphous;
TLC: Rf 0.31 (dichrolomethane:methanol:28% aqueous ammonia=90:10:1);
NMR (DMSO-$d_6$): δ 0.74-0.88 (m, 9H), 1.34-1.79 (m, 6H), 1.91-2.06 (m, 2H), 2.15-2.60 (m, 4H), 3.16-3.66 (m, 10H), 6.79-6.91 (m, 2H), 7.06-7.18 (m, 2H), 7.37-7.51 (m, 4H), 11.97-12.11 (m, 2H).

Example 40(9)

1-{4-[(9-cyclohexyl-3,9-diazaspiro[5.5]undec-3-yl)carbonyl]phenyl}-N,N-bis(H-imidazol-2-ylmethyl)methanamine Description: amorphous;
TLC: Rf 0.22 (dichrolomethane:methanol:28% aqueous ammonia=90:10:1);
NMR (CDCl$_3$): δ 1.00-1.34 (m, 6H), 1.35-1.70 (m, 8H), 1.70-1.92 (m, 4H), 2.25 (m, 1H), 2.44-2.60 (m, 4H), 3.39-3.42 (m, 2H), 3.54 (s, 4H), 3.58 (s, 2H), 3.64-3.80 (m, 2H), 7.01 (s, 4H), 7.25 (d, J=8.1 Hz, 2H), 7.32 (d, J=8.1 Hz, 2H), 11.20-12.11 (m, 2H).

Example 40(10)

1-(1H-imidazol-2-yl)-N-(1H-imidazol-2-ylmethyl)-N-(4-{[9-(2-thienylmethyl)-3,9-diazaspiro[5.5]undec-3-yl]carbonyl}benzyl)methanamine Description: amorphous;
TLC: Rf 0.24 (dichrolomethane:methanol:28% aqueous ammonia=90:10:1);
NMR (CDCl$_3$): δ 1.34-1.68 (m, 8H), 2.40-2.52 (m, 4H), 3.30-3.40 (m, 2H), 3.53 (s, 4H), 3.57 (s, 2H), 3.67-3.80 (m, 4H), 6.89 (dd, J=3.6, 1.2 Hz, 1H), 6.94 (dd, J=5.1, 3.6 Hz, 1H), 7.00 (s, 4H), 7.22 (dd, J=5.1, 1.2 Hz, 1H), 7.25 (d, J=8.1 Hz, 2H), 7.31 (d, J=8.1 Hz, 2H).

Example 40(11)

1-(1H-imidazol-2-yl)-N-(1H-imidazol-2-ylmethyl)-N-[4-({9-[(3-methyl-2-thienyl)methyl]-3,9-diazaspiro[5.5]undec-3-yl}carbonyl)benzyl]methanamine Description: amorphous;
TLC: Rf 0.24 (dichrolomethane:methanol:28% aqueous ammonia=90:10:1);
NMR (CDCl$_3$): δ 1.34-1.68 (m, 8H), 2.19 (s, 3H), 2.39-2.52 (m, 4H), 3.28-3.40 (m, 2H), 3.53 (s, 4H), 3.56 (s, 2H), 3.62 (s, 2H), 3.65-3.80 (m, 2H), 6.78 (d, J=5.1 Hz, 1H), 7.00 (s, 4H), 7.12 (d, J=5.1 Hz, 1H), 7.25 (d, J=8.1 Hz, 2H), 7.31 (d, J=8.1 Hz, 2H).

Example 40(12)

1-{trans-4-[(8-cyclohexyl-2,8-diazaspiro[4.5]dec-2-yl)carbonyl]cyclohexyl}-N,N-bis(1H-imidazol-2-ylmethyl)methanamine Description: amorphous;
TLC: Rf 0.47 (ethyl acetate:methanol:28% aqueous ammonia=40:10:2);
NMR (CDCl$_3$): δ 0.75-2.10 (m, 25H), 2.16-2.72 (m, 8H), 3.29-3.26 (m, 2H), 3.42-3.58 (m, 2H), 3.61 (s, 4H), 7.03 (s, 4H).

Example 40(13)

1-{4-[(8-cycloheptyl-2,8-diazaspiro[4.5]dec-2-yl)carbonyl]phenyl}-N,N-bis(H-imidazol-2-ylmethyl)methanamine

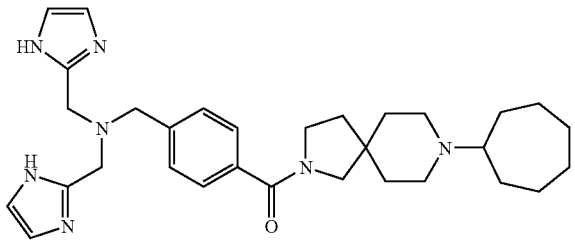

Description: amorphous;

TLC: Rf 0.14 (dichrolomethane:methanol:28% aqueous ammonia=90:10:1);

NMR (DMSO-$d_6$): δ 1.16-1.78 (m, 18H), 2.12-2.60 (m, 5H), 3.15-3.62 (m, 10H), 6.82-6.88 (m, 2H), 7.09-7.15 (m, 2H), 7.39-7.49 (m, 4H), 11.97-12.09 (m, 2H).

Example 40(14)

1-(4-{[8-(cyclopentylmethyl)-2,8-diazaspiro[4.5]dec-2-yl]carbonyl}phenyl)-N,N-bis(1H-imidazol-2-ylmethyl)methanamine

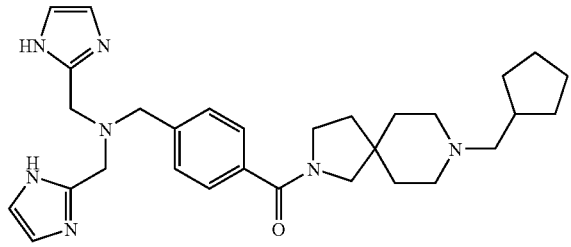

Description: amorphous;

TLC: Rf 0.15 (dichrolomethane:methanol:28% aqueous ammonia=90:10:1);

NMR (DMSO-$d_6$): δ 0.96-1.81 (m, 15H), 1.95-2.59 (m, 6H), 3.17-3.65 (m, 10H), 6.82-6.88 (m, 2H), 7.09-7.15 (m, 2H), 7.39-7.49 (m, 4H), 11.99-12.11 (m, 2H).

Example 40(15)

1-(4-{[8-(cyclopropylmethyl)-2,8-diazaspiro[4.5]dec-2-yl]carbonyl}phenyl)-N,N-bis(1H-imidazol-2-ylmethyl)methanamine Description: amorphous;

TLC: Rf 0.15 (dichrolomethane:methanol:28% aqueous ammonia=90:10:1);

NMR (DMSO-$d_6$): δ −0.06-0.12 (m, 2H), 0.32-0.51 (m, 2H), 0.61-0.93 (m, 1H), 1.35-1.81 (m, 6H), 2.03-2.62 (m, 6H), 3.16-3.66 (m, 10H), 6.78-6.91 (m, 2H), 7.05-7.19 (m, 2H), 7.36-7.52 (m, 4H), 12.00-12.14 (m, 2H).

Example 40(16)

1-{4-[(2-cyclohexyl-2,7-diazaspiro[3.5]non-7-yl)carbonyl]phenyl}-N,N-bis(H-imidazol-2-ylmethyl)methanamine Description: amorphous;

TLC: Rf 0.20 (dichrolomethane:methanol:28% aqueous ammonia=90:10:1);

NMR (CDCl$_3$): δ 0.88-1.30 (m, 6H), 1.50-1.90 (m, 8H), 1.97 (m, 1H), 3.04 (s, 4H), 3.24-3.42 (m, 2H), 3.54 (s, 4H), 3.59 (s, 2H), 3.60-3.77 (m, 2H), 7.02 (s, 4H), 7.26 (d, J=8.1 Hz, 2H), 7.34 (d, J=8.1 Hz, 2H).

Example 40(17)

1-(1H-imidazol-2-yl)-N-(1H-imidazol-2-ylmethyl)-N-[4-({7-[(3-methyl-2-thienyl)methyl]-2,7-diazaspiro[3.5]non-2-yl}carbonyl)benzyl]methanamine

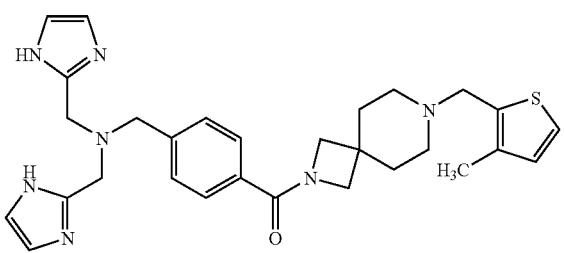

Description: amorphous;

TLC: Rf 0.27 (dichrolomethane:methanol:28% aqueous ammonia=90:10:1);

NMR (CDCl$_3$): δ 1.76-1.88 (m, 4H), 2.17 (s, 3H), 2.28-2.52 (m, 4H), 3.57 (s, 2H), 3.58 (s, 4H), 3.62 (s, 2H), 3.89 (s, 2H), 3.98 (s, 2H), 6.78 (d, J=5.1 Hz, 1H), 7.02 (s, 4H), 7.11 (d, J=5.1 Hz, 1H), 7.38 (d, J=8.1 Hz, 2H), 7.53 (d, J=8.1 Hz, 2H).

Example 40(18)

1-(1H-imidazol-2-yl)-N-(1H-imidazol-2-ylmethyl)-N-[4-({2-[(3-methyl-2-thienyl)methyl]-2,7-diazaspiro[3.5]non-7-yl}carbonyl)benzyl]methanamine Description: amorphous;

TLC: Rf 0.27 (dichrolomethane:methanol:28% aqueous ammonia=90:10:1);

NMR (CDCl$_3$): δ 1.64-1.92 (m, 4H), 2.19 (s, 3H), 3.11 (s, 4H), 3.24-3.40 (m, 2H), 3.54 (s, 4H), 3.59 (s, 2H), 3.60-3.80 (m, 4H), 6.79 (d, J=5.1 Hz, 1H), 7.02 (s, 4H), 7.11 (d, J=5.1 Hz, 1H), 7.25 (d, J=8.1 Hz, 2H), 7.34 (d, J=8.1 Hz, 2H).

Example 40(19)

1-{4-[(7-cyclohexyl-2,7-diazaspiro[3.5]non-2-yl)carbonyl]phenyl}-N,N-bis(H-imidazol-2-ylmethyl)methanamine

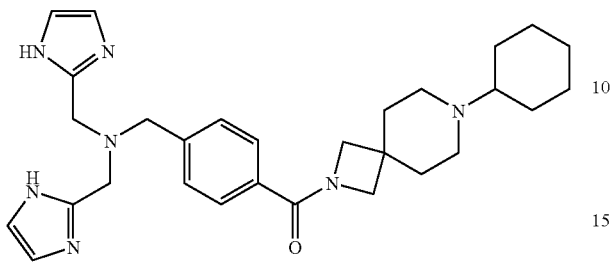

Description: amorphous;
TLC: Rf 0.25 (dichrolomethane:methanol:28% aqueous ammonia=90:10:1);
NMR (CDCl$_3$): δ 1.00-1.32 (m, 6H), 1.62 (m, 1H), 1.70-1.90 (m, 7H), 2.26 (m, 1H), 2.40-2.57 (m, 4H), 3.59 (s, 4H), 3.64 (s, 2H), 3.88 (s, 2H), 3.97 (s, 2H), 7.04 (s, 4H), 7.41 (d, J=8.1 Hz, 2H), 7.56 (d, J=8.1 Hz, 2H).

Example 40(20)

1-{4-[(9-cyclohexyl-2,9-diazaspiro[5.5]undec-2-yl)carbonyl]phenyl}-N,N-bis(H-imidazol-2-ylmethyl)methanamine

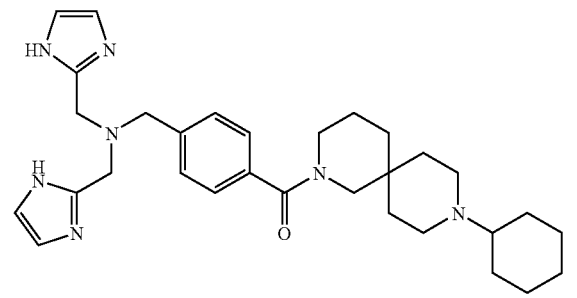

Description: amorphous;
TLC: Rf 0.25 (dichrolomethane:methanol:28% aqueous ammonia=90:10:1);
NMR (CDCl$_3$): δ 0.96-2.78 (m, 23H), 3.17 (m, 1H), 3.33 (m, 1H), 3.48-3.80 (m, 8H), 7.03 (s, 4H), 7.23-7.30 (m, 2H), 7.35 (d, J=8.1 Hz, 2H), 11.30-12.11 (m, 2H).

Example 40(21)

1-(1H-imidazol-2-yl)-N-(1H-imidazol-2-ylmethyl)-N-[4-({9-[(3-methyl-2-thienyl)methyl]-1-oxa-4,9-diazaspiro[5.5]undec-4-yl}carbonyl)benzyl]methanamine

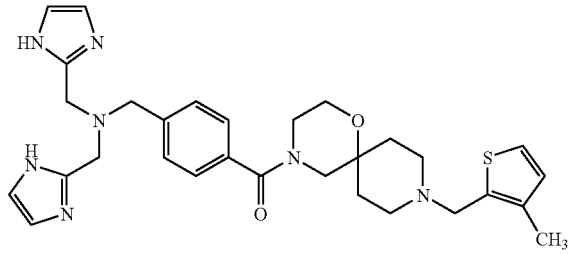

Description: amorphous;
TLC: Rf 0.38 (dichrolomethane:methanol:28% aqueous ammonia=90:10:1);
NMR (CDCl$_3$): δ 1.22-1.48 (m, 2H), 1.60-1.98 (m, 2H), 2.08-2.63 (m, 7H), 3.18-3.85 (m, 14H), 6.77 (d, J=5.1 Hz, 1H), 7.06 (s, 4H), 7.11 (d, J=5.1 Hz, 1H), 7.27 (d, J=8.1 Hz, 2H), 7.37 (d, J=8.1 Hz, 2H).

Example 40(22)

1-(1H-imidazol-2-yl)-N-(1H-imidazol-2-ylmethyl)-N-{4-[(7-isobutyl-2,7-diazaspiro[3.5]non-2-yl)carbonyl]benzyl}methanamine

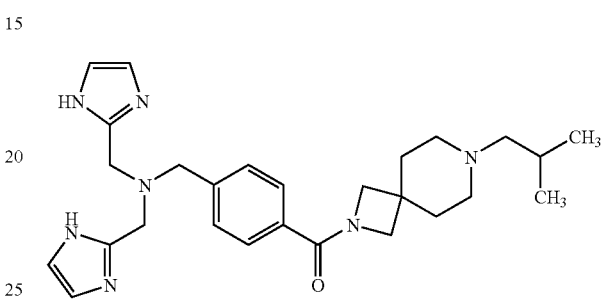

Description: amorphous;
TLC: Rf 0.29 (dichrolomethane:methanol:28% aqueous ammonia=90:10:1);
NMR (CDCl$_3$): δ 0.87 (d, J=6.6 Hz, 6H), 1.70-1.88 (m, 5H), 1.97-2.04 (m, 2H), 2.18-2.40 (m, 4H), 3.59 (s, 4H), 3.63 (s, 2H), 3.86 (s, 2H), 3.97 (s, 2H), 7.03 (s, 4H), 7.40 (d, J=8.1 Hz, 2H), 7.55 (d, J=8.1 Hz, 2H).

Example 40(23)

1-(1H-imidazol-2-yl)-N-(1H-imidazol-2-ylmethyl)-N-{4-[(2-isobutyl-2,7-diazaspiro[3.5]non-7-yl)carbonyl]benzyl}methanamine Description: amorphous;
TLC: Rf 0.29 (dichrolomethane:methanol:28% aqueous ammonia=90:10:1);
NMR (CDCl$_3$): δ 0.87 (d, J=6.6 Hz, 6H), 1.50-1.90 (m, 5H), 2.24-2.30 (m, 2H), 3.03 (s, 4H), 3.25-3.40 (m, 2H), 3.50-3.74 (m, 8H), 7.04 (s, 4H), 7.28 (d, J=8.1 Hz, 2H), 7.37 (d, J=8.1 Hz, 2H).

Example 40(24)

1-(4-{[8-(1-ethylpropyl)-2,8-diazaspiro[4.5]dec-2-yl]carbonyl}phenyl)-N,N-bis(1H-imidazol-2-ylmethyl)methanamine

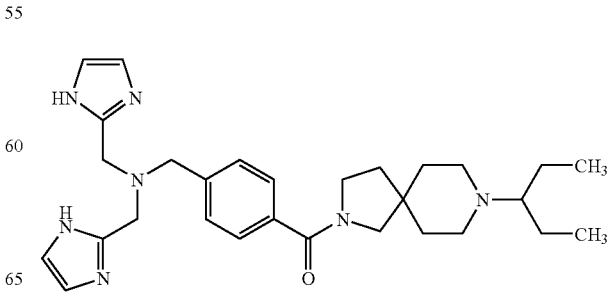

Description: amorphous;
TLC: Rf 0.58 (dichrolomethane:methanol:28% aqueous ammonia=40:10:1);
NMR (DMSO-$d_6$): δ 0.73-0.91 (m, 6H), 1.09-1.82 (m, 10H), 1.97-2.65 (m, 5H), 3.13-3.67 (m, 10H), 6.78-6.91 (m, 2H), 7.04-7.19 (m, 2H), 7.36-7.51 (m, 4H), 11.97-12.13 (m, 2H).

Example 40(25)

1-(1H-imidazol-2-yl)-N-(1H-imidazol-2-ylmethyl)-N-{4-[(8-isopropyl-2,8-diazaspiro[4.5]dec-2-yl)carbonyl]benzyl}methanamine Description: amorphous;
TLC: Rf 0.22 (dichrolomethane:methanol:28% aqueous ammonia=90:10:1);
NMR (CDCl$_3$): δ 0.98-1.10 (m, 6H), 1.50-1.88 (m, 6H), 2.25-2.80 (m, 5H), 3.22-3.74 (m, 10H), 7.03 (s, 4H), 7.32-7.44 (m, 4H).

Example 40(26)

1-(1H-imidazol-2-yl)-N-(1H-imidazol-2-ylmethyl)-N-{4-[(9-isobutyl-2,9-diazaspiro[5.5]undec-2-yl)carbonyl]benzyl}methanamine

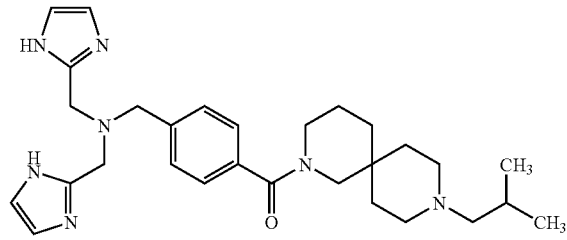

Description: amorphous;
TLC: Rf 0.25 (dichrolomethane:methanol:28% aqueous ammonia=90:10:1);
NMR (CDCl$_3$): δ 0.72-0.98 (m, 6H), 1.20-2.54 (m, 15H), 3.12-3.40 (m, 2H), 3.45-3.80 (m, 8H), 7.04 (s, 4H), 7.27 (d, J=8.1 Hz, 2H), 7.34 (d, J=8.1 Hz, 2H).

Example 40(27)

1-(1H-imidazol-2-yl)-N-(1H-imidazol-2-ylmethyl)-N-[4-({9-[(3-methyl-2-thienyl)methyl]-2,9-diazaspiro[5.5]undec-2-yl}carbonyl)benzyl]methanamine

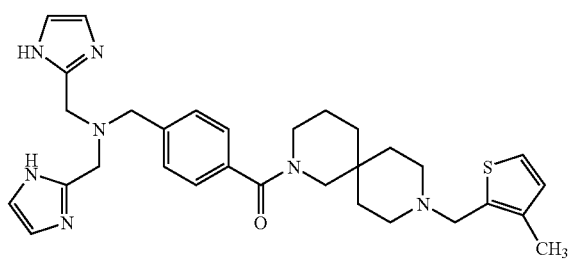

Description: amorphous;
TLC: Rf 0.29 (dichrolomethane:methanol:28% aqueous ammonia=90:10:1);
NMR (CDCl$_3$): δ 1.22-1.72 (m, 8H), 2.00-2.65 (m, 7H), 3.10-3.80 (m, 12H), 6.76 (m, 1H), 7.04 (s, 4H), 7.09 (m, 1H), 7.26 (d, J=8.1 Hz, 2H), 7.35 (d, J=8.1 Hz, 2H).

Example 40(28)

1-(1H-imidazol-2-yl)-N-(1H-imidazol-2-ylmethyl)-N-{4-[(9-isobutyl-3,9-diazaspiro[5.5]undec-3-yl)carbonyl]benzyl}methanamine

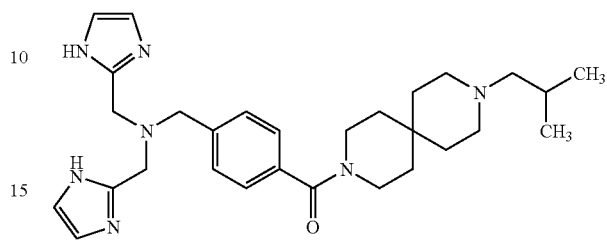

Description: amorphous;
TLC: Rf 0.24 (dichrolomethane:methanol:28% aqueous ammonia=90:10:1);
NMR (CDCl$_3$): δ 0.88 (d, J=6.6 Hz, 6H), 1.32-1.68 (m, 8H), 1.77 (m, 1H), 2.06 (d, J=7.5 Hz, 2H), 2.26-2.43 (m, 4H), 3.30-3.41 (m, 2H), 3.54 (s, 4H), 3.58 (s, 2H), 3.66-3.78 (m, 2H), 7.02 (s, 4H), 7.26 (d, J=8.1 Hz, 2H), 7.33 (d, J=8.1 Hz, 2H).

Example 40(29)

1-(1H-imidazol-2-yl)-N-(1H-imidazol-2-ylmethyl)-N-{4-[(9-isobutyl-1-oxa-4,9-diazaspiro[5.5]undec-4-yl)carbonyl]benzyl}methanamine

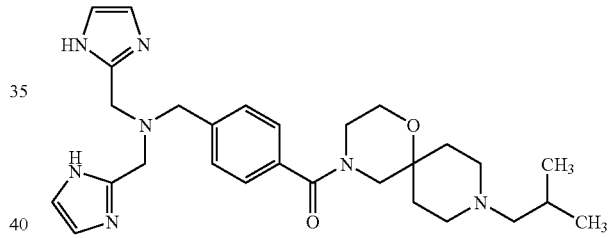

Description: amorphous;
TLC: Rf 0.24 (dichrolomethane:methanol:28% aqueous ammonia=90:10:1);
NMR (CDCl$_3$): δ 0.78-0.98 (m, 6H), 1.35 (m, 1H), 1.64-1.92 (m, 4H), 1.98-2.58 (m, 6H), 3.18-3.88 (m, 12H), 7.05 (s, 4H), 7.27 (d, J=8.1 Hz, 2H), 7.37 (d, J=8.1 Hz, 2H).

Example 40(30)

1-{4-[(9-cyclohexyl-1-oxa-4,9-diazaspiro[5.5]undec-4-yl)carbonyl]phenyl}-N,N-bis(1H-imidazol-2-ylmethyl)methanamine

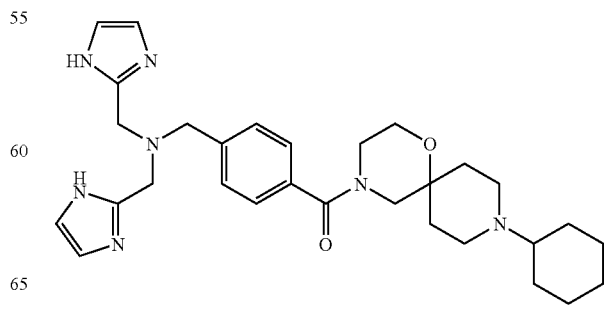

Example 40(31)

1-(1H-imidazol-2-yl)-N-{4-[(8-isobutyl-2,8-diazaspiro[4.5]dec-2-yl)carbonyl]benzyl}-N-[(1-methyl-1H-imidazol-2-yl)methyl]methanamine

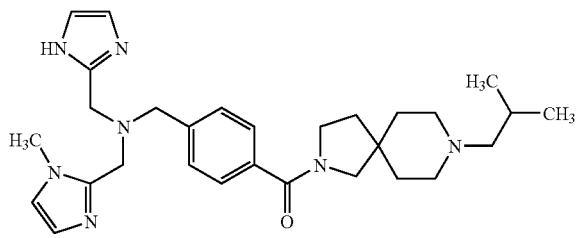

Description: amorphous;
TLC: Rf 0.55 (ethyl acetate:methanol:28% aqueous ammonia=40:10:2);
NMR (CDCl$_3$): δ 0.85 (d, J=6.6 Hz, 3H), 0.90 (d, J=6.6 Hz, 3H), 1.40-1.91 (m, 7H), 2.02 (d, J=7.2 Hz, 1H), 2.08 (d, J=7.2 Hz, 1H), 2.12-2.56 (m, 4H), 3.26 (s, 1H), 3.44-3.53 (m, 4H), 3.55-3.63 (m, 5H), 3.65-3.76 (m, 3H), 6.89 (s, 1H), 7.01 (s, 1H), 7.08 (s, 1H), 7.13 (s, 1H), 7.38-7.55 (m, 4H), 12.28-12.50 (m, 1H).

Example 40(32)

1-(1H-imidazol-2-yl)-N-{4-[(9-isobutyl-1-oxa-4,9-diazaspiro[5.5]undec-4-yl)carbonyl]benzyl}-N-[(1-methyl-1H-imidazol-2-yl)methyl]methanamine

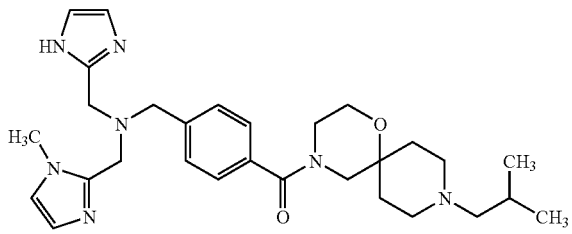

Description: amorphous;
TLC: Rf 0.61 (ethyl acetate:methanol:28% aqueous ammonia=40:10:2);
NMR (CDCl$_3$): δ 0.78-0.92 (m, 6H), 1.13-1.90 (m, 5H), 1.94-2.58 (m, 6H), 3.08-3.85 (m, 8H), 3.49 (s, 2H), 3.60 (s, 3H), 3.71 (s, 2H), 6.89 (d, J=1.2 Hz, 1H), 7.02 (d, J=1.2 Hz, 1H), 7.09 (s, 1H), 7.13 (s, 1H), 7.37 (d, J=7.8 Hz, 2H), 7.48 (d, J=7.8 Hz, 2H), 12.29-12.50 (m, 1H).

Example 40(33)

1-(1H-imidazol-2-yl)-N-{4-[(9-isobutyl-3,9-diazaspiro[5.5]undec-3-yl)carbonyl]benzyl}-N-[(1-methyl-1H-imidazol-2-yl)methyl]methanamine Description: amorphous;
TLC: Rf 0.66 (ethyl acetate:methanol:28% aqueous ammonia=40:10:2);
NMR (CDCl$_3$): δ 0.88 (d, J=6.6 Hz, 6H), 1.32-1.64 (m, 8H), 1.67-1.84 (m, 1H), 2.07 (d, J=7.2 Hz, 2H), 2.28-2.38 (m, 4H), 3.30-3.42 (m, 2H), 3.48 (s, 2H), 3.59 (s, 3H), 3.59-3.60 (m, 2H), 3.64-3.76 (m, 4H), 6.89 (d, J=1.2 Hz, 1H), 7.01 (d, J=1.2 Hz, 1H), 7.09 (s, 1H), 7.13 (s, 1H), 7.37 (d, J=8.1 Hz, 2H), 7.45 (d, J=8.1 Hz, 2H), 12.40 (s, 1H).

Example 40(34)

1-{4-[(9-cyclopentyl-2,9-diazaspiro[5.5]undec-2-yl)carbonyl]phenyl}-N,N-bis(H-imidazol-2-ylmethyl)methanamine Description: amorphous;
TLC: Rf 0.18 (dichrolomethane:methanol:28% aqueous ammonia=90:10:1);
NMR (CDCl$_3$): δ 1.19-1.96 (m, 16H), 2.09-2.78 (m, 5H), 3.18 (m, 1H), 3.33 (m, 1H), 3.47-3.80 (m, 8H), 7.04 (s, 4H), 7.26-7.31 (m, 2H), 7.35 (d, J=8.4 Hz, 2H).

Example 40(35)

1-(1H-imidazol-2-yl)-N-(1H-imidazol-2-ylmethyl)-N-(4-{[9-(tetrahydro-2H-pyran-4-yl)-2,9-diazaspiro[5.5]undec-2-yl]carbonyl}benzyl)methanamine Description: amorphous;
TLC: Rf 0.18 (dichrolomethane:methanol:28% aqueous ammonia=90:10:1);
NMR (CDCl$_3$): δ 1.20-1.83 (m, 12H), 2.10-2.78 (m, 5H), 3.10-3.80 (m, 12H), 3.85-4.08 (m, 2H), 7.04 (s, 4H), 7.25-7.30 (m, 2H), 7.35 (d, J=8.1 Hz, 2H).

Example 40(36)

1-[4-({8-[(2,4-dimethyl-1,3-thiazol-5-yl)methyl]-2,8-diazaspiro[4.5]dec-2-yl}carbonyl)phenyl]-N,N-bis(1H-imidazol-2-ylmethyl)methanamine Description: amorphous;
TLC: Rf 0.22 (dichrolomethane:methanol:28% aqueous ammonia=90:10:1);
NMR (DMSO-d$_6$): δ 1.33-1.80 (m, 6H), 2.11-2.59 (m, 10H), 3.18-3.64 (m, 12H), 6.80-6.90 (m, 2H), 7.08-7.17 (m, 2H), 7.38-7.50 (m, 4H), 12.00-12.10 (m, 2H).

Example 40(37)

1-(4-{[9-(2-ethylbutyl)-2,9-diazaspiro[5.5]undec-2-yl]carbonyl}phenyl)-N,N-bis(1H-imidazol-2-ylmethyl)methanamine

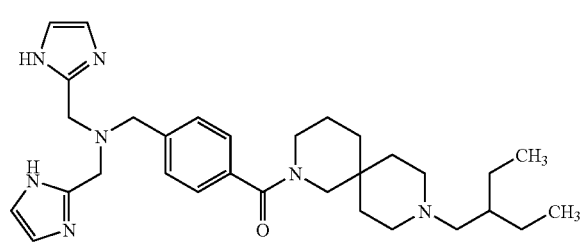

Description: amorphous;
TLC: Rf 0.23 (dichrolomethane:methanol:28% aqueous ammonia=90:10:1);
NMR (CDCl$_3$): δ 0.70-0.90 (m, 6H), 1.10-1.72 (m, 13H), 1.80-2.52 (m, 6H), 3.18 (m, 1H), 3.32 (m, 1H), 3.45-3.80 (m, 8H), 7.04 (s, 4H), 7.26 (d, J=8.1 Hz, 2H), 7.35 (d, J=8.1 Hz, 2H).

Example 40(38)

1-(4-{[9-(2,2-dimethylpropyl)-2,9-diazaspiro[5.5]
undec-2-yl]carbonyl}phenyl)-N,N-bis(1H-imidazol-
2-ylmethyl)methanamine Description: amorphous;
TLC: Rf 0.23 (dichrolomethane:methanol:28% aqueous ammonia=90:10:1);
NMR (CDCl$_3$): δ 0.70-0.90 (m, 9H), 1.20-1.70 (m, 8H), 1.85-2.20 (m, 1H), 1.95-2.20 (m, 2H), 2.30 (m, 1H), 2.42-2.60 (m, 2H), 3.18 (m, 1H), 3.31 (m, 1H), 3.45-3.78 (m, 8H), 7.03 (s, 4H), 7.25 (d, J=8.1 Hz, 2H), 7.28-7.35 (m, 2H).

Example 40(39)

1-(4-{[9-(cyclohexylmethyl)-2,9-diazaspiro[5.5]
undec-2-yl]carbonyl}phenyl)-N,N-bis(1H-imidazol-
2-ylmethyl)methanamine Description: amorphous;
TLC: Rf 0.23 (dichrolomethane:methanol:28% aqueous ammonia=90:10:1);
NMR (CDCl$_3$): δ 0.70-0.95 (m, 2H), 1.05-1.80 (m, 17H), 1.85-2.20 (m, 4H), 2.33 (m, 1H), 2.46 (m, 1H), 3.17 (m, 1H), 3.32 (m, 1H), 3.48-3.80 (m, 8H), 7.03 (s, 4H), 7.25 (d, J=7.8 Hz, 2H), 7.33 (d, J=7.8 Hz, 2H).

Example 40(40)

1-(1H-imidazol-2-yl)-N-(1H-imidazol-2-ylmethyl)-
N-(4-{[9-(2-methylbenzyl)-2,9-diazaspiro[5.5]un-
dec-2-yl]carbonyl}benzyl)methanamine Description: amorphous;
TLC: Rf 0.36 (dichrolomethane:methanol:28% aqueous ammonia=90:10:1);
NMR (CDCl$_3$): δ 1.18-1.75 (m, 8H), 1.95-2.59 (m, 7H), 3.10-3.80 (m, 12H), 7.02 (s, 4H), 7.04-7.18 (m, 4H), 7.24 (d, J=8.1 Hz, 2H), 7.26-7.38 (m, 2H).

Example 40(41)

1-(1H-imidazol-2-yl)-N-(1H-imidazol-2-ylmethyl)-
N-[4-({9-[(3-methoxy-2-thienyl)methyl]-2,9-diaza-
spiro[5.5]undec-2-yl}carbonyl)benzyl]methanamine Description: amorphous;
TLC: Rf 0.30 (dichrolomethane:methanol:28% aqueous ammonia=90:10:1);
NMR (CDCl$_3$): δ 1.20-1.72 (m, 8H), 2.08-2.35 (m, 2H), 2.40-2.64 (m, 2H), 3.15 (m, 1H), 3.31 (m, 1H), 3.40-3.75 (m, 10H), 3.79 (s, 3H), 6.79 (m, 1H), 7.03 (s, 4H), 7.09 (m, 1H), 7.24 (d, J=7.8 Hz, 2H), 7.33 (d, J=7.8 Hz, 2H).

Example 40(42)

1-(4-{[9-(1-ethylpropyl)-2,9-diazaspiro[5.5]undec-2-
yl]carbonyl}phenyl)-N,N-bis(H-imidazol-2-ylm-
ethyl)methanamine Description: amorphous;
TLC: Rf 0.30 (dichrolomethane:methanol:28% aqueous ammonia=90:10:1);
NMR (CDCl$_3$): δ 0.68-0.95 (m, 6H), 1.05-1.72 (m, 12H), 1.90-2.20 (m, 2H), 2.30 (m, 1H), 2.40-2.60 (m, 2H), 3.18 (m, 1H), 3.32 (m, 1H), 3.45-3.64 (m, 7H), 3.72 (m, 1H), 7.01 (s, 4H), 7.24 (d, J=7.8 Hz, 2H), 7.33 (d, J=7.8 Hz, 2H).

Example 40(43)

1-{4-[(9-cycloheptyl-2,9-diazaspiro[5.5]undec-2-yl)
carbonyl]phenyl}-N,N-bis(H-imidazol-2-ylmethyl)
methanamine Description: amorphous;
TLC: Rf 0.20 (dichrolomethane:methanol:28% aqueous ammonia=90:10:1);
NMR (CDCl$_3$): δ 1.20-2.04 (m, 20H), 2.24-2.83 (m, 5H), 3.15 (m, 1H), 3.35 (m, 1H), 3.50-3.78 (m, 8H), 7.03 (s, 4H), 7.25-7.32 (m, 2H), 7.38 (d, J=7.5 Hz, 2H).

Example 40(44)

(2-{[2-(4-{[bis(1H-imidazol-2-ylmethyl)amino]
methyl}benzoyl)-2,9-diazaspiro[5.5]undec-9-yl]
methyl}-3-thienyl)methanol Description: amorphous;
TLC: Rf 0.24 (dichrolomethane:methanol:28% aqueous ammonia=90:10:1);
NMR (CDCl$_3$): δ 1.05-1.72 (m, 8H), 2.10-2.80 (m, 4H), 3.08 (m, 1H), 3.25-3.75 (m, 11H), 4.45-4.65 (m, 2H), 6.96 (d, J=5.1 Hz, 1H), 7.03 (s, 4H), 7.08 (d, J=5.1 Hz, 1H), 7.25 (d, J=7.5 Hz, 2H), 7.36 (d, J=7.5 Hz, 2H).

Example 40(45)

1-(1H-imidazol-2-yl)-N-(1H-imidazol-2-ylmethyl)-
N-(4-{[9-(1-oxidotetrahydro-2H-thiopyran-4-yl)-2,9-
diazaspiro[5.5]undec-2-yl]carbonyl}benzyl)metha-
namine Description: amorphous;
TLC: Rf 0.11 (dichrolomethane:methanol:28% aqueous ammonia=90:10:1);
NMR (CDCl$_3$): δ 1.20-2.70 (m, 18H), 2.90-3.78 (m, 13H), 7.04 (s, 4H), 7.29 (d, J=8.1 Hz, 2H), 7.39 (d, J=8.1 Hz, 2H).

Example 40(46)

1-(1H-imidazol-2-yl)-N-(1H-imidazol-2-ylmethyl)-
N-(4-{[9-(tetrahydro-2H-thiopyran-4-yl)-2,9-diaza-
spiro[5.5]undec-2-yl]carbonyl}benzyl)methanamine Description: amorphous;
TLC: Rf 0.21 (dichrolomethane:methanol:28% aqueous ammonia=90:10:1);
NMR (CDCl$_3$): δ 1.20-1.80 (m, 12H), 1.90 (m, 1H), 2.05-2.28 (m, 2H), 2.35 (m, 1H), 2.50-2.76 (m, 5H), 3.17 (m, 1H), 3.33 (m, 1H), 3.45-3.64 (m, 7H), 3.72 (m, 1H), 7.04 (s, 4H), 7.23-7.30 (m, 2H), 7.37 (d, J=7.8 Hz, 2H).

Example 40(47)

1-{4-[(8-isobutyl-2,8-diazaspiro[4.5]dec-2-yl)carbo-
nyl]phenyl}-N,N-bis[(1-methyl-1H-imidazol-2-yl)
methyl]methanamine Description: amorphous;
TLC: Rf 0.49 (ethyl acetate:methanol:28% aqueous ammonia=40:10:2);
NMR (CDCl$_3$): δ 0.85 (d, J=6.3 Hz, 3H), 0.90 (d, J=6.3 Hz, 3H), 1.43-1.85 (m, 7H), 1.94-2.58 (m, 6H), 3.21 (s, 1H), 3.32 (s, 6H), 3.40-3.52 (m, 2H), 3.62-3.75 (m, 7H), 6.80 (s, 2H), 6.94 (s, 2H), 7.22-7.30 (m, 2H), 7.39-7.48 (m, 2H).

Example 40(48)

1-{4-[(9-isobutyl-3,9-diazaspiro[5.5]undec-3-yl)carbonyl]phenyl}-N,N-bis[(1-methyl-1H-imidazol-2-yl)methyl]methanamine Description: amorphous;
TLC: Rf 0.49 (ethyl acetate:methanol:28% aqueous ammonia=40:10:2);
NMR (CDCl$_3$): δ 0.89 (d, J=6.3 Hz, 6H), 1.30-1.64 (m, 8H), 1.69-1.86 (m, 1H), 2.08 (d, J=7.2 Hz, 2H), 2.26-2.42 (m, 4H), 3.33 (s, 8H), 3.69 (s, 8H), 6.80 (s, 2H), 6.93 (s, 2H), 7.25 (d, J=8.1 Hz, 2H), 7.33 (d, J=8.1 Hz, 2H).

Example 40(49)

1-(4-{[9-(1-ethylpropyl)-1-oxa-4,9-diazaspiro[5.5]undec-4-yl]carbonyl}phenyl)-N,N-bis(1H-imidazol-2-ylmethyl)methanamine

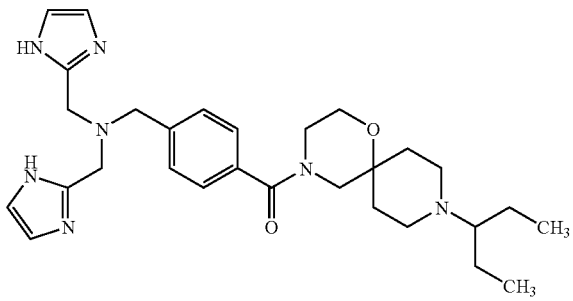

Description: amorphous;
TLC: Rf 0.26 (dichrolomethane:methanol:28% aqueous ammonia=90:10:1);
NMR (CDCl$_3$): δ 0.72-0.97 (m, 6H), 1.15-1.90 (m, 8H), 2.00-2.65 (m, 5H), 3.22 (m, 1H), 3.35-3.88 (m, 11H), 7.05 (s, 4H), 7.28 (d, J=8.1 Hz, 2H), 7.37 (d, J=8.1 Hz, 2H), 10.70-12.06 (m, 2H).

Example 40(50)

1-(4-{[9-(2-ethylbutyl)-1-oxa-4,9-diazaspiro[5.5]undec-4-yl]carbonyl}phenyl)-N,N-bis(1H-imidazol-2-ylmethyl)methanamine

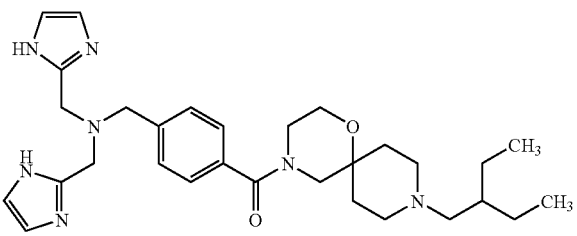

Description: amorphous;
TLC: Rf 0.28 (dichrolomethane:methanol:28% aqueous ammonia=90:10:1);
NMR (CDCl$_3$): δ 0.75-0.93 (m, 6H), 1.16-1.45 (m, 7H), 1.60-1.90 (m, 2H), 2.00-2.53 (m, 6H), 3.23 (m, 1H), 3.67-3.85 (m, 11H), 7.06 (s, 4H), 7.29 (d, J=7.8 Hz, 2H), 7.38 (d, J=7.8 Hz, 2H).

Example 40(51)

1-(4-{[9-(2,2-dimethylpropyl)-1-oxa-4,9-diazaspiro[5.5]undec-4-yl]carbonyl}phenyl)-N,N-bis(1H-imidazol-2-ylmethyl)methanamine Description: amorphous;
TLC: Rf 0.28 (dichrolomethane:methanol:28% aqueous ammonia=90:10:1);
NMR (CDCl$_3$): δ 0.73-0.95 (m, 9H), 1.24-1.45 (m, 2H), 1.40-1.90 (m, 2H), 1,94-2, 12 (m, 2H), 2.30-2.63 (m, 4H), 3.24 (m, 1H), 3.35-3.88 (m, 11H), 7.06 (s, 4H), 7.28 (d, J=8.1 Hz, 2H), 7.38 (d, J=8.1 Hz, 2H).

Example 40(52)

1-(1H-imidazol-2-yl)-N-(1H-imidazol-2-ylmethyl)-N-[4-({9-[(3-methoxy-2-thienyl)methyl]-1-oxa-4,9-diazaspiro[5.5]undec-4-yl}carbonyl)benzyl]methanamine Description: amorphous;
TLC: Rf 0.27 (dichrolomethane:methanol:28% aqueous ammonia=90:10:1);
NMR (CDCl$_3$): δ 1.24-1.46 (m, 2H), 1.63-1.94 (m, 2H), 2.22-2.69 (m, 4H), 3.21 (m, 1H), 3.32-3.86 (m, 16H), 6.08 (d, J=5.4 Hz, 1H), 7.06 (s, 4H), 7.10 (d, J=5.4 Hz, 1H), 7.27 (d, J=8.4 Hz, 2H), 7.37 (d, J=8.4 Hz, 2H).

Example 40(53)

(2-{[4-(4-{[bis(1H-imidazol-2-ylmethyl)amino]methyl}benzoyl)-1-oxa-4,9-diazaspiro[5.5]undec-9-yl]methyl}-3-thienyl)methanol Description: amorphous;
TLC: Rf 0.22 (dichrolomethane:methanol:28% aqueous ammonia=90:10:1);
NMR (CDCl$_3$): δ 1.08-1.30 (m, 2H), 1.80-1.95 (m, 2H), 2.25-2.70 (m, 4H), 3.17 (m, 1H), 3.35-3.85 (m, 13H), 4.55 (s, 2H), 6.96 (d, J=5.1 Hz, 1H), 7.05 (s, 4H), 7.09 (d, J=5.1 Hz, 1H), 7.26 (d, J=7.8 Hz, 2H), 7.37 (d, J=7.8 Hz, 2H).

Example 40(54)

1-{4-[(9-cycloheptyl-1-oxa-4,9-diazaspiro[5.5]undec-4-yl)carbonyl]phenyl}-N,N-bis(1H-imidazol-2-ylmethyl)methanamine Description: amorphous;
TLC: Rf 0.18 (dichrolomethane:methanol:28% aqueous ammonia=90:10:1);
NMR (CDCl$_3$): δ 1.20-1.93 (m, 16H), 2.34-2.65 (m, 5H), 3.20 (m, 1H), 3.33-3.85 (m, 11H), 7.06 (s, 4H), 7.28 (d, J=8.1 Hz, 2H), 7.37 (d, J=8.1 Hz, 2H), 10.82-11.81 (m, 2H).

Example 40(55)

1-{4-[(9-cyclopentyl-1-oxa-4,9-diazaspiro[5.5]undec-4-yl)carbonyl]phenyl}-N,N-bis(1H-imidazol-2-ylmethyl)methanamine Description: amorphous;
TLC: Rf 0.18 (dichrolomethane:methanol:28% aqueous ammonia=90:10:1);
NMR (CDCl$_3$): δ 1.22-1.98 (m, 12H), 2.26 (m, 1H), 3.22 (m, 1H), 3.35-3.88 (m, 11H), 7.06 (s, 4H), 7.29 (d, J=8.1 Hz, 2H), 7.38 (d, J=8.1 Hz, 2H).

Example 40(56)

1-(1H-imidazol-2-yl)-N-(1H-imidazol-2-ylmethyl)-N-(4-{[9-(tetrahydro-2H-pyran-4-yl)-1-oxa-4,9-diazaspiro[5.5]undec-4-yl]carbonyl}benzyl)methanamine Description: amorphous;
TLC: Rf 0.18 (dichrolomethane:methanol:28% aqueous ammonia=90:10:1);
NMR (CDCl$_3$): δ 1.20-1.95 (m, 8H), 2.33-2.65 (m, 5H), 3.15-3.85 (m, 14H), 3.92-4.06 (m, 2H), 7.05 (s, 4H), 7.28 (d, J=8.1 Hz, 2H), 7.37 (d, J=8.1 Hz, 2H).

Example 40(57)

1-(4-{[9-(cyclohexylmethyl)-1-oxa-4,9-diazaspiro[5.5]undec-4-yl]carbonyl}phenyl)-N,N-bis(1H-imidazol-2-ylmethyl)methanamine Description: amorphous;
TLC: Rf 0.20 (dichrolomethane:methanol:28% aqueous ammonia=90:10:1);
NMR (CDCl$_3$): δ 0.72-0.94 (m, 2H), 1.05-1.90 (m, 13H), 1.98-2.52 (m, 6H), 3.22 (m, 1H), 3.30-3.85 (m, 11H), 7.05 (s, 4H), 7.27 (d, J=7.8 Hz, 2H), 7.36 (d, J=7.8 Hz, 2H).

Example 40(58)

1-{4-[(9-isobutyl-1-oxa-4,9-diazaspiro[5.5]undec-4-yl)carbonyl]phenyl}-N,N-bis[(1-methyl-1H-imidazol-2-yl)methyl]methanamine Description: amorphous;
TLC: Rf 0.59 (ethyl acetate:methanol:28% aqueous ammonia=40:10:2);
NMR (CDCl$_3$): δ 0.86 (s, 6H), 1.16-1.93 (m, 5H), 1.95-2.54 (m, 6H), 3.05-3.87 (m, 6H), 3.34 (s, 6H), 3.69 (s, 6H), 6.80 (d, J=1.2 Hz, 2H), 6.94 (d, J=1.2 Hz, 2H), 7.22-7.38 (m, 4H).

Example 40(59)

1-{4-[2-(8-cyclohexyl-2,8-diazaspiro[4.5]dec-2-yl)-2-oxoethyl]phenyl}-N,N-bis(1H-imidazol-2-ylmethyl)methanamine TLC: Rf 0.38 (dichrolomethane:methanol:28% aqueous ammonia=9:1:0.1);
NMR (CDCl$_3$): δ 0.98-1.32 (m, 6H), 1.40-1.97 (m, 10H), 2.13-2.67 (m, 5H), 3.24-3.66 (m, 12H), 7.02 (s, 4H), 7.11-7.18 (m, 2H), 7.22-7.30 (m, 2H), 10.84-12.01 (m, 2H).

Example 40(60)

1-(1H-imidazol-2-yl)-N-(1H-imidazol-2-ylmethyl)-N-{4-[2-(8-isobutyl-2,8-diazaspiro[4.5]dec-2-yl)-2-oxoethyl]benzyl}methanamine

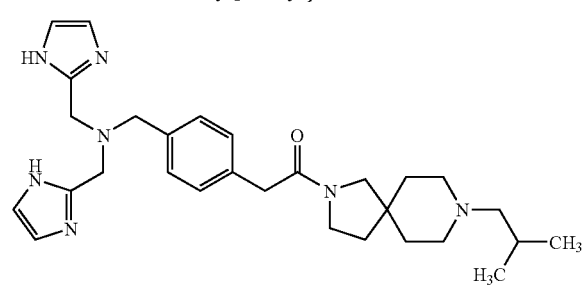

TLC: Rf 0.43 (dichrolomethane:methanol:28% aqueous ammonia=9:1:0.1);
NMR (CDCl$_3$): δ 0.83-0.91 (m, 6H), 1.48-1.86 (m, 7H), 2.01-2.07 (m, 2H), 2.11-2.51 (m, 4H), 3.25-3.66 (m, 12H), 7.02 (s, 4H), 7.11-7.19 (m, 2H), 7.23-7.31 (m, 2H), 10.60-12.03 (m, 2H).

Example 40(61)

1-(4-{[7-(1-ethylpropyl)-2,7-diazaspiro[3.5]non-2-yl]carbonyl}phenyl)-N,N-bis(1H-imidazol-2-ylmethyl)methanamine TLC: Rf 0.20 (dichrolomethane:methanol:28% aqueous ammonia=9:1:0.1);
NMR (CDCl$_3$): δ 0.87 (t, J=7.5 Hz, 6H), 1.19-1.50 (m, 4H), 1.68-1.82 (m, 4H), 2.13 (m, 1H), 2.32-2.50 (m, 4H), 3.59 (s, 4H), 3.62 (s, 2H), 3.87 (s, 2H), 3.96 (s, 2H), 7.02 (s, 4H), 7.39 (d, J=8.1 Hz, 2H), 7.55 (d, J=8.1 Hz, 2H).

Example 40(62)

1-(4-{[7-(2,2-dimethylpropyl)-2,7-diazaspiro[3.5]non-2-yl]carbonyl}phenyl)-N,N-bis(1H-imidazol-2-ylmethyl)methanamine TLC: Rf 0.20 (dichrolomethane:methanol:28% aqueous ammonia=9:1:0.1);
NMR (CDCl$_3$): δ 0.84 (s, 9H), 1.68-1.85 (m, 4H), 2.00 (s, 2H), 2.32-2.52 (m, 4H), 3.59 (s, 4H), 3.63 (s, 2H), 3.87 (s, 2H), 3.96 (s, 2H), 7.03 (s, 4H), 7.40 (d, J=8.1 Hz, 2H), 7.55 (d, J=8.1 Hz, 2H).

Example 40(63)

1-(4-{[2-(2,2-dimethylpropyl)-2,7-diazaspiro[3.5]non-7-yl]carbonyl}phenyl)-N,N-bis(1H-imidazol-2-ylmethyl)methanamine TLC: Rf 0.19 (dichrolomethane:methanol:28% aqueous ammonia=9:1:0.1);
NMR (CDCl$_3$): δ 0.85 (s, 9H), 1.60-1.92 (m, 4H), 2.21 (s, 2H), 3.07 (s, 4H), 3.22-3.40 (m, 2H), 3.54 (s, 4H), 3.58 (s, 2H), 3.62-3.78 (m, 2H), 7.01 (s, 4H), 7.25 (d, J=8.1 Hz, 2H), 7.33 (d, J=8.1 Hz, 2H).

Example 40(64)

1-(4-{[9-(1-ethylpropyl)-3,9-diazaspiro[5.5]undec-3-yl]carbonyl}phenyl)-N,N-bis(H-imidazol-2-ylmethyl)methanamine TLC: Rf 0.26 (dichrolomethane:methanol:28% aqueous ammonia=9:1:0.1);
NMR (CDCl$_3$): δ 0.89 (t, J=7.5 Hz, 6H), 1.21-1.63 (m, 12H), 2.13 (m, 1H), 2.40-2.52 (m, 4H), 3.30-3.40 (m, 2H), 3.54 (s, 4H), 3.58 (s, 2H), 3.65-3.80 (m, 2H), 7.01 (s, 4H), 7.26 (d, J=8.1 Hz, 2H), 7.33 (d, J=8.1 Hz, 2H).

Example 40(65)

1-{3-[(8-cyclohexyl-2,8-diazaspiro[4.5]dec-2-yl)carbonyl]phenyl}-N,N-bis(1H-imidazol-2-ylmethyl)methanamine TLC: Rf 0.41 (dichrolomethane:methanol:28% aqueous ammonia=9:1:0.1);
NMR (CDCl$_3$): δ 0.97-1.34 (m, 6H), 1.44-1.92 (m, 10H), 2.15-2.73 (m, 5H), 3.24-3.76 (m, 10H), 7.03 (s, 4H), 7.28-7.43 (m, 3H), 7.66-7.72 (m, 1H).

Example 40(66)

1-(1H-imidazol-2-yl)-N-(1H-imidazol-2-ylmethyl)-N-{3-[(8-isobutyl-2,8-diazaspiro[4.5]dec-2-yl)carbonyl]benzyl}methanamine TLC: Rf 0.46 (dichrolomethane:methanol:28% aqueous ammonia=9:1:0.1);
NMR (CDCl$_3$): δ 0.85 (d, J=6.6 Hz, 3H), 0.90 (d, J=6.6 Hz, 3H), 1.47-1.88 (m, 7H), 1.97-2.56 (m, 6H), 3.25-3.75 (m, 10H), 7.03 (s, 4H), 7.28-7.42 (m, 3H), 7.66-7.72 (m, 1H).

Example 40(67)

1-(4-{[9-(2,2-dimethylpropyl)-3,9-diazaspiro[5.5]undec-3-yl]carbonyl}phenyl)-N,N-bis(1H-imidazol-2-ylmethyl)methanamine TLC: Rf 0.26 (dichrolomethane:methanol:28% aqueous ammonia=9:1:0.1);
NMR (CDCl$_3$): δ 0.85 (s, 9H), 1.35-1.64 (m, 8H), 2.03 (s, 2H), 2.40-2.52 (m, 4H), 3.30-3.40 (m, 2H), 3.54 (s, 4H), 3.57 (s, 2H), 3.65-3.80 (m, 2H), 7.00 (s, 4H), 7.26 (d, J=8.1 Hz, 2H), 7.32 (d, J=8.1 Hz, 2H).

Example 40(68)

1-(4-{2-[8-(2,2-dimethylpropyl)-2,8-diazaspiro[4.5]dec-2-yl]-2-oxoethyl}phenyl)-N,N-bis(1H-imidazol-2-ylmethyl)methanamine TLC: Rf 0.35 (dichrolomethane:methanol:28% aqueous ammonia=9:1:0.1);
NMR (CDCl$_3$): δ 0.79-0.90 (m, 9H), 1.43-1.60 (m, 4H), 1.67-1.83 (m, 2H), 1.97-2.03 (m, 2H), 2.26-2.58 (m, 4H), 3.25-3.66 (m, 12H), 7.03 (s, 4H), 7.11-7.19 (m, 2H), 7.21-7.31 (m, 2H).

Example 40(69)

1-(1H-imidazol-2-yl)-N-(1H-imidazol-2-ylmethyl)-N-{4-[2-(8-isobutyl-2,8-diazaspiro[4.5]dec-2-yl)-1,1-dimethyl-2-oxoethyl]benzyl}methanamine TLC: Rf 0.20 (dichrolomethane:methanol:28% aqueous ammonia=9:1:0.1);
NMR (CDCl$_3$): δ 0.75-0.90 (m, 6H), 0.96-1.84 (m, 13H), 1.90-2.42 (m, 6H), 2.59-3.59 (m, 4H), 3.59-3.69 (m, 6H), 7.03-7.10 (m, 4H), 7.16-7.41 (m, 4H).

Example 40(70)

1-(4-{2-[8-(1-ethylpropyl)-2,8-diazaspiro[4.5]dec-2-yl]-2-oxoethyl}phenyl)-N,N-bis(1H-imidazol-2-ylmethyl)methanamine

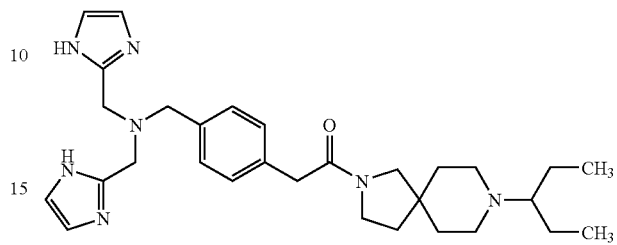

TLC: Rf 0.25 (dichrolomethane:methanol:28% aqueous ammonia=9:1:0.1);
NMR (CDCl$_3$): δ 0.88 (t, J=7.4 Hz, 6H), 1.18-1.57 (m, 8H), 1.66-1.84 (m, 2H), 2.06-2.19 (m, 1H), 2.26-2.57 (m, 4H), 3.26-3.35 (m, 2H), 3.48-3.57 (m, 2H), 3.59 (s, 6H), 3.62 (s, 2H), 7.02 (s, 4H), 7.11-7.20 (m, 2H), 7.23-7.31 (m, 2H).

Example 40(71)

2-{4-[(8-cyclohexyl-2,8-diazaspiro[4.5]dec-2-yl)carbonyl]phenyl}-N,N-bis(1H-imidazol-2-ylmethyl)ethanamine

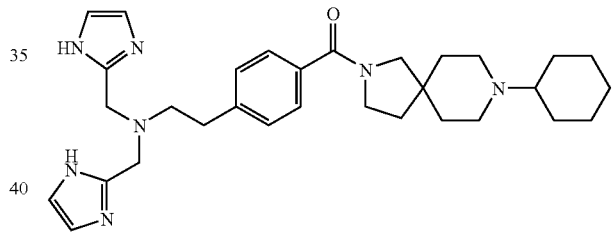

TLC: Rf 0.19 (dichrolomethane:methanol:28% aqueous ammonia=9:1:0.1);
NMR (CDCl$_3$): δ 0.97-1.35 (m, 6H), 1.46-2.00 (m, 10H), 2.12-2.90 (m, 9H), 3.20-3.75 (m, 8H), 7.01 (s, 4H), 7.11-7.19 (m, 2H), 7.33-7.41 (m, 2H).

Example 40(72)

1-(4-{[8-(1-ethylpropyl)-2,8-diazaspiro[4.5]dec-2-yl]carbonyl}phenyl)-N-(1H-imidazol-2-ylmethyl)-N-[(1-methyl-1H-imidazol-2-yl)methyl]methanamine

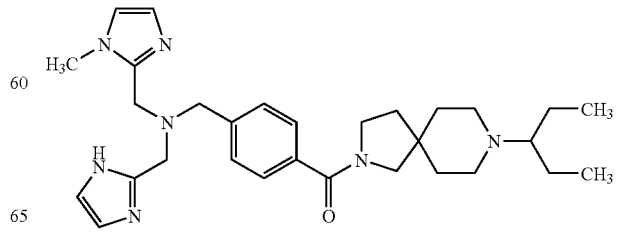

TLC: Rf 0.29 (dichrolomethane:methanol:28% aqueous ammonia=9:1:0.1);

NMR (CDCl₃): δ 0.80-0.96 (m, 6H), 1.18-1.82 (m, 10H), 2.13 (m, 1H), 2.26-2.60 (m, 4H), 3.21-3.74 (m, 13H), 6.88 (m, 1H), 7.01 (m, 1H), 7.08 (m, 1H), 7.13 (m, 1H), 7.40-7.51 (m, 4H).

Example 40(73)

1-(4-{[8-(2,2-dimethylpropyl)-2,8-diazaspiro[4.5]dec-2-yl]carbonyl}phenyl)-N-(1H-imidazol-2-ylmethyl)-N-[(1-methyl-1H-imidazol-2-yl)methyl]methanamine TLC: Rf 0.30 (dichrolomethane:methanol:28% aqueous ammonia=9:1:0.1);

NMR (CDCl₃): δ 0.80-0.88 (m, 9H), 1.48-1.85 (m, 6H), 1.97-2.07 (m, 2H), 2.27-2.60 (m, 4H), 3.22-3.73 (m, 13H), 6.89 (s, 1H), 7.00 (s, 1H), 7.07 (m, 1H), 7.13 (m, 1H), 7.40-7.50 (m, 4H).

Example 40(74)

1-(4-{[9-(2,2-dimethylpropyl)-1-oxa-4,9-diazaspiro[5.5]undec-4-yl]carbonyl}phenyl)-N-(1H-imidazol-2-ylmethyl)-N-[(1-methyl-1H-imidazol-2-yl)methyl]methanamine TLC: Rf 0.29 (dichrolomethane:methanol:28% aqueous ammonia=9:1:0.1);

NMR (CDCl₃): δ 0.72-0.92 (m, 9H), 1.60-1.85 (m, 4H), 1.90-2.10 (m, 2H), 2.27-2.62 (m, 4H), 3.15-3.85 (m, 15H), 6.89 (m, 1H), 7.01 (m, 1H), 7.08 (m, 1H), 7.13 (m, 1H), 7.36 (d, J=8.1 Hz, 2H), 7.48 (d, J=8.1 Hz, 2H).

Example 40(75)

1-(4-{[9-(1-ethylpropyl)-1-oxa-4,9-diazaspiro[5.5]undec-4-yl]carbonyl}phenyl)-N-(1H-imidazol-2-ylmethyl)-N-[(1-methyl-1H-imidazol-2-yl)methyl]methanamine

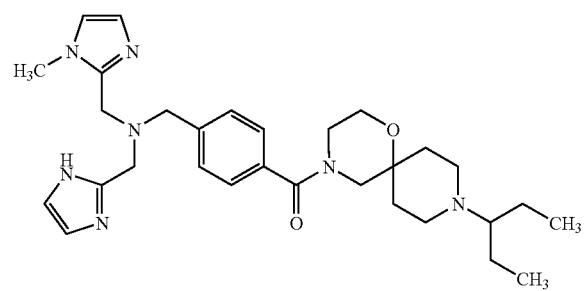

TLC: Rf 0.29 (dichrolomethane:methanol:28% aqueous ammonia=9:1:0.1);

NMR (CDCl₃): δ 0.72-0.95 (m, 6H), 1.15-1.85 (m, 8H), 2.10 (m, 1H), 2.22-2.62 (m, 4H), 3.15-3.85 (m, 15H), 6.89 (m, 1H), 7.01 (m, 1H), 7.08 (m, 1H), 7.13 (m, 1H), 7.36 (d, J=8.1 Hz, 2H), 7.48 (d, J=8.1 Hz, 2H).

Example 40(76)

1-{4-[(8-cyclohexyl-2,8-diazaspiro[4.5]dec-2-yl)carbonyl]phenyl}-N-(1H-imidazol-2-ylmethyl)-N-[(1-isobutyl-1H-imidazol-2-yl)methyl]methanamine TLC: Rf 0.42 (chloroform:methanol:28% aqueous ammonia=9:1:0.1);

NMR (CDCl₃): δ 0.84 (d, J=6.6 Hz, 6H), 0.91-1.38 (m, 6H), 1.38-2.86 (m, 16H), 3.20-3.32 (m, 1H), 3.36-3.54 (m, 5H), 3.57-3.74 (m, 6H), 6.83-6.94 (m, 1H), 6.98-7.05 (m, 1H), 7.05-7.18 (m, 2H), 7.34-7.60 (m, 4H).

Example 40(77)

1-(1H-imidazol-2-yl)-N-{4-[(8-isobutyl-2,8-diazaspiro[4.5]dec-2-yl)carbonyl]benzyl}-N-[(1-isobutyl-1H-imidazol-2-yl)methyl]methanamine TLC: Rf 0.35 (chloroform:methanol:28% aqueous ammonia=9:1:0.1);

NMR (CDCl₃): δ 0.72-0.99 (m, 12H), 1.29-2.68 (m, 14H), 2.92-3.32 (m, 1H), 3.37-3.57 (m, 5H), 3.57-3.82 (m, 6H), 6.85-6.93 (m, 1H), 6.97-7.07 (m, 1H), 7.10 (s, 2H), 7.33-7.56 (m, 4H).

Example 40(78)

1-(4-{[8-(1-ethylpropyl)-2,8-diazaspiro[4.5]dec-2-yl]carbonyl}phenyl)-N-(1H-imidazol-2-ylmethyl)-N-[(1-isobutyl-1H-imidazol-2-yl)methyl]methanamine

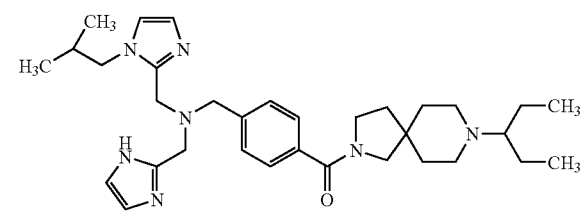

TLC: Rf 0.37 (chloroform:methanol:28% aqueous ammonia=9:1:0.1);

NMR (CDCl₃): δ 0.73-1.04 (m, 12H), 1.09-2.72 (m, 16H), 3.05-3.28 (m, 1H), 3.33-3.55 (m, 5H), 3.57-3.88 (m, 6H), 6.84-6.93 (m, 1H), 6.98-7.06 (m, 1H), 7.10 (s, 2H), 7.34-7.60 (m, 4H).

Example 40(79)

1-(4-{[8-(2,2-dimethylpropyl)-2,8-diazaspiro[4.5]dec-2-yl]carbonyl}phenyl)-N-(1H-imidazol-2-ylmethyl)-N-[(1-isobutyl-1H-imidazol-2-yl)methyl]methanamine TLC: Rf 0.50 (chloroform:methanol:28% aqueous ammonia=9:1:0.1);

NMR (CDCl₃): δ 0.65-0.97 (m, 15H), 1.29-1.89 (m, 6H), 1.89-2.17 (m, 3H), 2.20-2.68 (m, 4H), 3.17-3.32 (m, 1H), 3.34-3.55 (m, 5H), 3.57-3.82 (m, 6H), 6.85-6.93 (m, 1H), 6.98-7.06 (m, 1H), 7.11 (s, 2H), 7.36-7.52 (m, 4H).

Examples 41 (1) to Example 41(3)

The same operation as in Example 4→Example 2→Example 5 was performed, except for using a corresponding amine in place of the compound obtained in Example 3 in Example 19, and a corresponding amine in place of benzylamine in Example 2, to obtain the following compound.

Example 41 (1)

1-(1H-imidazol-2-yl)-N-(1H-imidazol-2-ylmethyl)-N-{4-[(8-isobutyl-2,8-diazaspiro[4.5]dec-2-yl)sulfonyl]benzyl}methanamine Description: amorphous;
TLC: Rf 0.35 (dichrolomethane:methanol:28% aqueous ammonia=90:10:1);
NMR (CDCl$_3$): δ 0.84 (d, J=6.6 Hz, 6H), 1.24-1.45 (m, 4H), 1.63 (t, J=7.2 Hz, 2H), 1.63-1.78 (m, 1H), 1.99 (d, J=7.2 Hz, 2H), 2.02-2.37 (m, 4H), 3.08 (s, 2H), 3.28 (t, J=7.2 Hz, 2H), 3.58 (s, 4H), 3.73 (s, 2H), 7.09 (s, 4H), 7.56 (d, J=8.1 Hz, 2H), 7.77 (d, J=8.1 Hz, 2H).

Example 41(2)

1-(1H-imidazol-2-yl)-N-(1H-imidazol-2-ylmethyl)-N-[4-({8-[(3-methyl-2-thienyl)methyl]-2,8-diazaspiro[4.5]dec-2-yl}sulfonyl)benzyl]methanamine Description: amorphous;
TLC: Rf 0.36 (dichrolomethane:methanol:28% aqueous ammonia=90:10:1);
NMR (CDCl$_3$): δ 1.27-1.46 (m, 4H), 1.63 (t, J=7.2 Hz, 2H), 2.12-2.49 (m, 4H), 2.15 (s, 3H), 3.08 (s, 2H), 3.28 (t, J=7.2 Hz, 2H), 3.54 (s, 2H), 3.57 (s, 4H), 3.72 (s, 2H), 6.76 (d, J=5.1 Hz, 1H), 7.09 (s, 4H), 7.10 (d, J=5.1 Hz, 1H), 7.56 (d, J=8.4 Hz, 2H), 7.76 (d, J=8.4 Hz, 2H).

Example 41(3)

1-{4-[(8-cyclohexyl-2,8-diazaspiro[4.5]dec-2-yl)sulfonyl]phenyl}-N,N-bis(1H-imidazol-2-ylmethyl)methanamine Description: amorphous;
TLC: Rf 0.24 (dichrolomethane:methanol:28% aqueous ammonia=90:10:1);
NMR (CDCl$_3$): δ 1.00-1.43 (m, 10H), 1.62 (t, J=7.2 Hz, 2H), 1.68-1.84 (m, 4H), 2.12-2.57 (m, 5H), 3.08 (s, 2H), 3.28 (t, J=7.2 Hz, 2H), 3.59 (s, 4H), 3.74 (s, 2H), 7.10 (s, 4H), 7.58 (d, J=8.7 Hz, 2H), 7.78 (d, J=8.7 Hz, 2H), 10.43-11.18 (m, 2H).

Example 42 tert-butyl 2-[4-(methoxycarbonyl)benzyl]-3-oxo-2,8-diazaspiro[4.5]decane-8-carboxylate Under an argon atmosphere, to an N,N-dimethylformamide (2 mL) solution of sodium hydride (60%, 94 mg), an N,N-dimethylformamide (4 mL) solution of tert-butyl 3-oxo-2,8-diazaspiro[4.5]decane-8-carboxylate (514 mg) was added at 0° C. The reaction solution was stirred at 50° C. for one hour. The solution was cooled to 0° C. and then an N,N-dimethylformamide (2 mL) solution of methyl 4-(bromomethyl)benzoate (442 mg) was added. The reaction solution was stirred at 0° C. for 30 minutes. To the reaction solution, 0.5N-hydrochloric acid (20 mL) was added. The aqueous layer was extracted twice with ethyl acetate. The aqueous layer was combined with the organic layer, washed in turn with water and saturated brine, and then dried over anhydrous magnesium sulfate. After removing the anhydrous magnesium sulfate by filtration, the filtrate was concentrated under reduced pressure. The residue was purified by silica gel chromatography (n-hexane:ethyl acetate=1:0→1:2) to obtain the title compound (553 mg) having the following physical properties.

Description: amorphous;
TLC: Rf 0.51 (n-hexane:ethyl acetate=2:1);
NMR (CDCl$_3$): δ 7.99 (d, J=8.7 Hz, 2H), 7.28 (d, J=8.7 Hz, 2H), 4.49 (m, 2H), 3.91 (s, 3H), 3.42 (m, 2H), 3.27 (m, 2H), 3.03 (s, 2H), 2.37 (s, 2H), 1.51 (m, 4H), 1.43 (s, 9H).

Example 43 tert-butyl 2-[4-(hydroxymethyl)benzyl]-3-oxo-2,8-diazaspiro[4.5]decane-8-carboxylate Under an argon atmosphere, to an anhydrous tetrahydrofuran (3 mL) solution of the compound (453 mg) obtained by the previous reaction, lithium borohydride (26 mg) was added. The reaction solution was stirred at 50° C. for 3 hours. The reaction solution was cooled to room temperature and an aqueous 0.5N-sodium hydroxide solution (10 mL) was added. The aqueous layer was extracted twice with ethyl acetate. The combined organic layer was washed with saturated brine and then dried over anhydrous magnesium sulfate. After removing the anhydrous magnesium sulfate by filtration, the filtrate was concentrated under reduced pressure. The residue was purified by silica gel chromatography (n-hexane:ethyl acetate=1:0→1:4) to obtain the title compound (365 mg) having the following physical properties.

TLC: Rf 0.18 (n-hexane:ethyl acetate=4:1);
NMR (CDCl$_3$): δ 7.33 (d, J=8.1 Hz, 2H), 7.21 (d, J=8.1 Hz, 2H), 4.68 (d, J=5.7 Hz, 2H), 4.43 (s, 2H), 3.44 (m, 2H), 3.23 (m, 2H), 3.03 (s, 2H), 2.36 (s, 2H), 1.51 (m, 4H), 1.43 (s, 9H).

Example 44 tert-butyl 2-(4-formylbenzyl)-3-oxo-2,8-diazaspiro[4.5]decane-8-carboxylate

To a dimethyl sulfoxide (7.5 mL)-ethyl acetate (1.5 mL) solution of the compound (332 mg) obtained in Example 43 and triethylamine (1.85 mL), a dimethyl sulfoxide (1.5 mL) solution of a sulfur trioxide-pyridine complex (430 mg) was added. The reaction solution was stirred at room temperature for 30 minutes. To the reaction solution, water (30 mL) was added. The aqueous layer was extracted twice with ethyl acetate. The aqueous layer was combined with the organic layer, washed in turn with water, 0.5N-hydrochloric acid, an aqueous saturated sodium hydrogen carbonate solution and saturated brine, and then dried over anhydrous magnesium sulfate. After removing the anhydrous magnesium sulfate by filtration, the filtrate was concentrated under reduced pressure. The residue was purified by silica gel chromatography (n-hexane:ethyl acetate=1:0→0:1) to obtain the title compound (335 mg) having the following physical properties.

TLC: Rf 0.38 (ethyl acetate);
NMR (CDCl$_3$): δ 10.01 (s, 1H), 7.87 (d, J=8.1 Hz, 2H), 7.40 (d, J=8.1 Hz, 2H), 4.53 (s, 2H), 3.46 (m, 2H), 3.25 (m, 2H), 3.07 (s, 2H), 2.39 (s, 2H), 1.51 (m, 4H), 1.44 (s, 9H).

Example 45 tert-butyl 2-(4-{[bis({1-[(dimethylamino)sulfonyl]-1H-imidazol-2-yl}methyl)amino]methyl}benzyl)-3-oxo-2,8-diazaspiro[4.5]decane-8-carboxylate With the compound (330 mg) produced in Example 44 and the compound (525 mg) produced in Example 3, the same operation as in Example 2 was performed to obtain the title compound (486 mg) having the following physical properties.
Description: amorphous;
TLC: Rf 0.19 (ethyl acetate:methanol=9:1);
NMR (CDCl₃): δ 7.31 (d, J=8.1 Hz, 2H), 7.23 (d, J=1.5 Hz, 2H), 7.13 (d, J=8.1 Hz, 2H), 6.99 (d, J=1.5 Hz, 2H), 4.41 (s, 2H), 4.16 (s, 4H), 4.06 (s, 2H), 3.44 (m, 2H), 3.25 (m, 2H), 3.02 (s, 2H), 2.81 (s, 12H), 2.35 (s, 2H), 1.52 (m, 4H), 1.44 (s, 9H).

Example 46

2-(4-{[bis(1H-imidazol-2-ylmethyl)amino]methyl}benzyl)-2,8-diazaspiro[4.5]decan-3-one A 2N-hydrochloric acid (5 mL) solution of the compound (480 mg) obtained in Example 45 was stirred at 80° C. for 3 hours. After the reaction solution was cooled to room temperature, the pH was adjusted to 12 with an aqueous 2N-sodium hydroxide solution. The aqueous layer was extracted four times with dichloromethane. The combined organic layer was washed with saturated brine and then dried over anhydrous magnesium sulfate. After removing the anhydrous magnesium sulfate by filtration, the filtrate was concentrated under reduced pressure. The residue was purified by silica gel chromatography (ethyl acetate:10%-saturated aqueous ammonia-methanol=1:0→7:3) to obtain the title compound (277 mg) having the following physical properties.
Description: amorphous;
TLC: Rf 0.32 (dichrolomethane:methanol:28% aqueous ammonia=70:30:3);
NMR (CDCl₃): δ 7.35 (d, J=8.1 Hz, 2H), 7.15 (d, J=8.1 Hz, 2H), 7.05 (s, 4H), 4.42 (s, 2H), 3.63 (s, 2H), 3.60 (s, 4H), 3.07 (s, 2H), 2.77 (t, J=5.1 Hz, 4H), 2.37 (s, 2H), 1.52 (m, 4H).

Example 47

2-(4-{[bis(1H-imidazol-2-ylmethyl)amino]methyl}benzyl)-8-isobutyl-2,8-diazaspiro[4.5]decan-3-one With the compound (50 mg) produced in Example 46 and isobutyl aldehyde (47 mg), the same operation as in Example 2 was performed to obtain the title compound (29 mg, 51%) having the following physical properties.

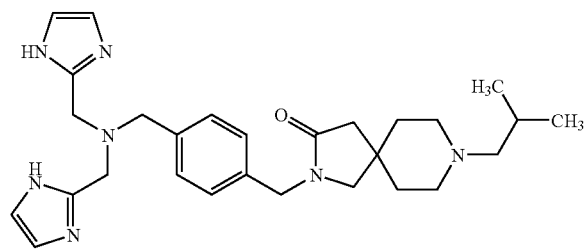

Description: amorphous;
TLC: Rf 0.30 (dichrolomethane:methanol:28% aqueous ammonia=90:10:1);
NMR (CDCl₃): δ 0.86 (d, J=6.6 Hz, 6H), 1.54-1.64 (m, 4H), 1.65-1.82 (m, 1H), 2.02 (d, J=7.2 Hz, 2H), 2.20-2.35 (m, 4H), 2.34 (s, 2H), 3.05 (s, 2H), 3.60 (s, 4H), 3.65 (s, 2H), 4.42 (s, 2H), 7.07 (s, 4H), 7.16 (d, J=8.1 Hz, 2H), 7.35 (d, J=8.1 Hz, 2H).

Example 48(1) to Example 48(14)

Except for using the corresponding carbonyl in Example 47 in place of isobutyl aldehyde, the same operation as in Example 47 was performed to obtain the following compound.

Example 48(1)

2-(4-{[bis(1H-imidazol-2-ylmethyl)amino]methyl}benzyl)-8-cyclohexyl-2,8-diazaspiro[4.5]decan-3-one Description: amorphous;
TLC: Rf 0.27 (dichrolomethane:methanol:28% aqueous ammonia=90:10:1);
NMR (CDCl₃): δ 1.00-1.33 (m, 6H), 1.54-1.68 (m, 4H), 1.70-1.88 (m, 4H), 2.17-2.31 (m, 1H), 2.33 (s, 2H), 2.38-2.59 (m, 4H), 3.05 (s, 2H), 3.60 (s, 4H), 3.63 (s, 2H), 4.42 (s, 2H), 7.05 (s, 4H), 7.14 (d, J=8.1 Hz, 2H), 7.34 (d, J=8.1 Hz, 2H).

Example 48(2)

2-(4-{[bis(1H-imidazol-2-ylmethyl)amino]methyl}benzyl)-8-[(3-methyl-2-thienyl)methyl]-2,8-diazaspiro[4.5]decan-3-one Description: amorphous;
TLC: Rf 0.38 (dichrolomethane:methanol:28% aqueous ammonia=90:10:1);
NMR (CDCl₃): δ 1.55-1.66 (m, 4H), 2.16 (s, 3H), 2.26-2.51 (m, 4H), 2.34 (s, 2H), 3.05 (s, 2H), 3.57 (s, 2H), 3.59 (s, 4H), 3.63 (s, 2H), 4.42 (s, 2H), 6.77 (d, J=5.1 Hz, 1H), 7.06 (s, 4H), 7.11 (d, J=5.1 Hz, 1H), 7.15 (d, J=8.1 Hz, 2H), 7.34 (d, J=8.1 Hz, 2H).

Example 48(3)

2-(4-{[bis(1H-imidazol-2-ylmethyl)amino]methyl}benzyl)-8-(2,2-dimethylpropyl)-2,8-diazaspiro[4.5]decan-3-one TLC: Rf 0.34 (dichrolomethane:methanol:28% aqueous ammonia=9:1:0.1);
NMR (CDCl₃): δ 0.82 (s, 9H), 1.50-1.61 (m, 4H), 1.99 (s, 2H), 2.33 (s, 2H), 2.36-2.46 (m, 4H), 3.05 (s, 2H), 3.59 (s, 4H), 3.63 (s, 2H), 4.41 (s, 2H), 7.05 (s, 4H), 7.13 (d, J=8.2 Hz, 2H), 7.33 (d, J=8.2 Hz, 2H).

Example 48(4)

2-(4-{[bis(1H-imidazol-2-ylmethyl)amino]methyl}benzyl)-8-(1-ethylpropyl)-2,8-diazaspiro[4.5]decan-3-one

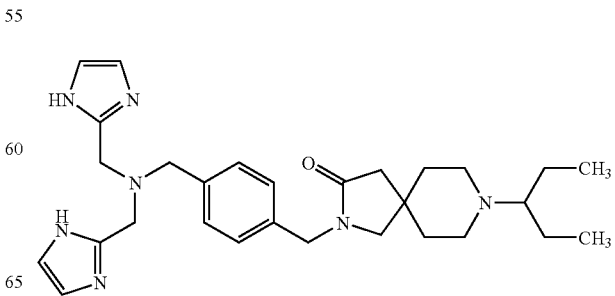

TLC: Rf 0.16 (dichrolomethane:methanol:28% aqueous ammonia=9:1:0.1);
NMR (CDCl$_3$): δ 0.86 (t, J=7.4 Hz, 6H), 1.16-1.49 (m, 4H), 1.49-1.65 (m, 4H), 2.05-2.17 (m, 1H), 2.33 (s, 2H), 2.36-2.47 (m, 4H), 3.05 (s, 2H), 3.59 (s, 4H), 3.62 (s, 2H), 4.41 (s, 2H), 7.05 (s, 4H), 7.13 (d, J=8.1 Hz, 2H), 7.33 (d, J=8.1 Hz, 2H).

Example 48(5)

2-(4-{[bis(1H-imidazol-2-ylmethyl)amino]methyl}benzyl)-8-cyclohexyl-2,8-diazaspiro[4.5]decan-1-one TLC: Rf 0.28 (dichrolomethane:methanol:28% aqueous ammonia=9:1:0.1);
NMR (CDCl$_3$): δ 1.01-2.10 (m, 16H), 2.20-2.41 (m, 3H), 2.83-2.96 (m, 2H), 3.13-3.22 (m, 2H), 3.58 (s, 4H), 3.61 (s, 2H), 4.41 (s, 2H), 7.06 (s, 4H), 7.09 (d, J=8.1 Hz, 2H), 7.29 (d, J=8.1 Hz, 2H).

Example 48(6)

2-(4-{[bis(1H-imidazol-2-ylmethyl)amino]methyl}benzyl)-8-isobutyl-2,8-diazaspiro[4.5]decan-1-one TLC: Rf 0.33 (dichrolomethane:methanol:28% aqueous ammonia=9:1:0.1);
NMR (CDCl$_3$): δ 0.90 (d, J=6.6 Hz, 6H), 1.35-1.47 (m, 2H), 1.70-1.86 (m, 1H), 1.86-2.13 (m, 8H), 2.76-2.86 (m, 2H), 3.14-3.22 (m, 2H), 3.59 (s, 4H), 3.60 (s, 2H), 4.42 (s, 2H), 7.06 (s, 4H), 7.09 (d, J=8.1 Hz, 2H), 7.31 (d, J=8.1 Hz, 2H).

Example 48(7)

2-(4-{[bis(1H-imidazol-2-ylmethyl)amino]methyl}benzyl)-8-(2,2-dimethylpropyl)-2,8-diazaspiro[4.5]decan-1-one

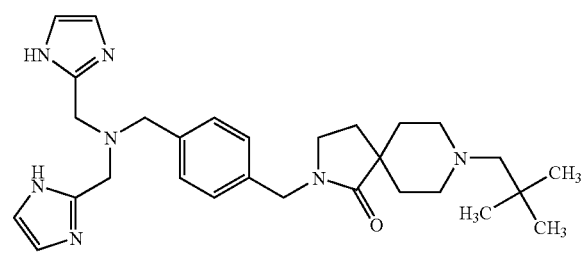

TLC: Rf 0.42 (dichrolomethane:methanol:28% aqueous ammonia=9:1:0.1);
NMR (CDCl$_3$): δ 0.87 (s, 9H), 1.29-1.40 (m, 2H), 1.87-1.97 (m, 2H), 1.98-2.13 (m, 4H), 2.20-2.35 (m, 2H), 2.72-2.84 (m, 2H), 3.12-3.22 (m, 2H), 3.60 (s, 4H), 3.61 (s, 2H), 4.42 (s, 2H), 7.07 (s, 4H), 7.10 (d, J=8.1 Hz, 2H), 7.31 (d, J=8.1 Hz, 2H).

Example 48(8)

2-(4-{[bis(1H-imidazol-2-ylmethyl)amino]methyl}benzyl)-8-(1-ethylpropyl)-2,8-diazaspiro[4.5]decan-1-one

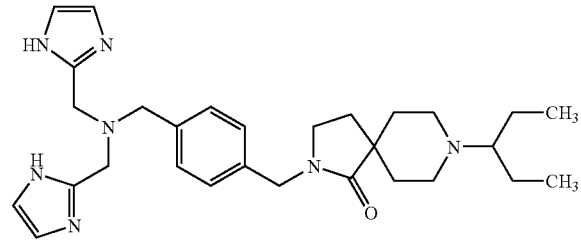

TLC: Rf 0.41 (dichrolomethane:methanol:28% aqueous ammonia=9:1:0.1);
NMR (CDCl$_3$): δ 0.90 (t, J=7.4 Hz, 6H), 1.21-1.56 (m, 6H), 1.86-2.07 (m, 4H), 2.10-2.22 (m, 1H), 2.29-2.43 (m, 2H), 2.64-2.78 (m, 2H), 3.13-3.21 (m, 2H), 3.59 (s, 4H), 3.61 (s, 2H), 4.41 (s, 2H), 7.06 (s, 4H), 7.09 (d, J=8.1 Hz, 2H), 7.30 (d, J=8.1 Hz, 2H).

Example 48(9)

2-(4-{[bis(1H-imidazol-2-ylmethyl)amino]methyl}benzyl)-9-cyclohexyl-2,9-diazaspiro[5.5]undecan-1-one TLC: Rf 0.16 (dichrolomethane:methanol:28% aqueous ammonia=9:1:0.1);
NMR (CDCl$_3$): δ 0.97-1.38 (m, 6H), 1.43-1.97 (m, 10H), 2.17-2.39 (m, 3H), 2.39-2.61 (m, 2H), 2.78-2.93 (m, 2H), 3.15-3.24 (m, 2H), 3.55 (s, 4H), 3.57 (s, 2H), 4.52 (s, 2H), 7.03 (d, J=8.1 Hz, 2H), 7.04 (s, 4H), 7.22 (d, J=8.1 Hz, 2H).

Example 48(10)

2-(4-{[bis(1H-imidazol-2-ylmethyl)amino]methyl}benzyl)-9-isobutyl-2,9-diazaspiro[5.5]undecan-1-one TLC: Rf 0.26 (dichrolomethane:methanol:28% aqueous ammonia=9:1:0.1);
NMR (CDCl$_3$): δ 0.90 (d, J=6.6 Hz, 6H), 1.45-1.58 (m, 2H), 1.70-1.88 (m, 4H), 2.03-2.42 (m, 7H), 2.66-2.78 (m, 2H), 3.16-3.25 (m, 2H), 3.57 (s, 4H), 3.58 (s, 2H), 4.52 (s, 2H), 7.02-7.10 (m, 6H), 7.21-7.28 (m, 2H).

Example 48(11)

2-(4-{[bis(1H-imidazol-2-ylmethyl)amino]methyl}benzyl)-9-(2,2-dimethylpropyl)-2,9-diazaspiro[5.5]undecan-1-one TLC: Rf 0.37 (dichrolomethane:methanol:28% aqueous ammonia=9:1:0.1);
NMR (CDCl$_3$): δ 0.86 (s, 9H), 1.39-1.51 (m, 2H), 1.68-1.88 (m, 4H), 2.05 (s, 2H), 2.24-2.47 (m, 4H), 2.64-2.75 (m, 2H), 3.16-3.24 (m, 2H), 3.57 (s, 4H), 3.58 (s, 2H), 4.52 (s, 2H), 7.07 (d, J=8.1 Hz, 2H), 7.05 (s, 4H), 7.23 (d, J=8.1 Hz, 2H).

Example 48(12)

2-(4-{[bis(1H-imidazol-2-ylmethyl)amino]methyl}benzyl)-9-(1-ethylpropyl)-2,9-diazaspiro[5.5]undecan-1-one

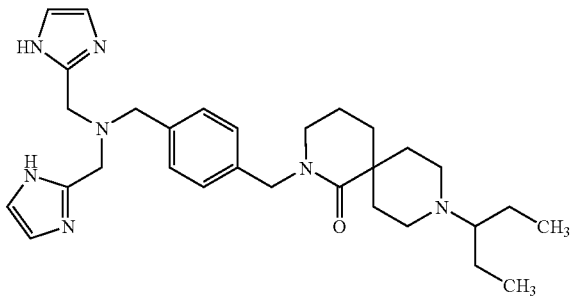

TLC: Rf 0.24 (dichrolomethane:methanol:28% aqueous ammonia=9:1:0.1);
NMR (CDCl$_3$): δ 0.90 (t, J=7.3 Hz, 6H), 1.18-1.89 (m, 10H), 2.08-2.33 (m, 3H), 2.39-2.55 (m, 2H), 2.57-2.72 (m, 2H), 3.16-3.24 (m, 2H), 3.57 (s, 4H), 3.60 (s, 2H), 4.52 (s, 2H), 7.04-7.09 (m, 6H), 7.21-7.27 (m, 2H).

Example 48(13)

3-(4-{[bis(1H-imidazol-2-ylmethyl)amino]methyl}benzyl)-8-cyclohexyl-1-oxa-3,8-diazaspiro[4.5]decan-2-one TLC: Rf 0.29 (dichrolomethane:methanol:28% aqueous ammonia=9:1:0.1);
NMR (CDCl$_3$): δ 0.97-1.99 (m, 14H), 2.23-2.40 (m, 1H), 2.49-2.77 (m, 4H), 3.13 (s, 2H), 3.60 (s, 4H), 3.64 (s, 2H), 4.40 (s, 2H), 7.06 (s, 4H), 7.19 (d, J=8.1 Hz, 2H), 7.38 (d, J=8.1 Hz, 2H).

Example 48(14)

3-(4-{[bis(1H-imidazol-2-ylmethyl)amino]methyl}benzyl)-8-(1-ethylpropyl)-1-oxa-3,8-diazaspiro[4.5]decan-2-one TLC: Rf 0.27 (dichrolomethane:methanol:28% aqueous ammonia=9:1:0.1);
NMR (CDCl$_3$): δ 0.87 (t, J=7.3 Hz, 6H), 1.19-1.52 (m, 4H), 1.60-1.74 (m, 2H), 1.82-1.94 (m, 2H), 2.10-2.22 (m, 1H), 2.36-2.49 (m, 2H), 2.61-2.74 (m, 2H), 3.14 (s, 2H), 3.60 (s, 4H), 3.63 (s, 2H), 4.40 (s, 2H), 7.06 (s, 4H), 7.18 (d, J=8.1 Hz, 2H), 7.37 (d, J=8.1 Hz, 2H).

Example 49 tert-butyl(dimethyl)[2-(4-methylphenyl)ethoxy]silane

To N,N-dimethylformamide (6 mL) solution of 2-(4-bromophenyl)ethanol (552 mg), imidazole (248 mg) and tert-butyldimethylsilyl chloride (453 mg) were added. The reaction solution was stirred at room temperature for 3 hours. To the reaction solution, 1N-hydrochloric acid (10 mL) was added. The aqueous layer was extracted twice with ethyl acetate. The combined organic layer was washed with water and saturated brine and then dried over anhydrous magnesium sulfate. After removing the anhydrous magnesium sulfate by filtration, the filtrate was concentrated under reduced pressure. The residue was purified by silica gel chromatography (n-hexane:ethyl acetate=1:0→97:3) to obtain the title compound (829 mg) having the following physical properties.
TLC: Rf 0.51 (n-hexane:ethyl acetate=50:1);
NMR (CDCl$_3$): δ 7.39 (d, J=8.4 Hz, 2H), 7.08 (d, J=8.4 Hz, 2H), 3.77 (t, J=6.9 Hz, 2H), 2.76 (t, J=6.9 Hz, 2H), 0.86 (s, 9H), −0.03 (s, 6H).

Example 50 tert-butyl 2-[4-(2-{[tert-butyl(dimethyl)silyl]oxy}ethyl)phenyl]-2,8-diazaspiro[4.5]decane-8-carboxylate Under an argon atmosphere, an anhydrous toluene (1 mL) solution of trisdibenzylideneacetone dipalladium (21 mg), biphenyl-2-yl(dicyclohexyl)phosphine (32 mg) and tert-butoxy potassium (306 mg) was stirred at room temperature for one hour. To this solution, an anhydrous toluene (2 mL) solution of the compound (714 mg) obtained in Example 49 and tert-butyl 2,8-diazaspiro[4.5]decane-8-carboxylate (594 mg) was added. The reaction solution was stirred at 100° C. for one hour. The reaction solution was cooled to room temperature, and then water (10 mL) was added. The aqueous layer was filtered through Celite (trade name). The aqueous layer was extracted with ethyl acetate. The combined organic layer was washed with saturated brine and then dried over anhydrous magnesium sulfate. After removing the anhydrous magnesium sulfate by filtration, the filtrate was concentrated under reduced pressure. The residue was purified by silica gel chromatography (n-hexane:ethyl acetate=98:2→77:23) to obtain the title compound (683 mg) having the following physical properties.
TLC: Rf 0.24 (n-hexane:ethyl acetate=19:1);
NMR (CDCl$_3$): δ 7.07 (d, J=8.4 Hz, 2H), 6.48 (d, J=8.4 Hz, 2H), 3.73 (t, J=6.9 Hz, 2H), 3.49 (m, 2H), 3.36 (m, 4H), 3.14 (s, 2H), 2.73 (t, J=6.9 Hz, 2H), 1.87 (t, J=6.9 Hz, 2H), 1.56 (m, 4H), 1.46 (s, 9H), 0.89 (s, 9H), −0.03 (s, 6H).

Example 51 tert-butyl 2-[4-(2-hydroxyethyl)phenyl]-2,8-diazaspiro[4.5]decane-8-carboxylate

To a tetrahydrofuran (4 mL) solution of the compound (657 mg) obtained in Example 50, a tetrahydrofuran solution (1.0N, 2.8 mL) of tetrabutylammonium fluoride was added. The reaction solution was stirred at room temperature for 4 hours. To the reaction solution, saturated brine (10 mL) was added. The aqueous layer was extracted with ethyl acetate. The combined organic layer was washed with saturated brine and then dried over anhydrous magnesium sulfate. After removing the anhydrous magnesium sulfate by filtration, the filtrate was concentrated under reduced pressure. The residue was purified by silica gel chromatography (n-hexane:ethyl acetate=67:33→36:67) to obtain the title compound (423 mg) having the following physical properties.
TLC: Rf 0.44 (n-hexane:ethyl acetate=1:1);
NMR (CDCl$_3$): δ 7.09 (d, J=8.4 Hz, 2H), 6.51 (d, J=8.4 Hz, 2H), 3.80 (dt, J=6.6, 6.6 Hz, 2H), 3.49 (m, 2H), 3.37 (m, 4H), 3.15 (s, 2H), 2.77 (t, J=6.6 Hz, 2H), 1.88 (t, J=6.9 Hz, 2H), 1.56 (m, 4H), 1.47 (s, 9H).

Example 52 tert-butyl 2-[4-(2-oxoethyl)phenyl]-2,8-diazaspiro[4.5]decane-8-carboxylate

The same operation as in Example 44 was performed, except for using the compound (210 mg) obtained in Example 51 in place of the compound obtained in Example 43, to obtain the title compound (73 mg) having the following physical properties.

TLC: Rf 0.80 (n-hexane:ethyl acetate=1:1);

NMR (CDCl$_3$): δ 9.69 (t, J=2.7 Hz, 1H), 7.07 (d, J=8.4 Hz, 2H), 6.54 (d, J=8.4 Hz, 2H), 3.57 (d, J=2.7 Hz, 2H), 3.48 (m, 2H), 3.37 (m, 4H), 3.16 (s, 2H), 1.89 (t, J=6.9 Hz, 2H), 1.56 (m, 4H), 1.47 (s, 9H).

Example 53 tert-butyl 2-(4-{2-[bis({1-[(dimethylamino)sulfonyl]-1H-imidazol-2-yl}methyl)amino]ethyl}phenyl)-2,8-diazaspiro[4.5]decane-8-carboxylate The same operation as in Example 2 was performed, except for using the compound (71 mg) obtained in Example 52 in place of the compound obtained in Example 1, and the compound (102 mg) obtained in Example 3 in place of benzylamine in Example 2, to obtain the title compound (131 mg) having the following physical properties.

TLC: Rf 0.43 (dichrolomethane:methanol:28% aqueous ammonia=90:10:1);

NMR (CDCl$_3$): δ 7.26 (m, 2H), 7.04 (d, J=8.4 Hz, 2H), 6.65 (m, 2H), 6.45 (d, J=8.4 Hz, 2H), 4.20 (s, 4H), 3.48 (m, 2H), 3.32 (m, 4H), 3.12 (s, 2H), 2.93 (m, 2H), 2.87 (s, 12H), 2.76 (m, 2H), 1.86 (t, J=6.9 Hz, 2H), 1.57 (m, 4H), 1.46 (s, 9H).

Example 54

2-[4-(2,8-diazaspiro[4.5]dec-2-yl)phenyl]-N,N-bis(1H-imidazol-2-ylmethyl)ethanamine The same operation as in Example 46 was performed, except for using the compound (166 mg) obtained in Example 53 in place of the compound obtained in Example 45 in Example 46, to obtain the title compound (92 mg) having the following physical properties.

TLC: Rf 0.21 (dichrolomethane:methanol:28% aqueous ammonia=40:10:1);

NMR (CDCl$_3$): δ 7.06 (d, J=8.4 Hz, 2H), 7.00 (s, 4H), 6.49 (d, J=8.4 Hz, 2H), 3.66 (s, 4H), 3.32 (t, J=6.9 Hz, 2H), 3.14 (s, 2H), 2.81 (m, 8H), 1.84 (t, J=6.9 Hz, 2H), 1.57 (m, 4H)

Example 55

2-[4-(8-cyclohexyl-2,8-diazaspiro[4.5]dec-2-yl)phenyl]-N,N-bis(1H-imidazol-2-ylmethyl)ethanamine

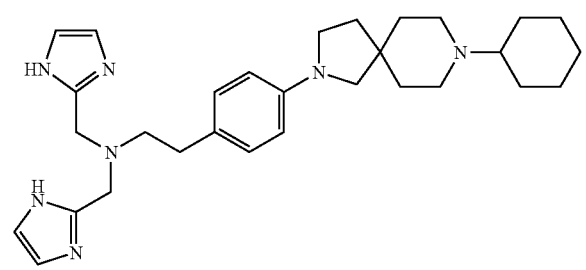

The same operation as in Example 2 was performed, except for using the compound (62 mg) obtained in Example 54 and cyclohexanone (21 mg), to obtain the title compound (36 mg) having the following physical properties.

Description: amorphous;

TLC: Rf 0.20 (dichrolomethane:methanol:28% aqueous ammonia=90:10:1);

NMR (CDCl$_3$): δ 1.03-1.35 (m, 6H), 1.53-1.95 (m, 10H), 2.19-2.88 (m, 9H), 3.09 (s, 2H), 3.26-3.35 (m, 2H), 3.66 (s, 4H), 6.44-6.52 (m, 2H), 6.99 (s, 4H), 7.01-7.09 (m, 2H).

Example 55(1)

2-[3-(8-cyclohexyl-2,8-diazaspiro[4.5]dec-2-yl)phenyl]-N,N-bis(1H-imidazol-2-ylmethyl)ethanamine The same operation as in Example 50→Example 51→Example 52→Example 53→Example 54→Example 55 was performed, except for using a corresponding alcohol in place of 4-(2-hydroxyethyl)bromobenzene in Example 49, to obtain the title compound (36 mg) having the following physical properties.

Description: amorphous;

TLC: Rf 0.22 (dichrolomethane:methanol:28% aqueous ammonia=90:10:1);

NMR (CDCl$_3$): δ 1.03-1.37 (m, 6H), 1.52-1.98 (m, 10H), 2.24-2.41 (m, 1H), 2.43-2.72 (m, 4H), 2.74-2.92 (m, 4H), 3.09 (s, 2H), 3.30 (t, J=6.9 Hz, 2H), 3.68 (s, 4H), 6.35-6.45 (m, 2H), 6.47-6.55 (m, 1H), 6.99 (s, 4H), 7.15 (t, J=7.8 Hz, 1H).

Example 56

N,N-dimethyl-2-({[(1-methyl-1H-imidazol-2-yl)methyl]amino}methyl)-1H-imidazole-1-sulfonamide To a 1% acetic acid-dimethylformamide (40 mL) solution of benzylamine (2.32 g) and 2-formyl-N,N-dimethyl-1H-imidazole-1-sulfonamide (4.00 g) synthesized in Example 1, sodium triacetoxyborohydride (4.18 g) was added. The reaction solution was stirred at room temperature for 15 hours. To the reaction solution, an aqueous 5N-sodium hydroxide solution was added, followed by extraction twice with dichloromethane. The organic layer was washed with saturated brine and then dried over anhydrous magnesium sulfate. After removing the anhydrous magnesium sulfate by filtration, the filtrate was concentrated. The residue was purified by silica gel chromatography (n-hexane:ethyl acetate=4:1→ethyl acetate:methanol=9:1). To a 1% acetic acid-dimethylformamide (40 mL) solution of the obtained compound and 1-methyl-1H-imidazole-2-carbaldehyde (2.38 g), sodium triacetoxyborohydride (4.18 g) was added. The reaction solution was stirred at room temperature for 15 hours. To the reaction solution, an aqueous 5N-sodium hydroxide solution was added, followed by extraction twice with dichloromethane. The organic layer was washed with saturated brine and then dried over anhydrous magnesium sulfate. After removing the anhydrous magnesium sulfate by filtration, the filtrate was concentrated. The residue was purified by silica gel chromatography (ethyl acetate:methanol=9:1→ethyl acetate:methanol: 28% aqueous ammonia=29:1:0.2) to obtain a compound (3.10 g). The same operation as in Example 3, except for using the obtained compound, and then the obtained crude product was purified by silica gel chromatography (ethyl acetate:methanol=9:1) to obtain the title compound (1.66 g) having the following physical properties.

TLC: Rf 0.54 (ethyl acetate:methanol:28% aqueous ammonia=4:1:0.2);

NMR (CDCl$_3$): δ 2.88 (s, 6H), 3.69 (s, 3H), 3.94 (s, 2H), 4.07 (s, 2H), 6.82 (d, J=1.3 Hz, 1H), 6.89 (d, J=1.3 Hz, 1H), 6.99 (d, J=1.7 Hz, 1H), 7.23 (d, J=1.7 Hz, 1H).

Example 57

4-{[8-(2,2-dimethylpropyl)-2,8-diazaspiro[4.5]dec-2-yl]methyl}-N-(1H-imidazol-2-ylmethyl)-N-[(1-methyl-1H-imidazol-2-yl)methyl]benzamide The same operation as in Example 4→Example 5→Example 8 was performed, except for using the amine obtained in Example 56 in place of 2,2'-[iminobis(methylene)]bis(N,N-dimethyl-1H-imidazole-1-sulfonamide) in Example 4, to obtain the title compound having the following physical properties.

TLC: Rf 0.33 (dichrolomethane:methanol:28% aqueous ammonia=9:1:0.1);

NMR (DMSO-d$_6$): δ 0.80 (s, 9H), 1.37-1.57 (m, 6H), 1.95 (s, 2H), 2.23-2.55 (m, 6H), 2.27 (s, 2H), 3.52 (s, 3H), 3.57-3.77 (m, 2H), 4.36-4.80 (m, 4H), 6.77-6.96 (m, 2H), 7.00-7.14 (m, 2H), 7.28 (d, J=8.1 Hz, 2H), 7.43 (d, J=8.1 Hz, 2H), 12.07-12.44 (m, 1H).

Example 57(1) to Example 57(7)

The same operation as in Example 56→Example 57 was performed, except for using a corresponding aldehyde in place of 1-methyl-1H-imidazole-2-carbaldehyde in Example 56, and a corresponding amine in place of 8-(2,2-dimethylpropyl)-2,8-diazaspiro[4.5]decane in Example 57, to obtain the following compound.

Example 57(1)

N-(1H-imidazol-2-ylmethyl)-4-[(2-isobutyl-2,8-diazaspiro[4.5]dec-8-yl)methyl]-N-[(1-methyl-1H-imidazol-2-yl)methyl]benzamide TLC: Rf 0.24 (dichrolomethane:methanol:28% aqueous ammonia=9:1:0.1);

NMR (DMSO-d$_6$): δ 0.83 (d, J=6.6 Hz, 6H), 1.36-1.55 (m, 6H), 1.55-1.72 (m, 1H), 2.07 (d, J=7.5 Hz, 2H), 2.18-2.34 (m, 6H), 2.37-2.46 (m, 2H), 3.41 (s, 3H), 3.57-3.75 (m, 2H), 4.39-4.78 (m, 4H), 6.79-6.94 (m, 2H), 7.00-7.15 (m, 2H), 7.28 (d, J=8.1 Hz, 2H), 7.35-7.50 (m, J=8.1 Hz, 2H), 12.05-12.47 (m, 1H).

Example 57(2)

4-{[2-(2,2-dimethylpropyl)-2,8-diazaspiro[4.5]dec-8-yl]methyl}-N-(1H-imidazol-2-ylmethyl)-N-[(1-methyl-1H-imidazol-2-yl)methyl]benzamide TLC: Rf 0.23 (dichrolomethane:methanol:28% aqueous ammonia=9:1:0.1);

NMR (DMSO-d$_6$): δ 0.83 (s, 9H), 1.36-1.58 (m, 6H), 2.14 (s, 2H), 2.17-2.35 (m, 4H), 2.40 (s, 2H), 2.54-2.65 (m, 2H), 3.41 (s, 3H), 3.52-3.77 (m, 2H), 4.34-4.80 (m, 4H), 6.78-6.94 (m, 2H), 7.01-7.16 (m, 2H), 7.28 (d, J=8.2 Hz, 2H), 7.43 (d, J=8.2 Hz, 2H), 12.09-12.48 (m, 1H).

Example 57(3)

4-{[2-(1-ethylpropyl)-2,8-diazaspiro[4.5]dec-8-yl]methyl}-N-(1H-imidazol-2-ylmethyl)-N-[(1-methyl-1H-imidazol-2-yl)methyl]benzamide TLC: Rf 0.25 (dichrolomethane:methanol:28% aqueous ammonia=9:1:0.1);

NMR (DMSO-d$_6$): δ 0.78 (t, J=7.4 Hz, 6H), 1.20-1.56 (m, 10H), 1.91-2.03 (m, 1H), 2.19-2.35 (m, 6H), 2.44-2.53 (m, 2H), 3.41 (s, 3H), 3.55-3.77 (m, 2H), 4.41-4.75 (m, 4H), 6.77-6.93 (m, 2H), 7.02-7.13 (m, 2H), 7.28 (d, J=8.1 Hz, 2H), 7.37-7.47 (m, J=8.1 Hz, 2H), 12.13-12.46 (m, 1H).

Example 57(4)

4-[(8-cyclohexyl-2,8-diazaspiro[4.5]dec-2-yl)methyl]-N-(1H-imidazol-2-ylmethyl)-N-[(1-isobutyl-1H-imidazol-2-yl)methyl]benzamide TLC: Rf 0.44 (chloroform:methanol:28% aqueous ammonia=9:1:0.1);

NMR (CDCl$_3$): δ 0.64-1.38 (m, 13H), 1.44-2.14 (m, 10H), 2.11-2.27 (m, 1H), 2.32 (s, 2H), 2.40-2.66 (m, 6H), 3.56 (s, 2H), 3.97 (d, J=7.5 Hz, 2H), 4.36-4.89 (m, 4H), 6.47-7.00 (m, 1H), 6.96-7.20 (m, 3H), 7.30-7.57 (m, 4H).

Example 57(5)

N-(1H-imidazol-2-ylmethyl)-4-[(8-isobutyl-2,8-diazaspiro[4.5]dec-2-yl)methyl]-N-[(1-isobutyl-1H-imidazol-2-yl)methyl]benzamide TLC: Rf 0.39 (chloroform:methanol:28% aqueous ammonia=9:1:0.1);

NMR (CDCl$_3$): δ 0.87 (d, J=6.6 Hz, 6H), 0.97 (d, J=6.2 Hz, 6H), 1.37-1.90 (m, 7H), 2.02 (d, J=7.1 Hz, 2H), 2.05-2.10 (m, 1H), 2.16-2.44 (m, 6H), 2.53 (t, J=6.9 Hz, 2H), 3.56 (s, 2H), 3.98 (d, J=7.3 Hz, 2H), 4.33-4.93 (m, 4H), 6.79-6.95 (m, 1H), 6.97-7.18 (m, 3H), 7.28-7.56 (m, 4H).

Example 57(6)

4-{[8-(1-ethylpropyl)-2,8-diazaspiro[4.5]dec-2-yl]methyl}-N-(1H-imidazol-2-ylmethyl)-N-[(1-isobutyl-1H-imidazol-2-yl)methyl]benzamide

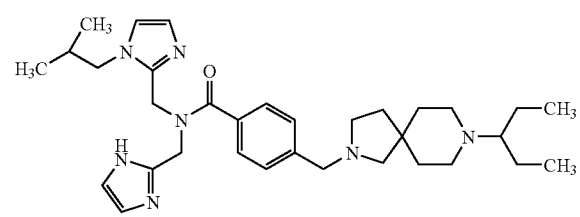

TLC: Rf 0.40 (chloroform:methanol:28% aqueous ammonia=9:1:0.1);

NMR (CDCl$_3$): δ 0.87 (t, J=7.4 Hz, 6H), 0.97 (d, J=6.4 Hz, 6H), 1.16-1.68 (m, 7H), 1.79-1.93 (m, 4H), 1.97-2.15 (m, 1H), 2.32 (s, 2H), 2.33-2.45 (m, 4H), 2.52 (t, J=6.9 Hz, 2H), 3.56 (s, 2H), 3.97 (d, J=7.0 Hz, 2H), 4.29-5.00 (m, 4H), 6.73-6.97 (m, 1H), 6.98-7.19 (m, 3H), 7.28-7.59 (m, 4H).

Example 57(7)

4-{[8-(2,2-dimethylpropyl)-2,8-diazaspiro[4.5]dec-2-yl]methyl}-N-(1H-imidazol-2-ylmethyl)-N-[(1-isobutyl-1H-imidazol-2-yl)methyl]benzamide TLC: Rf 0.45 (chloroform:methanol:28% aqueous ammonia=9:1:0.1);
NMR (CDCl$_3$): δ 0.84 (s, 9H), 0.97 (d, J=6.4 Hz, 6H), 1.40-1.85 (m, 6H), 1.88-2.15 (m, 3H), 2.22-2.46 (m, 6H), 2.47-2.65 (m, 2H), 3.56 (s, 2H), 3.97 (d, J=7.1 Hz, 2H), 4.40-4.93 (m, 4H), 6.80-6.96 (m, 1H), 6.96-7.17 (m, 3H), 7.29-7.52 (m, 4H).

Example 58

1-(1-methyl-1H-imidazol-2-yl)-N-[(1-methyl-1H-imidazol-2-yl)methyl]methanamine

The same operation as in Example 2→Example 3 was performed, except for using 1-methyl-1H-imidazole-2-carbaldehyde in place of 2-formyl-N,N-dimethyl-1H-imidazole-1-sulfonamide in Example 2, to obtain the title compound having the following physical properties.
TLC: Rf 0.63 (chloroform:methanol:28% aqueous ammonia=4:1:0.2);
NMR (CDCl$_3$): δ 3.63 (s, 6H), 3.87 (s, 4H), 6.82 (s, 2H), 6.93 (s, 2H).

Example 59

4-{[8-(2,2-dimethylpropyl)-2,8-diazaspiro[4.5]dec-2-yl]methyl}-N,N-bis[(1-methyl-1H-imidazol-2-yl)methyl]benzamide The same operation as in Example 4→Example 8 was performed, except for using the amine obtained in Example 58 in place of 2,2'-[iminobis(methylene)]bis(N,N-dimethyl-1H-imidazole-1-sulfonamide) in Example 4, to obtain the title compound having the following physical properties.
TLC: Rf 0.53 (dichrolomethane:methanol:28% aqueous ammonia=9:1:0.1);
NMR (CDCl$_3$): δ 0.83 (s, 9H), 1.46-1.67 (m, 6H), 1.97 (s, 2H), 2.31 (s, 2H), 2.29-2.46 (m, 4H), 2.52 (t, J=6.9 Hz, 2H), 3.34-3.53 (m, 3H), 3.55 (s, 2H), 3.65-3.90 (m, 3H), 4.54-4.93 (m, 4H), 6.73-6.83 (m, 2H), 6.87-7.07 (m, 2H), 7.30 (d, J=8.2 Hz, 2H), 7.56 (d, J=8.2 Hz, 2H).

Example 60

1-(4-{[8-(1-ethylpropyl)-2,8-diazaspiro[4.5]dec-2-yl]carbonyl}phenyl)-N,N-bis[(1-methyl-1H-imidazol-2-yl)methyl]methanamine The same operation as in Example 4→Example 8 was performed, except for using 8-(1-ethylpropyl)-2,8-diazaspiro[4.5]decane in place of 2,2'-[iminobis(methylene)]bis(N,N-dimethyl-1H-imidazole-1-sulfonamide) in Example 4, and the amine obtained in Example 58 in place of trans-4-piperidin-1-ylcyclohexaneamine in Example 8, to obtain the title compound having the following physical properties.
TLC: Rf 0.30 (dichrolomethane:methanol:28% aqueous ammonia=9:1:0.1);
NMR (CDCl$_3$): δ 0.80-0.96 (m, 6H), 1.18-1.84 (m, 10H), 2.14 (m, 1H), 2.24-2.60 (m, 4H), 3.16-3.75 (m, 16H), 6.78-6.82 (m, 2H), 6.90-6.93 (m, 2H), 7.22-7.30 (m, 2H), 7.43 (d, J=7.8 Hz, 2H).

Example 60(1) to Example 60(3)

The same operation was carried out, except for using a corresponding amine in place of 8-(1-ethylpropyl)-2,8-diazaspiro[4.5]decane in Example 60, to obtain the following compound.

Example 60(1)

1-(4-{[8-(2,2-dimethylpropyl)-2,8-diazaspiro[4.5]dec-2-yl]carbonyl}phenyl)-N,N-bis[(1-methyl-1H-imidazol-2-yl)methyl]methanamine TLC: Rf 0.31 (dichrolomethane:methanol:28% aqueous ammonia=9:1:0.1);
NMR (CDCl$_3$): δ 0.80-0.89 (m, 9H), 1.40-1.83 (m, 6H), 1.96-2.07 (m, 2H), 2.22-2.60 (m, 4H), 3.18-3.73 (m, 16H), 6.80 (s, 2H), 6.93 (s, 2H), 7.21-7.30 (m, 2H), 7.40-7.46 (m, 2H).

Example 60(2)

1-(4-{[9-(2,2-dimethylpropyl)-1-oxa-4,9-diazaspiro[5.5]undec-4-yl]carbonyl}phenyl)-N,N-bis[(1-methyl-1H-imidazol-2-yl)methyl]methanamine TLC: Rf 0.34 (dichrolomethane:methanol:28% aqueous ammonia=9:1:0.1);
NMR (CDCl$_3$): δ 0.72-0.90 (m, 9H), 1.55-1.85 (m, 4H), 1.95-2.10 (m, 2H), 2.28-2.62 (m, 4H), 3.12-3.80 (m, 18H), 6.79-6.81 (m, 2H), 6.92-6.94 (m, 2H), 7.27-7.34 (m, 4H).

Example 60(3)

1-(4-{[9-(1-ethylpropyl)-1-oxa-4,9-diazaspiro[5.5]undec-4-yl]carbonyl}phenyl)-N,N-bis[(1-methyl-1H-imidazol-2-yl)methyl]methanamine

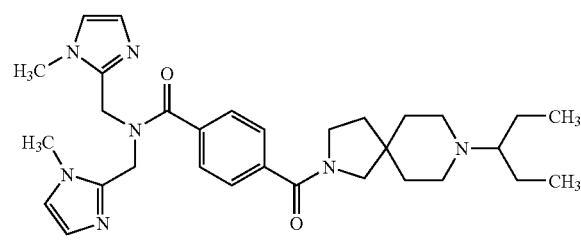

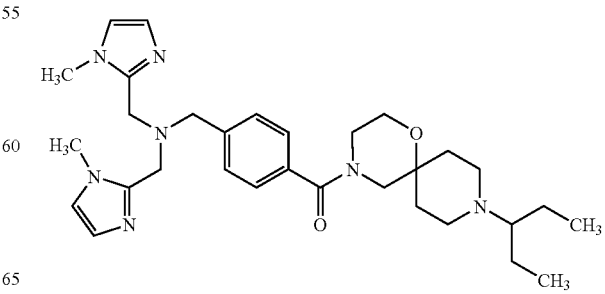

TLC: Rf 0.34 (dichrolomethane:methanol:28% aqueous ammonia=9:1:0.1);

NMR (CDCl$_3$): δ 0.77-0.95 (m, 6H), 1.12-1.85 (m, 8H), 2.10 (m, 1H), 2.22-2.63 (m, 4H), 3.10-3.83 (m, 18H), 6.78-6.81 (m, 2H), 6.92-6.94 (m, 2H), 7.24-7.34 (m, 4H).

Example 61

Ethyl{4-[(tert-butoxycarbonyl)amino]piperidin-1-yl}(oxo)acetate 4-(tert-butoxycarbonylamino)piperidine (150 mg) was added to acetonitrile (5 mL), and triethylamine (0.21 mL) and ethyloxalyl chloride (0.11 mL) were added dropwise at 0° C. The reaction solution was stirred for 30 minutes and an aqueous saturated sodium hydrogen carbonate solution was added, followed by extraction with ethyl acetate. The organic layer was washed in turn with water and saturated brine, dried over anhydrous magnesium sulfate and then concentrated under reduced pressure to obtain the title compound (235 mg) having the following physical properties.

TLC: Rf 0.48 (hexane:ethyl acetate=1:1);

NMR (CDCl$_3$): δ 1.37 (t, J=6.00 Hz, 3H), 1.37-1.50 (m, 2H), 1.44 (s, 9H), 1.96-2.08 (m, 2H), 2.80-2.93 (m, 1H), 3.10-3.23 (m, 1H), 3.59-3.75 (m, 2H), 4.26-4.44 (m, 3H), 4.58 (d, J=7.32 Hz, 1H).

Example 62

{4-[(tert-butoxycarbonyl)amino]piperidin-1-yl}(oxo)acetic Acid

To an ethanol (3 mL) solution of the compound (235 mg) obtained in Example 61, 2N— sodium hydroxide water (0.75 mL) was added. The reaction solution was stirred for 15 hours, and then concentrated by adding 2N hydrochloric acid to obtain the title compound (240 mg) having the following physical properties.

TLC: Rf 0.20 (chloroform:methanol:28% aqueous ammonia=4:1:0.2);

NMR (CD$_3$OD): δ 1.28-1.53 (m, 2H), 1.43 (s, 9H), 1.86-1.98 (m, 2H), 2.87-3.00 (m, 1H), 3.18-3.29 (m, 1H), 3.56-3.68 (m, 1H), 3.68-3.82 (m, 1H), 4.18-4.37 (m, 1H).

Example 63 tert-butyl {1-[(8-isobutyl-2,8-diazaspiro[4.5]dec-2-yl)(oxo)acetyl]piperidin-4-yl}carbamate The compound (240 mg) obtained in Example 62, 8-(2-methylpropyl)-2,8-diazaspiro[4.5]decane (133 mg), N,N,N',N'-tetramethyl-ortho-(7-azabenzotriazol-1-yl)uronium hexafluorophosphate (518 mg) and diisopropyl ethylamine (0.24 mL) were added to dimethylformamide (5 mL), followed by stirring for 2 hours. To the reaction solution, saturated brine was added, followed by extraction with dichloromethane. The organic layer was dried over anhydrous magnesium sulfate and then concentrated under reduced pressure. The residue was purified by silica gel chromatography (ethyl acetate:methanol=9:1→ethyl acetate:methanol:28% aqueous ammonia=29:1:0.2→8:1:0.2) to obtain the title compound (236 mg) having the following physical properties.

TLC: Rf 0.78 (ethyl acetate:methanol:28% aqueous ammonia=8:1:0.2);

NMR (CDCl$_3$): δ 0.90 (d, J=6.59 Hz, 6H), 1.32-1.87 (m, 9H), 1.44 (s, 9H), 1.93-2.18 (m, 4H), 2.24-2.39 (m, 2H), 2.40-2.60 (m, 2H), 2.78-2.94 (m, 1H), 3.07-3.19 (m, 1H), 3.21-3.33 (m, 1H), 3.36 (s, 1H), 3.55 (t, J=7.41 Hz, 2H), 3.64-3.77 (m, 2H), 4.36-4.47 (m, 1H), 4.48-4.60 (m, 1H).

Example 64

1-[(8-isobutyl-2,8-diazaspiro[4.5]dec-2-yl)(oxo)acetyl]piperidine-4-amine

Except for using the compound (236 mg) produced in Example 63, the same operation as in Example 25 was performed to obtain the title compound (144 mg) having the following physical properties.

TLC: Rf 0.29 (dichrolomethane:methanol:28% aqueous ammonia=4:1:0.2);

NMR (CDCl$_3$): δ 0.81 (d, J=6.59, 6H), 1.12-1.91 (m, 11H), 1.99 (d, J=9.00 Hz, 2H), 2.08-2.46 (m, 4H), 2.70-2.90 (m, 1H), 2.97-3.12 (m, 1H), 3.17-3.23 (m, 1H), 3.25-3.32 (m, 1H), 3.42-3.55 (m, 2H), 3.53-3.76 (m, 2H), 4.23-4.42 (m, 1H).

Example 65

N,N-bis(1H-imidazol-2-ylmethyl)-1-[(8-isobutyl-2,8-diazaspiro[4.5]dec-2-yl)(oxo)acetyl]-4-piperidinamine The same operation as in Example 2 was performed, except for using the compound (144 mg) obtained in Example 64 in place of benzylamine, and 1H-imidazole-2-carbaldehyde (158 mg) in place of the compound obtained in Example 1, to obtain the title compound having the following physical properties.

TLC: Rf 0.42 (dichrolomethane:methanol:28% aqueous ammonia=8:1:0.2);

NMR (CDCl$_3$): δ 0.84-0.94 (m, 6H), 1.32-2.00 (m, 11H), 2.02-2.11 (m, 2H), 2.17-2.32 (m, 2H), 2.35-2.53 (m, 2H), 2.59-2.85 (m, 2H), 2.95-3.10 (m, 1H), 3.15-3.91 (m, 9H), 4.42-4.56 (m, 1H), 7.03 (s, 4H).

Example 65(1) to Example 65(9)

Except for using the corresponding amine in place of 4-(tert-butoxycarbonylamino)piperidine in Example 61 and using the corresponding amine in place of 8-(2-methylpropyl)-2,8-diazaspiro[4.5]decane in Example 61, the same operation as in Example 61→Example 62→Example 63→Example 64→Example 65 was performed to obtain the following compound.

Example 65(1)

1-(1H-imidazol-2-yl)-N-(1H-imidazol-2-ylmethyl)-N-({1-[(8-isobutyl-2,8-diazaspiro[4.5]dec-2-yl)(oxo)acetyl]-4-piperidinyl}methyl)methanamine TLC: Rf 0.40 (dichrolomethane:methanol:28% aqueous ammonia=8:1:0.2);

NMR (CDCl$_3$): δ 0.84-0.91 (m, 6H), 0.97-1.21 (m, 2H), 1.46-1.97 (m, 10H), 2.02-2.11 (m, 2H), 2.17-2.52 (m, 6H), 2.60-2.78 (m, 1H), 2.97-3.11 (m, 1H), 3.17-3.38 (m, 2H), 3.41-3.71 (m, 7H), 4.39-4.53 (m, 1H), 7.04 (s, 4H).

Example 65(2)

1-[3-(8-benzyl-2,8-diazaspiro[4.5]dec-2-yl)-3-oxo-propanoyl]-N,N-bis(1H-imidazol-2-ylmethyl)-4-piperidinamine

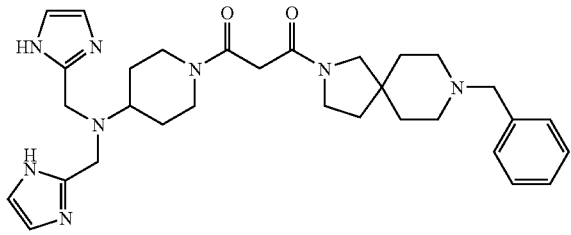

TLC: Rf 0.43 (dichrolomethane:methanol:28% aqueous ammonia=8:1:0.2);
NMR (CDCl$_3$): δ 1.21-1.98 (m, 10H), 2.20-2.40 (m, 2H), 2.42-2.64 (m, 3H), 2.69-2.82 (m, 1H), 2.96-3.13 (m, 1H), 3.24-3.63 (m, 8H), 3.66-3.83 (m, 4H), 3.83-3.97 (m, 1H), 4.48-4.61 (m, 1H), 7.01 (s, 4H), 7.20-7.37 (m, 5H).

Example 65(3)

1-[3-(8-cyclohexyl-2,8-diazaspiro[4.5]dec-2-yl)-3-oxopropanoyl]-N,N-bis(1H-imidazol-2-ylmethyl)-3-pyrrolidinamine

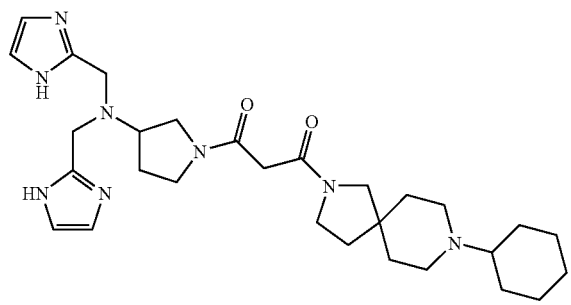

TLC: Rf 0.50 (dichrolomethane:methanol:28% aqueous ammonia=4:1:0.2);
NMR (CDCl$_3$): δ 0.84-1.92 (m, 16H), 1.97-2.21 (m, 2H), 2.22-2.36 (m, 1H), 2.36-2.52 (m, 2H), 2.55-2.68 (m, 2H), 3.09-4.02 (m, 15H), 7.03 (d, J=1.2 Hz, 4H).

Example 65(4)

1-[3-(8-cyclohexyl-2,8-diazaspiro[4.5]dec-2-yl)-3-oxopropanoyl]-N,N-bis(1H-imidazol-2-ylmethyl)-4-piperidinamine

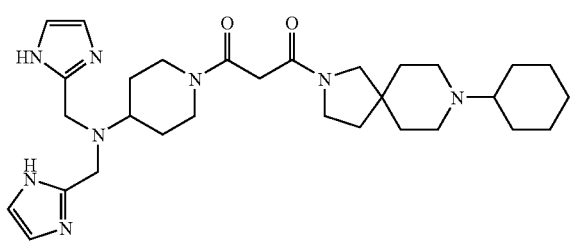

TLC: Rf 0.42 (dichrolomethane:methanol:28% aqueous ammonia=4:1:0.2);
NMR (CDCl$_3$): δ 0.96-2.02 (m, 20H), 2.19-2.81 (m, 7H), 2.96-3.12 (m, 1H), 3.22-3.93 (m, 11H), 4.46-4.62 (m, 1H), 7.06 (s, 4H).

Example 65(5)

1-{3-[8-(1-ethylpropyl)-2,8-diazaspiro[4.5]dec-2-yl]-3-oxopropanoyl}-N,N-bis(1H-imidazol-2-ylmethyl)-4-piperidinamine

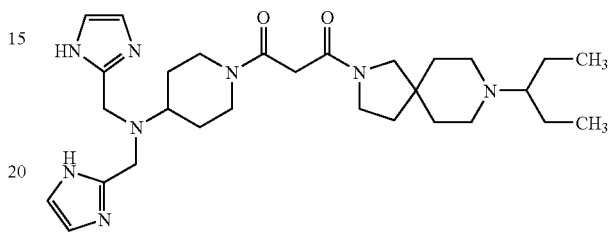

TLC: Rf 0.33 (dichrolomethane:methanol:28% aqueous ammonia=8:1:0.2);
NMR (CDCl$_3$): δ 0.83-0.95 (m, 6H), 1.19-1.99 (m, 14H), 2.09-2.22 (m, 1H), 2.32-2.64 (m, 5H), 2.66-2.80 (m, 1H), 2.97-3.11 (m, 1H), 3.22-3.66 (m, 6H), 3.67-3.82 (m, 4H), 3.82-3.94 (m, 1H), 4.49-4.61 (m, 1H), 7.01 (s, 4H).

Example 65(6)

1-{3-[8-(2,2-dimethylpropyl)-2,8-diazaspiro[4.5]dec-2-yl]-3-oxopropanoyl}-N,N-bis(1H-imidazol-2-ylmethyl)-4-piperidinamine TLC: Rf 0.38 (dichrolomethane:methanol:28% aqueous ammonia=8:1:0.2);
NMR (CDCl$_3$): δ 0.84 (s, 9H), 1.19-1.98 (m, 10H), 1.99-2.06 (m, 2H), 2.30-2.65 (m, 5H), 2.65-2.83 (m, 1H), 2.96-3.12 (m, 1H), 3.22-3.64 (m, 6H), 3.65-3.82 (m, 4H), 3.81-3.94 (m, 1H), 4.45-4.62 (m, 1H), 7.01 (s, 4H).

Example 65(7)

N,N-bis(1H-imidazol-2-ylmethyl)-1-[3-(8-isobutyl-2,8-diazaspiro[4.5]dec-2-yl)-3-oxopropanoyl]-4-piperidinamine TLC: Rf 0.70 (dichrolomethane:methanol:28% aqueous ammonia=4:1:0.2);
NMR (CDCl$_3$): δ 0.88 (d, J=6.6 Hz, 6H), 1.21-1.98 (m, 11H), 2.00-2.11 (m, 2H), 2.15-2.35 (m, 2H), 2.35-2.49 (m, 2H), 2.49-2.63 (m, 1H), 2.65-2.80 (m, 1H), 2.97-3.10 (m, 1H), 3.23-3.65 (m, 6H), 3.66-3.81 (m, 4H), 3.81-3.91 (m, 1H), 4.49-4.60 (m, 1H), 7.00 (s, 4H).

Example 65(8)

1-(1H-imidazol-2-yl)-N-(1H-imidazol-2-ylmethyl)-N-({1-[3-(8-isobutyl-2,8-diazaspiro[4.5]dec-2-yl)-3-oxopropanoyl]-4-piperidinyl}methyl)methanamine TLC: Rf 0.41 (dichrolomethane:methanol:28% aqueous ammonia=8:1:0.2);
NMR (CDCl$_3$): δ 0.88 (d, J=6.6 Hz, 6H), 1.02-1.95 (m, 12H), 2.01-2.10 (m, 2H), 2.13-2.51 (m, 6H), 2.52-2.67 (m, 1H), 2.98-3.16 (m, 1H), 3.24-3.57 (m, 6H), 3.60 (s, 4H), 3.80-3.93 (m, 1H), 4.48-4.62 (m, 1H), 7.03 (s, 4H).

Example 65(9)

1-[4-(8-cyclohexyl-2,8-diazaspiro[4.5]dec-2-yl)-4-oxobutanoyl]-N,N-bis(1H-imidazol-2-ylmethyl)-4-piperidinamine TLC: Rf 0.46 (dichrolomethane:methanol:28% aqueous ammonia=8:1:0.2);
NMR (CDCl$_3$): δ 0.79-1.95 (m, 20H), 2.18-3.07 (m, 12H), 3.21-3.67 (m, 4H), 3.70-3.84 (m, 4H), 3.86-4.00 (m, 1H), 4.47-4.61 (m, 1H), 7.01 (s, 4H).

Example 66

Methyl {4-[(tert-butoxycarbonyl)amino]piperidin-1-yl}acetate 4-(tert-butoxycarbonylamino)piperidine (1.2 g) and potassium carbonate (1.2 g) were suspended in dimethylformamide (20 mL), and then methyl bromoacetate (0.62 mL) was added. The reaction solution was stirred for one hour and water was added, followed by extraction with ethyl acetate. The organic layer was washed in turn with water and saturated brine, and dried over anhydrous magnesium sulfate, and then the filtrate was concentrated. The residue was purified by silica gel chromatography (hexane:ethyl acetate=2:1→0:1) to obtain the title compound (1.36 g) having the following physical properties.
TLC: Rf 0.79 (ethyl acetate:methanol:28% aqueous ammonia=8:1:0.2);
NMR (CDCl$_3$): δ 1.44 (s, 9H), 1.46-1.61 (m, 2H), 1.87-2.00 (m, 2H), 2.19-2.34 (m, 2H), 2.83-2.94 (m, 2H), 3.21 (s, 2H), 3.39-3.56 (m, 1H), 3.72 (s, 3H), 4.60 (d, J=6.77 Hz, 1H).

Example 67

{4-[(tert-butoxycarbonyl)amino]piperidin-1-yl}acetic acid

Except for using the compound produced in Example 66 in place of the compound produced in Example 61, the same operation as in Example 62 was performed to obtain the title compound having the following physical properties.
TLC: Rf 0.10 (chloroform:methanol:28% aqueous ammonia=4:1:0.2);
NMR (DMSO-d$_6$): δ 1.37 (s, 9H), 1.47-1.63 (m, 2H), 1.73-1.85 (m, 2H), 2.61-2.73 (m, 2H), 3.07-3.21 (m, 2H), 3.28 (s, 2H), 3.29-3.43 (m, 1H), 6.91 (d, J=7.14 Hz, 1H).

Example 68 tert-butyl {1-[2-(8-cyclohexyl-2,8-diazaspiro[4.5]dec-2-yl)-2-oxoethyl]piperidin-4-yl}carbamate Except for using the compound produced in Example 67 in place of the compound produced in Example 62 and using 8-cyclohexyl-2,8-diazaspiro[4.5]decane in place of 8-(2-methylpropyl)-2,8-diazaspiro[4.5]decane, the same operation as in Example 63 was performed to obtain the title compound having the following physical properties.
TLC: Rf 0.60 (ethyl acetate:methanol:28% aqueous ammonia=4:1:0.2);
NMR (CDCl$_3$): δ 0.97-1.98 (m, 20H), 1.44 (s, 9H), 2.12-2.34 (m, 3H), 2.36-2.68 (m, 4H), 2.83-2.94 (m, 2H), 3.05-3.12 (m, 2H), 3.28-3.35 (m, 2H), 3.41-3.59 (m, 3H), 4.40-4.53 (m, 1H).

Example 69

1-[2-(8-cyclohexyl-2,8-diazaspiro[4.5]dec-2-yl)-2-oxoethyl]piperidine-4-amine

Except for using the compound produced in Example 68 in place of the compound produced in Example 63, the same operation as in Example 64 was performed to obtain the title compound having the following physical properties.
TLC: Rf 0.29 (chloroform:methanol:28% aqueous ammonia=4:1:0.2);
NMR (CDCl$_3$): δ 0.96-1.94 (m, 20H), 2.16 (t, J=11.44 Hz, 2H), 2.23-2.36 (m, 1H), 2.37-2.73 (m, 5H), 2.82-2.91 (m, 2H), 3.08 (s, 1H), 3.10 (s, 1H), 3.32 (s, 1H), 3.36 (s, 1H), 3.50 (t, J=7.32 Hz, 1H), 3.57 (t, J=7.05 Hz, 1H).

Example 70

1-[2-(8-cyclohexyl-2,8-diazaspiro[4.5]dec-2-yl)-2-oxoethyl]-N,N-bis(1H-imidazol-2-ylmethyl)-4-piperidinamine Except for using the compound (30 mg) produced in Example 69 in place of the compound produced in Example 64, the same operation as in Example 65 was performed to obtain the title compound having the following physical properties.
TLC: Rf 0.80 (dichrolomethane:methanol:28% aqueous ammonia=4:1:0.2);
NMR (CDCl$_3$): δ 0.98-1.94 (m, 20H), 1.98-2.11 (m, 2H), 2.21-2.36 (m, 1H), 2.37-2.69 (m, 5H), 2.90-3.03 (m, 2H), 3.06 (s, 1H), 3.07 (s, 1H), 3.31 (s, 2H), 3.45-3.60 (m, 2H), 3.77 (s, 4H), 7.00 (s, 4H).

Example 70(1) to Example 70(2)

Except for using the corresponding amine in place of 4-(tert-butoxycarbonylamino)piperidine and using corresponding bromide in place of methyl bromoacetate, the same operation as in Example 61 was performed to obtain the compound of the present invention having the following physical properties.

Example 70(1)

1-[3-(8-cyclohexyl-2,8-diazaspiro[4.5]dec-2-yl)-3-oxopropyl]-N,N-bis(1H-imidazol-2-ylmethyl)-4-piperidinamine

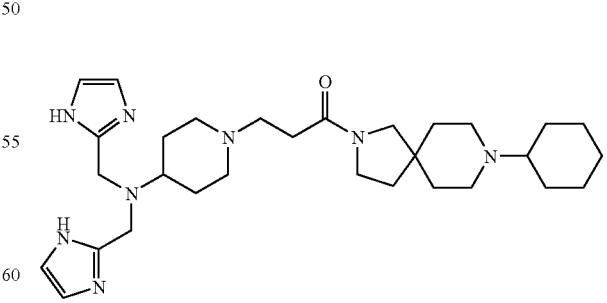

TLC: Rf 0.69 (dichrolomethane:methanol:28% aqueous ammonia=4:1:0.2);
NMR (CDCl$_3$): δ 0.97-2.10 (m, 22H), 2.22-2.74 (m, 10H), 2.87-2.98 (m, 2H), 3.25 (s, 1H), 3.30 (s, 1H), 3.43-3.55 (m, 2H), 3.76 (s, 2H), 3.80 (s, 2H), 7.00 (s, 2H), 7.01 (s, 2H).

Example 70(2)

1-{1-[2-(8-cyclohexyl-2,8-diazaspiro[4.5]dec-2-yl)-2-oxoethyl]-4-piperidinyl}-N,N-bis(1H-imidazol-2-ylmethyl)methanamine

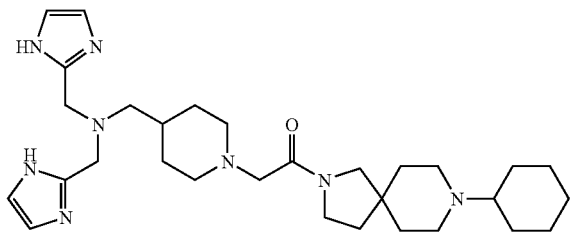

TLC: Rf 0.38 (dichrolomethane:methanol:28% aqueous ammonia=4:1:0.2);

NMR (CDCl$_3$): δ 0.97-1.91 (m, 21H), 1.94-2.10 (m, 2H), 2.19-2.68 (m, 5H), 2.34 (d, J=7.1 Hz, 2H), 2.82-2.96 (m, 2H), 3.07 (s, 1H), 3.08 (s, 1H), 3.32 (s, 1H), 3.37 (s, 1H), 3.45-3.68 (m, 2H), 3.60 (s, 4H), 7.03 (s, 4H).

Biological Examples

Efficacy of the compound of the present invention, for example the fact that the compound of the present invention has CXCR4 antagonistic activity, has been demonstrated by the following experiment.

A measuring method of the present invention was modified to improve accuracy and/or sensitivity of the measurement for evaluating the compound of the present invention. The detailed experimental methods are shown bellow.

As mentioned above, a more direct procedure is a screening a compound that prevents for HIV from binding to CXCR4, which is a receptor on CD4+ cell, on an assay system using HIV viruses. However, using HIV viruses for a large-scale screening is not practical due to its difficult handling. On the other hand, both of T cell-directed (X4) HIV-1 and SDF-1 bind to CXCR4 and therefore CXCR4 binding sites at both of HIV-side and SDF-1-side as well as SDF-1- and HIV-binding sites at the CXCR4 side may presumably have any common characteristics. Thus, to find a compound inhibiting absorption of HIV viruses to a cell that is a different mechanism from those of pre-existing anti-AIDS drugs (reverse transcriptase inhibitors and protease inhibitors), an assay system using an endogenous ligand for CXCR4, SDF-1 instead of HIV may be available.

Specifically, as a system of screening a compound that inhibits the binding between SDF-1 and CXCR4, for example a system of measuring the binding between iodine-labeled SDF-1 and a human T cell strain in which CXCR4 is known to be expressed is operable. The identical idea is possible since macrophage (R5) HIV and RANTES, MIP-1α, and MIP-1β all bind to CCR5.

[Test Methods]

Test Example 1

Study for Inhibition of Binding Human SDF-1 to CEM Cells

To human T cell strain CEM cells in a binding buffer (containing HEPES and BSA), the test compound and $^{125}$I-SDF-1 (NEN) were added and the mixture was incubated at 4° C. for 60 minutes. The reacted CEM cells were rapidly filtrated with a GF/B membrane filter plate (Packard) to adsorb. The plate was washed with PBS three times and then dried. Microscint+20 (Packard) was added thereto. An amount of the radioactivity bound to the CEM cells was measured using Top Count (Packard) and inhibition (%) of the test compound was calculated according to the following equation:

Inhibition=$\{(Et-Ea)/(Et-Ec)\} \times 100$ wherein

Et: amount of radioactivity when the test compound is not added,

Ec: amount of radioactivity when non-radioactive SDF-1 (Pepro Tech) is added in an amount of 1000 times as much as $^{125}$I-SDF-1 as a test compound, and Ea: amount of radioactivity when the test compound is added.

All compounds of the present invention shown in the Example exhibited inhibition of 50% or more in a concentration of 10 μM. For example, IC$_{50}$ value for compound 8(113) was 15 nM.

Test Example 2

Measurement of the Influence of a Compound of the Present Invention on Blood Pressure and Heart Rate A rat is anesthetized with urethane (1.2 g/kg subcutaneous administration). After neck midline dissection, a catheter for measuring blood pressure is inserted into a right common carotid artery. Then, after dissecting inguinal region, a catheter for chemical injection is inserted into a femoral vein and fixed. A catheter for measurement of blood pressure is connected to a pressure transducer and then the pressure waveform is recorded on a thermal writing pen recorder through an amplifier for strain compression (AP-641G (manufactured by NIHON KOHDEN CORPORATION)). In this case, regarding a heart rate, a value through a cardiotachometer (AT-601 G (manufactured by NIHON KOHDEN CORPORATION)) using the pressure waveform obtained from the amplifier for strain compression as a trigger is recorded on a thermal writing pen recorder. The test compound is dissolved in a 10% solubilizing agent/physiological saline solution (volume ratio of polyoxyethylene hydroxystearate:propylene glycol:physiological saline=7:3:190) so as to adjust the concentration to 0.1, 0.3, 1, 3 or 10 mg/mL to prepare solutions. Each solution is intravenous administered at 1 mL/Kg through the caudal vein over about 10 seconds. Accumulative administration of stepwise increasing in dosage is carried out to an individual.

Test Example 3

Measurement of Maximum Plasma Level (Cmax) and Bioavailability (BA)

A test compound is weighed, dissolved in Solutol (trade name; manufactured by BASF-TAKEDA Vitamins Ltd.)/propylene glycol=7/3 which is heated to 60° C. and adjusted to 20 mg/mL; thereafter, the test compound is diluted by 10 times with distilled water for injection, and further diluted by 2 times with saline solution, by which intravenously administered solution is eventually made. The test compound is weighed, dissolved in Solutol (trade name; manufactured by BASF-TAKEDA Vitamins Ltd.)/propylene glycol=7/3 which is heated to 60° C., and adjusted to 20 mg/mL; thereafter, the test compound is diluted by 10 times with distilled water for injection, by which orally administered solution is eventually made. Intravenous administration is performed by rapid single administration (n=3) of intravenously administered solution (1 mg/kg) from the tail vein of Crl:CD(SD) Rat (male, manufactured by CHARLES RIVER LABORATORIES JAPAN, INC). Oral administration is performed by forced administration (n=3) of orally administered solution (10 mg/kg) into the stomach of Crl:CD(SD) Rat (male, manufactured by CHARLES RIVER LABORATORIES JAPAN, INC.) using a sonde. The administration is conducted under fasting conditions; water is freely ingested. A 0.35 mL blood sample is taken from cervical vein by using Heparinized Syringe at 15 minutes, 30 minutes, 1 hour, 2 hours, 4 hours, 6 hours, 8 hours, and 24 hours after administration. The obtained blood is stored in ice, and after centrifugation at 12,000 rpm for 5 minutes, blood plasma is fractionated. The blood plasma is preserved at a temperature of −80° C. The sample of blood plasma preserved at a temperature of −80° C. is dissolved; inner standard solution (100 µL) and acetonitrile (2 mL) are added to the blood plasma sample 100 µL and stirred; and the sample is centrifuged at 2,500 rpm for 10 minutes. After the supernatant is evaporated to dryness by means of a centrifugal concentrator, 67% dimethyl sulfoxide solution (150 µL) is added to the residue and dissolves them again; and 20 µL of the solution is analyzed by means of LC/MS/MS.

The analysis by means of LC/MS/MS should be performed, for example, under the following conditions:
[LC Conditions]
Measurement device: Waters 2795 (manufactured by Waters Corporation)
Analytical column: Unison UK-C18, 3.0 µm particle size, 2.0 mm×30 mm (manufactured by Imtakt Corporation)
Analytical column temperature: Room temperature
Flow rate: 200 µL/min
Moving bed: 5 mM IPC-PFAA-7 solution/acetonitrile (9/1→1/9)
[MS/MS Conditions]
Measurement device: Quatro micro API (manufactured by Micromass Communications Inc.)
Method for ionization: ES+
Capillary electric potential: 3.30 kV
Source temperature: 120° C.
Desolvation temperature: 350° C.
Multiplier: 650 V
The monitor ion which was suitable for each sample was selected.

The concentration transition in the rat blood plasma of the test compound is analyzed by means of non-compartment analysis method by using WinNonlin 4.0.1 (manufactured by Pharsight Corporation) to calculate the maximum blood concentration Cmax and the area under the blood concentration curve AUC.

BA is calculated by means of the following formula:

$$BA(\%)=\{(AUC_{p.o.}/Dose_{p.o.})/(AUC_{i.v.}/Dose_{i.v.})\} \times 100$$

$AUC_{p.o.}$: AUC in oral administration
$Dose_{p.o.}$: Amount of the drug orally administered
$AUC_{i.v.}$: AUC in intravenous administration
$Dose_{i.v.}$: Amount of the drug intravenously administered The maximum blood concentration Cmax of the compound of the present invention indicated good values. For example, the maximum blood concentrations Cmax of Example 8 (113), Example 40 (68), Example 40 (72) and Example 65 (4) were as shown in Table 1.

| Compound | Cmax (ng/mL) |
| --- | --- |
| Example 8(113) | 80 |
| Example 8(114) | 46 |
| Example 40(68) | 175 |
| Example 40(72) | 157 |
| Example 65(4) | 420 |

Test Example 4

Investigation with a Phospholipidosis Detecting System Using Fluorescent Labeling Phospholipidosis Analog (i) Phospholipid Accumulation Measurement 100 µL/well as required (1 dose 2 wells) of cell suspension of CHL/IU (cell line derived from a Chinese hamster lung) adjusted by MEM ($7 \times 10^4$ cells/mL) adjusted by MEM (minimum essential medium) culture medium was added to a 96-well plate (96-well clear-bottom plate), and cultured for about 24 hours. After culture, the supernatant of the 96-well plate was removed, and the 100 µL/well compounds of each concentration dissolved and suspended in a minimum essential medium (MEM) including 25 µmol/L nitrobenzoxadiazole dipalmitoyl phosphatidylethanolamine (NBD-PE) (hereinafter abbreviated as a NPD-PE medium) were added and treated for about 24 hours. The treatment concentrations of each compound were set to be 6.25, 12.5, 25, 50 and 100 µmol/L. The positive control substance was set to be amiodarone hydrochloride, and the treatment concentrations were set to be 1.25, 2.5, 5, 10 and 20 µmol/L. In addition, 5 untreated controls (only MEM) and 5 NBD-PE controls (made by means of adding a 1/100 amount of DMSO to the NBD-PE culture medium) were set per compound, and cultured in the same manner. After finishing the culture, the cultures were washed twice with Phosphate buffered saline (hereinafter abbreviated as PBS) (−) 100 µL/well, and the MEM (100 µL) was added to all of the treatment wells including 2 empty wells for WST-1 background controls and cultured for about a half hour. The fluorescence intensities of each well were measured by using a microplate reader (manufactured by Molecular Devices Inc., SPECTRA max M2; the excitation wavelength 485 nm/the fluorescence wavelength 535 nm).

(ii) Analysis

Using the average values of each dose×2 wells, a phospholipid increase rate (%) to the NBD-PE control was calculated by using the following calculating formula:

Phospholipid increase rate(%)=100×{(test article fluorescence intensity−untreated control fluorescence intensity)/(*NBD-PE* control fluorescence intensity−untreated control fluorescence intensity (iii) Cytotoxicity Assay The 96-well plate measured in the phospholipid accumulation measurement was measured by means of Plate Reader (manufactured by Molecular Devices Inc., SPECTRA max M2) with the main wavelength of 450 nm and the correct wavelength of 690 nm to calculate a Pre value. An amount of 5 µL/well of Premix WS T-1 was added to each of the 96 hole plates by which Pre measurement was conducted. After culture for 2 to 4 hours, the 96-well plate was measured as well as the Pre measurement to calculate an Aft value. Then, the background control value was subtracted from the each measured value. A value which was calculated by subtracting the Pre value from the Aft value was used, then the cell growth rate (%) was calculated by using the following calculating formula:

Cell growth rate(%)=100×{(test article OD)/(NBD-PE control OD)}

(iv) Determination

A test dose that indicated value of equal to or more than 25% of the maximum phospholipid accumulation increase rate of amiodarone which was the positive control was determined as positive. In addition, the dose whose cell growth rate was equal to or less than 50% in the cytotoxicity assay was not used for determination of existence or nonexistence of a phospholipidosis inductive effect.

As a result, it was found that the compound of the present invention had a low phospholipidosis inductive effect in vitro experiment system.

| Compound | The rate of increase of phopholipid accumulation (%) (compound dose: 50 μM) | Judgement |
|---|---|---|
| Example 8(113) | 10 | negative |
| Example 40(68) | 18 | negative |
| Example 40(72) | 16 | negative |
| Example 65(4) | 12 | negative |

Test Example 5

Artificial Lipid Membrane Binding Account by Using Biacore (Registered Trademark) S51 System (i) Liposome Adjustment 10 mM of 1,2-Dioleoyl-sn-Glycero-3-Phosphate, Monosodium Salt (hereinafter abbreviated as DOPA) chloroform solution was evaporated to dryness by means of an aspirator, and 0.6 mL of PBS/5% dimethyl sulfoxide (hereinafter abbreviated as DMSO) was added. The chloroform solution was fully suspended by means of a vortex mixer, and the freezing and thawing were repeated for 5 times. Liposome was created by means of a liposome adjustment instrument (manufactured by Avestin Inc.) and 2 syringes, and was diluted to 0.5 mM with PBS/5% DMSO just prior to immobilization.

(ii) Measurement Compound Adjustment

The 38 μL of 1×PBS is added to 2 μL DMSO solution (10 mM), and further the 360 μL 1×PBS/5% DMSO was added; the 50 μM of final concentration in the 1×PBS/5% DMSO was adjusted and measured.

(iii) Analysis

All of the following analysis used Biacore® S51 system; the measurement conditions were set by Biacore® S51 Control Soft.

The measurement temperature was set to be 37° C., and the 1×PBS/5% DMSO (pH 7.4 or PH 6.0) was used as a buffer. Series S Sensor Chip L1 was used for a sensor chip. The DOPA was immobilized in one of the measuring spots on the sensor surface, and the central spot was used as a reference.

Immobilization of liposome was conducted at a flow rate of 10 μL/min for about 3 minutes; then the compound was added at a flow rate of 30 μL/min and the interaction was measured. The measurement conditions are as follows:

Assay buffer: PBS/5% DMSO (pH 7.4 or PH 6.0)
Measurement temperature: 37° C.
Sensor chip: Series S Sensor Chip L1

Flow rate: 10 μL/min at the time of the liposome immobilization; 30 μL/min at the time of the measurement of interaction with the compound Regeneration: 20 mMCHAPS (3-[(3-Cholamidopropyl) dimethylammonio]-1-propanesulfonate), Isopropanol/50 mM sodium hydroxide solution=40/60 (volume ratio) mixture (60 seconds)

(iv) Data Processing

The data processing was conducted by means of method of Abdiche et al. (Analytical biochemistry, 328, 233-243 (2004)) by using Biacore S51 Evaluation Soft.

Regarding the value of binding response (RU) in which the value of reference was subtracted, it was divided by a sample molecular weight after minute error of the DMSO concentration included in the sample solution was corrected. In addition, the value obtained here was divided by an amount of capture at the time of the cycle because the value obtained here was proportional to the amount of capture of the liposome; further, the value was multiplied by a million to be considered as a corrected value (Corrected value=1000000× RU (test compound)/molecular quantity (test compound) RU (liposome)).

Propranolol, Amiodarone, Desipramine, Imipramine and Procaine were added as the controls, and it was recognized that the variation of the binding response was within ca. 10 to 15%.

(v) Determination

The compound, in which a value of the binding response after the correction was equal to or more than 150, was determined as positive.

As a result, it was found that the compound of the present invention had a low phospholipidosis inductive effect in vitro experiment system.

| Compound | Corrected value of binding response (RU) | Judgement |
|---|---|---|
| Example 8(113) | 66.6 | negative |
| Example 8(114) | 80.7 | negative |
| Example 40(68) | 77.6 | negative |
| Example 40(72) | 72.0 | negative |
| Example 65(4) | 36.0 | negative |

Formulation Examples

Formulation Example 1

N,N-bis(1H-imidazol-2-ylmethyl)-4-[(2-isobutyl-2,8-diazaspiro[4.5]dec-8-yl)methyl]benzamide (200 g), calcium carboxymethyl cellulose (disintegrant, 20.0 g), magnesium stearate (lubricants, 10.0 g) and microcrystalline cellulose (870 g) were mixed by a conventional method and then compressed to obtain 10,000 tablets each containing 20 mg of an active ingredient.

Formulation Example 2

N,N-bis(1H-imidazol-2-ylmethyl)-4-[(2-isobutyl-2,8-diazaspiro[4.5]dec-8-yl)methyl]benzamide (100 g), mannitol (2 kg) and distilled water (50 L) were mixed by a conventional method and filtered with a dust filter, and then each ampoule was filled with 5 mL of the obtained mixture and subjected to heat sterilization in an autoclave to obtain 10,000 ampoules each containing 10 mg of an active ingredient.

INDUSTRIAL APPLICABILITY

The compound of the present invention has CXCR4 antagonistic activity and is therefore useful as a preventive and/or therapeutic agent for CXCR4-mediated diseases. Accordingly, the compound of the present invention can be available as a drug. For example, the compound of the present invention is useful as a preventive and/or therapeutic agent for inflammatory and immune diseases (for example, rheumatoid arthritis, arthritis, systemic lupus erythematosus, retinopathy, macular degeneration, pulmonary fibrosis, transplanted organ rejection, etc.), allergic diseases, infections (for example, human immunodeficiency virus infection, acquired immunodeficiency syndrome, etc.), cancerous diseases (for example, cancer, cancer metastasis, etc.), cardiac or vascular disease (for example, arteriosclerosis, myocardial infarction, stenocardia, cerebral infarction, chronic occlusive disease, etc.), psychoneurotic diseases, cerebral diseases, and metabolic diseases, or an agent for regeneration therapy. In addition, the compound of the present invention is therefore useful as a preventive and/or therapeutic agent for cancerous diseases or infections.

The invention claimed is:

1. 1-(4-{[9-(2-ethylbutyl)-1-oxa-4,9-diazaspiro[5.5]undec-4-yl]carbonyl}phenyl)-N,N-bis(1H-imidazol-2-ylmethyl)methanamine, a salt thereof or an N-oxide thereof.

2. A compound which is 1-(4-{[9-(2-ethylbutyl)-1-oxa-4,9-diazaspiro[5.5]undec-4-yl]carbonyl}phenyl)-N,N-bis(1H-imidazol-2-ylmethyl)methanamine.

3. A pharmaceutical composition which comprises 1-(4-{[9-(2-ethylbutyl)-1-oxa-4,9-diazaspiro [5.5]undec-4-yl]carbonyl}phenyl)-N,N-bis(1H-imidazol-2-ylmethyl)methanamine, a salt thereof or an N-oxide thereof, and a pharmaceutically acceptable carrier.

* * * * *